(12) United States Patent
Liu et al.

(10) Patent No.: US 11,661,605 B2
(45) Date of Patent: May 30, 2023

(54) PRODUCTION METHOD FOR PROTEIN

(71) Applicant: Kao Corporation, Tokyo (JP)

(72) Inventors: Shenghao Liu, Wakayama (JP);
Yasushi Kageyama, Wakayama (JP);
Mika Terai, Sakai (JP)

(73) Assignee: Kao Corporation, Tokyo (JP)

( * ) Notice: Subject to any disclaimer, the term of this patent is extended or adjusted under 35 U.S.C. 154(b) by 83 days.

(21) Appl. No.: 16/961,331

(22) PCT Filed: Jan. 11, 2019

(86) PCT No.: PCT/JP2019/000618
§ 371 (c)(1),
(2) Date: Jul. 10, 2020

(87) PCT Pub. No.: WO2019/139108
PCT Pub. Date: Jul. 18, 2019

(65) Prior Publication Data
US 2020/0370059 A1 Nov. 26, 2020

(30) Foreign Application Priority Data
Jan. 12, 2018 (JP) .............................. JP2018-003491

(51) Int. Cl.
*C12N 15/75* (2006.01)
*C07K 14/32* (2006.01)

(52) U.S. Cl.
CPC .............. *C12N 15/75* (2013.01); *C07K 14/32* (2013.01)

(58) Field of Classification Search
CPC ....... C12N 15/75; C07K 14/32; C07K 14/325
See application file for complete search history.

(56) References Cited

U.S. PATENT DOCUMENTS

| | | | |
|---|---|---|---|
| 6,270,760 B1 | 8/2001 | Adams et al. | |
| 8,389,685 B2 * | 3/2013 | Takimura ............... | C07K 14/32 435/243 |
| 2004/0248279 A1 | 12/2004 | Sawada et al. | |
| 2005/0271642 A1 | 12/2005 | Asano et al. | |
| 2009/0081726 A1 | 3/2009 | Kodama et al. | |
| 2012/0183998 A1 | 7/2012 | Kawahara et al. | |

FOREIGN PATENT DOCUMENTS

| | | | |
|---|---|---|---|
| JP | S62-294080 A | | 12/1987 |
| JP | S63-17687 A | | 1/1988 |
| JP | S63-133999 A | | 6/1988 |
| JP | H04278092 | * | 10/1992 |
| JP | 2007-130013 A | | 5/2007 |
| JP | 4336082 B2 | | 9/2009 |
| JP | 4485341 B2 | | 6/2010 |
| JP | 2011-160686 | * | 8/2011 |
| JP | 4955358 B2 | | 3/2012 |
| JP | 2017-79639 A | | 5/2017 |
| JP | 2018-070565 A | | 5/2018 |
| JP | 2018-177656 A | | 11/2018 |
| WO | WO 95/02695 A1 | | 1/1995 |
| WO | WO 2011/049227 A1 | | 4/2011 |
| WO | WO 2016/007355 A1 | | 1/2016 |
| WO | WO 2017/123946 A1 | | 7/2017 |
| WO | WO 2018/136459 | * | 7/2018 |

OTHER PUBLICATIONS

AddGene Plasmid: pHY300PLK Plasmid map and Description—Retrived from < https://www.addgene.org/vector-database/3107/ > on Apr. 28, 2022.*
Kodama et al., 2012. "Approaches for Improving Protein Production in Multiple Protease-Deficient Bacillus subtilis Host Strains", in Advances in Applied Biotechnology, Prof. Marian Petre (Ed.), ISBN: 978-953-307-820-5, InTech.*
NCBI B. subtilis sigA gene information. Retrieved from < www.ncbi.nlm.nih.gov/gene/937897 > Retrieved on Oct. 25, 2022.*
The extended European search report including the supplementary European search report and the European search opinion, for EP application No. 19738051.2, dated Dec. 13, 2021, from the European Patent Office, Munich, Germany.
Yoshisue H, et al., "Identification of a promoter for the crystal protein-encoding gene cryIVB from *Bacillus thuringiensis* subsp. *israelensis*," G

(56) References Cited

OTHER PUBLICATIONS

International Preliminary Report on Patentability (IPRP), Chapter I of the Patent Cooperation Treaty, including the Written Opinion, for PCT/JP2019/000618; I.A. fd Jan. 11, 2019, dated Jul. 14, 2020, by the International Bureau of WIPO, Geneva, Switzerland.

Singh, A. et al., "Protein recovery from inclusion bodies of *Escherichia coli* using mild solubilization process." Microb Cell Fact. 2015; 14:41. Published Mar. 25, 2015. doi:10.1186/s12934-015-0222-8.

Higashibata, H, "The elements of obtaining a high expression of heterologous protein in *E. coli*." Biotechnology, vol. 91, pp. 96-100 (2013).

Schumann, W. et al., "Production of recombinant proteins in *Escherichia coli*," Genetics and Molecular Biology (Brazil), 27, 3, 442-453 (2004).

Gomes, AR et al., "An Overview of Heterologous Expression Host Systems for the Production of Recombinant Proteins," Adv. Anim. Vet. Sci. 4(7):346-356 (2016).

Ferrer-Miralles, N. et al., "Bacterial cell factories for recombinant protein production; expanding the catalogue." Microbial Cell Factories 2013 12:113.

Agaisse, H et al., "How does *Bacillus thuringiensis* produce so much insecticidal crystal protein?" J Bacteriol. 1995;177(21):6027-6032. doi:10.1128/jb.177.21.6027-6032.1995.

Deng, C et al., "Regulation of *cry* gene expression in *Bacillus thuringiensis*." Toxins (Basel). 2014;6(7):2194-2209. Published Jul. 23, 2014. doi:10.3390/toxins6072194.

Hu, Y et al., "*Bacillus subtilis* strain engineered for treatment of soil-transmitted helminth diseases." Appl Environ Microbiol. 2013;79(18):5527-5532. doi: 10.1128/AEM.01854-13.
Durmaz, E et al., "Intracellular and Extracellular Expression of *Bacillus thuringiensis* Crystal Protein Cry5B in *Lactococcus lactis* for Use as an Anthelminthic." Appl Environ Microbiol. 2015;82(4):1286-1294. Published Dec. 18, 2015. doi:10.1128/AEM.02365-15.
Yang, CY et al., . Enterotoxigenicity and cytotoxicity of *Bacillus thuringiensis* strains and development of a process for Cry1Ac production. J Agric Food Chem. 2003;51(1):100-105. doi:10.1021/j10258631.
Shivakumar AG, et al., "Gene dosage effect on the expression of the delta-endotoxin genes of *Bacillus thuringiensis* subsp. *kurstaki* in *Bacillus subtilis* and *Bacillus megaterium*," Gene. Jun. 30, 1989; 79(1):21-31. doi: 10.1016/0378-1119(89)90089-9. PMID: 2550328.
Ochoa-Zarzosa, A. et al. Chapter 9: "Shuttle vectors of *Bacillus thuringiensis*, " in E. Sansinemea (ed.), *Bacillus thuringiensis Biotechnology*, Springer Science+Business Media B.V., 2012, pp. 175-184.
Chen, Hong, "Principles and Applications of Genetic Engineering," Beijing: China Agriculture Press, pp. 223-226, Jan. 31, 2004.

* cited by examiner

[Figure 1-A]
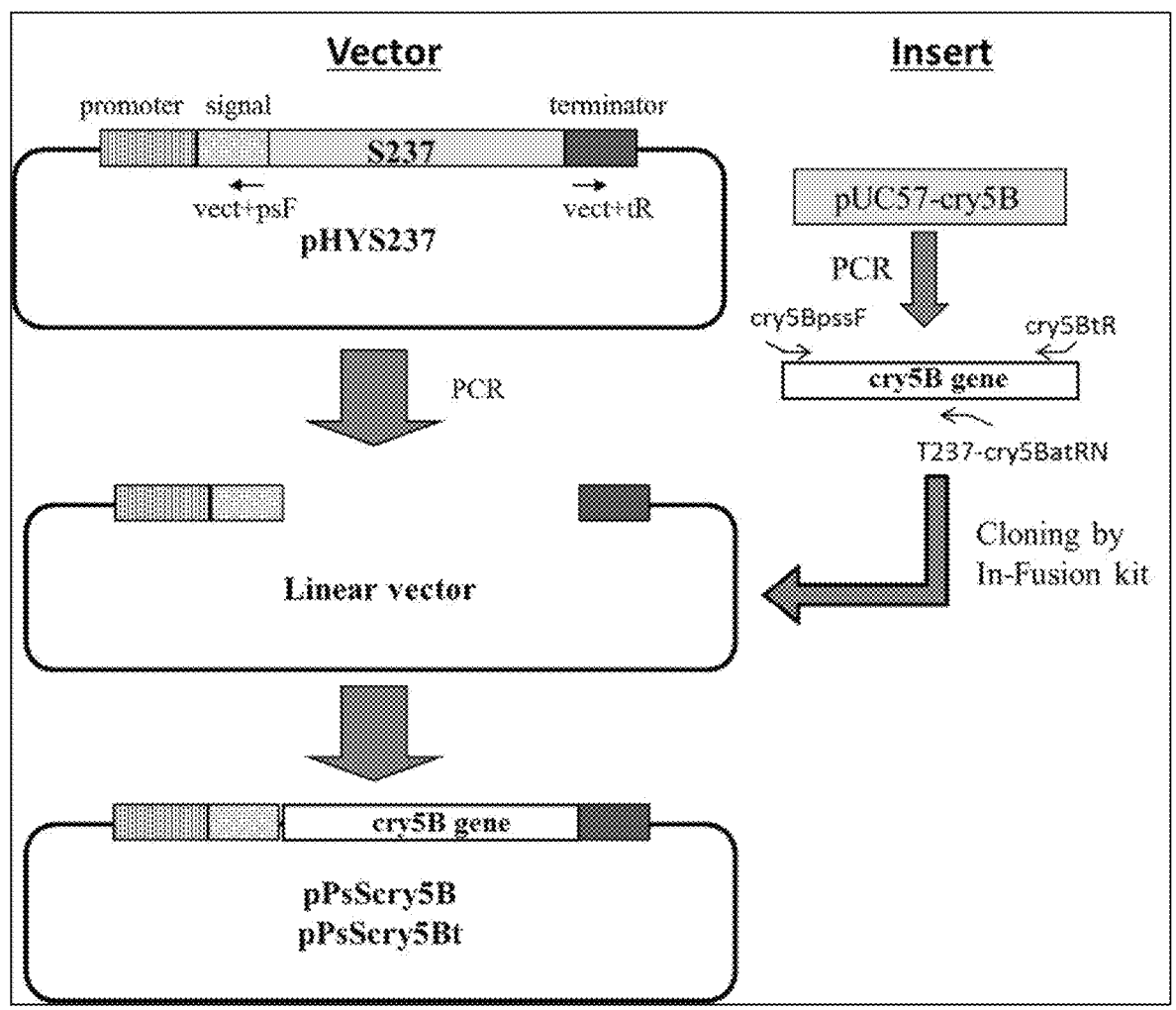

[Figure 1-B]
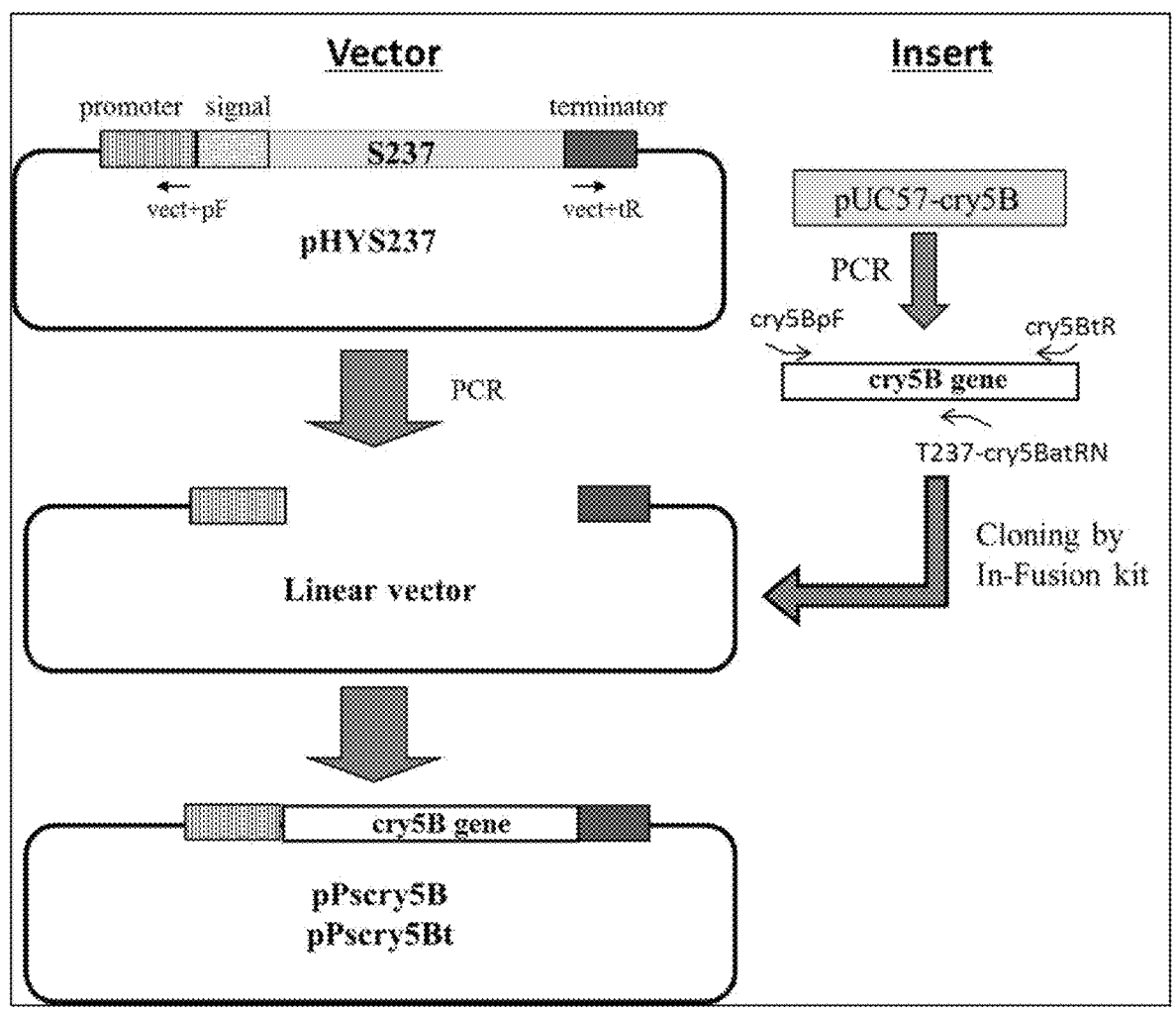

[Figure 1-C]
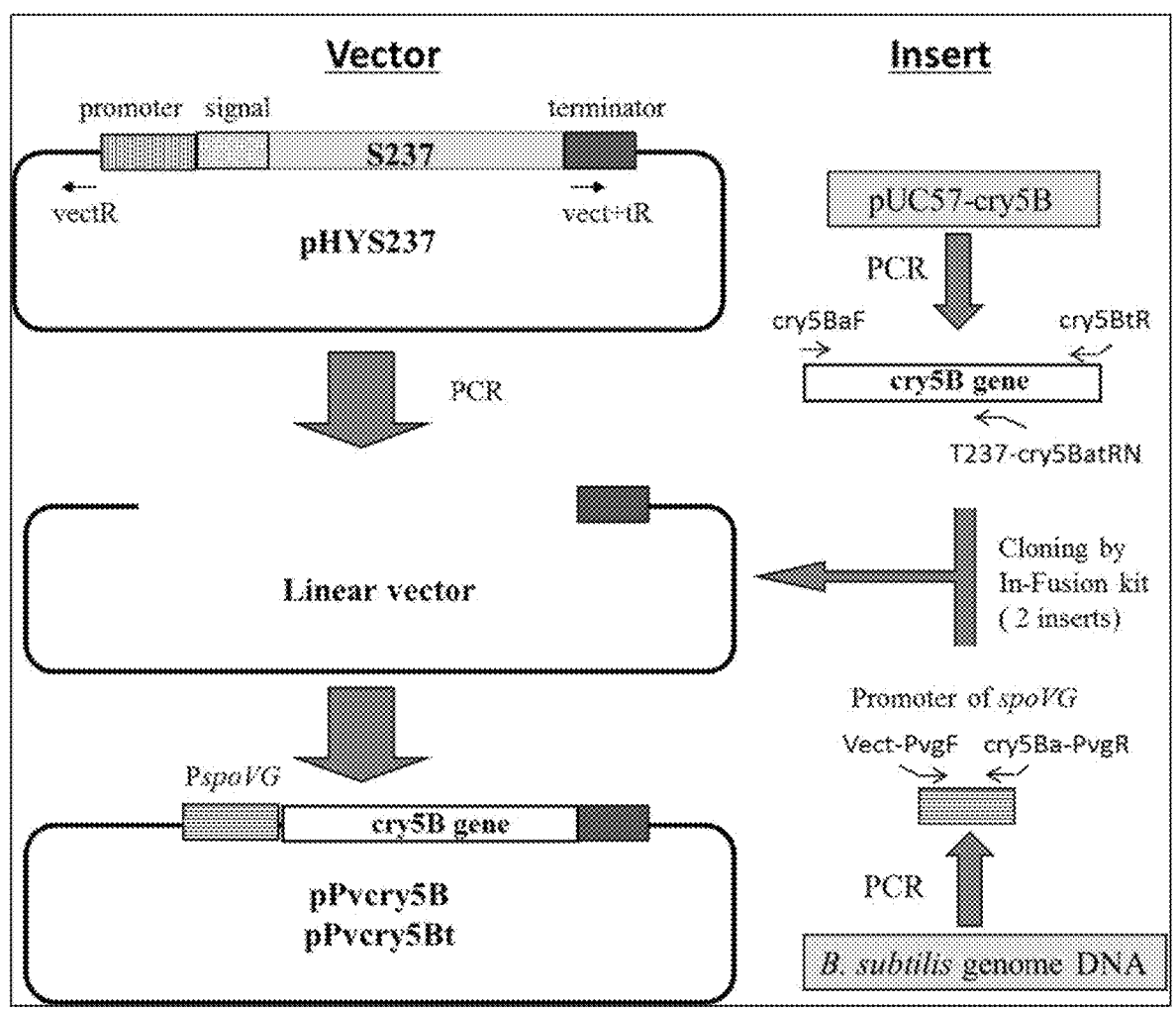

[Figure 1-D]
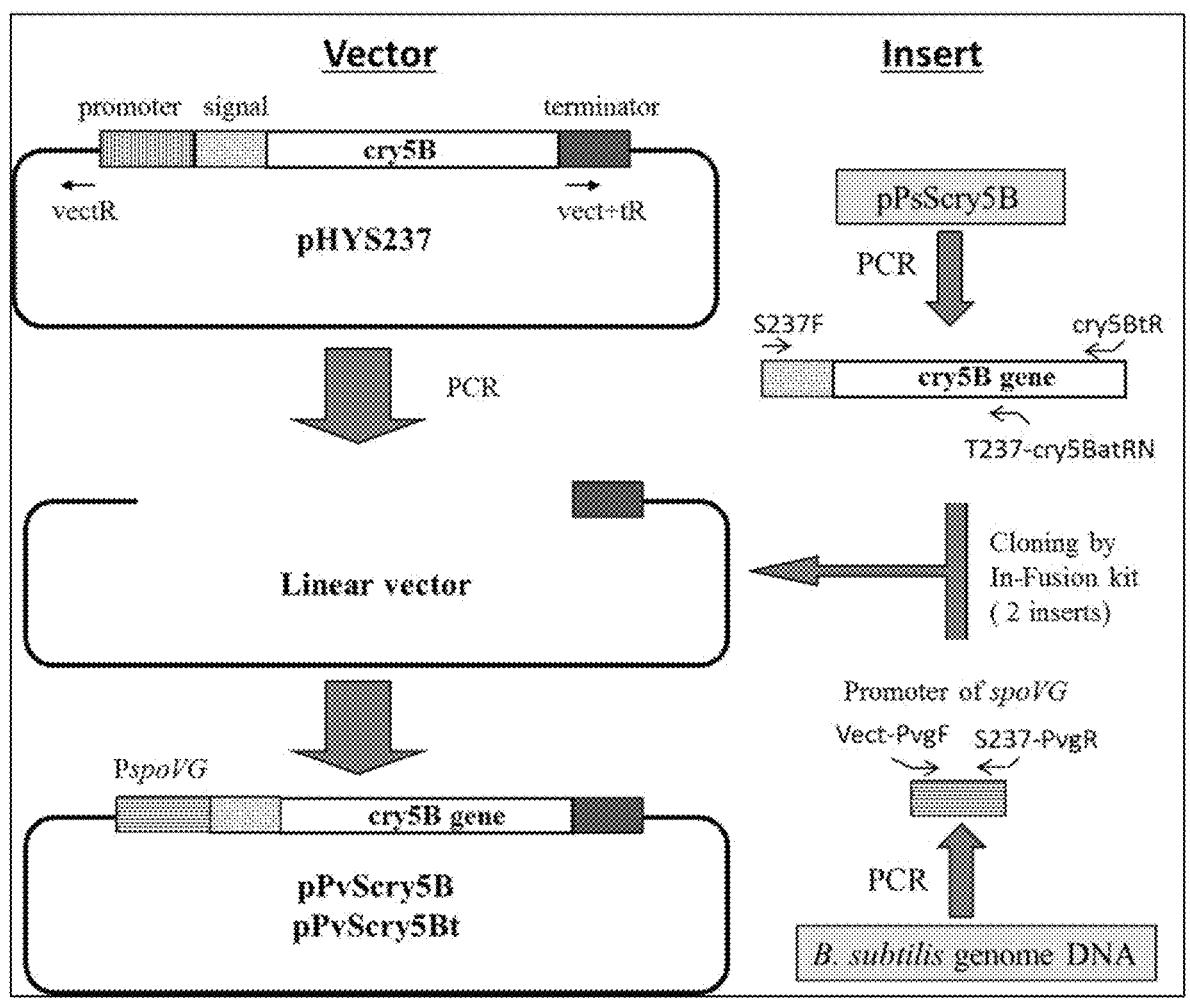

[Figure 2]
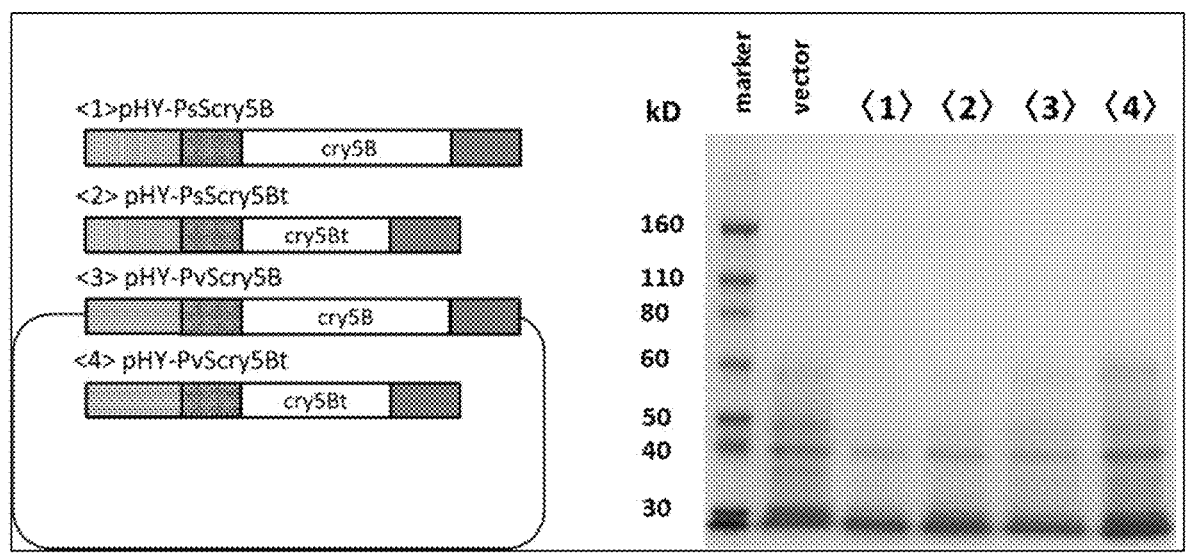

[Figure 3]
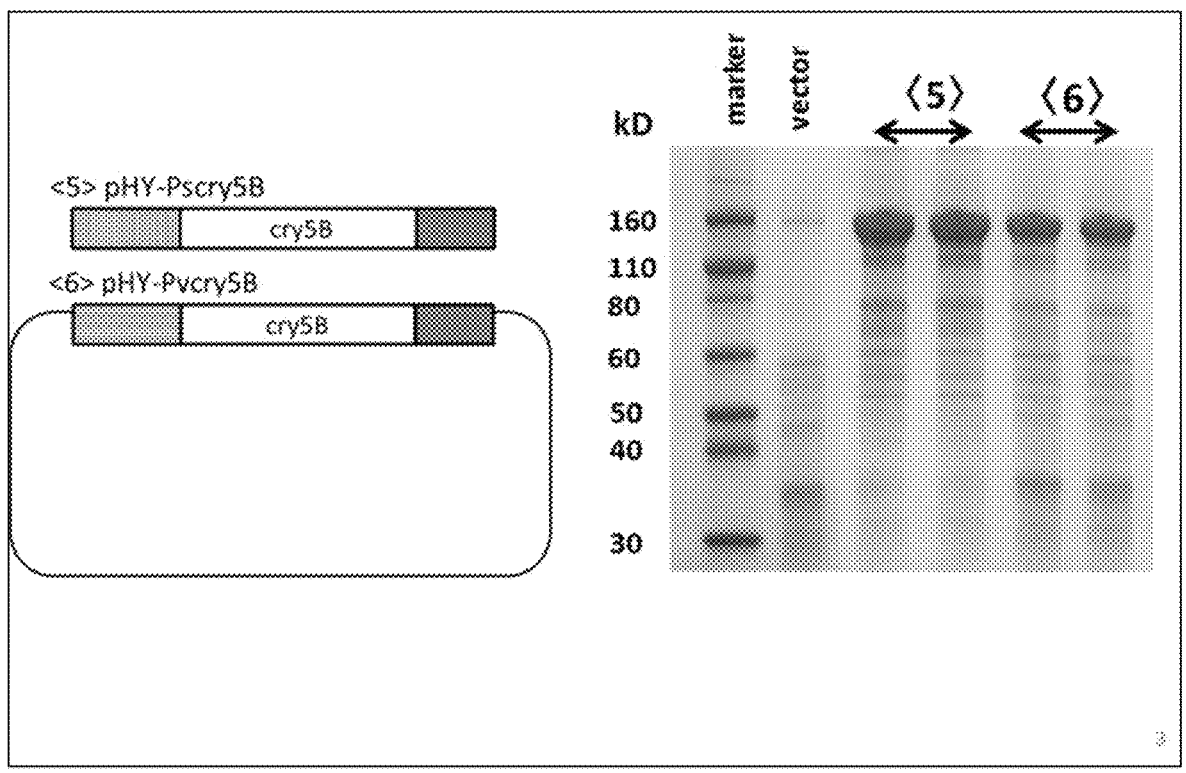

[Figure 4-A]
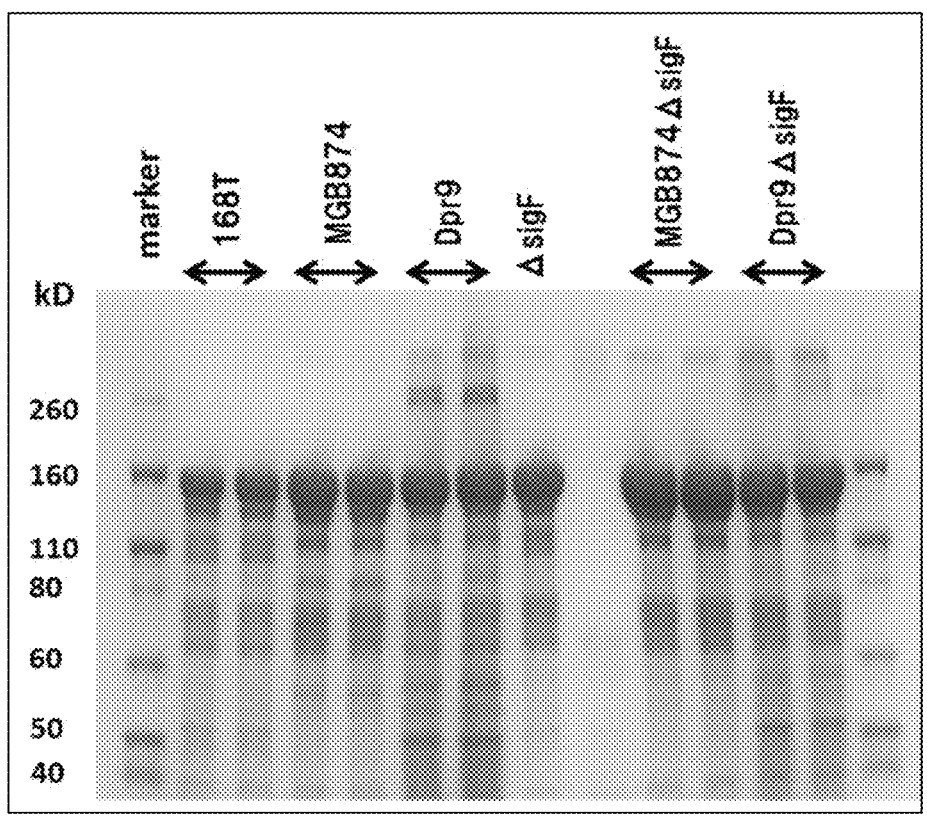

[Figure 4-B]
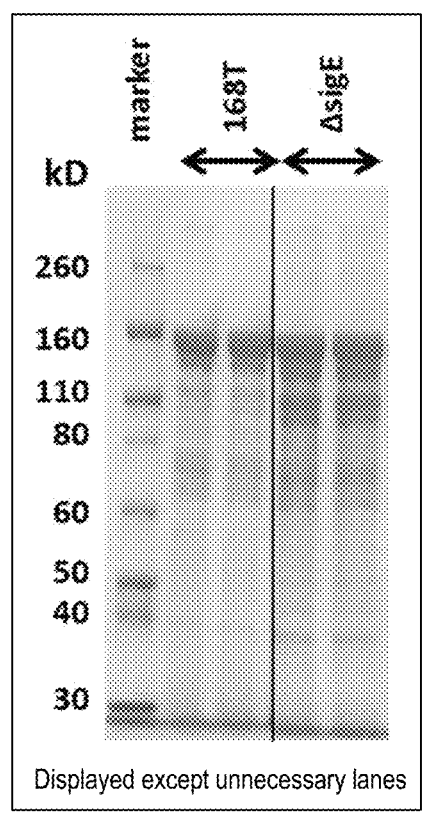

[Figure 5]

[Figure 6]
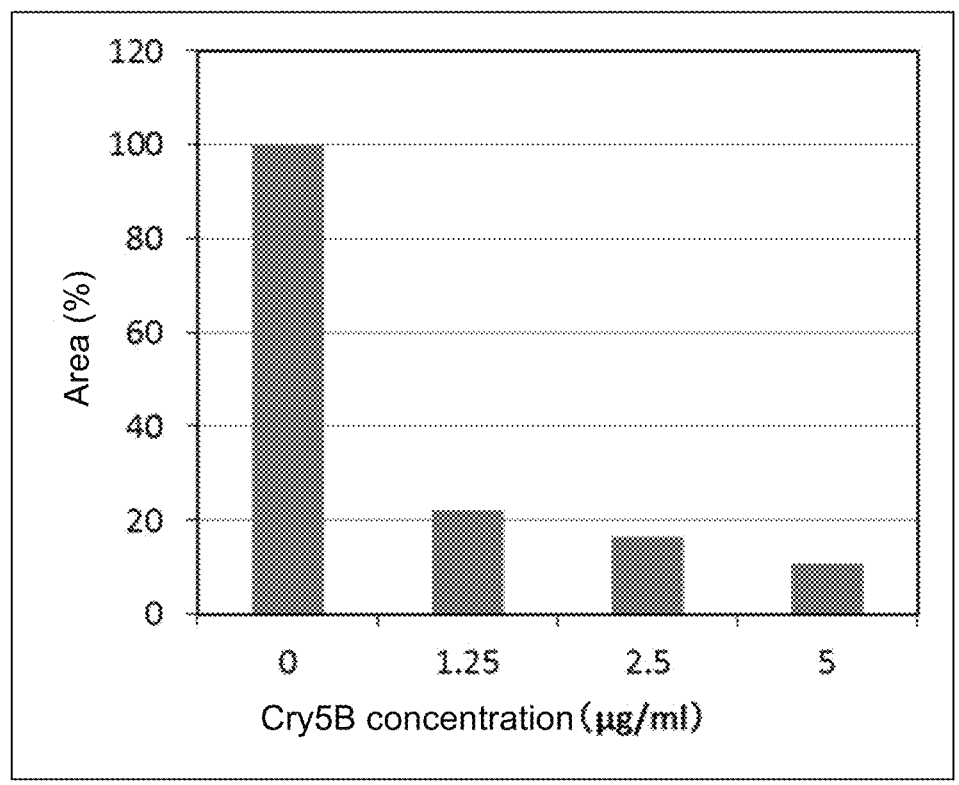

[Figure 7]
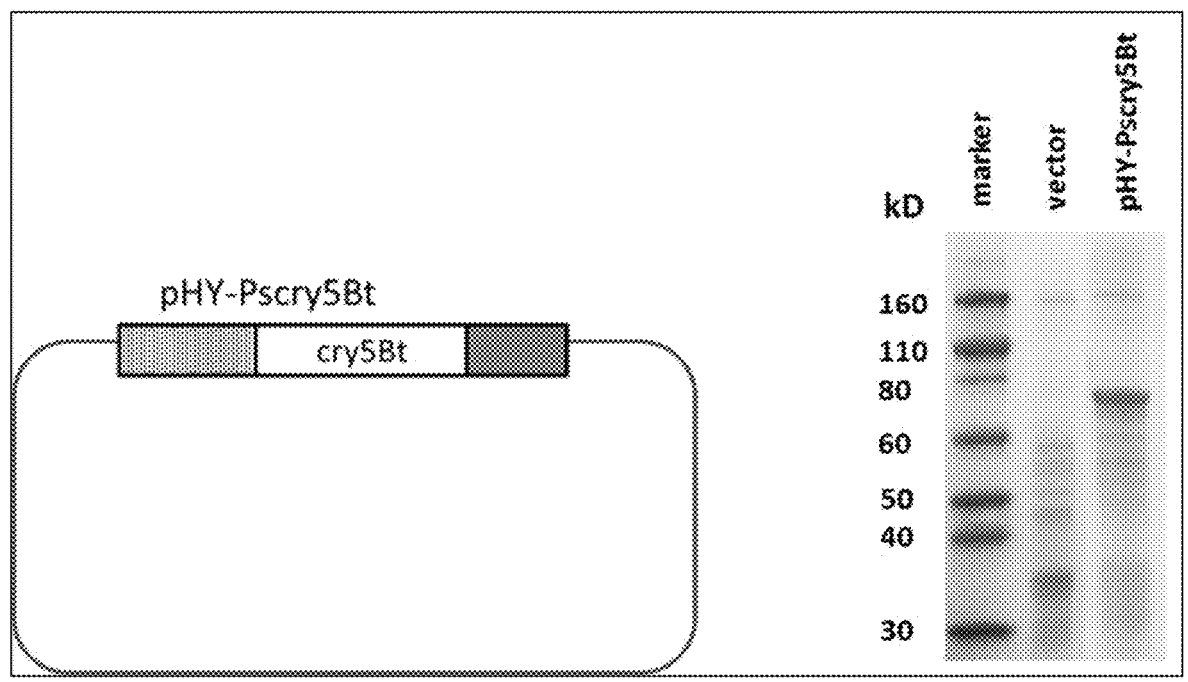

[Figure 8]
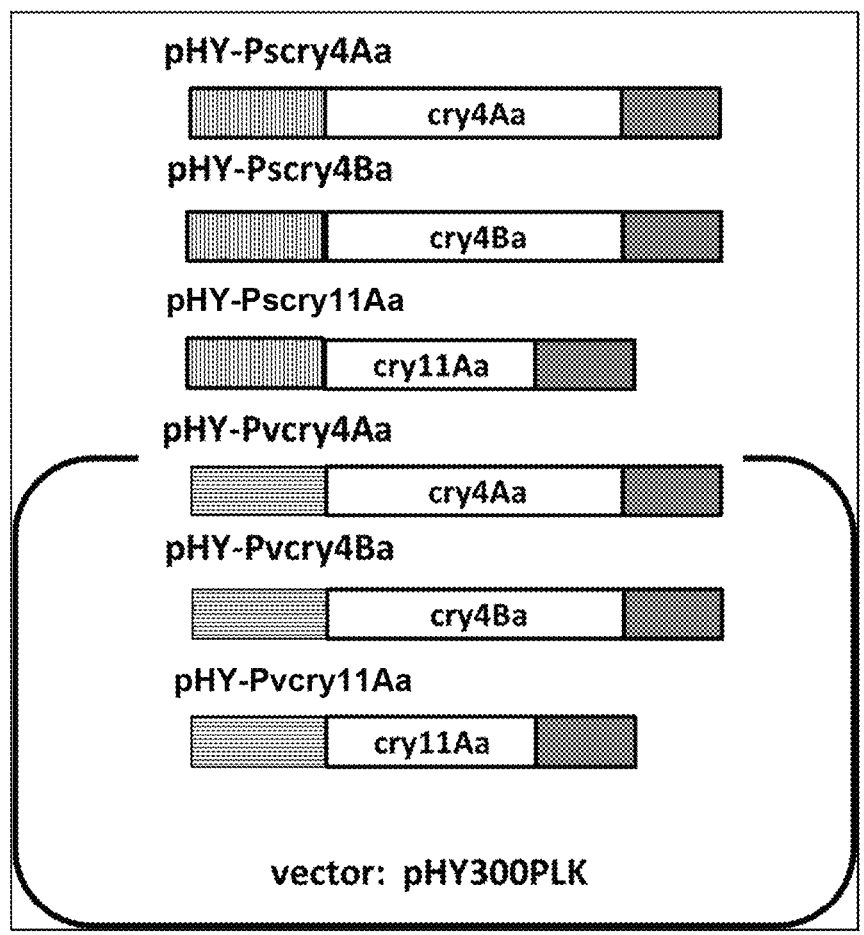

[Figure 9]
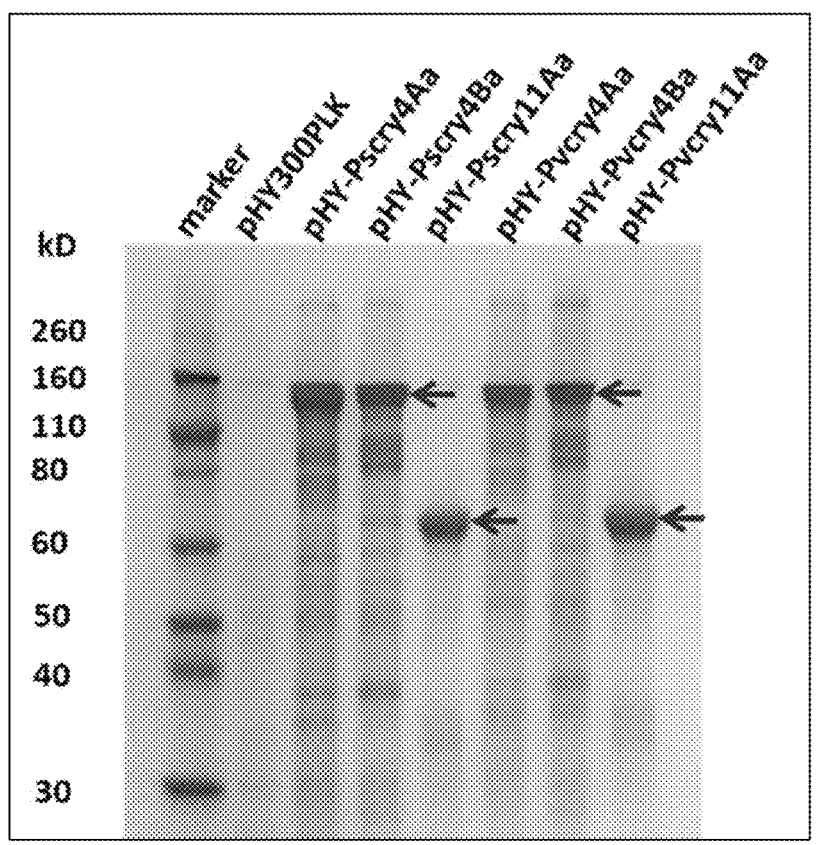

PRODUCTION METHOD FOR PROTEIN

FIELD OF THE INVENTION

The present invention relates to a method for producing a Cry protein by using a *Bacillus* bacterium.

BACKGROUND OF THE INVENTION

Generally, when a large amount of protein is intracellularly expressed by using *Escherichia coli*, the protein is often collected as an insoluble/inactive aggregate (modified protein) called an inclusion body. In this case, in order to recover a biological activity of the protein, a procedure that solubilizes the aggregate and activates (refolding) the protein is required (Non Patent Literature 1). When an active protein cannot be obtained even by the procedure, the expression level of the protein is regulated so as not to form an inclusion body (Non Patent Literatures 2, 3). In another case, when a heterologous protein is intracellularly produced, it is also necessary to adjust expression of a promoter and the copy number of plasmids, in consideration of effect of the heterologous protein on a host (Non Patent Literatures 2, 3).

In contrast, when an extracellular protein is expressed, it is not necessary to consider formation of an inclusion body and effect of concentration of the protein on a host. Up to present, studies for enhancing expression by using a high-expression promoter in combination with a high-copy-number plasmid and releasing suppression of a promoter have been conducted (Patent Literature 1). As a host suitable for extracellular production of protein, a *Bacillus* bacterium, particularly *Bacillus subtilis* has been reported (Non Patent Literatures 4, 5). In addition, *Bacillus subtilis* has been recognized particularly as a highly safe microorganism. In this respect, *Bacillus subtilis* is advantageous as a host.

*Bacillus thuringiensis* is a microorganism producing various insecticidal crystal proteins (hereinafter, referred to as "Cry proteins") and used as a biological agrochemical (Non Patent Literature 6). Generally, a plasmid encoding a Cry protein gene (cry gene) that *Bacillus thuringiensis* has is a large theta-replicating plasmid of low-copy-number. In contrast, a rolling circle replicating plasmid such as a plasmid encoding a replication protein (RepB), which is set forth in SEQ ID NO: 9 and functions to replicate *Bacillus subtilis*, is commonly known to be high copy number. In this point, the rolling circle replicating plasmid differs from the theta-replicating plasmid of low-copy-number (Non Patent Literature 7). When the Cry protein is intracellularly produced by using *Bacillus thuringiensis* from a Cry protein gene (cry gene) on its plasmid, the cry-gene copy number reaches a saturation. From this, it is suggested that the production amount is not increased by increasing the number of copies (Non Patent Literature 6). When a cry gene is cloned into a high-copy-number plasmid, physiological equilibrium changes, with the result that inhibition of sporulation is observed (Non Patent Literature 6). It is suggested that formation of a crystal structure of Cry protein and solubility thereof are influenced by various factors such as a secondary structure and additional constitution components (Non Patent Literature 6). Thus, it has been considered unlikely that a large amount of the protein can be produced simply by enhancing cry gene expression. For example, when *Bacillus thuringiensis*-derived Cry5B protein is expressed in *Bacillus subtilis* PY79, the productivity of the protein in *Bacillus subtilis* PY79 is reported to be as low as only 10 mg/L in contrast to the productivity in *Bacillus thuringiensis* is 75 mg/L (Non Patent Literature 8, Patent Literature 2). Also, it is reported that when Cry5B protein gene is expressed by using a high-copy-number plasmid under control of a high-expression promoter in *Lactococcus lactis*, the productivity of the protein in *Bacillus thuringiensis* is as low as a detection level by western blot (Non Patent Literature 9).

As described above, means that have been generally studied for improving expression of an extracellular protein are not always applicable to production of intracellular proteins, and a means for efficiently and highly expressing, in particular, Cry protein, has not yet been found.

PATENT LITERATURE

Patent Literature 1: WO2011/049227A1
Patent Literature 2: WO2016/007355A1
Patent Literature 3: WO2017/123946A1

NON PATENT LITERATURE

Non Patent Literature 1: Singh A, Upadhyay V, Upadhyay A K, Singh S M, Panda A K (2015) Protein recovery from inclusion bodies of *Escherichia coli* using mild solubilization process; Microb Cell Fact.; 25:14-41.

Non Patent Literature 2: Hiroki Higashibata (2013), ABC for highly expressing heterologous protein using *Escherichia coli* as a host; Biotechnology, 91, 96-100

Non Patent Literature 3: CHUMANN, Wolfgang and FERREIRA, Luis Carlos S. (2004) Production of recombinant proteins in *Escherichia coli*. Genet. Mol. Biol. [online]., 27 (3), 442-453.

Non Patent Literature 4: Gomes A R, Byregowda S M, Veeregowda B M, Balamurugan V (2016). An overview of heterologous expression host systems for the production of recombinant proteins; Adv. Anim. Vet. Sci. 4 (7): 346-356.

Non Patent Literature 5: Ferrer-Miralles and Villaverde (2013). Bacterial cell factories for recombinant protein production; expanding the catalogue. Microbial Cell Factories, 12: 113

Non Patent Literature 6: HERVE' A. et al. How Does *Bacillus thuringiensis* Produce SO Much Insecticidal Crystal Protein; J. of Bacteriology 1995, 177 (21), 6027-6032

Non Patent Literature 7: Deng C, Peng Q, Song F, Lereclus D (2014) Regulation of cry gene expression in *Bacillus thuringiensis*; Toxins. 6: 2194-2209

Non Patent Literature 8: Yan Hu et al. *Bacillus subtilis* Strain Engineered for Treatment of Soil-Transmitted Helminth Diseases, Applied and Environmental Microbiology 2013, 79 (18): 5527-5532

Non Patent Literature 9: Durmaz E. et al. Intracellular and Extracellular Expression of *Bacillus thuringiensis* Crystal Protein Cry5B in *Lactococcus lactis* for Use as an Anthelminthic, Applied and Environmental Microbiology 2016, 82 (4): 1286-1294

SUMMARY OF THE INVENTION

The present invention provides the following 1) and 2).

1) A method for producing a Cry protein or a culture product comprising the Cry protein, comprising transforming a *Bacillus* bacterium with an expression plasmid incorporating a gene encoding the Cry protein operably linked to a regulatory region comprising a σA-dependent promoter or a σH-dependent promoter, and culturing the transformed cell, wherein the expression plasmid comprises a polynucleotide encoding a replication protein consisting of the amino acid sequence set forth in SEQ ID NO: 9 or a protein having an identity of 80% or more with the amino acid sequence of the replication protein and involved in replication initiation.

2) An expression plasmid for expressing a Cry protein in a *Bacillus* bacterium, comprising a polynucleotide encoding a replication protein consisting of the amino acid sequence set forth in SEQ ID NO: 9 or a protein having an identity of 80% or more with the amino acid sequence of the replication protein and involved in replication initiation, wherein a gene encoding the Cry protein is operably linked to a regulatory region comprising a σA-dependent promoter or a σH-dependent promoter.

BRIEF DESCRIPTION OF DRAWINGS

FIG. 1-A shows construction of a Cry5B expression plasmid (pPsScry5B and pPsScry5Bt). The arrows represent the positions and directions of primers. The names of primers are shown above or below the arrows.

FIG. 1-B shows construction of a Cry5B expression plasmid (pPscry5B and pPscry5Bt). The arrows represent the positions and directions of primers. The names of primers are shown above and below the arrows.

FIG. 1-C shows construction of a Cry5B expression plasmid (pPvcry5B and pPvcry5Bt). The arrows represent the positions and directions of primers. The names of primers are shown above and below the arrows.

FIG. 1-D shows construction of a Cry5B expression plasmid (pPvScry5B and pPvScry5Bt). The arrows represent the positions and directions of primers. The names of primers are shown above and below the arrows.

FIG. 2 shows expression of Cry5B and Cry5Bt by a plasmid having a secretion signal.

FIG. 3 shows expression of Cry5B by a plasmid having no secretion signal.

FIG. 4-A shows expression (1) of Cry5B by using a *Bacillus subtilis* mutant strain.

FIG. 4-B shows expression (2) of Cry5B by using a *Bacillus subtilis* mutant strain.

FIG. 5 shows photographs of nematodes in L1 growth assay.

FIG. 6 shows the areas of nematodes, more specifically, values at different concentrations of Cry5B protein based on the area of a control (regarded as 100%)

FIG. 7 shows expression of Cry5Bt by a plasmid having no secretion signal.

FIG. 8 shows plasmids expressing a mosquitocidal protein (pHY-Pscry4Aa, pHY-Pscry4Ba, pHY-Pscry11Aa, pHY-Pvcry4Aa, pHY-Pvcry4Ba, pHY-Pvcry11Aa).

FIG. 9 shows expression of a mosquitocidal protein.

DETAILED DESCRIPTION OF THE INVENTION

The present invention relates to a provision of a method for intracellularly producing a large amount of a Cry protein in a *Bacillus* bacterium.

The present inventors conducted studies on intracellular production of a Cry protein by a *Bacillus* bacterium, preferably *Bacillus subtilis*. As a result, they surprisingly found that a significantly large amount of a Cry protein is intracellularly produced by using a predetermined high-expression plasmid used for extracellular production of a protein, and that the Cry protein thus produced has an activity equivalent to that of a wild-type protein.

According to the present invention, there is provided a high-expression system for a Cry protein using a *Bacillus* bacterium, preferably, *Bacillus subtilis*. Using the system, it is possible to efficiently produce a Cry protein or a culture product containing the Cry protein.

In the specification, the identities between amino acid sequences and between nucleotide sequences are calculated by the Lipman-Pearson method (Lipman, D J., Pearson. W R.: Science, 227, 1435-1441, 1985). Specifically, the identity is calculated by analysis using homology analysis (Search homology) program of genetic information processing software, Genetyx-Win (Software Development) and performed by setting the "unit size to compare (ktup)" at 2.

In the specification, the term "one or several" used in connection with deletion, substitution, addition or insertion of amino acid(s) or nucleotide(s) in an amino acid sequence or a nucleotide sequence, can be, for example, 1 to 12, preferably 1 to 8, and more preferably 1 to 4, unless otherwise specified. In the specification, "addition" of amino acid(s) or nucleotide(s) includes addition of one to several amino acids or nucleotides to one or both ends of a sequence.

In the specification, "stringent conditions" in connection with hybridization refer to conditions described in Molecular Cloning-A LABORATORY MANUAL THIRD EDITION (Joseph Sambrook, David W. Russell, Cold Spring Harbor Laboratory Press, 2001). More specifically, examples thereof include conditions where hybridization is performed by incubating a solution containing 6×SSC (1×SSC composition: 0.15 M sodium chloride, 0.015 M sodium citrate, pH 7.0), 0.5% SDS, 5×Denhardt and 100 mg/mL herring sperm DNA together with a probe at a constant temperature of 65° C. for 8 to 16 hours.

In the specification, the upstream and downstream regions of a gene refer to a region following the 5' end and 3' end of a target gene or target region, respectively. The upstream and downstream regions of a gene are not limited respectively to the upstream region and downstream region of a translation initiation site of the gene, unless otherwise specified.

In the specification, the transcription initiation regulatory region is a region containing a promoter and a transcription initiation site, and the translation initiation regulatory region is a site corresponding to the Shine-Dalgarno (SD) sequence, which forms a ribosome binding site together with an initiation codon (Shine, J., Dalgarno, L.: Proc. Natl. Acad. Sci. USA., 71, 1342-1346, 1974).

In the present invention, a Cry protein refers to a crystalline insecticidal protein produced by *Bacillus thuringiensis*. Cry proteins are classified into classes from Cry1 to Cry75 based on the primary structure of the proteins (Microbiology and Molecular Biology Reviews (1998) 62, 807-813. Revision of the Nomenclature for the *Bacillus thuringiensis* Pesticidal Crystal Proteins, www.lifesci.sussex.ac.uk/Home/Neil#Crickmore/Bt/(Dec. 7, 2017)). Each of the classes is further divided into subclasses based on the degree of sequence analogy. For example, 100 or more types of Cry proteins belong to Cry1 class. Major Cry proteins are listed in the following Tables 1-1 to 1-3. Note that, the access numbers shown in Tables are GenBank Accession Nos.

TABLE 1-1

| Cry protein | Accession No. | NCBI Protein | NCBI Nuc | Authors | Year | Strain/Other ID |
|---|---|---|---|---|---|---|
| Cry1Aa1 | AAA22353 | 142765 | 142764 | Schnepf et al | 1985 | Bt kurstaki HD1 |
| Cry1Ab1 | AAA22330 | 142720 | 142719 | Wabiko et al | 1986 | Bt berliner 1715 |
| Cry1Ba1 | CAA29898 | | | Brizzard & Whiteley | 1988 | Bt *thuringiensis* HD2 |
| Cry1Ac1 | AAA22331 | | | Adang et al | 1985 | Bt kurstaki HD73 |
| Cry2Aa1 | AAA22335 | | | Donovan et al | 1989 | Bt kurstaki |
| Cry1Fa1 | AAA22348 | | | Chambers et al | 1991 | Bt aizawai EG6346 |
| Cry2Ab1 | AAA22342 | | | Widner & Whiteley | 1989 | Bt kurstaki HD1 |
| Cry2Ba1 | KC156658 | | | Sampson et al | 2012 | ARP026 |
| Cry3Aa1 | AAA22336 | | | Herrnstadt et al | 1987 | Bt san diego |
| Cry3Ba1 | CAA34983 | | | Sick et al | 1990 | Bt tolworthi 43F |
| Cry4Aa1 | CAA68485 | | | Ward & Ellar | 1987 | Bt *israelensis* |
| Cry4Ba1 | CAA30312 | | | Chungjatpornchai et al | 1988 | Bt *israelensis* 4Q2-72 |
| Cry5Aa1 | AAA67694 | | | Narva et al | 1994 | Bt darmstadiensis PS17 |
| Cry5Ba1 | AAA68598 | | | Foncerrada & Narva | 1997 | Bt PS86Q3 |
| Cry6Aa1 | AAA22357 | | | Narva et al | 1993 | Bt PS52A1 |
| Cry6Ba1 | AAA22358 | | | Narva et al | 1991 | Bt PS69D1 |
| Cry7Aa1 | AAA22351 | | | Lambert et al | 1992 | Bt galleriae PGSI245 |
| Cry8Aa1 | AAA21117 | | | Narva & Fu | 1992 | Bt kumamotoensis |
| Cry9Aa1 | CAA41122 | | | Shevelev et al | 1991 | Bt galleriae |
| Cry10Aa1 | AAA22614 | | | Thorne et al | 1986 | Bt *israelensis* |
| Cry11Aa1 | AAA22352 | | | Donovan et al | 1988 | Bt *israelensis* |
| Cry11Ba1 | CAA60504 | | | Delecluse et al | 1995 | Bt jegathesan 367 |
| Cry12Aa1 | AAA22355 | | | Narva et al | 1991 | Bt PS33F2 |
| Cry13Aa1 | AAA22356 | | | Narva et al | 1992 | Bt PS63B |
| Cry14Aa1 | AAA21516 | | | Narva et al | 1994 | Bt sotto PS80JJ1 |
| Cry15Aa1 | AAA22333 | | | Brown & Whiteley | 1992 | Bt thompsoni |
| Cry16Aa1 | CAA63860 | | | Barloy et al | 1996 | Cb malaysia CH18 |

TABLE 1-2

| Cry protein | Accession No. | NCBI Protein | NCBI Nuc | Authors | Year | Strain/Other ID |
|---|---|---|---|---|---|---|
| Cry17Aa1 | CAA67841 | | | Barloy et al | 1998 | Cb malaysia CH18 |
| Cry18Aa1 | CAA67506 | | | Zhang et al | 1997 | *Paenibacillus popilliae* |
| Cry19Aa1 | CAA68875 | | | Rosso & Delecluse | 1996 | Bt jegathesan 367 |
| Cry20Aa1 | AAB93476 | | | Lee & Gill | 1997 | Bt fukuokaensis |
| Cry21Aa1 | I32932 | | | Payne et al | 1996 | |
| Cry21Ba1 | BAC06484 | | | Sato & Asano | 2002 | Bt roskildiensis |
| Cry22Aa1 | I34547 | | | Payne et al | 1997 | |
| Cry23Aa1 | AAF76375 | | | Donovan et al | 2000 | Bt |
| Cry24Aa1 | AAC61891 | | | Kawalek and Gill | 1998 | Bt jegathesan |
| Cry25Aa1 | AAC61892 | | | Kawalek and Gill | 1998 | Bt jegathesan |
| Cry26Aa1 | AAD25075 | | | Wojciechowska et al | 1999 | Bt finitimus B-1166 |
| Cry27Aa1 | BAA82796 | | | Saitoh | 1999 | Bt higo |
| Cry28Aa1 | AAD24189 | | | Wojciechowska et al | 1999 | Bt finitimus B-1161 |
| Cry29Aa1 | CAC80985 | | | Delecluse et al | 2000 | Bt medellin |
| Cry30Aa1 | CAC80986 | | | Delecluse et al | 2000 | Bt medellin |
| Cry31Aa1 | BAB11757 | | | Saitoh & Mizuki | 2000 | Bt 84-HS-1-11 |
| Cry32Aa1 | AAG36711 | | | Balasubramanian et al | 2001 | Bt *yunnanensis* |
| Cry33Aa1 | AAL26871 | | | Kim et al | 2001 | Bt dakota |
| Cry34Ab1 | AAG41671 | | | Moellenbeck et all | 2001 | Bt PS149B1 |
| Cry35Ab1 | AAG41672 | | | Moellenbeck et al | 2001 | Bt PS149B1 |
| Cry36Aa1 | AAK64558 | | | Rupar et al | 2001 | Bt |
| Cry39Aa1 | BAB72016 | | | Ito et al | 2001 | Bt aizawai |
| Cry40Aa1 | BAB72018 | | | Ito et al | 2001 | Bt aizawai |
| Cry41Aa1 | BAD35157 | | | Yamashita et al | 2003 | Bt A1462 |
| Cry42Aa1 | BAD35166 | | | Yamashita et al | 2003 | Bt A1462 |
| Cry43Aa1 | BAD15301 | | | Yokoyama and Tanaka | 2003 | P. *lentimorbus* semadara |
| Cry44Aa1 | BAD08532 | | | Ito et al | 2004 | Bt entomocidus INA288 |

TABLE 1-3

| Cry protein | Accession No. | NCBI Protein | NCBI Nuc | Authors | Year | Strain/Other ID |
|---|---|---|---|---|---|---|
| Cry45Aa1 | BAD22577 | | | Okumura et al | 2004 | Bt 89-T-34-22 |
| Cry46Aa1 | BAC79010 | | | Ito et al | 2004 | Bt dakota |
| Cry47Aa1 | AAY24695 | | | Kongsuwan et al | 2005 | Bt CAA890 |
| Cry48Aa1 | CAJ18351 | | | Jones and Berry | 2005 | Bs IAB59 |

TABLE 1-3-continued

| Cry protein | Accession No. | NCBI Protein | NCBI Nuc | Authors | Year | Strain/Other ID |
|---|---|---|---|---|---|---|
| Cry50Aa1 | BAE86999 | 89885725 | 89885724 | Ohgushi et al | 2006 | Bt sotto |
| Cry51Aa1 | ABI14444 | 112253719 | 112253718 | Meng et al | 2006 | Bt F14-1 |
| Cry52Aa1 | EF613489 | | | Shu et al | 2010 | Bt Y41 |
| Cry53Aa1 | EF633476 | | | Shu et al | 2010 | Bt Y41 |
| Cry54Aa1 | ACA52194 | 169261091 | 169261090 | Tan et al | 2009 | Bt MC28 |
| Cry55Aa1 | ABW88932 | | | Guo et al | 2008 | YBT 1518 |
| Cry56Aa1 | ACU57499 | 256033941 | 256033940 | Zhu et al | 2010 | Bt Ywc2-8 |
| Cry57Aa1 | ACN87261 | 225348555 | 225348554 | Noguera & Ibarra | 2009 | Bt kim |
| Cry58Aa1 | ACN87260 | 225348553 | 225348552 | Noguera & Ibarra | 2009 | Bt entomocidus |
| Cry59Aa1 | ACR43758 | 239638225 | 239638224 | Noguera & Ibarra | 2009 | Bt kim LBIT-980 |
| Cry60Aa1 | ACU24782 | 255653180 | 255653179 | Sun and Park | 2009 | Bt jegathesan |
| Cry61Aa1 | HM035087 | | 327505548 | Geng et al | 2010 | Sbt009 |
| Cry62Aa1 | HM054509 | | 302753235 | Zhu et al | 2010 | ST7 |
| Cry63Aa1 | BAI44028 | 260268375 | | Nagamatsu et al | 2010 | MO19 |
| Cry64Aa1 | BAJ05397 | 294661779 | | Ekino et al | 2010 | Bt tohokuensis |
| Cry65Aa1 | HM461868 | | 328833581 | Geng et al | 2010 | SBt 003 |
| Cry66Aa1 | AEB52311 | | 339186760 | Sun et al | 2010 | SBt 021 |
| Cry67Aa1 | HM485582 | | 339186762 | Sun et al | 2010 | SBt 009 |
| Cry68Aa1 | HQ113114 | | 327466752 | Peng Guan et al | 2012 | Bt MC28 |
| Cry69Aa1 | HQ401006 | | 332139130 | Peng Guan | 2011 | Bt MC28 |
| Cry70Aa1 | JN646781 | | | Qiao Li | 2015 | Bt hs18-1 |
| Cry71Aa1 | JX025568 | | | Qiao Li et al | 2016 | Bt Hs18-1 |
| Cry72Aa1 | JX025569 | | | Qiao Li et al | 2016 | Bt Hs18-1 |

Among the Cry proteins listed above, Cry1A protein, Cry1F protein, Cry2A protein, Cry34A protein, Cry35A protein, Cry3A protein, Cry3B protein, Cry21 protein, Cry14A protein, CryσA protein, Cry13 protein, Cry5B protein, Cry4Aa protein, Cry4Ba protein and Cry11Aa protein are more suitably produced by the method of the present invention; and Cry5B protein, Cry4Aa protein, Cry4Ba protein and Cry11Aa protein are more suitably produced.

A Cry5B protein is a nematocidal protein known to be effective to soil-transmitted helminth infections (Cappello M et al. Proc. Natl. Acad. Sci. U.S.A. 103: 15154-15159, Hu Y et al. PLoS Negl. Trop. Dis. 4: e614). For example, the amino acid sequence of Cry5B protein is set forth in SEQ ID NO: 2 in the Sequence Listing and the nucleotide sequence of a gene encoding the protein is set forth in SEQ ID NO: 1 in the Sequence Listing.

Cry4Aa protein, Cry4Ba protein and Cry11Aa protein are known as proteins having an insecticidal activity to mosquitos (FEMS Microbiol Lett 266 (2007) 163-169, Mhalakshmi A at al. Advances Microbiol. 2 (2012) 216-226).

For examples, the amino acid sequence of Cry4Aa protein is set forth in SEQ ID NO: 4 of the Sequence Listing and the nucleotide sequence of a gene encoding the protein is set forth in SEQ ID NO: 3 of the Sequence Listing.

For example, the amino acid sequence of Cry4Ba protein is set forth in SEQ ID NO: 6 of the Sequence Listing and the nucleotide sequence of a gene encoding the protein is set forth in SEQ ID NO: 5 of the Sequence Listing.

For example, the amino acid sequence of Cry11Aa protein is set forth in SEQ ID NO: 8 of the Sequence Listing and the nucleotide sequence of a gene encoding the protein is set forth in SEQ ID NO: 7 of the Sequence Listing.

Naturally occurring proteins of these are well known to have mutant proteins having one to several amino acid mutations due to gene mutations caused by difference in, e.g., ecotype, or the presence of analogous isozyme(s).

Because of this, other than the Cry proteins listed in Table 1, mutants of the Cry proteins, which have addition, substitution of one to several amino acid residues or deletion of one to several amino acid residues in the amino acid sequences consisting of the Cry proteins and have an equivalent insecticidal activity are included in the Cry protein of the present invention.

For example, in the cases of Cry5B protein, Cry4Aa protein, Cry4Ba protein and Cry11Aa protein, the following (A) to (C) are included:

(A) a protein consisting of the amino acid sequence set forth in SEQ ID NO: 2, 4, 6 or 8;

(B) a protein consisting of an amino acid having deletion, substitution, addition or insertion of one or several amino acids with respect to the amino acid sequence set forth in SEQ ID NO: 2, 4, 6 or 8 and having an insecticidal activity; and (C) A protein consisting of an amino acid sequence having an identity of 80% or more, more preferably 90% or more, more preferably 95% or more, more preferably 96% or more, more preferably 97% or more, more preferably 98% or more, and more preferably 99% or more with the amino acid sequence set forth in SEQ ID NO: 2, 4, 6 or 8 and having an insecticidal activity.

A gene encoding the Cry protein (also referred to as cry gene) of the present invention is not particularly limited in type; in other words, the gene may be any one of naturally occurring DNA, recombinant DNA and chemically synthesized DNA, and either a genomic DNA clone or a cDNA clone.

The cry gene of the present invention typically refers to any one of the cry genes listed in Table 1. Among the naturally occurring genes, a small number of mutations are present due to difference in, e.g., ecotype, or the presence of analogous isozymes, as is well known to those skilled in the art. Accordingly, examples of the cry gene of the present invention are not limited to the genes listed in Table 1 and include all genes as long as they encode the aforementioned Cry proteins.

For example, in the cases of cry5B gene, cry4Aa gene, cry4Ba gene and cry11Aa gene, the following (a) to (f) are included:

(a) a polynucleotide consisting of the nucleotide sequence set forth in SEQ ID NO: 1, 3, 5 or 7;

(b) a polynucleotide consisting of a nucleotide sequence having an identity of 80% or more, more preferably 90% or more, more preferably 95% or more, more preferably 96% or more, more preferably 97% or more, more preferably 98% or more, and more preferably 99% or more with the nucleotide sequence set forth in SEQ ID NO: 1, 3, 5 or 7 and encoding a protein having an insecticidal activity;

(c) a polynucleotide hybridizing with a complementary strand of the polynucleotide consisting of the nucleotide sequence set forth in SEQ ID NO: 1, 3, 5 or 7 under stringent conditions and encoding a protein having an insecticidal activity;

(d) a polynucleotide encoding a protein consisting of the amino acid sequence set forth in SEQ ID NO: 2, 4, 6 or 8;

(e) A polynucleotide encoding a protein consisting of an amino acid sequence having deletion, substitution, addition or insertion of one or several amino acids with respect to the amino acid set forth in SEQ ID NO: 2, 4, 6 or 8 and having an insecticidal activity; and (f) a polynucleotide encoding a protein consisting of an amino acid sequence having an identity of 80% or more, more preferably 90% or more, more preferably 95% or more, more preferably 96% or more, more preferably 97% or more, more preferably 98% or more, and more preferably 99% or more with the amino acid sequence set forth in SEQ ID NO: 2 and having an insecticidal activity.

In the present invention, a Cry protein or a culture product containing a Cry protein is produced by incorporating the cry gene mentioned above operably linked to a regulatory region containing a σA-dependent promoter or a σH-dependent promoter into an expression plasmid, transforming a *Bacillus* bacterium with the plasmid, and culturing the transformed cell. As the expression plasmid, a plasmid containing a polynucleotide encoding a replication protein consisting of the amino acid sequence set forth in SEQ ID NO: 9 or a protein having an identity of 80% or more with the amino acid sequence of the replication protein and involved in replication initiation, is used.

The replication protein (Rep) is an initiator protein functioning in replication initiation of a plasmid. The plasmid used in the present invention, contains the replication protein set forth in SEQ ID NO: 9 required for replication in *Bacillus subtilis*. For example, the replication protein set forth in SEQ ID NO: 9 is present in pAMα1. Two types of replication proteins for pAMα1 are known; however, the replication protein to be used in the present invention is a protein, which consists of the amino acid sequence set forth in SEQ ID NO: 9. Also, a protein having an identity of 80% or more, more preferably 90% or more, more preferably 95% or more, more preferably 96% or more, more preferably 97% or more, more preferably 98% or more, and more preferably 99% or more with the amino acid sequence of the replication protein and involved in replication initiation can be used similarly to the protein. As such a plasmid replication protein, for example, a protein having an amino acid having deletion, substitution or addition of one or several amino acids with respect to the amino acid sequence set forth in SEQ ID NO: 9 is included. For example, mutant proteins described in JP-B-5361484 are mentioned; more specifically, proteins, which are obtained by substituting at least one amino acid residue selected from the group consisting of amino acid residues at (a) 48-position, (b) 262-position, (c) 149-position and (d) 198-position of the amino acid sequence set forth in SEQ ID NO: 9 with a predetermined amino acid residue, are mentioned.

The above plasmid includes, other than a polynucleotide encoding a replication protein, e.g., polynucleotides encoding a protein involved in initiation replication. Other than these, the plasmid can also appropriately include e.g., a drug resistance gene and a multicloning site.

Examples of the plasmid suitably used in the present invention include pHY300PLK and the plasmids described in JP-B-5361484.

Plasmid pHY300PLK can be constructed of DNA molecules derived from *E. coli* plasmid, pACYC177, and *Streptococcus faecalis* plasmid, pAMα1, by use of a shuttle vector, which can transform DNA of both *Escherichia coli* and *Bacillus subtilis*, and RepB is contained in the replication region of pAMα1.

A gene encoding a desired Cry protein is operably linked to a regulatory region containing a σA factor-dependent promoter or a σH factor-dependent promoter in the plasmid to construct a recombinant plasmid (expression vector) which can produce a Cry protein in bacterial cells of *Bacillus subtilis*.

The "gene operably linked to a regulatory region" herein refers to a gene arranged expressibly under control of the regulatory region.

The promoter herein is present upstream of the coding region of a predetermined gene and defined as a region having a function to control transcription of the gene by interaction with RNA polymerase. More specifically, the promoter refers to a region consisting of about 200 to 600 nucleotides and present upstream of the coding region of the predetermined gene.

As the regulatory region including a promoter, a transcription initiation regulatory region and translation initiation regulatory region are mentioned. The regulatory region preferably has a function to enhance expression of a gene present downstream thereof in a host and more preferably a function to constitutively express a downstream gene or enhancing expression thereof.

The σA factor-dependent promoter and σH factor-dependent promoter are promoters working before a spore coat protein deposition period in the sporulation phase for spore-forming microorganisms.

The regulatory region containing a σA-dependent promoter or a σH-dependent promoter is preferably selected from regulatory regions different from the regulatory region of a gene encoding a Cry protein in the microorganism from which the gene is derived.

Examples of the σA factor-dependent promoter include, but are not particularly limited to, *Bacillus subtilis* phage SP01 promoter (Proc. Natl. Acd. Sci. USA. (1984) 81: 439-443.) and promoters of veg gene, amyE (amylase) gene, aprE (subtilisin) gene and S237 (S237 cellulase, JP-A-2000-210081) gene. Examples of the σH factor-dependent promoter include, but are not particularly limited to, promoters of cite gene, spoVS gene and spoVG (Proc. Natl. Acd. Sci. USA. (1986) 83: 9438-9442.) gene.

In the present invention, as the GA factor-dependent promoter, a promoter of a cellulase gene of *Bacillus* sp. KSM-S237 strain is more preferable. As the σH factor-dependent promoter, a promoter of spoVG gene (BG10112) of *Bacillus subtilis* Marburg No. 168 (*Bacillus subtilis* 168 strain) is more preferable.

As the regulatory region containing a σA factor-dependent promoter, the regulatory region of a cellulase gene of *Bacillus* sp. KSM-S237 strain is suitably mentioned. The regulatory region is more specifically a transcription initiation regulatory region and a translation initiation region (SEQ ID NO: 10) of the cellulase gene, preferably the nucleotide sequence set forth in SEQ ID NO: 10, or a nucleotide sequence having an identity of 80% or more, more preferably 90% or more, further preferably 95% or more, and still further preferably 98% or more with the nucleotide sequence set forth in SEQ ID NO: 10, or any one of the above nucleotide sequences partly having a deletion. The nucleotide sequence having an identity of 80% or more, more preferably 90% or more, further preferably 95% or more and still further preferably 98% or more with the nucleotide sequence set forth in SEQ ID NO: 10 refers to a sequence having the above identity and maintaining a function as a σA factor-dependent promoter, i.e., function involved in transcription and translation of the gene. The nucleotide sequence partly having a deletion is a sequence having a deletion but maintaining a function as a σA factor-dependent promoter, i.e., function involved in transcription and translation of the gene. Among the σA factor-dependent promoters, a more preferable σA factor-dependent promoter includes a promoter consisting of the nucleotide sequence set forth in SEQ ID NO: 11. The promoter is a promoter consisting of a sequence of the regulatory region of a cellulase gene of the Bacillus sp. KSM-S237 strain mentioned above, from which a Cre-like sequence has been deleted (JP-A-2011-103875), and having a sequence identity of 95% with the nucleotide sequence set forth in SEQ ID NO: 10.

Herein, the phrase "functions as a σA factor-dependent promoter" means that transcription is specifically controlled by the σA factor which is an RNA polymerase. The specificity thereof can be evaluated by ligating a reporter gene to a site downstream of the polynucleotide to be evaluated, and observing expression of the reporter gene in the presence or absence of the σA factor.

As the regulatory region containing a σH factor-dependent promoter, the regulatory region of spoVG gene of Bacillus subtilis Marburg No. 168 (Bacillus subtilis 168 strain) is preferably mentioned. The regulatory region is more specifically a transcription initiation regulatory region and a translation initiation region of the spoVG gene (BG10112) (SEQ ID NO: 12), preferably the nucleotide sequence set forth in SEQ ID NO: 12 or a nucleotide sequence having an identity of 80% or more, more preferably 90% or more, further preferably 95% or more and still further preferably 98% or more with the nucleotide sequence set forth in SEQ ID NO: 12 or any one of the above nucleotide sequences partly having a deletion. The nucleotide sequence having an identity of 80% or more, more preferably 90% or more, further preferably 95% or more and still further preferably 98% or more with the nucleotide sequence set forth in SEQ ID NO: 12 refers to a sequence having the above identity and maintaining a function as a σH factor-dependent promoter, i.e., a function involved in transcription and translation of the gene. The nucleotide sequence partly having a deletion is a sequence having a deletion but maintaining a function as a σH factor-dependent promoter, i.e., a function involved in transcription and translation of a gene. Herein, the phrase "function as a σH factor-dependent promoter" means that transcription is specifically controlled by the σH factor which is an RNA polymerase. The specificity thereof can be evaluated by ligating a reporter gene to a site downstream of the polynucleotide to be evaluated, and observing expression of the reporter gene in the presence or absence of a σH factor.

Insertion into a plasmid containing the cry gene and the regulatory region can be carried out by a method ordinarily used in the technical field. For example, fragments of the cry gene and the regulatory region may be amplified by, e.g., PCR, inserted into a plasmid by, e.g., a restriction enzyme method and linked. Alternatively, a fragment prepared by ligating the fragments of the gene and the regulatory region in advance may be inserted into a plasmid. In this case, the regulatory region fragment and the cry gene fragment are arranged on the plasmid in this order from the upstream and ligated. For convenient sake, a commercially available ligation kit (for example, manufactured by, e.g., Takara Bio Inc.) can be used.

Examples of a method for introducing a constructed plasmid into a host cell include the calcium chloride method and the calcium chloride/rubidium chloride method described in Sambrook, J. et al., Molecular Cloning, A Laboratory Manual (2nd edition), Cold Spring Harbor Laboratory, 1.74 (1989), an electroporation method, an electroinjection method, a chemical treatment method with, e.g., PEG, and a method using a gene gun.

As the host cell to which the above expression plasmid is to be introduced, a Bacillus bacterium, preferably Bacillus subtilis, Bacillus megaterium or Bacillus brevis, is used. The Bacillus bacterium to be used may be a wild type or a mutant type. Specific examples of the microorganism belonging to the genus Bacillus include Bacillus subtilis, Bacillus cereus, Bacillus thuringiensis, Bacillus anthracis, Bacillus stearotheromophilus, Bacillus coagulans, Bacillus megaterium, Bacillus halodurans, Bacillus brevis (BreviBacillus brevis), Bacillus choshinensis (Brevibacillus choshinensis), Bacillus pumilus, Bacillus alcalophilus, Bacillus amylolyticus, Bacillus amyloliquefaciens, Bacillus liqueniformis, Bacillus polymyxa (Paenibacillus polymyxa), Bacillus sphaericus, Bacillus firmus, Bacillus clausii and Bacillus macerans. Note that, Bacillus brevis is classified into the genus Brevibacillus and sometimes represented as, e.g., BreviBacillus brevis or Brevibacillus choshinensis, depending on the strain; Bacillus polymyxa is classified into the genus Paenibacillus and sometimes represented as Paenibacillus polymyxa; and Bacillus stearotheromophilus is classified into the genus Geobacillus and sometimes represented as Geobacillus stearotheromophilus. However, in the specification, Bacillus brevis, Bacillus polymyxa, and Bacillus stearotheromophilus are all defined as bacteria belonging to the genus Bacillus. More specifically, in the present invention, the microorganisms belonging to the genus Bacillus are interpreted as including microorganisms represented as Brevibacillus brevis and Brevibacillus choshinensis, a microorganism represented as Paenibacillus polymyxa and a microorganism represented as Geobacillus stearotheromophilus. Note that, microorganisms belonging to the genus Bacillus can be purchased from culture collections.

Examples of a wild-type Bacillus include Bacillus subtilis Marburg No. 168 (Bacillus subtilis 168 strain). A Bacillus subtilis mutant strain is not particularly limited as long as it is suitable for producing a Cry protein and, for example, a Bacillus subtilis strain having deletion of the regions unnecessary for survival, proliferation and protein production from the genome of the wild-type strain thereof; a Bacillus subtilis strain having a deletion of a predetermined protease gene; a Bacillus subtilis strain having a deletion of a factor gene specific to a sporulation phase, or a Bacillus subtilis strain having these mutations in combination, is mentioned.

A Bacillus subtilis mutant strain having a wide region deleted in the genome has a genome having a wide region deleted compared to the genome of a wild-type Bacillus subtilis strain (for example, Bacillus subtilis 168 strain); for example, mutant strains described in JP-B-4955358 are mentioned. Examples thereof include Bacillus subtilis mutant strains having a deletion of at least one region selected from the group consisting of prophage 6 (yoaV-yob0) region, prophage 1 (ybbU-ybdE) region, prophage 4 (yjcM-yjdJ) region, PBSX (ykdA-xlyA) region, prophage 5 (ynxB-dut) region, prophage 3 (ydiM-ydjC) region, spb (yodU-ypqP) region, pks (pksA-ymaC) region, skin (spoIVCB-spoIIIC) region, pps (ppsE-ppsA) region, prophage 2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, prophage 7 (yrkM-yraK, or yrkS-yraK) region, sbo-ywhH region, yybP-yyaJ region and yncM-fosB region in the genome of wild-type *Bacillus subtilis* strain; and preferably include *Bacillus subtilis* MGB874 strain having deletions of all of prophage 6 (yoaV-yob0) region, prophage 1 (ybbU-ybdE) region, prophage 4 (yjcM-yjdJ) region, PBSX (ykdA-xlyA) region, prophage 5 (ynxB-dut) region, prophage 3 (ydiM-ydjC) region, spb (yodU-ypqP) region, pks (pksA-ymaC) region, skin (spoIVCB-spoIIIC) region, pps (ppsE-ppsA) region, prophage 2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, prophage 7 (yrkS-yraK) region, sbo-ywhH region, yybP-yyaJ region and yncM-fosB region. The MGB874 strain mentioned above is available from the National Bio Resource Project (NBRP) of the National Institute of Genetics (www.shigen.nig.ac.jp/bsub/kaoListAction.do). Further, an example of an MGB874 mutant strain is a *Bacillus subtilis* mutant stain (MGB874abrB* ΔkinA) described in JP-A-2017-79639 which is obtained by genetic modification to constitutively express abrB gene or an equivalent gene thereto and in which kinA gene is deleted or inactivated.

Examples of a *Bacillus subtilis* strain having a predetermined protease gene deleted, include *Bacillus subtilis*, which is described in JP-B-4485341 and has a deletion or inactivation of aprX gene of *Bacillus subtilis* and at least one gene selected from the group consisting of aprE, nprB, nprE, bpr, vpr, mpr, epr and wprA of *Bacillus subtilis*; and preferably a *Bacillus subtilis* strain (Dpr9 strain) having nonuple deletions of aprX, aprE, nprB, nprE, bpr, vpr, mpr, epr and wprA genes.

A *Bacillus subtilis* strain having a deletion of sporulation phase-specific σ factor gene includes *Bacillus subtilis* strains, which are described in JP-B-4336082 and have a deletion or inactivation of at least one gene selected from the group consisting of sigF, sigG and sigE; preferably a sigE-deficient strain (ΔsigE strain) and a sigF-deficient strain (ΔsigF strain); and more preferably a sigF-deficient strain (ΔsigF strain).

In view of production of a Cry protein, an MGB874ΔsigF mutant strain obtained by deleting sigF from the MGB874 strain mentioned above and a Dpr9ΔsigF mutant strain obtained by deleting sigF from the Dpr9 strain mentioned above are more preferably used.

The Cry protein of the present invention can be expressed (produced) by culturing a transformed *Bacillus subtilis* containing an expression vector prepared as described above in a nutrition medium. The nutrient medium preferably contains a carbon source and an inorganic or organic nitrogen source necessary for growth of *Bacillus subtilis* (transformant). Examples of the carbon source include glucose, dextran, soluble starch, sucrose and methanol. Examples of the inorganic or organic nitrogen source include ammonium salts, nitrates, amino acids, corn steep liquor, peptone, casein, meat extract, soybean meal and potato extract. If desired, other nutrients (e.g., inorganic salts (e.g., sodium chloride, calcium chloride, sodium dihydrogen phosphate, magnesium chloride), vitamins and antibiotics (e.g., tetracycline, neomycin, kanamycin, spectinomycin, erythromycin)) may be contained. Culturing is performed by a method known in the art. Culture conditions, such as temperature, aeration/stirring conditions, medium pH and culture time, are appropriately selected so as to produce a large amount of the protein of the present invention.

A culture product containing a Cry protein of the present invention and obtained by culturing as mentioned above can be obtained by collecting host cells by a process such as centrifugation and filtration, and suspending the collected host cells in an appropriate buffer (for example, a buffer such as a Tris buffer, phosphate buffer, HEPES buffer, MES buffer having a concentration of about 10 M to 100 mM (desirably in the range of pH 5.0 to 9.0) or water. The host cells can be further crushed by appropriately using known cell disruption means such as lysozyme, freeze-thaw, sonication, French press and bead disruption in combination and subjected to centrifugation to collect the Cry protein. The above culture product can be sterilized by adding a bactericidal substance such as carvacrol followed by incubation (Patent Literature 3).

The collected Cry protein can be appropriately purified by utilizing a sucrose density gradient method, a recrystallization method, ion exchange chromatography, gel filtration, hydrophobic chromatography, isoelectric chromatography and affinity column using a polyclonal antibody against a Cry protein as a ligand.

In connection with the embodiments mentioned above, the following aspects of the present invention are further disclosed.

<1> A method for producing a Cry protein or a culture product comprising the Cry protein, comprising transforming a *Bacillus* bacterium with an expression plasmid incorporating a gene encoding the Cry protein operably linked to a regulatory region comprising a σA-dependent promoter or a σH-dependent promoter, and culturing the transformed cell, wherein the expression plasmid comprises a polynucleotide encoding a replication protein consisting of the amino acid sequence set forth in SEQ ID NO: 9 or a protein having an identity of 80% or more, more preferably 90% or more, more preferably 95% or more, more preferably 96% or more, more preferably 97% or more, more preferably 98% or more, and more preferably 99% or more with the amino acid sequence of the replication protein and involved in replication initiation.

<2> The method according to <1>, wherein the regulatory region comprising a σA-dependent promoter or a σH-dependent promoter differs from a regulatory region of a gene encoding the Cry protein in a microorganism from which the gene is derived.

<3> The method according to <1> or <2>, wherein the regulatory region comprising a σA-dependent promoter or a σH-dependent promoter is a regulatory region of spoVG gene or a regulatory region of a cellulase gene of *Bacillus* sp. KSM-S237 strain.

<4> The method according to <3>, wherein the regulatory region of a cellulase gene of *Bacillus* sp. KSM-S237 strain is a transcription initiation regulatory region and a translation initiation region of the gene.

<5> The method according to any one of <1> to <4>, wherein the *Bacillus* bacterium is *Bacillus subtilis*, *Bacillus megaterium* or *Bacillus brevis*.

<6> The method according to any one of <1> to <4>, wherein the *Bacillus* bacterium is *Bacillus subtilis*.

<7> The method according to <6>, wherein the *Bacillus subtilis* is *Bacillus subtilis* 168 strain.

<8> The method according to <6> or <7>, wherein the *Bacillus subtilis* is a *Bacillus subtilis* strain having a genome in which at least one region selected from the group consisting of prophage 6 region, prophage 1 region, prophage 4 region, PBSX region, prophage 5 region, prophage 3 region, spb region, pks region, skin region, pps region, prophage 2 region, ydcL-ydeK-ydhU region, yisB-yitD region, yunA-yurT region, cgeE-ypmQ region, yeeK-yesX region, pdp-rocR region, ycxB-sipU region, SKIN-Pro7 region, sbo-ywhH region, yybP-yyaJ region and yncM-fosB region is deleted.

<9

ID NO: 10, and maintaining a function involved in transcription and a function involved in translation of the gene as a σA factor-dependent promoter.

<37> The expression plasmid or *Bacillus subtilis* according to any one of <18> to <34>, wherein the regulatory region comprising a σH-dependent promoter is a regulatory region of a spoVG gene of *Bacillus subtilis* Marburg No. 168 (*Bacillus subtilis* 168 strain).

<38> The expression plasmid or *Bacillus subtilis* according to <37>, wherein the regulatory region of spoVG gene is a sequence having a nucleotide sequence having an identity of 80% or more, more preferably 90% or more, further preferably 95% or more and still further preferably 98% or more with the nucleotide sequence set forth in SEQ ID NO: 12, and maintaining a function involved in transcription and a function involved in translation of the gene as a σH factor-dependent promoter.

EXAMPLES

Example 1

Production of Culture Product Containing Cry5B Protein

1. Synthesis of Artificial Gene

*Bacillus thuringiensis* YBT-1518-derived insecticidal protein gene cry5B (GenBank: CP005935.1, SEQ ID NO: 1) was artificially synthesized by GenScript Biotech Corporation (U.S.A.). The synthesized gene (3738 bp) was cloned into a KpnI-HindIII site of pUC57 to obtain pUC57-cry5B.

2. Construction of Expression Plasmid

In construction of all expression plasmids, pHY300PLK (Takara Bio Inc.) was used as a vector and S237 cellulase gene-derived sequence was used as a terminator. A promoter derived from S237 cellulase gene [Hakamada et al, Biosci. Biotechnol. Biochem., 64 (2000), 2281-2289] or spoVG gene of *Bacillus subtilis* 168 strain, was used. A signal sequence derived from S237 cellulase is used or not used. Full length Cry5B gene (cry5B) or truncated (cry5Bt) was used. Eight types of plasmids were prepared by using these in combination (FIGS. 1-A to D). The full length of cry5B gene (3738 bp) is set forth in SEQ ID NO: 1. The nucleotide sequence from nucleotide Nos. 2095-3738 is the region to be decomposed within the intestine of a nematode; whereas, the nucleotide sequence from nucleotide Nos. 1-2094 is a sequence encoding crystal toxin, which is activated after the decomposition [Hui et al, 2012, Biochemistry, vol 11, p 9911-21]. The full-length cry5B gene has the whole sequence of nucleotide Nos. 1-3738; whereas the truncated gene thereof has a sequence of nucleotide Nos. 1-2094.

Construction was carried out in accordance with the method instructed by the protocol of In-Fusion (R) HD EcoDry™ Cloning Kit. The processes for producing individual plasmids were shown in FIGS. 1-A to D.

2.1 Construction of pPsScry5B and pPsScry5Bt

Using a primer set of vect+psF and vect+tR, shown in Table 2 and pHYS237 DNA as a template, a vector containing the promoter, signal and terminator regions of S237 was amplified. Next, using pUC57-cry5B DNA as a template and a primer set of cry5BpssF and cry5BtR (or T237-cry5BatRN), an insert of full-length (or truncated) cry5B gene was amplified by PCR. Subsequently, using In-Fusion (R) HD EcoDry™ Cloning Kit (company: Clontech), the vector and the insert were ligated, and thereafter, *Escherichia coli* HB101 competent cells (Takara Bio Inc.) were transformed with the resultant construct. Transformants were screened based on tetracycline resistance, confirmed by colony PCR and designated as pPsScry5B (or pPsScry5Bt) (FIG. 1-A). The plasmid was extracted, further confirmed by PCR and checked for the digestion pattern of the plasmid by use of restriction enzymes EcoRI, SpeI and XbaI.

TABLE 2

| No | Name of primer | Sequence (5'-3') | SEQ ID NO: |
|---|---|---|---|
| 1 | vectR | GGGAATTCCTGTTATAAAAA | 13 |
| 2 | S237F | ATGATGTTAAGAAAGAAAACA | 14 |
| 3 | vect-PvgF | ATAACAGGAATTCCCTAAGAAAAGTGATTCTGGGA | 15 |
| 4 | S237-PvgR | TCTTTCTTAACATCATAGTAGTTCACCACCTTTTCC | 16 |
| 5 | T237-cry5BatRN | AACTAGTTTAATAGATTATTGGATTTTTGGAACAAACTC | 17 |
| 6 | cry5BpF | TATTTAGGAGGTAATATGATGGCAACAATTAATGAGTT | 18 |
| 7 | cry5BpssF | CCGGCAGCTCTTGCAATGGCAACAATTAATGAGTT | 19 |
| 8 | cry5BtR | AACTAGTTTAATAGATTATTGATTATTATTCATAC | 20 |
| 9 | vect+psF | TGCAAGAGCTGCCGGAAATA | 21 |
| 10 | vect+tR | TCTATTAAACTAGTTATAGG | 22 |
| 11 | vect+pF | ATTACCTCCTAAATATTTTT | 23 |
| 12 | cry5BaF | GCAACAATTAATGAGTTGTATCC | 24 |
| 13 | cry5BaF1 | CGTTCAAAATCATCCGTAAATG | 25 |

TABLE 2-continued

| No | Name of primer | Sequence (5'-3') | SEQ ID NO: |
|---|---|---|---|
| 14 | cry5BaR1 | AAATGCATGAACCACTTCCAC | 26 |
| 15 | cry5BatR | ATTGGATTTTTGGAACAAACTC | 27 |
| 16 | S237Pfw | TAAAAGTAGAAGACAAAGGA | 28 |
| 17 | S237fw | CGATATATGTAAGCGGTTAAC | 29 |
| 18 | S237rv | CAATTTAAAATCGCTACCCT | 30 |
| 19 | cry5Ba-PvgR | AACTCATTAATTGTTGCCATAGTAGTTCACCACCTTTTCC | 31 |
| 20 | vectR-F | TTTTTATAACAGGAATTCCC | 32 |
| 21 | SEQ-P1 | GGATCAACTTTGGGAGAGAG | 33 |
| 22 | SEQ-P2 | CAAGTAGTAATAATATAGAT | 34 |
| 23 | SEQ-P3 | GCAACAATTAATGAGTTGTA | 35 |
| 24 | SEQ-P4 | AGTACACCAGAAAGAGTAAT | 36 |
| 25 | SEQ-P5 | TCAAGGTGGTAAATTAGATT | 37 |
| 26 | SEQ-P6 | TCACGTCCTGATCAAAAAAT | 38 |
| 27 | SEQ-P7 | TACCTGCTGGAAGTTTCTAT | 39 |
| 28 | SEQ-P8 | ACAGAGGCCGAAATGTAGTA | 40 |
| 29 | SEQ-P9 | ACAGCATATGACCAAGAACG | 41 |
| 30 | SEQ-P10 | GAGAATATGTGGAAACACAC | 42 |
| 31 | frag1-F | CATACCCTTACTTGATCAAAGGTTG | 43 |
| 32 | frag1-R | AACAGGGTTATTACAATCACAGTGA | 44 |
| 33 | frag2-F | AATGGTAACAATGCAGTTAAACTTT | 45 |
| 34 | frag2-R | AAGCTTCTAGAGATCTGCAGGTCGA | 46 |

2.2 Construction of pPscry5B and pPscry5Bt

Using a primer set of vect+pF and vect+tR, shown in Table 2, and pHYS237 DNA as a template, a vector containing the promoter and terminator regions of S237 was amplified. Next, using pUC57-cry5B DNA as a template and a primer set of cry5BpF and cry5BtR (or T237-cry5BatRN), an insert of full-length (or truncated) cry5B gene was amplified by PCR. Subsequently, using In-Fusion (R) HD EcoDry™ Cloning Kit (company: Clontech), the vector and the insert were ligated and *Escherichia coli* HB101 competent cells (Takara Bio Inc.) were transformed with the resultant construct. Transformants were screened based on tetracycline resistance, confirmed by colony PCR and designated as pPscry5B (or pPscry5Bt) (FIG. 1-B). The plasmid was extracted, further confirmed by PCR and checked for the digestion pattern of the plasmid by use of restriction enzymes EcoRI, SpeI and XbaI.

2.3 Construction of pPvcry5B and pPvcry5Bt

Using a primer set of vectR and vect+tR, shown in Table 2 and pHYS237 DNA as a template, a vector containing a terminator region of S237 was amplified. Next, using pUC57-cry5B DNA as a template and a primer set of cry5BaF and cry5BtR (or T237-cry5BatRN), an insert of full-length (or truncated) cry5B gene was amplified by PCR. Also, using a primer set of Vect-PvgF and cry5Ba-PvgR, and genomic DNA of *Bacillus subtilis* 168 strain as a template, a promoter region of spoVG gene was amplified as a second insert. Subsequently, using In-Fusion (R) HD EcoDry™ Cloning Kit (company: Clontech), the vector and the second insert were ligated and *Escherichia coli* HB101 competent cells (Takara Bio Inc.) were transformed with the resultant construct. Transformants were screened based on tetracycline resistance, confirmed by colony PCR and designated as pPvcry5B (or pPvcry5Bt) (FIG. 1-C). The plasmid was extracted, further confirmed by PCR and checked for the digestion pattern of the plasmid by use of restriction enzymes EcoRI, SpeI and XbaI.

2.4 Construction of pPvScry5B and pPvScry5Bt

Using a primer set of vectR and vect+tR, shown in Table 2 and pHYS237 DNA as a template, a vector containing a terminator region of S237 was amplified. Next, using pPsScry5B DNA as a template and a primer set of S237F and cry5BtR (or T237-cry5BatRN), an insert of full-length (or truncated) cry5B gene having a signal sequence of S237 ligated thereto was amplified by PCR. Also, using a primer set of Vect-PvgF and S237-PvgR, and genomic DNA of *Bacillus subtilis* 168 strain as a template, a promoter region of spoVG gene was amplified as a second insert. Subsequently, using In-Fusion (R) HD EcoDry™ Cloning Kit (company: Clontech), the vector and the second insert were ligated, and thereafter, *Escherichia coli* HB101 competent cells (Takara Bio Inc.) were transformed with the resultant construct. Transformants were screened based on tetracycline resistance, confirmed by colony PCR and designated as pPvScry5B (or pPvScry5Bt) (FIG. 1-D). The plasmid was extracted, further confirmed by PCR and checked for the digestion pattern of the plasmid by use of restriction enzymes EcoRI, SpeI and XbaI.

3. Sequencing of Plasmid

Eight types of plasmids thus constructed were subjected to sequencing. Templates for sequencing was prepared by PCR. With respect to 4 types of full-length cry5B plasmids, 5' and 3' side fragments of each plasmid were prepared by use of primers frag1-F and frag1-R or frag2-F and frag2-R shown in Table 2. With respect to four types of truncated cry5B plasmids, fragments were prepared by use of primers frag1-F and frag2-R shown in Table 2. The PCR products of them were subjected to sequencing using 10 primers of SEQ-P1 to SEQ-P10 shown in Table 2. As a result of the analysis, no mutation was found in all plasmids. From this, it was confirmed that all plasmids were successfully constructed as designed.

4. Expression of Cry5B Protein and Truncated Cry5B (Cry5Bt) protein in Wild-Type *Bacillus Subtilis* Strain by Plasmid Having Secretion Signal Tryptophan auxotrophy-recovered *Bacillus subtilis* 168 strain (168T strain) (JP-A-2017-79640) were transformed with the four types of constructed plasmids having a secretion signal (FIGS. 1-A, D). The obtained transformants were cultured in a 2×L/mal medium containing 2% (w/v) of Bacto Tryptone, 1.0% (w/v) of yeast extract, 1.0% (w/v) of sodium chloride, 0.00075% (w/v) of manganese sulfate pentahydrate (manufactured by Wako Pure Chemical Industries, Ltd.), 7.5% (w/v) of maltose monohydrate (manufactured by Wako Pure Chemical Industries, Ltd.) and 0.0015% (w/v) of tetracycline hydrochloride for 3 days at 30° C. while shaking at 250 rpm. Each of the culture solutions (1 mL) was centrifuged at 15000 rpm and 4° C. to separate into a culture supernatant and cells. The prepared culture supernatant was checked for Cry5B expression by SDS-PAGE, and as a result, no Cry5B band was observed (FIG. 2).

5. Expression of Cry5B Protein by Plasmid Having No Secretion Signal in Wild Type *Bacillus Subtilis* Strain Among the constructed plasmids having no secretion signal (FIGS. 1-B, C), two types of plasmids <5> and <6> (FIG. 3) for expressing Cry5B protein were used herein. Tryptophan auxotrophy-recovered *Bacillus subtilis* 168 strains (168T strain) were transformed with plasmids <5> and <6>. The obtained transformants were each cultured in a 2×L/mal medium for 3 days at 30° C. while shaking at 250 rpm. Each of the culture solutions (1 mL) was centrifuged at 15000 rpm and 4° C. to separate into a culture supernatant and cells. The cell pellets were washed with 1×PBS, and then suspended in 1 mL of 1×PBS. To the suspensions, 1 mg/mL lysozyme was added and the mixtures were kept warm at 37° C. for one hour. Subsequently, the cells were crushed by sonication using BIORUPTOR (Cosmo Bio) for 30 seconds. After sonication was repeated 20 times, the crushed cells were centrifuged at 15000 rpm and 4° C. for 30 minutes. The supernatants were discarded and the precipitates were suspended in 1 mL of 1×PBS to obtain cell lysates. The prepared cell lysates were checked for Cry5B expression by SDS-PAGE, and as a result, high expression by pHY-Pscry5B (<5>) and pHY-Pvcry5B (<6>) was confirmed. Plasmids pHY-Pscry5B and pHY-Pvcry5B have a full-length of 140 kD, which matched with estimated sizes (FIG. 3).

6. Expression of Cry5B Protein in *Bacillus Subtilis* Mutant Strain (1)

A *Bacillus subtilis* mutant strain in which a large region of the genome of wild type *Bacillus subtilis* strain is deleted (MGB874 strain; JP-B-4955358), a protease deficient strain (Dpr9 strain; JP-B-4485341), sigF deficient strain (ΔsigF strain; JP-B-4336082), MGB874ΔsigF strain and Dpr9ΔsigF strain were used as hosts and each transformed with pHY-Pscry5B. MGB874ΔsigF strain and Dpr9ΔsigF strain, MGB874abrB*ΔkinA strain (JP-A-2017-79639) were prepared in the same manner as in ΔsigF strain by removing sigF from MGB874 and Dpr9 strain, respectively. Similarly to the above Section 4, culturing was carried out in a 2×L/mal medium and the prepared cell lysates were analyzed for Cry5B expression by SDS-PAGE. As a result, it was found that bands of Cry5B expressed in MGB874 strain, Dpr9 strain, sigF deficient strain, MGB874ΔsigF strain and Dpr9ΔsigF strain are clearly thick compared to that of a wild-type 168T strain (FIG. 4-A).

7. Expression of Cry5B Protein in *Bacillus Subtilis* Mutant (2)

A sigE deficient strain (ΔsigE strain; JP-B-4336082) was used as a host and transformed with pHY-Pscry5B. Similarly to the above Section 4, culturing was carried out in the 2×L/mal medium and the prepared cell lysate was analyzed for Cry5B expression by SDS-PAGE. As a result, it was found that the band of Cry5B in sigE deficient strain is apparently thick (FIG. 4-B).

8. Expression of Cry5B Protein in *Bacillus Megaterium*

Plasmid pHY-Pscry5B for expressing Cry5B protein was introduced to *Bacillus megaterium* ATCC 14581 strain (hereinafter referred to as 14581 strain) by a protoplast method. The obtained recombinant strain was cultured in the 2×L/mal medium in the same manner as in Example 1, Section 5, and the prepared cell lysate was analyzed for Cry5B expression by SDS-PAGE. As a result, in a transformant having pHY-Pscry5B introduced therein, a thick Cry5B band was observed.

9. Quantification of Cry5B Protein Expressed

Using image software, ImageJ, (rsb.info.nih.gov/ij/download.html) developed by the National Institute of Health (NIH), bands on SDS-PAGE were quantified. Bovine serum albumin (BSA) (manufactured by Wako Pure Chemical Industries, Ltd.) as a standard protein, and Cry5B expressed in pHY-Pscry5B transformant were subjected to SDS-PAGE and staining was carried out by Bio-Safe™ Coomassie (BIO-RAD) while shaking for one hour. After color was removed by ion-exchange water, the gel was photographed.

The brightness of individual bands in an image of SDS-PAGE was analyzed by ImageJ to prepare a BSA calibration curve. Based on this calibration curve, the amounts of Cry5B proteins were calculated (Table 3, Table 4, Table 5). As shown in Table 3, Cry5B productivity in wild type Bacillus subtilis strain was 1.1 g/L, which was found to be 15 times as high as the value (75 mg/L) produced by a recombinant and described in literatures. The productivity was further improved twice or more by using MGB874ΔsigF strain.

TABLE 3

Productivity of Cry5B protein (1)

| Host strain | Amount of Cry5B produced (g/L) |
|---|---|
| 168T | 1.1 |
| MGB874 | 1.7 |
| Dpr9 | 1.7 |
| ΔsigF | 1.8 |
| MGB874ΔsigF | 2.5 |
| Dpr9ΔsigF | 2.0 |
| MGB874abrB*ΔkinA | 1.9 |

TABLE 4

Productivity of Cry5B protein (2)

| Host strain | Amount of Cry5B produced (g/L) |
|---|---|
| 168T | 1.2 |
| ΔsigE | 1.7 |

TABLE 5

Productivity of Cry5B protein (3)

| Host strain | Amount of Cry5B produced (g/L) |
|---|---|
| 14581 strain | 1.3 |

10. Evaluation of Cry5B Activity

10.1 Preparation of Egg-Bearing Adult Insect

A solution containing 750 μL of an *Escherichia coli* (*E. coli* OP50-1) solution (1 g wet-weight/6 mL S medium), 100 μL of a streptomycin (1 mg/mL) solution and 1000 L1 larvae (*Caenorhabditis elegans*) was dropped on an NGM plate and cultured in an incubator at 20° C. for 3 to 4 days to obtain egg-bearing adult insects.

10.2 Preparation of First-Stage (L1) Larvae

The NGM plate (Table 6) on which nematodes were cultured was washed about three times with S basal buffer and all were transferred to a 15 mL centrifuge tube. The supernatant was discarded and nematodes precipitated were transferred to a 1.5 mL-Eppendorf tube. After allowed to stand still for a while, the supernatant up to 1 mL was removed. To the Eppendorf tube, 250 μL of 4M NaOH and 250 μL of a sodium hypochlorite solution (Wako) were added and slightly stirred. After allowed to stand still for 3 minutes, the tube was spun down by a bench-top mini-centrifuge for about 30 seconds. The supernatant was removed while remaining a precipitate, and S basal buffer was added up to 1.5 mL. After slightly stirred, the tube was spun down for about 30 seconds. This operation was repeated three times. The total amount of the egg precipitate thus obtained was transferred to a petri dish of 35 mm in diameter, cultured at 20° C. for about 24 hours to obtain a first-stage larvae (L1 larva) hatched.

10.3 L1 Growth Assay

In accordance with a method of Bischof et al. (Methods in Molecular Biology, vol. 331, pp 139-154, *C. elegans*: Methods and applications, Edited by: K. Strange, Humana Press), L1 growth assay was carried out. To individual wells of a 48-well flat-bottom plate, 20 μL of a 1 g/35 mL *Escherichia coli* solution, 20 μL of a 1 mg/mL streptomycin solution, 10 L1-larvae and an appropriate amount of Cry5B protein expressed in *Bacillus subtilis* were added and the total amount was adjusted with S medium (Table 7) to 200 μL. As the amount of Cry5B protein, 1.25, 2.5 and 5 μg/mL were used. As the control, *Bacillus subtilis* to which a vector (pHY300PLK) was introduced was used. After culturing was carried out at 20° C. for 3 days, the nematodes in individual wells were photographed by a camera (FIG. 5). Based on the image photographed, outlines of the nematodes were drawn by use of Image J and the area thereof was calculated. The results are shown in FIG. 6. The growth of nematode was significantly suppressed by use of Cry5B; more specifically, the growth was suppressed by about 80%, even at a concentration of 1.25 μg/mL, compared to the control. From the results, it was demonstrated that Cry5B expressed in *Bacillus subtilis* is toxic to nematodes.

Medium component (1) NGM:

TABLE 6

| | |
|---|---|
| <A> | |
| NaCl | 3.0 g |
| Agar powder | 17.0 g |
| Cholesterol (5 mL/mL in EtOH) | 1.0 mL |
| Ultrapure water | 973 mL |
| <B> | |
| 1M $CaCl_2$ | 1.0 mL |
| 1M $MgSO_4$ | 1.0 mL |
| 1M phosphate buffer solution (pH 6.0) | 25 mL |

After A and B were separately sterilized, they were mixed.

(2) S basal buffer: 0.1M NaCl, 0.05M $KHPO_4$ (pH6.0)

(3) S medium:

TABLE 7

| <A> S basal | |
|---|---|
| NaCl | 5.8 g |
| 1M phosphate buffer solution (pH 6.0) | 50 mL |
| Cholesterol (5 mg/mL in EtOH) | 1 mL |
| Ultrapure water | 923 mL |

TABLE 7-continued

| <B> | |
|---|---|
| 1M citrate buffer solution (pH 6.0) | 10 mL |
| Aqueous trace metal solution | 10 mL |
| 1M CaCl$_2$ | 3 mL |
| 1M MgSO$_4$ | 3 mL |

*Aqueous trace metal solution:
EDTA•Na$_2$ 1.86 g
FeSO$_4$•7H$_2$O 0.69 g
MnCl$_2$•4H$_2$O 0.20 g
ZnSO$_4$•7H$_2$O 0.29 g
CuSO$_4$•5H$_2$O 0.025 g
Ultrapure water 1000 mL After A and B were separately sterilized, they were mixed.

11. Expression of Truncated Cry5B (Cry5Bt) Protein by Plasmid Having No Secretion Signal in Wild Type *Bacillus Subtilis* Strain Plasmid pHY-Pscry5Bt <7> of truncated Cry5B (Cry5Bt) having no secretion signal was used herein. A tryptophan auxotrophy-recovered *Bacillus subtilis* 168 strain (168T strain) was transformed with the plasmid, and the obtained transformant was cultured in a 2×L/mal medium for 3 days at 30° C. while shaking at 250 rpm. The culture solution (1 mL) was centrifuged at 15000 rpm and 4° C. to separate into a culture supernatant and cells. The cell pellet was washed with 1×PBS, and then suspended in 1 mL of 1×PBS. To the suspension, 1 mg/mL lysozyme was added and the mixture was kept warm at 37° C. for one hour. Subsequently, the cells were crushed by sonication using BIORUPTOR (Cosmo Bio) for 30 seconds. After sonication was repeated 20 times, the crushed cells were centrifuged at 15000 rpm and 4° C. for 30 minutes. The supernatant was discarded and the precipitate was suspended in 1 mL of 1×PBS to obtain a cell lysate. The prepared cell lysate was checked for Cry5Bt expression by SDS-PAGE (FIG. 7). As a result, it was confirmed that pHY-Pscry5Bt was highly expressed. The size of the protein band was 79 kD, which was matched with the estimated size of truncated Cry5B.

Example 2

Production of Mosquitocidal Proteins (Cry4Aa, Cry4Ba, Cry11Aa)

1. Synthesis of Artificial Gene

*Bacillus thuringiensis* serovar israelensis-derived insecticidal protein genes, cry4Aa (GenBank: YP_001573833, SEQ ID NO: 3), cry4Ba (GenBank: NC_010076, SEQ ID NO: 5) and cry11Aa (GenBank: NC_010076, SEQ ID NO: 7) were artificially synthesized by GenScript Biotech Corporation (U.S.A.). The synthesized genes were each cloned into a KpnI-HindIII site of pUC57 to obtain plasmids of pUC57-cry4Aa, pUC57-cry4Ba and pUC57-cry11Aa, respectively.

2. Construction of Expression Plasmid

In construction of all expression plasmids, pHY300PLK was used as a vector and an S237 cellulase gene-derived sequence was used as a terminator. A promoter derived from S237 cellulase gene [Hakamada et al, Biosci. Biotechnol. Biochem., 64 (2000), 2281-2289] often handled in our laboratory or derived from spoVG gene of *Bacillus subtilis* 168 strain was used. Using these in combination with the three genes: cry4Aa, cry4Ba and cry11 Aa, 6 types of plasmids shown in FIG. 8 were produced. The promoter of S237 cellulase gene was used for pHY-Pscry4Aa, pHY-Pscry4Ba and pHY-Pscry11Aa; and the promoter of the spoVG gene of *Bacillus subtilis* 168 strain was used for pHY-Pvcry4Aa, pHY-Pvcry4Ba and pHY-Pvcry11Aa. Construction was carried out in accordance with the method instructed by the protocol of In-Fusion (R) HD EcoDry™ Cloning Kit.

2.1 Construction of pHY-Pscry4Aa, pHY-Pscry4Ba and pHY-Pscry11Aa

Using a primer set of vect+pF and vect+tR shown in Table 8 and pHYS237 DNA as a template, a vector containing S237 promoter and terminator regions was amplified. Next, using pUC57-cry4Aa DNA as a template and a primer set of cry4AFPS and cry4ART, an insert of cry4Aa gene was amplified by PCR. Subsequently, using In-Fusion (R) HD EcoDry™ Cloning Kit (company: Clontech), the vector and the insert were ligated and *Escherichia coli* HB101 competent cells (Takara Bio Inc.) were transformed with the resultant construct. Transformants were screened based on tetracycline resistance, confirmed by colony PCR and designated as pHY-Pscry4Aa. The plasmid was extracted, confirmed by PCR and checked for the digestion pattern of the plasmid by use of restriction enzymes.

Similarly to the above, using pUC57-cry4Ba DNA as a template and a primer set of cry4BFPS and cry4BRT, cry4Ba gene was amplified by PCR. Further, using pUC57-cry11Aa DNA as a template and a primer set of cry11AFPS and cry11ART, an insert of cry11Aa gene was amplified by PCR. In this manner, pHY-Pscry4Ba and pHY-Pscry11Aa were constructed.

TABLE 8

| Name of primer | Sequence | SEQ ID NO: |
|---|---|---|
| vect+pF | ATTACCTCCTAAATATTTTT | 47 |
| Vect+pvgF | AGTAGTTCACCACCTTTTCC | 48 |
| vect+tR | TCTATTAAACTAGTTATAGG | 49 |
| cry4AFPS | TATTTAGGAGGTAATATGATGAATCCT TATCAAAATAA | 50 |
| cry4AFPV | GGAAAAGGTGGTGAACTACTATGAATC CTTATCAAAATAA | 51 |
| cry4ART | CCTATAACTAGTTTAATAGATCACTCG TTCATGCAAATTA | 52 |
| cry4BFPS | TATTTAGGAGGTAATATGATGAATTCA GGCTATCCGTT | 53 |
| cry4BFPV | GGAAAAGGTGGTGAACTACTATGAATT CAGGCTATCCGTT | 54 |
| cry4BRT | CCTATAACTAGTTTAATAGATCACTCG TTCATGCAAATTA | 55 |
| cry11AFPS | TATTTAGGAGGTAATATGATGGAAGAT AGTTCTTTAGA | 56 |

TABLE 8-continued

| Name of primer | Sequence | SEQ ID NO: |
|---|---|---|
| cry11AFPV | GGAAAAGGTGGTGAACTACTATGGAAGATAGTTCTTTAGA | 57 |
| cry11ART | CCTATAACTAGTTTAATAGACTACTTTAGTAACGGATTAA | 58 |

2.2 Construction of pHY-Pvcry4Aa, pHY-Pvcry4Ba and pHY-Pvcry11Aa

Using a primer set of vect+pvgF and vect+tR, shown in Table 8, and pHY-Pscry5B (refer to Example of Cry5B) as a template, a vector containing the promoter region of spoVG gene and the terminator region of S237 cellulase gene was amplified. Next, using pUC57-cry4Aa DNA as a template and a primer set of cry4AFPV and cry4ART, an insert of cry4Aa gene was amplified by PCR. Subsequently, using In-Fusion (R) HD EcoDry™ Cloning Kit (company: Clontech), the vector and the insert were ligated. *Escherichia coli* HB101 competent cells were transformed (Takara Bio Inc.) with the resultant construct. Transformants were screened based on tetracycline resistance, confirmed by colony PCR and designated as pHY-Pvcry4Aa. The plasmid was extracted, confirmed by PCR and check for the digestion pattern of the plasmid by use of restriction enzymes.

Similarly to the above, using pUC57-cry4Ba DNA as a template and a primer set of cry4BFPV and cry4BRT, a cry4Ba gene was amplified by PCR. Further, using pUC57-cry11Aa DNA as a template and a primer set of cry11AFPV and cry11ART, an insert of cry11Aa gene was amplified by PCR. In this manner, pHY-Pvcry4Ba and pHY-Pvcry11Aa were constructed.

3. Expression of Mosquitocidal Protein in *Bacillus Subtilis*

Six types of plasmids constructed (FIG. 8) were used herein. Tryptophan auxotrophy-recovered *Bacillus subtilis* 168 strain (168T strain) was transformed with each of the six plasmids. The obtained transformants were cultured in a 2×L/mal medium for 3 days at 30° C. while shaking at 250 rpm. The culture solution (1 mL) was centrifuged at 15000 rpm and 4° C. to separate into a culture supernatant and cells. After the cell pellets were washed with 1×PBS and suspended in 1 mL of 1×PBS. To the suspensions, 1 mg/mL lysozyme was added and the mixtures were kept warm at 37° C. for one hour. Subsequently, the cells were crushed by sonication using Biorupter (Cosmo Bio) for 30 seconds. After sonication was repeated 20 times, the crushed cells were centrifuged at 15000 rpm and 4° C. for 30 minutes. The supernatants were discarded and the precipitates were suspended in 1 mL of 1×PBS to obtain cell lysates. The prepared cell lysates were checked for protein expression by SDS-PAGE. As a result, the protein was highly expressed in all plasmids, as shown in FIG. 9.

4. Quantification of a Mosquitocidal Protein Expressed

Using image software, ImageJ, (rsb.info.nih.gov/ij/download.html) developed by the National Institute of Health (NIH), bands on SDS-PAGE were quantified. As a standard protein, bovine serum albumin (BSA) was used. The brightness of individual bands in an image of SDS-PAGE was analyzed by ImageJ to prepare a BSA calibration curve. Based on the calibration curve, the amounts of individual mosquitocidal proteins were calculated. As shown in Table 9, productivities of them were confirmed to fall within the range of 0.6 to 0.7 g/L.

TABLE 9

Productivity of Mosquitocidal protein

| Plasmid | Amount of Mosquitocidal protein produced (g/L) |
|---|---|
| pHY-Pscry4Aa | 0.70 |
| pHY-Pscry4Ba | 0.69 |
| pHY-Pscry11Aa | 0.55 |
| pHY-Pvcry4Aa | 0.58 |
| pHY-Pvcry4Ba | 0.60 |
| pHY-Pvcry11Aa | 0.59 |

5. Evaluation of Activity of Mosquitocidal Protein

5.1 Preparation of Mosquito Larva

Tiger mosquito, *Aedes albopictus*, was purchased from SUMIKA TECHNOSERVICE CORPORATION, hatched and put in use. A plastic pan was filled with water up to a height of about 1 cm and a paper filter on which eggs were deposited was placed in the pan. After hatched, feed (TetraMin baby) for tropical fish was given to mosquito larvae every day. Mosquito larvae on day 5 after hatch were used for activity evaluation.

5.2 Evaluation of Mosquitocidal Activity

In accordance with the method of Leetachewa et al. (BMB reports, 47 (2014), 546-551), Cry4Aa, Cry4Ba and Cry11Aa expressed in *Bacillus subtilis* were evaluated for the mosquitocidal activity. A 24-well flat-bottom plate was used herein. To each well, 5-day-old mosquito larvae (10 larvae) were added. The concentration of a mosquitocidal protein was set at 50 μg/mL. A total amount of a sample was adjusted with water up to 1 mL. After the larvae were allowed to stand still at 25° C. for 24 hours, the number of dead mosquito larvae was counted and a mortality rate was calculated. The results are shown in Table 10. Compared to a control (a mortality rate of 0%), the mortality rates of Cry4Aa, Cry4Ba and Cry11Aa were 93.3%, 93.3% and 76.7%, respectively. From the results, it was confirmed that the mosquitocidal proteins expressed in *Bacillus subtilis* have a high mosquitocidal effect.

TABLE 10

Mosquitocidal effect of mosquitocidal protein on mosquito larvae

| Mosquitocidal protein | Mortality rate (%) |
|---|---|
| Control | 0 |
| Cry4Aa | 93.3 |
| Cry4Ba | 93.3 |
| Cry11Aa | 76.7 |

SEQUENCE LISTING

<160> NUMBER OF SEQ ID NOS: 58

<210> SEQ ID NO 1
<211> LENGTH: 3738
<212> TYPE: DNA
<213> ORGANISM: Bacillus thuringiensis
<220> FEATURE:
<221> NAME/KEY: CDS
<222> LOCATION: (1)..(3738)

<400> SEQUENCE: 1

```
atg gca aca att aat gag ttg tat cca gtt cct tat aat gtg cta gct       48
Met Ala Thr Ile Asn Glu Leu Tyr Pro Val Pro Tyr Asn Val Leu Ala
1               5                   10                  15 cat cca att aaa gaa gtc gat gat cct tat tct tgg tca aat tta tta       96
His Pro Ile Lys Glu Val Asp Asp Pro Tyr Ser Trp Ser Asn Leu Leu
            20                  25                  30 aag ggt ata caa gaa ggt tgg gaa gaa tgg gga aaa aca gga caa aaa      144
Lys Gly Ile Gln Glu Gly Trp Glu Glu Trp Gly Lys Thr Gly Gln Lys
        35                  40                  45 aaa ctt ttt gaa gac cat ctt acg att gca tgg aat ctt tat aaa aca      192
Lys Leu Phe Glu Asp His Leu Thr Ile Ala Trp Asn Leu Tyr Lys Thr
    50                  55                  60 gga aaa tta gat tat ttc gct ttg aca aaa gca tca ata tca ttg att      240
Gly Lys Leu Asp Tyr Phe Ala Leu Thr Lys Ala Ser Ile Ser Leu Ile
65                  70                  75                  80 gga ttt att cca ggg gca gaa gca gca gtt ccc ttt att aat atg ttt      288
Gly Phe Ile Pro Gly Ala Glu Ala Ala Val Pro Phe Ile Asn Met Phe
                85                  90                  95 gta gac ttt gtt tgg cct aaa tta ttt ggt gcg aat aca gaa gga aaa      336
Val Asp Phe Val Trp Pro Lys Leu Phe Gly Ala Asn Thr Glu Gly Lys
            100                 105                 110 gat caa cag ttg ttt aat gct atc atg gat gca gtt aat aaa atg gta      384
Asp Gln Gln Leu Phe Asn Ala Ile Met Asp Ala Val Asn Lys Met Val
        115                 120                 125 gat aat aag ttc tta agt tat aat ctt agt aca ctt aat aaa aca att      432
Asp Asn Lys Phe Leu Ser Tyr Asn Leu Ser Thr Leu Asn Lys Thr Ile
    130                 135                 140 gaa gga ctt caa ggt aat tta ggc cta ttt caa aat gct ata caa gta      480
Glu Gly Leu Gln Gly Asn Leu Gly Leu Phe Gln Asn Ala Ile Gln Val
145                 150                 155                 160 gcc att tgt caa ggc agt aca cca gaa aga gta att ttt gat caa aat      528
Ala Ile Cys Gln Gly Ser Thr Pro Glu Arg Val Ile Phe Asp Gln Asn
                165                 170                 175 tgt aca cca tgt aat cca aat caa cct tgt aaa gat gat ttg gat aga      576
Cys Thr Pro Cys Asn Pro Asn Gln Pro Cys Lys Asp Asp Leu Asp Arg
            180                 185                 190 gtt gct tca cgt ttt gat acg gct aat tct caa ttc aca cag cat tta      624
Val Ala Ser Arg Phe Asp Thr Ala Asn Ser Gln Phe Thr Gln His Leu
        195                 200                 205 cca gaa ttt aaa aat cct tgg tcg gat gaa aac tct act cag gaa ttt      672
Pro Glu Phe Lys Asn Pro Trp Ser Asp Glu Asn Ser Thr Gln Glu Phe
    210                 215                 220 aaa aga aca tct gtt gaa tta act tta cca atg tat aca aca gta gct      720
Lys Arg Thr Ser Val Glu Leu Thr Leu Pro Met Tyr Thr Thr Val Ala
225                 230                 235                 240 acg tta cat ctt tta tta tat aaa gga tat ata gaa ttt atg aca aaa      768
Thr Leu His Leu Leu Leu Tyr Lys Gly Tyr Ile Glu Phe Met Thr Lys
                245                 250                 255 tgg aat ttt cac aat gaa caa tat tta aat aat tta aag gta gaa tta      816
Trp Asn Phe His Asn Glu Gln Tyr Leu Asn Asn Leu Lys Val Glu Leu
```

```
                    260                 265                 270
caa caa ttg ata cac tca tat tca gaa act gtt cgt aca agt ttc ctt         864
Gln Gln Leu Ile His Ser Tyr Ser Glu Thr Val Arg Thr Ser Phe Leu
        275                 280                 285 caa ttt tta cct acc ttg aat aat cgt tca aaa tca tcc gta aat gct         912
Gln Phe Leu Pro Thr Leu Asn Asn Arg Ser Lys Ser Ser Val Asn Ala
290                 295                 300 tat aac cgt tat gtc cgc aat atg act gtt aac tgt tta gat att gct         960
Tyr Asn Arg Tyr Val Arg Asn Met Thr Val Asn Cys Leu Asp Ile Ala
305                 310                 315                 320 gct aca tgg cct aca ttt gat aca cat aat tat cat caa ggt ggt aaa        1008
Ala Thr Trp Pro Thr Phe Asp Thr His Asn Tyr His Gln Gly Gly Lys
            325                 330                 335 tta gat tta act cgt att att ctt tca gat aca gca gga cca ata gaa        1056
Leu Asp Leu Thr Arg Ile Ile Leu Ser Asp Thr Ala Gly Pro Ile Glu
            340                 345                 350 gaa tat act act ggc gac aaa act tca gga cct gaa cat agt aac att        1104
Glu Tyr Thr Thr Gly Asp Lys Thr Ser Gly Pro Glu His Ser Asn Ile
            355                 360                 365 aca cca aat aat att cta gat aca cca tct cca aca tat cag cac tca        1152
Thr Pro Asn Asn Ile Leu Asp Thr Pro Ser Pro Thr Tyr Gln His Ser
370                 375                 380 ttt gta tct gtt gat tct att gta tat tct aga aaa gaa tta caa caa        1200
Phe Val Ser Val Asp Ser Ile Val Tyr Ser Arg Lys Glu Leu Gln Gln
385                 390                 395                 400 tta gac ata gct act tat agt aca aat aat agt aat aat tgt cac cct        1248
Leu Asp Ile Ala Thr Tyr Ser Thr Asn Asn Ser Asn Asn Cys His Pro
                405                 410                 415 tat gga tta cga ctt tca tat aca gat gga agc aga tat gat tat gga        1296
Tyr Gly Leu Arg Leu Ser Tyr Thr Asp Gly Ser Arg Tyr Asp Tyr Gly
            420                 425                 430 gat aat caa cct gat ttt act act tcc aat aac aat tat tgt cat aat        1344
Asp Asn Gln Pro Asp Phe Thr Thr Ser Asn Asn Asn Tyr Cys His Asn
            435                 440                 445 agc tat act gcc cct att aca ctt gtg aat gca cga cat tta tat aat        1392
Ser Tyr Thr Ala Pro Ile Thr Leu Val Asn Ala Arg His Leu Tyr Asn
450                 455                 460 gca aaa ggc tct tta caa aat gta gaa tct tta gtg gtt agt act gta        1440
Ala Lys Gly Ser Leu Gln Asn Val Glu Ser Leu Val Val Ser Thr Val
465                 470                 475                 480 aat ggt gga agt ggt tca tgc att tgt gat gca tgg att aat tat tta        1488
Asn Gly Gly Ser Gly Ser Cys Ile Cys Asp Ala Trp Ile Asn Tyr Leu
                485                 490                 495 cgt cct cct caa aca agt aaa aat gaa tca cgt cct gat caa aaa att        1536
Arg Pro Pro Gln Thr Ser Lys Asn Glu Ser Arg Pro Asp Gln Lys Ile
            500                 505                 510 aat gtt ttg tat cca ata aca gaa act gta aat aag ggg act gga gga        1584
Asn Val Leu Tyr Pro Ile Thr Glu Thr Val Asn Lys Gly Thr Gly Gly
            515                 520                 525 aat tta gga gtt att tct gcc tat gtt cca atg gaa ctt gta cca gaa        1632
Asn Leu Gly Val Ile Ser Ala Tyr Val Pro Met Glu Leu Val Pro Glu
530                 535                 540 aac gtt att gga gat gtt aat gct gat act aaa ttg cca ctt aca caa        1680
Asn Val Ile Gly Asp Val Asn Ala Asp Thr Lys Leu Pro Leu Thr Gln
545                 550                 555                 560 tta aag ggc ttt cca ttt gaa aaa tat ggt tct gag tat aat aat cgg        1728
Leu Lys Gly Phe Pro Phe Glu Lys Tyr Gly Ser Glu Tyr Asn Asn Arg
                565                 570                 575 ggt atc tct ctt gtt cgc gaa tgg ata aat ggt aac aat gca gtt aaa        1776
Gly Ile Ser Leu Val Arg Glu Trp Ile Asn Gly Asn Asn Ala Val Lys
```

```
                Gly Ile Ser Leu Val Arg Glu Trp Ile Asn Gly Asn Asn Ala Val Lys
                                580                 585                 590 cct tct aat agt caa tct gtt ggc ata caa att acg aat caa acc aaa      1824
Leu Ser Asn Ser Gln Ser Val Gly Ile Gln Ile Thr Asn Gln Thr Lys
            595                 600                 605 caa aaa tat gaa ata cgt tgc cgt tat gcg agt aaa gga gat aat aat      1872
Gln Lys Tyr Glu Ile Arg Cys Arg Tyr Ala Ser Lys Gly Asp Asn Asn
610                 615                 620 gtt tat ttt aat gtg gat tta agt gaa aat cca ttt aga aat tcc att      1920
Val Tyr Phe Asn Val Asp Leu Ser Glu Asn Pro Phe Arg Asn Ser Ile
625                 630                 635                 640 tct ttt gga tct act gaa agt tct gtt gta gga gta caa ggt gaa aat      1968
Ser Phe Gly Ser Thr Glu Ser Ser Val Val Gly Val Gln Gly Glu Asn
                645                 650                 655 gga aag tat ata ttg aaa tca atc aca acg gta gaa ata cct gct gga      2016
Gly Lys Tyr Ile Leu Lys Ser Ile Thr Thr Val Glu Ile Pro Ala Gly
            660                 665                 670 agt ttc tat gtt cat ata aca aac caa ggt tct tca gat ctc ttt tta      2064
Ser Phe Tyr Val His Ile Thr Asn Gln Gly Ser Ser Asp Leu Phe Leu
            675                 680                 685 gat cgt att gag ttt gtt cca aaa atc caa ttc caa ttc tgt gat aat      2112
Asp Arg Ile Glu Phe Val Pro Lys Ile Gln Phe Gln Phe Cys Asp Asn
690                 695                 700 aat aat ctt cac tgt gat tgt aat aac cct gtt gac acc gat tgt aca      2160
Asn Asn Leu His Cys Asp Cys Asn Asn Pro Val Asp Thr Asp Cys Thr
705                 710                 715                 720 ttt tgt tgc gtt tgc act agt ctt act gat tgt gat tgt aat aac cct      2208
Phe Cys Cys Val Cys Thr Ser Leu Thr Asp Cys Asp Cys Asn Asn Pro
                725                 730                 735 cgt ggc cta gat tgt acg cta tgt tgt cag gta gaa aat cag cta cct      2256
Arg Gly Leu Asp Cys Thr Leu Cys Cys Gln Val Glu Asn Gln Leu Pro
            740                 745                 750 tct ttt gtg aca ctt aca gat tta caa aat att acg aca caa gta aat      2304
Ser Phe Val Thr Leu Thr Asp Leu Gln Asn Ile Thr Thr Gln Val Asn
            755                 760                 765 gca tta gtt gca tcg agc gaa cat gat aca ctt gca aca gac gtg agt      2352
Ala Leu Val Ala Ser Ser Glu His Asp Thr Leu Ala Thr Asp Val Ser
770                 775                 780 gat tat gag att gaa gaa gtt gta ctg aaa gta gat gca tta tct ggt      2400
Asp Tyr Glu Ile Glu Glu Val Val Leu Lys Val Asp Ala Leu Ser Gly
785                 790                 795                 800 gaa gtg ttt gga aaa gag aaa aaa gca ttg cgt aaa ttg gta aat cac      2448
Glu Val Phe Gly Lys Glu Lys Lys Ala Leu Arg Lys Leu Val Asn His
                805                 810                 815 aca aaa cgt tta agc aaa gcg cgt aac ctc ttg ata gga gga aat ttt      2496
Thr Lys Arg Leu Ser Lys Ala Arg Asn Leu Leu Ile Gly Gly Asn Phe
            820                 825                 830 gat aac ttg gat gct tgg tac aga ggc cga aat gta gta aac gta tct      2544
Asp Asn Leu Asp Ala Trp Tyr Arg Gly Arg Asn Val Val Asn Val Ser
            835                 840                 845 gat cat gaa cta ttt aag agt gat cat gta tta ttg cca cca cca aca      2592
Asp His Glu Leu Phe Lys Ser Asp His Val Leu Leu Pro Pro Pro Thr
850                 855                 860 ctg tac tca tct tat atg ttc caa aaa gta gag gaa tcg aaa tta aaa      2640
Leu Tyr Ser Ser Tyr Met Phe Gln Lys Val Glu Glu Ser Lys Leu Lys
865                 870                 875                 880 gcg aat aca cgt tat act gtg tct ggt ttt att gca cat gca gaa gat      2688
Ala Asn Thr Arg Tyr Thr Val Ser Gly Phe Ile Ala His Ala Glu Asp
                885                 890                 895
```

| | | |
|---|---|---|
| tta gaa att gtt gtg tct cgt tat ggg caa gaa gtg aag aaa gtg gtt<br>Leu Glu Ile Val Val Ser Arg Tyr Gly Gln Glu Val Lys Lys Val Val<br>                        900                    905                910 | 2736 | |
| caa gtt cca tat gga gaa gca ttc cca ttg aca tcg agg gga gcg att<br>Gln Val Pro Tyr Gly Glu Ala Phe Pro Leu Thr Ser Arg Gly Ala Ile<br>         915                    920                    925 | 2784 | |
| tgt tgc cct cca cgt tct aca tgt aat gga aaa cct gct gat cca cat<br>Cys Cys Pro Pro Arg Ser Thr Cys Asn Gly Lys Pro Ala Asp Pro His<br>930                    935                    940 | 2832 | |
| ttc ttt agt tac agt att gat gtg gga aca tta gat gta gaa gca aac<br>Phe Phe Ser Tyr Ser Ile Asp Val Gly Thr Leu Asp Val Glu Ala Asn<br>945                    950                    955                    960 | 2880 | |
| cct ggt atc gaa ttg ggt ctt cgt att gta gaa cga act gga atg gca<br>Pro Gly Ile Glu Leu Gly Leu Arg Ile Val Glu Arg Thr Gly Met Ala<br>                        965                    970                    975 | 2928 | |
| cgt gta agt aat tta gaa att cgt gaa gat cgt cca tta aag aaa aat<br>Arg Val Ser Asn Leu Glu Ile Arg Glu Asp Arg Pro Leu Lys Lys Asn<br>                  980                    985                    990 | 2976 | |
| gaa ctc cgc aat gta caa cgt gca  gca aga aat tgg aga  aca gca tat<br>Glu Leu Arg Asn Val Gln Arg Ala  Ala Arg Asn Trp Arg  Thr Ala Tyr<br>         995                    1000                1005 | 3024 | |
| gac caa gaa cgt gca gaa gta  acg gcc ttg att caa  cct gta tta<br>Asp Gln Glu Arg Ala Glu Val  Thr Ala Leu Ile Gln  Pro Val Leu<br>1010                    1015                1020 | 3069 | |
| aat caa atc aat gcg ttg tat  gaa aat gaa gat tgg  aat cga gca<br>Asn Gln Ile Asn Ala Leu Tyr  Glu Asn Glu Asp Trp  Asn Arg Ala<br>1025                    1030                1035 | 3114 | |
| att cgt tct gga gtt tct tat  cat gac tta gaa gca  att gtt tta<br>Ile Arg Ser Gly Val Ser Tyr  His Asp Leu Glu Ala  Ile Val Leu<br>1040                    1045                1050 | 3159 | |
| cca aca tta cca aaa tta aat  cat tgg ttt atg tct  gat atg tta<br>Pro Thr Leu Pro Lys Leu Asn  His Trp Phe Met Ser  Asp Met Leu<br>1055                    1060                1065 | 3204 | |
| ggg gaa caa ggt tcc att tta  gct caa ttt caa gaa  gca tta gat<br>Gly Glu Gln Gly Ser Ile Leu  Ala Gln Phe Gln Glu  Ala Leu Asp<br>1070                    1075                1080 | 3249 | |
| cgt gcg tat acg caa ctc gaa  gaa agt aca att ctg  cat aat ggt<br>Arg Ala Tyr Thr Gln Leu Glu  Glu Ser Thr Ile Leu  His Asn Gly<br>1085                    1090                1095 | 3294 | |
| cat ttc aca aca gat gca gca  aat tgg acg ata gaa  ggc gat gca<br>His Phe Thr Thr Asp Ala Ala  Asn Trp Thr Ile Glu  Gly Asp Ala<br>1100                    1105                1110 | 3339 | |
| cat cat gcg ata tta gaa gat  ggt aga cgc gta tta  cgt ctt cca<br>His His Ala Ile Leu Glu Asp  Gly Arg Arg Val Leu  Arg Leu Pro<br>1115                    1120                1125 | 3384 | |
| gat tgg tct tct agc gtt tca  caa acc att gaa ata  gaa aat ttt<br>Asp Trp Ser Ser Ser Val Ser  Gln Thr Ile Glu Ile  Glu Asn Phe<br>1130                    1135                1140 | 3429 | |
| gat cca gat aaa gaa tat cag  tta gtt ttc cat gca  caa gga gaa<br>Asp Pro Asp Lys Glu Tyr Gln  Leu Val Phe His Ala  Gln Gly Glu<br>1145                    1150                1155 | 3474 | |
| gga acg gtc tcc ctt caa cat  ggt gaa gaa gga gaa  tat gtg gaa<br>Gly Thr Val Ser Leu Gln His  Gly Glu Glu Gly Glu  Tyr Val Glu<br>1160                    1165                1170 | 3519 | |
| aca cac ccg cat aag tct gcg  aat ttt aca act tca  cac cgt caa<br>Thr His Pro His Lys Ser Ala  Asn Phe Thr Thr Ser  His Arg Gln<br>1175                    1180                1185 | 3564 | |
| gga gtc aca ttt gaa aca aat  aaa gta aca gtt gaa  att acc tca<br>Gly Val Thr Phe Glu Thr Asn  Lys Val Thr Val Glu  Ile Thr Ser<br>1190                    1195                1200 | 3609 | |

-continued

```
gaa gat gga gaa ttc cta gtc gat cat att gcg ctt gtg gaa gct         3654
Glu Asp Gly Glu Phe Leu Val Asp His Ile Ala Leu Val Glu Ala
    1205                1210                1215 cct ctt cct aca gat gac caa agt tca gat gga aat acg act tcc         3699
Pro Leu Pro Thr Asp Asp Gln Ser Ser Asp Gly Asn Thr Thr Ser
1220                1225                1230 aat acg aat agc aat aca agt atg aat aat aat caa taa                 3738
Asn Thr Asn Ser Asn Thr Ser Met Asn Asn Asn Gln
    1235                1240                1245

<210> SEQ ID NO 2
<211> LENGTH: 1245
<212> TYPE: PRT
<213> ORGANISM: Bacillus thuringiensis

<400> SEQUENCE: 2

Met Ala Thr Ile Asn Glu Leu Tyr Pro Val Pro Tyr Asn Val Leu Ala
1               5                   10                  15

His Pro Ile Lys Glu Val Asp Pro Tyr Ser Trp Ser Asn Leu Leu
            20                  25                  30

Lys Gly Ile Gln Glu Gly Trp Glu Trp Gly Lys Thr Gly Gln Lys
        35                  40                  45

Lys Leu Phe Glu Asp His Leu Thr Ile Ala Trp Asn Leu Tyr Lys Thr
    50                  55                  60

Gly Lys Leu Asp Tyr Phe Ala Leu Thr Lys Ala Ser Ile Ser Leu Ile
65                  70                  75                  80

Gly Phe Ile Pro Gly Ala Glu Ala Ala Val Pro Phe Ile Asn Met Phe
                85                  90                  95

Val Asp Phe Val Trp Pro Lys Leu Phe Gly Ala Asn Thr Glu Gly Lys
            100                 105                 110

Asp Gln Gln Leu Phe Asn Ala Ile Met Asp Ala Val Asn Lys Met Val
        115                 120                 125

Asp Asn Lys Phe Leu Ser Tyr Asn Leu Ser Thr Leu Asn Lys Thr Ile
    130                 135                 140

Glu Gly Leu Gln Gly Asn Leu Gly Leu Phe Gln Asn Ala Ile Gln Val
145                 150                 155                 160

Ala Ile Cys Gln Gly Ser Thr Pro Glu Arg Val Ile Phe Asp Gln Asn
                165                 170                 175

Cys Thr Pro Cys Asn Pro Asn Gln Pro Cys Lys Asp Leu Asp Arg
            180                 185                 190

Val Ala Ser Arg Phe Asp Thr Ala Asn Ser Gln Phe Thr Gln His Leu
        195                 200                 205

Pro Glu Phe Lys Asn Pro Trp Ser Asp Glu Asn Ser Thr Gln Glu Phe
    210                 215                 220

Lys Arg Thr Ser Val Glu Leu Thr Leu Pro Met Tyr Thr Thr Val Ala
225                 230                 235                 240

Thr Leu His Leu Leu Leu Tyr Lys Gly Tyr Ile Glu Phe Met Thr Lys
                245                 250                 255

Trp Asn Phe His Asn Glu Gln Tyr Leu Asn Asn Leu Lys Val Glu Leu
            260                 265                 270

Gln Gln Leu Ile His Ser Tyr Ser Glu Thr Val Arg Thr Ser Phe Leu
        275                 280                 285

Gln Phe Leu Pro Thr Leu Asn Asn Arg Ser Lys Ser Ser Val Asn Ala
    290                 295                 300

Tyr Asn Arg Tyr Val Arg Asn Met Thr Val Asn Cys Leu Asp Ile Ala
```

```
              305                 310                 315                 320
Ala Thr Trp Pro Thr Phe Asp Thr His Asn Tyr His Gln Gly Gly Lys
                325                 330                 335

Leu Asp Leu Thr Arg Ile Ile Leu Ser Asp Thr Ala Gly Pro Ile Glu
                340                 345                 350

Glu Tyr Thr Thr Gly Asp Lys Thr Ser Gly Pro Glu His Ser Asn Ile
                355                 360                 365

Thr Pro Asn Asn Ile Leu Asp Thr Pro Ser Pro Thr Tyr Gln His Ser
370                 375                 380

Phe Val Ser Val Asp Ser Ile Val Tyr Ser Arg Lys Glu Leu Gln Gln
385                 390                 395                 400

Leu Asp Ile Ala Thr Tyr Ser Thr Asn Asn Ser Asn Asn Cys His Pro
                405                 410                 415

Tyr Gly Leu Arg Leu Ser Tyr Thr Asp Gly Ser Arg Tyr Asp Tyr Gly
                420                 425                 430

Asp Asn Gln Pro Asp Phe Thr Thr Ser Asn Asn Asn Tyr Cys His Asn
                435                 440                 445

Ser Tyr Thr Ala Pro Ile Thr Leu Val Asn Ala Arg His Leu Tyr Asn
                450                 455                 460

Ala Lys Gly Ser Leu Gln Asn Val Glu Ser Leu Val Val Ser Thr Val
465                 470                 475                 480

Asn Gly Gly Ser Gly Ser Cys Ile Cys Asp Ala Trp Ile Asn Tyr Leu
                485                 490                 495

Arg Pro Pro Gln Thr Ser Lys Asn Glu Ser Arg Pro Asp Gln Lys Ile
                500                 505                 510

Asn Val Leu Tyr Pro Ile Thr Glu Thr Val Asn Lys Gly Thr Gly Gly
                515                 520                 525

Asn Leu Gly Val Ile Ser Ala Tyr Val Pro Met Glu Leu Val Pro Glu
                530                 535                 540

Asn Val Ile Gly Asp Val Asn Ala Asp Thr Lys Leu Pro Leu Thr Gln
545                 550                 555                 560

Leu Lys Gly Phe Pro Phe Glu Lys Tyr Gly Ser Glu Tyr Asn Asn Arg
                565                 570                 575

Gly Ile Ser Leu Val Arg Glu Trp Ile Asn Gly Asn Asn Ala Val Lys
                580                 585                 590

Leu Ser Asn Ser Gln Ser Val Gly Ile Gln Ile Thr Asn Gln Thr Lys
                595                 600                 605

Gln Lys Tyr Glu Ile Arg Cys Arg Tyr Ala Ser Lys Gly Asp Asn Asn
                610                 615                 620

Val Tyr Phe Asn Val Asp Leu Ser Glu Asn Pro Phe Arg Asn Ser Ile
625                 630                 635                 640

Ser Phe Gly Ser Thr Glu Ser Ser Val Val Gly Val Gln Gly Glu Asn
                645                 650                 655

Gly Lys Tyr Ile Leu Lys Ser Ile Thr Thr Val Glu Ile Pro Ala Gly
                660                 665                 670

Ser Phe Tyr Val His Ile Thr Asn Gln Gly Ser Ser Asp Leu Phe Leu
                675                 680                 685

Asp Arg Ile Glu Phe Val Pro Lys Ile Gln Phe Gln Phe Cys Asp Asn
                690                 695                 700

Asn Asn Leu His Cys Asp Cys Asn Pro Val Asp Thr Asp Cys Thr
705                 710                 715                 720

Phe Cys Cys Val Cys Thr Ser Leu Thr Asp Cys Asp Cys Asn Asn Pro
                725                 730                 735
```

-continued

```
Arg Gly Leu Asp Cys Thr Leu Cys Cys Gln Val Glu Asn Gln Leu Pro
            740                 745                 750

Ser Phe Val Thr Leu Thr Asp Leu Gln Asn Ile Thr Thr Gln Val Asn
            755                 760                 765

Ala Leu Val Ala Ser Ser Glu His Asp Thr Leu Ala Thr Asp Val Ser
            770                 775                 780

Asp Tyr Glu Ile Glu Glu Val Val Leu Lys Val Asp Ala Leu Ser Gly
785                 790                 795                 800

Glu Val Phe Gly Lys Glu Lys Lys Ala Leu Arg Lys Leu Val Asn His
            805                 810                 815

Thr Lys Arg Leu Ser Lys Ala Arg Asn Leu Leu Ile Gly Gly Asn Phe
            820                 825                 830

Asp Asn Leu Asp Ala Trp Tyr Arg Gly Arg Asn Val Val Asn Val Ser
            835                 840                 845

Asp His Glu Leu Phe Lys Ser Asp His Val Leu Leu Pro Pro Pro Thr
            850                 855                 860

Leu Tyr Ser Ser Tyr Met Phe Gln Lys Val Glu Glu Ser Lys Leu Lys
865                 870                 875                 880

Ala Asn Thr Arg Tyr Thr Val Ser Gly Phe Ile Ala His Ala Glu Asp
            885                 890                 895

Leu Glu Ile Val Val Ser Arg Tyr Gly Gln Glu Val Lys Lys Val Val
            900                 905                 910

Gln Val Pro Tyr Gly Glu Ala Phe Pro Leu Thr Ser Arg Gly Ala Ile
            915                 920                 925

Cys Cys Pro Pro Arg Ser Thr Cys Asn Gly Lys Pro Ala Asp Pro His
            930                 935                 940

Phe Phe Ser Tyr Ser Ile Asp Val Gly Thr Leu Asp Val Glu Ala Asn
945                 950                 955                 960

Pro Gly Ile Glu Leu Gly Leu Arg Ile Val Glu Arg Thr Gly Met Ala
            965                 970                 975

Arg Val Ser Asn Leu Glu Ile Arg Glu Asp Arg Pro Leu Lys Lys Asn
            980                 985                 990

Glu Leu Arg Asn Val Gln Arg Ala Ala Arg Asn Trp Arg Thr Ala Tyr
            995                 1000                1005

Asp Gln Glu Arg Ala Glu Val Thr Ala Leu Ile Gln Pro Val Leu
    1010                1015                1020

Asn Gln Ile Asn Ala Leu Tyr Glu Asn Glu Asp Trp Asn Arg Ala
    1025                1030                1035

Ile Arg Ser Gly Val Ser Tyr His Asp Leu Glu Ala Ile Val Leu
    1040                1045                1050

Pro Thr Leu Pro Lys Leu Asn His Trp Phe Met Ser Asp Met Leu
    1055                1060                1065

Gly Glu Gln Gly Ser Ile Leu Ala Gln Phe Gln Glu Ala Leu Asp
    1070                1075                1080

Arg Ala Tyr Thr Gln Leu Glu Glu Ser Thr Ile Leu His Asn Gly
    1085                1090                1095

His Phe Thr Thr Asp Ala Ala Asn Trp Thr Ile Glu Gly Asp Ala
    1100                1105                1110

His His Ala Ile Leu Glu Asp Gly Arg Arg Val Leu Arg Leu Pro
    1115                1120                1125

Asp Trp Ser Ser Ser Val Ser Gln Thr Ile Glu Ile Glu Asn Phe
    1130                1135                1140
```

-continued

| | | | | | | | | | | | |
|---|---|---|---|---|---|---|---|---|---|---|---|
| Asp | Pro | Asp | Lys | Glu | Tyr | Gln | Leu | Val | Phe | His | Ala | Gln | Gly | Glu |
| | 1145 | | | | 1150 | | | | 1155 | | |

Gly Thr Val Ser Leu Gln His Gly Glu Glu Gly Glu Tyr Val Glu
    1160                1165                1170

Thr His Pro His Lys Ser Ala Asn Phe Thr Thr Ser His Arg Gln
    1175                1180                1185

Gly Val Thr Phe Glu Thr Asn Lys Val Thr Val Glu Ile Thr Ser
    1190                1195                1200

Glu Asp Gly Glu Phe Leu Val Asp His Ile Ala Leu Val Glu Ala
    1205                1210                1215

Pro Leu Pro Thr Asp Asp Gln Ser Ser Asp Gly Asn Thr Thr Ser
    1220                1225                1230

Asn Thr Asn Ser Asn Thr Ser Met Asn Asn Asn Gln
    1235                1240                1245

<210> SEQ ID NO 3
<211> LENGTH: 3543
<212> TYPE: DNA
<213> ORGANISM: Bacillus thuringiensis
<220> FEATURE:
<221> NAME/KEY: CDS
<222> LOCATION: (1)..(3543)

<400> SEQUENCE: 3

```
atg aat cct tat caa aat aaa aat gaa tat gaa aca tta aat gct tca      48
Met Asn Pro Tyr Gln Asn Lys Asn Glu Tyr Glu Thr Leu Asn Ala Ser
1               5                   10                  15 caa aaa aaa tta aat ata tct aat aat tat aca aga tat cca ata gaa      96
Gln Lys Lys Leu Asn Ile Ser Asn Asn Tyr Thr Arg Tyr Pro Ile Glu
            20                  25                  30 aat agt cca aaa caa tta tta caa agt aca aat tat aaa gat tgg ctc     144
Asn Ser Pro Lys Gln Leu Leu Gln Ser Thr Asn Tyr Lys Asp Trp Leu
        35                  40                  45 aat atg tgt caa cag aat cag cag tat ggt gga gat ttt gaa act ttt     192
Asn Met Cys Gln Gln Asn Gln Gln Tyr Gly Gly Asp Phe Glu Thr Phe
    50                  55                  60 att gat agt ggt gaa ctc agt gcc tat act att gta gtt ggg acc gta     240
Ile Asp Ser Gly Glu Leu Ser Ala Tyr Thr Ile Val Val Gly Thr Val
65                  70                  75                  80 ctg act ggt ttc ggg ttc aca aca ccc tta gga ctt gct tta ata ggt     288
Leu Thr Gly Phe Gly Phe Thr Thr Pro Leu Gly Leu Ala Leu Ile Gly
                85                  90                  95 ttt ggt aca tta ata cca gtt ctt ttt cca gcc caa gac caa tct aac     336
Phe Gly Thr Leu Ile Pro Val Leu Phe Pro Ala Gln Asp Gln Ser Asn
            100                 105                 110 aca tgg agt gac ttt ata aca caa act aaa aat att ata aaa aaa gaa     384
Thr Trp Ser Asp Phe Ile Thr Gln Thr Lys Asn Ile Ile Lys Lys Glu
        115                 120                 125 ata gca tca aca tat ata agt aat gct aat aaa att tta aac agg tcg     432
Ile Ala Ser Thr Tyr Ile Ser Asn Ala Asn Lys Ile Leu Asn Arg Ser
    130                 135                 140 ttt aat gtt atc agc act tat cat aat cac ctt aaa aca tgg gag aat     480
Phe Asn Val Ile Ser Thr Tyr His Asn His Leu Lys Thr Trp Glu Asn
145                 150                 155                 160 aat cca aac cca caa aat act cag gat gta agg aca caa atc cag cta     528
Asn Pro Asn Pro Gln Asn Thr Gln Asp Val Arg Thr Gln Ile Gln Leu
                165                 170                 175 gtt cat tac cat ttt caa aat gtc att cca gag ctt gta aac tct tgt     576
Val His Tyr His Phe Gln Asn Val Ile Pro Glu Leu Val Asn Ser Cys
            180                 185                 190
```

```
cct cct aat cct agt gat tgc gat tac tat aac ata cta gta tta tct        624
Pro Pro Asn Pro Ser Asp Cys Asp Tyr Tyr Asn Ile Leu Val Leu Ser
        195                 200                 205 agt tat gca caa gca gca aac tta cat ctg act gta tta aat caa gcc        672
Ser Tyr Ala Gln Ala Ala Asn Leu His Leu Thr Val Leu Asn Gln Ala
    210                 215                 220 gtc aaa ttt gaa gcg tat tta aaa aac aat cga caa ttc gat tat tta        720
Val Lys Phe Glu Ala Tyr Leu Lys Asn Asn Arg Gln Phe Asp Tyr Leu
225                 230                 235                 240 gag cct ttg cca aca gca att gat tat tat cca gta ttg act aaa gct        768
Glu Pro Leu Pro Thr Ala Ile Asp Tyr Tyr Pro Val Leu Thr Lys Ala
            245                 250                 255 ata gaa gat tac act aat tat tgt gta aca act tat aaa aaa gga tta        816
Ile Glu Asp Tyr Thr Asn Tyr Cys Val Thr Thr Tyr Lys Lys Gly Leu
        260                 265                 270 aat tta att aaa acg acg cct gat agt aat ctt gat gga aat ata aac        864
Asn Leu Ile Lys Thr Thr Pro Asp Ser Asn Leu Asp Gly Asn Ile Asn
    275                 280                 285 tgg aac aca tac aat acg tat cga aca aaa atg act act gct gta tta        912
Trp Asn Thr Tyr Asn Thr Tyr Arg Thr Lys Met Thr Thr Ala Val Leu
290                 295                 300 gat ctt gtt gca ctc ttt cct aat tat gat gta ggt aaa tat cca ata        960
Asp Leu Val Ala Leu Phe Pro Asn Tyr Asp Val Gly Lys Tyr Pro Ile
305                 310                 315                 320 ggt gtc caa tct gaa ctt act cga gaa att tat cag gta ctt aac ttc       1008
Gly Val Gln Ser Glu Leu Thr Arg Glu Ile Tyr Gln Val Leu Asn Phe
            325                 330                 335 gaa gaa agc ccc tat aaa tat tat gac ttt caa tat caa gag gat tca       1056
Glu Glu Ser Pro Tyr Lys Tyr Tyr Asp Phe Gln Tyr Gln Glu Asp Ser
        340                 345                 350 ctt aca cgt aga ccg cat tta ttt act tgg ctt gat tct ttg aat ttt       1104
Leu Thr Arg Arg Pro His Leu Phe Thr Trp Leu Asp Ser Leu Asn Phe
    355                 360                 365 tat gaa aaa gcg caa act act cct aat aat ttt ttc acc agc cat tat       1152
Tyr Glu Lys Ala Gln Thr Thr Pro Asn Asn Phe Phe Thr Ser His Tyr
370                 375                 380 aat atg ttt cat tac aca ctt gat aat ata tcc caa aaa tct agt gtt       1200
Asn Met Phe His Tyr Thr Leu Asp Asn Ile Ser Gln Lys Ser Ser Val
385                 390                 395                 400 ttt gga aat cac aat gta act gat aaa tta aaa tct ctt ggt ttg gca       1248
Phe Gly Asn His Asn Val Thr Asp Lys Leu Lys Ser Leu Gly Leu Ala
            405                 410                 415 aca aat att tat att ttt tta tta aat gtc ata agc tta gat aat aaa       1296
Thr Asn Ile Tyr Ile Phe Leu Leu Asn Val Ile Ser Leu Asp Asn Lys
        420                 425                 430 tat cta aat gat tat aat aat att agt aaa atg gat ttt ttt ata act       1344
Tyr Leu Asn Asp Tyr Asn Asn Ile Ser Lys Met Asp Phe Phe Ile Thr
    435                 440                 445 aat ggt act aga ctt ttg gag aaa gaa ctt aca gca gga tct ggg caa       1392
Asn Gly Thr Arg Leu Leu Glu Lys Glu Leu Thr Ala Gly Ser Gly Gln
450                 455                 460 ata act tat gat gta aat aaa aat att ttc ggg tta cca att ctt aaa       1440
Ile Thr Tyr Asp Val Asn Lys Asn Ile Phe Gly Leu Pro Ile Leu Lys
465                 470                 475                 480 cga aga gag aat caa gga aac cct acc ctt ttt cca aca tat gat aac       1488
Arg Arg Glu Asn Gln Gly Asn Pro Thr Leu Phe Pro Thr Tyr Asp Asn
            485                 490                 495 tat agt cat att tta tca ttt att aaa agt ctt agt atc cct gca aca       1536
Tyr Ser His Ile Leu Ser Phe Ile Lys Ser Leu Ser Ile Pro Ala Thr
```

-continued

```
                500                  505                  510
tat aaa act caa gtg tat acg ttt gct tgg aca cac tct agt gtt gat      1584
Tyr Lys Thr Gln Val Tyr Thr Phe Ala Trp Thr His Ser Ser Val Asp
        515                  520                  525 cct aaa aat aca att tat aca cat tta act acc caa att cca gct gta      1632
Pro Lys Asn Thr Ile Tyr Thr His Leu Thr Thr Gln Ile Pro Ala Val
530                 535                  540 aaa gcg aat tca ctt ggg act gct tct aag gtt gtt caa gga cct ggt      1680
Lys Ala Asn Ser Leu Gly Thr Ala Ser Lys Val Val Gln Gly Pro Gly
545                 550                  555                  560 cat aca gga ggg gat tta att gat ttc aaa gat cat ttc aaa att aca      1728
His Thr Gly Gly Asp Leu Ile Asp Phe Lys Asp His Phe Lys Ile Thr
                565                  570                  575 tgt caa cac tca aat ttt caa caa tcg tat ttt ata aga att cgt tat      1776
Cys Gln His Ser Asn Phe Gln Gln Ser Tyr Phe Ile Arg Ile Arg Tyr
                580                  585                  590 gct tca aat gga agc gca aat act cga gct gtt ata aat ctt agt atc      1824
Ala Ser Asn Gly Ser Ala Asn Thr Arg Ala Val Ile Asn Leu Ser Ile
        595                  600                  605 cca ggg gta gca gaa ctg ggt atg gca ctc aac ccc act ttt tct ggt      1872
Pro Gly Val Ala Glu Leu Gly Met Ala Leu Asn Pro Thr Phe Ser Gly
610                 615                  620 aca gat tat acg aat tta aaa tat aaa gat ttt cag tac tta gaa ttt      1920
Thr Asp Tyr Thr Asn Leu Lys Tyr Lys Asp Phe Gln Tyr Leu Glu Phe
625                 630                  635                  640 tct aac gag gtg aaa ttt gct cca aat caa aac ata tct ctt gtg ttt      1968
Ser Asn Glu Val Lys Phe Ala Pro Asn Gln Asn Ile Ser Leu Val Phe
                645                  650                  655 aat cgt tcg gat gta tat aca aac aca aca gta ctt att gat aaa att      2016
Asn Arg Ser Asp Val Tyr Thr Asn Thr Thr Val Leu Ile Asp Lys Ile
                660                  665                  670 gaa ttt ctg cca att act cgt tct ata aga gag gat aga gag aaa caa      2064
Glu Phe Leu Pro Ile Thr Arg Ser Ile Arg Glu Asp Arg Glu Lys Gln
        675                  680                  685 aaa tta gaa aca gta caa caa ata att aat aca ttt tat gca aat cct      2112
Lys Leu Glu Thr Val Gln Gln Ile Ile Asn Thr Phe Tyr Ala Asn Pro
690                 695                  700 ata aaa aac act tta caa tca gaa ctt aca gat tat gac ata gat caa      2160
Ile Lys Asn Thr Leu Gln Ser Glu Leu Thr Asp Tyr Asp Ile Asp Gln
705                 710                  715                  720 gcc gca aat ctt gtg gaa tgt att tct gaa gaa tta tat cca aaa gaa      2208
Ala Ala Asn Leu Val Glu Cys Ile Ser Glu Glu Leu Tyr Pro Lys Glu
                725                  730                  735 aaa atg ctg tta tta gat gaa gtt aaa aat gcg aaa caa ctt agt caa      2256
Lys Met Leu Leu Leu Asp Glu Val Lys Asn Ala Lys Gln Leu Ser Gln
                740                  745                  750 tct cga aat gta ctt caa aac ggg gat ttt gaa tcg gct acg ctt ggt      2304
Ser Arg Asn Val Leu Gln Asn Gly Asp Phe Glu Ser Ala Thr Leu Gly
        755                  760                  765 tgg aca aca agt gat aat atc aca att caa gaa gat gat cct att ttt      2352
Trp Thr Thr Ser Asp Asn Ile Thr Ile Gln Glu Asp Asp Pro Ile Phe
770                 775                  780 aaa ggg cat tac ctt cat atg tct ggg gcg aga gac att gat ggt acg      2400
Lys Gly His Tyr Leu His Met Ser Gly Ala Arg Asp Ile Asp Gly Thr
785                 790                  795                  800 ata ttt ccg acc tat ata ttc caa aaa att gat gaa tca aaa tta aaa      2448
Ile Phe Pro Thr Tyr Ile Phe Gln Lys Ile Asp Glu Ser Lys Leu Lys
                805                  810                  815 ccg tat aca cgt tac cta gta agg gga ttt gta gga agt agt aaa gat      2496
```

|  |  |  |  |  |  |  |  |  |  |  |  |  |  |
|---|---|---|---|---|---|---|---|---|---|---|---|---|---|
| Pro | Tyr | Thr | Arg | Tyr | Leu | Val | Arg | Gly | Phe | Val | Gly | Ser | Ser | Lys | Asp |
|  |  |  | 820 |  |  |  | 825 |  |  |  | 830 |  |  |

```
gta gaa cta gtg gtt tca cgc tat ggg gaa gaa att gat gcc atc atg      2544
Val Glu Leu Val Val Ser Arg Tyr Gly Glu Glu Ile Asp Ala Ile Met
            835                 840                 845 aat gtt cca gct gat tta aac tat ctg tat cct tct acc ttt gat tgt      2592
Asn Val Pro Ala Asp Leu Asn Tyr Leu Tyr Pro Ser Thr Phe Asp Cys
850                 855                 860 gaa ggg tct aat cgt tgt gag acg tcc gct gtg ccg gct aac att ggg      2640
Glu Gly Ser Asn Arg Cys Glu Thr Ser Ala Val Pro Ala Asn Ile Gly
865                 870                 875                 880 aac act tct gat atg ttg tat tca tgc caa tat gat aca ggg aaa aag      2688
Asn Thr Ser Asp Met Leu Tyr Ser Cys Gln Tyr Asp Thr Gly Lys Lys
                885                 890                 895 cat gtc gta tgt cag gat tcc cat caa ttt agt ttc act att gat aca      2736
His Val Val Cys Gln Asp Ser His Gln Phe Ser Phe Thr Ile Asp Thr
        900                 905                 910 ggg gca tta gat aca aat gaa aat ata ggg gtt tgg gtc atg ttt aaa      2784
Gly Ala Leu Asp Thr Asn Glu Asn Ile Gly Val Trp Val Met Phe Lys
            915                 920                 925 ata tct tct cca gat gga tac gca tca tta gat aat tta gaa gta att      2832
Ile Ser Ser Pro Asp Gly Tyr Ala Ser Leu Asp Asn Leu Glu Val Ile
930                 935                 940 gaa gaa ggg cca ata gat ggg gaa gca ctg tca cgc gtg aaa cac atg      2880
Glu Glu Gly Pro Ile Asp Gly Glu Ala Leu Ser Arg Val Lys His Met
945                 950                 955                 960 gag aag aaa tgg aac gat caa atg gaa gca aaa cgt tcg gaa aca caa      2928
Glu Lys Lys Trp Asn Asp Gln Met Glu Ala Lys Arg Ser Glu Thr Gln
                965                 970                 975 caa gca tat gat gta gcg aaa caa gcc att gat gct tta ttc aca aat      2976
Gln Ala Tyr Asp Val Ala Lys Gln Ala Ile Asp Ala Leu Phe Thr Asn
        980                 985                 990 gta caa gat gag gct tta cag ttt gat acg aca ctc gct caa att cag      3024
Val Gln Asp Glu Ala Leu Gln Phe Asp Thr Thr Leu Ala Gln Ile Gln
            995                 1000                1005 tac gct gag tat ttg gta caa tcg att cca tat gtg tac aat gat          3069
Tyr Ala Glu Tyr Leu Val Gln Ser Ile Pro Tyr Val Tyr Asn Asp
    1010                1015                1020 tgg ttg tca gat gtt cca ggt atg aat tat gat atc tat gta gag          3114
Trp Leu Ser Asp Val Pro Gly Met Asn Tyr Asp Ile Tyr Val Glu
1025                1030                1035 ttg gat gca cga gtg gca caa gcg cgt tat ttg tat gat aca aga          3159
Leu Asp Ala Arg Val Ala Gln Ala Arg Tyr Leu Tyr Asp Thr Arg
    1040                1045                1050 aat att att aaa aat ggt gat ttt aca caa ggg gta atg ggg tgg          3204
Asn Ile Ile Lys Asn Gly Asp Phe Thr Gln Gly Val Met Gly Trp
1055                1060                1065 cat gta act gga aat gca gac gta caa caa ata gat ggt gtt tct          3249
His Val Thr Gly Asn Ala Asp Val Gln Gln Ile Asp Gly Val Ser
    1070                1075                1080 gta ttg gtt cta tct aat tgg agt gct ggc gta tct caa aat gtc          3294
Val Leu Val Leu Ser Asn Trp Ser Ala Gly Val Ser Gln Asn Val
1085                1090                1095 cat ctc caa cat aat cat ggg tat gtc tta cgt gtt att gcc aaa          3339
His Leu Gln His Asn His Gly Tyr Val Leu Arg Val Ile Ala Lys
    1100                1105                1110 aaa gaa gga cct gga aat ggg tat gtc acg ctt atg gat tgt gag          3384
Lys Glu Gly Pro Gly Asn Gly Tyr Val Thr Leu Met Asp Cys Glu
1115                1120                1125
```

-continued

```
gag aat caa gaa aaa ttg acg ttt acg tct tgt gaa gaa gga tat    3429
Glu Asn Gln Glu Lys Leu Thr Phe Thr Ser Cys Glu Glu Gly Tyr
    1130            1135                1140 att acg aag aca gta gat gta ttc cca gat aca gat cgt gta cga    3474
Ile Thr Lys Thr Val Asp Val Phe Pro Asp Thr Asp Arg Val Arg
1145                1150                1155 att gag ata ggc gaa acc gaa ggt tcg ttt tat atc gaa agc att    3519
Ile Glu Ile Gly Glu Thr Glu Gly Ser Phe Tyr Ile Glu Ser Ile
    1160            1165                1170 gaa tta att tgc atg aac gag tga                                3543
Glu Leu Ile Cys Met Asn Glu
    1175            1180
```

<210> SEQ ID NO 4
<211> LENGTH: 1180
<212> TYPE: PRT
<213> ORGANISM: Bacillus thuringiensis

<400> SEQUENCE: 4

```
Met Asn Pro Tyr Gln Asn Lys Asn Glu Tyr Glu Thr Leu Asn Ala Ser
1               5                   10                  15

Gln Lys Lys Leu Asn Ile Ser Asn Asn Tyr Thr Arg Tyr Pro Ile Glu
            20                  25                  30

Asn Ser Pro Lys Gln Leu Leu Gln Ser Thr Asn Tyr Lys Asp Trp Leu
        35                  40                  45

Asn Met Cys Gln Gln Asn Gln Gln Tyr Gly Gly Asp Phe Glu Thr Phe
    50                  55                  60

Ile Asp Ser Gly Glu Leu Ser Ala Tyr Thr Ile Val Val Gly Thr Val
65                  70                  75                  80

Leu Thr Gly Phe Gly Phe Thr Thr Pro Leu Gly Leu Ala Leu Ile Gly
                85                  90                  95

Phe Gly Thr Leu Ile Pro Val Leu Phe Pro Ala Gln Asp Gln Ser Asn
            100                 105                 110

Thr Trp Ser Asp Phe Ile Thr Gln Thr Lys Asn Ile Ile Lys Lys Glu
        115                 120                 125

Ile Ala Ser Thr Tyr Ile Ser Asn Ala Asn Lys Ile Leu Asn Arg Ser
    130                 135                 140

Phe Asn Val Ile Ser Thr Tyr His Asn His Leu Lys Thr Trp Glu Asn
145                 150                 155                 160

Asn Pro Asn Pro Gln Asn Thr Gln Asp Val Arg Thr Gln Ile Gln Leu
                165                 170                 175

Val His Tyr His Phe Gln Asn Val Ile Pro Glu Leu Val Asn Ser Cys
            180                 185                 190

Pro Pro Asn Pro Ser Asp Cys Asp Tyr Tyr Asn Ile Leu Val Leu Ser
        195                 200                 205

Ser Tyr Ala Gln Ala Ala Asn Leu His Leu Thr Val Leu Asn Gln Ala
    210                 215                 220

Val Lys Phe Glu Ala Tyr Leu Lys Asn Asn Arg Gln Phe Asp Tyr Leu
225                 230                 235                 240

Glu Pro Leu Pro Thr Ala Ile Asp Tyr Tyr Pro Val Leu Thr Lys Ala
                245                 250                 255

Ile Glu Asp Tyr Thr Asn Tyr Cys Val Thr Thr Tyr Lys Lys Gly Leu
            260                 265                 270

Asn Leu Ile Lys Thr Thr Pro Asp Ser Asn Leu Asp Gly Asn Ile Asn
        275                 280                 285

Trp Asn Thr Tyr Asn Thr Tyr Arg Thr Lys Met Thr Thr Ala Val Leu
```

```
            290                 295                 300
Asp Leu Val Ala Leu Phe Pro Asn Tyr Asp Val Gly Lys Tyr Pro Ile
305                 310                 315                 320
Gly Val Gln Ser Glu Leu Thr Arg Glu Ile Tyr Gln Val Leu Asn Phe
                325                 330                 335
Glu Glu Ser Pro Tyr Lys Tyr Tyr Asp Phe Gln Tyr Gln Glu Asp Ser
                340                 345                 350
Leu Thr Arg Arg Pro His Leu Phe Thr Trp Leu Asp Ser Leu Asn Phe
                355                 360                 365
Tyr Glu Lys Ala Gln Thr Thr Pro Asn Asn Phe Phe Thr Ser His Tyr
                370                 375                 380
Asn Met Phe His Tyr Thr Leu Asp Asn Ile Ser Gln Lys Ser Ser Val
385                 390                 395                 400
Phe Gly Asn His Asn Val Thr Asp Lys Leu Lys Ser Leu Gly Leu Ala
                405                 410                 415
Thr Asn Ile Tyr Ile Phe Leu Leu Asn Val Ile Ser Leu Asp Asn Lys
                420                 425                 430
Tyr Leu Asn Asp Tyr Asn Asn Ile Ser Lys Met Asp Phe Phe Ile Thr
                435                 440                 445
Asn Gly Thr Arg Leu Leu Glu Lys Glu Leu Thr Ala Gly Ser Gly Gln
                450                 455                 460
Ile Thr Tyr Asp Val Asn Lys Asn Ile Phe Gly Leu Pro Ile Leu Lys
465                 470                 475                 480
Arg Arg Glu Asn Gln Gly Asn Pro Thr Leu Phe Pro Thr Tyr Asp Asn
                485                 490                 495
Tyr Ser His Ile Leu Ser Phe Ile Lys Ser Leu Ser Ile Pro Ala Thr
                500                 505                 510
Tyr Lys Thr Gln Val Tyr Thr Phe Ala Trp Thr His Ser Ser Val Asp
                515                 520                 525
Pro Lys Asn Thr Ile Tyr Thr His Leu Thr Thr Gln Ile Pro Ala Val
                530                 535                 540
Lys Ala Asn Ser Leu Gly Thr Ala Ser Lys Val Val Gln Gly Pro Gly
545                 550                 555                 560
His Thr Gly Gly Asp Leu Ile Asp Phe Lys Asp His Phe Lys Ile Thr
                565                 570                 575
Cys Gln His Ser Asn Phe Gln Gln Ser Tyr Phe Ile Arg Ile Arg Tyr
                580                 585                 590
Ala Ser Asn Gly Ser Ala Asn Thr Arg Ala Val Ile Asn Leu Ser Ile
                595                 600                 605
Pro Gly Val Ala Glu Leu Gly Met Ala Leu Asn Pro Thr Phe Ser Gly
                610                 615                 620
Thr Asp Tyr Thr Asn Leu Lys Tyr Lys Asp Phe Gln Tyr Leu Glu Phe
625                 630                 635                 640
Ser Asn Glu Val Lys Phe Ala Pro Asn Gln Asn Ile Ser Leu Val Phe
                645                 650                 655
Asn Arg Ser Asp Val Tyr Thr Asn Thr Thr Val Leu Ile Asp Lys Ile
                660                 665                 670
Glu Phe Leu Pro Ile Thr Arg Ser Ile Arg Glu Asp Arg Glu Lys Gln
                675                 680                 685
Lys Leu Glu Thr Val Gln Gln Ile Ile Asn Thr Phe Tyr Ala Asn Pro
                690                 695                 700
Ile Lys Asn Thr Leu Gln Ser Glu Leu Thr Asp Tyr Asp Ile Asp Gln
705                 710                 715                 720
```

```
Ala Ala Asn Leu Val Glu Cys Ile Ser Glu Glu Leu Tyr Pro Lys Glu
            725                 730                 735

Lys Met Leu Leu Leu Asp Glu Val Lys Asn Ala Lys Gln Leu Ser Gln
            740                 745                 750

Ser Arg Asn Val Leu Gln Asn Gly Asp Phe Glu Ser Ala Thr Leu Gly
            755                 760                 765

Trp Thr Thr Ser Asp Asn Ile Thr Ile Gln Glu Asp Asp Pro Ile Phe
            770                 775                 780

Lys Gly His Tyr Leu His Met Ser Gly Ala Arg Asp Ile Asp Gly Thr
785                 790                 795                 800

Ile Phe Pro Thr Tyr Ile Phe Gln Lys Ile Asp Glu Ser Lys Leu Lys
                    805                 810                 815

Pro Tyr Thr Arg Tyr Leu Val Arg Gly Phe Val Gly Ser Ser Lys Asp
            820                 825                 830

Val Glu Leu Val Val Ser Arg Tyr Gly Glu Glu Ile Asp Ala Ile Met
            835                 840                 845

Asn Val Pro Ala Asp Leu Asn Tyr Leu Tyr Pro Ser Thr Phe Asp Cys
850                 855                 860

Glu Gly Ser Asn Arg Cys Glu Thr Ser Ala Val Pro Ala Asn Ile Gly
865                 870                 875                 880

Asn Thr Ser Asp Met Leu Tyr Ser Cys Gln Tyr Asp Thr Gly Lys Lys
                    885                 890                 895

His Val Val Cys Gln Asp Ser His Gln Phe Ser Phe Thr Ile Asp Thr
                    900                 905                 910

Gly Ala Leu Asp Thr Asn Glu Asn Ile Gly Val Trp Val Met Phe Lys
            915                 920                 925

Ile Ser Ser Pro Asp Gly Tyr Ala Ser Leu Asp Asn Leu Glu Val Ile
            930                 935                 940

Glu Glu Gly Pro Ile Asp Gly Glu Ala Leu Ser Arg Val Lys His Met
945                 950                 955                 960

Glu Lys Lys Trp Asn Asp Gln Met Glu Ala Lys Arg Ser Glu Thr Gln
                965                 970                 975

Gln Ala Tyr Asp Val Ala Lys Gln Ala Ile Asp Ala Leu Phe Thr Asn
            980                 985                 990

Val Gln Asp Glu Ala Leu Gln Phe Asp Thr Thr Leu Ala Gln Ile Gln
            995                1000                1005

Tyr Ala Glu Tyr Leu Val Gln Ser Ile Pro Tyr Val Tyr Asn Asp
       1010                1015                1020

Trp Leu Ser Asp Val Pro Gly Met Asn Tyr Asp Ile Tyr Val Glu
       1025                1030                1035

Leu Asp Ala Arg Val Ala Gln Ala Arg Tyr Leu Tyr Asp Thr Arg
       1040                1045                1050

Asn Ile Ile Lys Asn Gly Asp Phe Thr Gln Gly Val Met Gly Trp
       1055                1060                1065

His Val Thr Gly Asn Ala Asp Val Gln Gln Ile Asp Gly Val Ser
       1070                1075                1080

Val Leu Val Leu Ser Asn Trp Ser Ala Gly Val Ser Gln Asn Val
       1085                1090                1095

His Leu Gln His Asn His Gly Tyr Val Leu Arg Val Ile Ala Lys
       1100                1105                1110

Lys Glu Gly Pro Gly Asn Gly Tyr Val Thr Leu Met Asp Cys Glu
       1115                1120                1125
```

-continued

```
Glu Asn  Gln Glu Lys Leu Thr  Phe Thr Ser Cys Glu  Glu Gly Tyr
    1130                 1135                 1140

Ile Thr  Lys Thr Val Asp Val  Phe Pro Asp Thr Asp  Arg Val Arg
    1145                 1150                 1155

Ile Glu  Ile Gly Glu Thr Glu  Gly Ser Phe Tyr Ile  Glu Ser Ile
    1160                 1165                 1170

Glu Leu  Ile Cys Met Asn Glu
    1175                 1180

<210> SEQ ID NO 5
<211> LENGTH: 3411
<212> TYPE: DNA
<213> ORGANISM: Bacillus thuringiensis
<220> FEATURE:
<221> NAME/KEY: CDS
<222> LOCATION: (1)..(3411)

<400> SEQUENCE: 5 atg aat tca ggc tat ccg tta gcg aat gac tta caa ggg tca atg aaa       48
Met Asn Ser Gly Tyr Pro Leu Ala Asn Asp Leu Gln Gly Ser Met Lys
1               5                   10                  15 aac acg aac tat aaa gat tgg cta gcc atg tgt gaa aat aac caa cag       96
Asn Thr Asn Tyr Lys Asp Trp Leu Ala Met Cys Glu Asn Asn Gln Gln
            20                  25                  30 tat ggc gtt aat cca gct gcg att aat tct tct tca gtt agt acc gct      144
Tyr Gly Val Asn Pro Ala Ala Ile Asn Ser Ser Ser Val Ser Thr Ala
        35                  40                  45 tta aaa gta gct gga gct atc ctt aaa ttt gta aac cca cct gca ggt      192
Leu Lys Val Ala Gly Ala Ile Leu Lys Phe Val Asn Pro Pro Ala Gly
    50                  55                  60 act gtc tta acc gta ctt agc gcg gtg ctt cct att ctt tgg ccg act      240
Thr Val Leu Thr Val Leu Ser Ala Val Leu Pro Ile Leu Trp Pro Thr
65                  70                  75                  80 aat act cca acg cct gaa aga gtt tgg aat gat ttc atg acc aat aca      288
Asn Thr Pro Thr Pro Glu Arg Val Trp Asn Asp Phe Met Thr Asn Thr
                85                  90                  95 ggg aat ctt att gat caa act gta aca gct tat gta cga aca gat gca      336
Gly Asn Leu Ile Asp Gln Thr Val Thr Ala Tyr Val Arg Thr Asp Ala
            100                 105                 110 aat gca aaa atg acg gtt gtg aaa gat tat tta gat caa tat aca act      384
Asn Ala Lys Met Thr Val Val Lys Asp Tyr Leu Asp Gln Tyr Thr Thr
        115                 120                 125 aaa ttt aac act tgg aaa aga gag cct aat aac cag tcc tat aga aca      432
Lys Phe Asn Thr Trp Lys Arg Glu Pro Asn Asn Gln Ser Tyr Arg Thr
    130                 135                 140 gca gta ata act caa ttt aac tta acc agt gcc aaa ctt cga gag acc      480
Ala Val Ile Thr Gln Phe Asn Leu Thr Ser Ala Lys Leu Arg Glu Thr
145                 150                 155                 160 gca gtt tat ttt agc aac tta gta ggt tat gaa tta ttg tta tta cca      528
Ala Val Tyr Phe Ser Asn Leu Val Gly Tyr Glu Leu Leu Leu Leu Pro
                165                 170                 175 ata tac gca caa gta gca aat ttc aat tta ctt tta ata aga gat ggc      576
Ile Tyr Ala Gln Val Ala Asn Phe Asn Leu Leu Leu Ile Arg Asp Gly
            180                 185                 190 ctc ata aat gca caa gaa tgg tct tta gca cgt agt gct ggt gac caa      624
Leu Ile Asn Ala Gln Glu Trp Ser Leu Ala Arg Ser Ala Gly Asp Gln
        195                 200                 205 cta tat aac act atg gtg cag tac act aaa gaa tat att gca cat agc      672
Leu Tyr Asn Thr Met Val Gln Tyr Thr Lys Glu Tyr Ile Ala His Ser
    210                 215                 220
```

```
att aca tgg tat aat aaa ggt tta gat gta ctt aga aat aaa tct aat         720
Ile Thr Trp Tyr Asn Lys Gly Leu Asp Val Leu Arg Asn Lys Ser Asn
225                 230                 235                 240 gga caa tgg att acg ttt aat gat tat aaa aga gag atg act att caa         768
Gly Gln Trp Ile Thr Phe Asn Asp Tyr Lys Arg Glu Met Thr Ile Gln
            245                 250                 255 gta tta gat ata ctc gct ctt ttt gcc agt tat gat cca cgt cga tac         816
Val Leu Asp Ile Leu Ala Leu Phe Ala Ser Tyr Asp Pro Arg Arg Tyr
                260                 265                 270 cct gcg gac aaa ata gat aat acg aaa cta tca aaa aca gaa ttt aca         864
Pro Ala Asp Lys Ile Asp Asn Thr Lys Leu Ser Lys Thr Glu Phe Thr
            275                 280                 285 aga gag att tat aca gct tta gta gaa tct cct tct agt aaa tct ata         912
Arg Glu Ile Tyr Thr Ala Leu Val Glu Ser Pro Ser Ser Lys Ser Ile
290                 295                 300 gca gca ctg gag gca gca ctt aca cga gat gtt cat tta ttc act tgg         960
Ala Ala Leu Glu Ala Ala Leu Thr Arg Asp Val His Leu Phe Thr Trp
305                 310                 315                 320 cta aag aga gta gat ttc tgg acc aat act ata tat caa gat tta aga        1008
Leu Lys Arg Val Asp Phe Trp Thr Asn Thr Ile Tyr Gln Asp Leu Arg
            325                 330                 335 ttt tta tct gcc aat aaa att ggg ttt tca tat aca aat tct tct gca        1056
Phe Leu Ser Ala Asn Lys Ile Gly Phe Ser Tyr Thr Asn Ser Ser Ala
                340                 345                 350 atg caa gaa agt gga att tat gga agt tct ggt ttt ggt tca aat ctt        1104
Met Gln Glu Ser Gly Ile Tyr Gly Ser Ser Gly Phe Gly Ser Asn Leu
            355                 360                 365 act cat caa att caa ctt aat tct aat gtt tat aaa act tct atc aca        1152
Thr His Gln Ile Gln Leu Asn Ser Asn Val Tyr Lys Thr Ser Ile Thr
370                 375                 380 gat act agc tcc ccc tct aat cga gtt aca aaa atg gat ttc tac aaa        1200
Asp Thr Ser Ser Pro Ser Asn Arg Val Thr Lys Met Asp Phe Tyr Lys
385                 390                 395                 400 att gat ggt act ctt gcc tct tat aat tca aat ata aca cca act cct        1248
Ile Asp Gly Thr Leu Ala Ser Tyr Asn Ser Asn Ile Thr Pro Thr Pro
            405                 410                 415 gaa ggt tta agg acc aca ttt ttt gga ttt tca aca aat gag aac aca        1296
Glu Gly Leu Arg Thr Thr Phe Phe Gly Phe Ser Thr Asn Glu Asn Thr
                420                 425                 430 cct aat caa cca act gta aat gat tat acg cat att tta agc tat ata        1344
Pro Asn Gln Pro Thr Val Asn Asp Tyr Thr His Ile Leu Ser Tyr Ile
            435                 440                 445 aaa act gat gtt ata gat tat aac agt aac agg gtt tca ttt gct tgg        1392
Lys Thr Asp Val Ile Asp Tyr Asn Ser Asn Arg Val Ser Phe Ala Trp
450                 455                 460 aca cat aag att gtt gac cct aat aat caa ata tac aca gat gct atc        1440
Thr His Lys Ile Val Asp Pro Asn Asn Gln Ile Tyr Thr Asp Ala Ile
465                 470                 475                 480 aca caa gtt ccg gcc gta aaa tct aac ttc ttg aat gca aca gct aaa        1488
Thr Gln Val Pro Ala Val Lys Ser Asn Phe Leu Asn Ala Thr Ala Lys
            485                 490                 495 gta atc aag gga cct ggt cat aca ggg ggg gat cta gtt gct ctt aca        1536
Val Ile Lys Gly Pro Gly His Thr Gly Gly Asp Leu Val Ala Leu Thr
                500                 505                 510 agc aat ggt act cta tca ggc aga atg gag att caa tgt aaa aca agt        1584
Ser Asn Gly Thr Leu Ser Gly Arg Met Glu Ile Gln Cys Lys Thr Ser
            515                 520                 525 att ttt aat gat cct aca aga agt tac gga tta cgc ata cgt tat gct        1632
Ile Phe Asn Asp Pro Thr Arg Ser Tyr Gly Leu Arg Ile Arg Tyr Ala
530                 535                 540
```

-continued

| | | |
|---|---|---|
| gca aat agt cca att gta ttg aat gta tca tat gta tta caa gga gtt<br>Ala Asn Ser Pro Ile Val Leu Asn Val Ser Tyr Val Leu Gln Gly Val<br>545                      550                    555                  560 | 1680 |
| tct aga gga aca acg att agt aca gaa tct acg ttt tca aga cct aat<br>Ser Arg Gly Thr Thr Ile Ser Thr Glu Ser Thr Phe Ser Arg Pro Asn<br>                    565                    570                    575 | 1728 |
| aat ata ata cct aca gat tta aaa tat gaa gag ttt aga tac aaa gat<br>Asn Ile Ile Pro Thr Asp Leu Lys Tyr Glu Glu Phe Arg Tyr Lys Asp<br>                  580                    585                    590 | 1776 |
| cct ttt gat gca att gta ccg atg aga tta tct tct aat caa ctg ata<br>Pro Phe Asp Ala Ile Val Pro Met Arg Leu Ser Ser Asn Gln Leu Ile<br>              595                    600                    605 | 1824 |
| act ata gct att caa cca tta aac atg act tca aat aat caa gtg att<br>Thr Ile Ala Ile Gln Pro Leu Asn Met Thr Ser Asn Asn Gln Val Ile<br>610                        615                    620 | 1872 |
| att gac aga atc gaa att att cca atc act caa tct gta tta gat gag<br>Ile Asp Arg Ile Glu Ile Ile Pro Ile Thr Gln Ser Val Leu Asp Glu<br>625                      630                    635                  640 | 1920 |
| aca gag aac caa aat tta gaa tca gaa cga gaa gtt gtg aat gca ctg<br>Thr Glu Asn Gln Asn Leu Glu Ser Glu Arg Glu Val Val Asn Ala Leu<br>                    645                    650                    655 | 1968 |
| ttt aca aat gac gcg aaa gat gca tta aac att gga acg aca gat tat<br>Phe Thr Asn Asp Ala Lys Asp Ala Leu Asn Ile Gly Thr Thr Asp Tyr<br>                  660                    665                    670 | 2016 |
| gac ata gat caa gcc gca aat ctt gtg gaa tgt att tct gaa gaa tta<br>Asp Ile Asp Gln Ala Ala Asn Leu Val Glu Cys Ile Ser Glu Glu Leu<br>675                        680                    685 | 2064 |
| tat cca aaa gaa aaa atg ctg tta tta gat gaa gtt aaa aat gcg aaa<br>Tyr Pro Lys Glu Lys Met Leu Leu Leu Asp Glu Val Lys Asn Ala Lys<br>              690                    695                    700 | 2112 |
| caa ctt agt caa tct cga aat gta ctt caa aac ggg gat ttt gaa tcg<br>Gln Leu Ser Gln Ser Arg Asn Val Leu Gln Asn Gly Asp Phe Glu Ser<br>705                      710                    715                  720 | 2160 |
| gct acg ctt ggt tgg aca aca agt gat aat atc aca att caa gaa gat<br>Ala Thr Leu Gly Trp Thr Thr Ser Asp Asn Ile Thr Ile Gln Glu Asp<br>                    725                    730                    735 | 2208 |
| gat cct att ttt aaa ggg cat tac ctt cat atg tct ggg gcg aga gac<br>Asp Pro Ile Phe Lys Gly His Tyr Leu His Met Ser Gly Ala Arg Asp<br>              740                    745                    750 | 2256 |
| att gat ggt acg ata ttt ccg acc tat ata ttc caa aaa att gat gaa<br>Ile Asp Gly Thr Ile Phe Pro Thr Tyr Ile Phe Gln Lys Ile Asp Glu<br>                  755                    760                    765 | 2304 |
| tca aaa tta aaa ccg tat aca cgt tac cta gta agg gga ttt gta gga<br>Ser Lys Leu Lys Pro Tyr Thr Arg Tyr Leu Val Arg Gly Phe Val Gly<br>770                        775                    780 | 2352 |
| agt agt aaa gat gta gaa cta gtg gtt tca cgc tat ggg gaa gaa att<br>Ser Ser Lys Asp Val Glu Leu Val Val Ser Arg Tyr Gly Glu Glu Ile<br>785                      790                    795                  800 | 2400 |
| gat gcc atc atg aat gtt cca gct gat tta aac tat ctg tat cct tct<br>Asp Ala Ile Met Asn Val Pro Ala Asp Leu Asn Tyr Leu Tyr Pro Ser<br>                  805                    810                    815 | 2448 |
| acc ttt gat tgt gaa ggg tct aat cgt tgt gag acg tcc gct gtg ccg<br>Thr Phe Asp Cys Glu Gly Ser Asn Arg Cys Glu Thr Ser Ala Val Pro<br>              820                    825                    830 | 2496 |
| gct aac att ggg aac act tct gat atg ttg tat tca tgc caa tat gat<br>Ala Asn Ile Gly Asn Thr Ser Asp Met Leu Tyr Ser Cys Gln Tyr Asp<br>835                        840                    845 | 2544 |
| aca ggg aaa aag cat gtc gta tgt cag gat tcc cat caa ttt agt ttc<br>Thr Gly Lys Lys His Val Val Cys Gln Asp Ser His Gln Phe Ser Phe | 2592 |

```
                850                 855                 860
act att gat aca ggg gca tta gat aca aat gaa aat ata ggg gtt tgg       2640
Thr Ile Asp Thr Gly Ala Leu Asp Thr Asn Glu Asn Ile Gly Val Trp
865                 870                 875                 880 gtc atg ttt aaa ata tct tct cca gat gga tac gca tca tta gat aat       2688
Val Met Phe Lys Ile Ser Ser Pro Asp Gly Tyr Ala Ser Leu Asp Asn
                885                 890                 895 tta gaa gta att gaa gaa ggg cca ata gat ggg gaa gca ctg tca cgc       2736
Leu Glu Val Ile Glu Glu Gly Pro Ile Asp Gly Glu Ala Leu Ser Arg
    900                 905                 910 gtg aaa cac atg gag aag aaa tgg aac gat caa atg gaa gca aaa cgt       2784
Val Lys His Met Glu Lys Lys Trp Asn Asp Gln Met Glu Ala Lys Arg
915                 920                 925 tcg gaa aca caa caa gca tat gat gta gcg aaa caa gcc att gat gct       2832
Ser Glu Thr Gln Gln Ala Tyr Asp Val Ala Lys Gln Ala Ile Asp Ala
    930                 935                 940 tta ttc aca aat gta caa gat gag gct tta cag ttt gat acg aca ctc       2880
Leu Phe Thr Asn Val Gln Asp Glu Ala Leu Gln Phe Asp Thr Thr Leu
945                 950                 955                 960 gct caa att cag tac gct gag tat ttg gta caa tcg att cca tat gtg       2928
Ala Gln Ile Gln Tyr Ala Glu Tyr Leu Val Gln Ser Ile Pro Tyr Val
                965                 970                 975 tac aat gat tgg ttg tca gat gtt cca ggt atg aat tat gat atc tat       2976
Tyr Asn Asp Trp Leu Ser Asp Val Pro Gly Met Asn Tyr Asp Ile Tyr
        980                 985                 990 gta gag ttg gat gca cga gtg gca caa gcg cgt tat ttg tat gat aca       3024
Val Glu Leu Asp Ala Arg Val Ala Gln Ala Arg Tyr Leu Tyr Asp Thr
    995                 1000                1005 aga aat att att aaa aat ggt gat ttt aca caa ggg gta atg ggg           3069
Arg Asn Ile Ile Lys Asn Gly Asp Phe Thr Gln Gly Val Met Gly
1010                1015                1020 tgg cat gta act gga aat gca gac gta caa caa ata gat ggt gtt           3114
Trp His Val Thr Gly Asn Ala Asp Val Gln Gln Ile Asp Gly Val
1025                1030                1035 tct gta ttg gtt cta tct aat tgg agt gct ggc gta tct caa aat           3159
Ser Val Leu Val Leu Ser Asn Trp Ser Ala Gly Val Ser Gln Asn
1040                1045                1050 gtc cat ctc caa cat aat cat ggg tat gtc tta cgt gtt att gcc           3204
Val His Leu Gln His Asn His Gly Tyr Val Leu Arg Val Ile Ala
1055                1060                1065 aaa aaa gaa gga cct gga aat ggg tat gtc acg ctt atg gat tgt           3249
Lys Lys Glu Gly Pro Gly Asn Gly Tyr Val Thr Leu Met Asp Cys
1070                1075                1080 gag gag aat caa gaa aaa ttg acg ttt acg tct tgt gaa gaa gga           3294
Glu Glu Asn Gln Glu Lys Leu Thr Phe Thr Ser Cys Glu Glu Gly
1085                1090                1095 tat att acg aag aca gta gat gta ttc cca gat aca gat cgt gta           3339
Tyr Ile Thr Lys Thr Val Asp Val Phe Pro Asp Thr Asp Arg Val
1100                1105                1110 cga att gag ata ggc gaa acc gaa ggt tcg ttt tat atc gaa agc           3384
Arg Ile Glu Ile Gly Glu Thr Glu Gly Ser Phe Tyr Ile Glu Ser
1115                1120                1125 att gaa tta att tgc atg aac gag tga                                   3411
Ile Glu Leu Ile Cys Met Asn Glu
                1130                1135

<210> SEQ ID NO 6
<211> LENGTH: 1136
<212> TYPE: PRT
<213> ORGANISM: Bacillus thuringiensis
```

```
<400> SEQUENCE: 6

Met Asn Ser Gly Tyr Pro Leu Ala Asn Asp Leu Gln Gly Ser Met Lys
1               5                   10                  15

Asn Thr Asn Tyr Lys Asp Trp Leu Ala Met Cys Glu Asn Asn Gln Gln
            20                  25                  30

Tyr Gly Val Asn Pro Ala Ala Ile Asn Ser Ser Val Ser Thr Ala
        35                  40                  45

Leu Lys Val Ala Gly Ala Ile Leu Lys Phe Val Asn Pro Pro Ala Gly
    50                  55                  60

Thr Val Leu Thr Val Leu Ser Ala Val Leu Pro Ile Leu Trp Pro Thr
65                  70                  75                  80

Asn Thr Pro Thr Pro Glu Arg Val Trp Asn Asp Phe Met Thr Asn Thr
                85                  90                  95

Gly Asn Leu Ile Asp Gln Thr Val Thr Ala Tyr Val Arg Thr Asp Ala
            100                 105                 110

Asn Ala Lys Met Thr Val Val Lys Asp Tyr Leu Asp Gln Tyr Thr Thr
            115                 120                 125

Lys Phe Asn Thr Trp Lys Arg Glu Pro Asn Asn Gln Ser Tyr Arg Thr
    130                 135                 140

Ala Val Ile Thr Gln Phe Asn Leu Thr Ser Ala Lys Leu Arg Glu Thr
145                 150                 155                 160

Ala Val Tyr Phe Ser Asn Leu Val Gly Tyr Glu Leu Leu Leu Leu Pro
                165                 170                 175

Ile Tyr Ala Gln Val Ala Asn Phe Asn Leu Leu Leu Ile Arg Asp Gly
            180                 185                 190

Leu Ile Asn Ala Gln Glu Trp Ser Leu Ala Arg Ser Ala Gly Asp Gln
    195                 200                 205

Leu Tyr Asn Thr Met Val Gln Tyr Thr Lys Glu Tyr Ile Ala His Ser
    210                 215                 220

Ile Thr Trp Tyr Asn Lys Gly Leu Asp Val Leu Arg Asn Lys Ser Asn
225                 230                 235                 240

Gly Gln Trp Ile Thr Phe Asn Asp Tyr Lys Arg Glu Met Thr Ile Gln
                245                 250                 255

Val Leu Asp Ile Leu Ala Leu Phe Ala Ser Tyr Asp Pro Arg Arg Tyr
            260                 265                 270

Pro Ala Asp Lys Ile Asp Asn Thr Lys Leu Ser Lys Thr Glu Phe Thr
            275                 280                 285

Arg Glu Ile Tyr Thr Ala Leu Val Glu Ser Pro Ser Ser Lys Ser Ile
    290                 295                 300

Ala Ala Leu Glu Ala Ala Leu Thr Arg Asp Val His Leu Phe Thr Trp
305                 310                 315                 320

Leu Lys Arg Val Asp Phe Trp Thr Asn Thr Ile Tyr Gln Asp Leu Arg
                325                 330                 335

Phe Leu Ser Ala Asn Lys Ile Gly Phe Ser Tyr Thr Asn Ser Ser Ala
            340                 345                 350

Met Gln Glu Ser Gly Ile Tyr Gly Ser Ser Gly Phe Gly Ser Asn Leu
    355                 360                 365

Thr His Gln Ile Gln Leu Asn Ser Asn Val Tyr Lys Thr Ser Ile Thr
    370                 375                 380

Asp Thr Ser Ser Pro Ser Asn Arg Val Thr Lys Met Asp Phe Tyr Lys
385                 390                 395                 400

Ile Asp Gly Thr Leu Ala Ser Tyr Asn Ser Asn Ile Thr Pro Thr Pro
```

-continued

```
            405                 410                 415
Glu Gly Leu Arg Thr Thr Phe Phe Gly Phe Ser Thr Asn Glu Asn Thr
                420                 425                 430
Pro Asn Gln Pro Thr Val Asn Asp Tyr Thr His Ile Leu Ser Tyr Ile
            435                 440                 445
Lys Thr Asp Val Ile Asp Tyr Asn Ser Asn Arg Val Ser Phe Ala Trp
        450                 455                 460
Thr His Lys Ile Val Asp Pro Asn Asn Gln Ile Tyr Thr Asp Ala Ile
465                 470                 475                 480
Thr Gln Val Pro Ala Val Lys Ser Asn Phe Leu Asn Ala Thr Ala Lys
                485                 490                 495
Val Ile Lys Gly Pro His Thr Gly Gly Asp Leu Val Ala Leu Thr
                500                 505                 510
Ser Asn Gly Thr Leu Ser Gly Arg Met Glu Ile Gln Cys Lys Thr Ser
            515                 520                 525
Ile Phe Asn Asp Pro Thr Arg Ser Tyr Gly Leu Arg Ile Arg Tyr Ala
        530                 535                 540
Ala Asn Ser Pro Ile Val Leu Asn Val Ser Tyr Val Leu Gln Gly Val
545                 550                 555                 560
Ser Arg Gly Thr Thr Ile Ser Thr Glu Ser Thr Phe Ser Arg Pro Asn
                565                 570                 575
Asn Ile Ile Pro Thr Asp Leu Lys Tyr Glu Glu Phe Arg Tyr Lys Asp
            580                 585                 590
Pro Phe Asp Ala Ile Val Pro Met Arg Leu Ser Ser Asn Gln Leu Ile
        595                 600                 605
Thr Ile Ala Ile Gln Pro Leu Asn Met Thr Ser Asn Asn Gln Val Ile
610                 615                 620
Ile Asp Arg Ile Glu Ile Ile Pro Ile Thr Gln Ser Val Leu Asp Glu
625                 630                 635                 640
Thr Glu Asn Gln Asn Leu Glu Ser Glu Arg Glu Val Val Asn Ala Leu
                645                 650                 655
Phe Thr Asn Asp Ala Lys Asp Ala Leu Asn Ile Gly Thr Thr Asp Tyr
            660                 665                 670
Asp Ile Asp Gln Ala Ala Asn Leu Val Glu Cys Ile Ser Glu Glu Leu
        675                 680                 685
Tyr Pro Lys Glu Lys Met Leu Leu Leu Asp Glu Val Lys Asn Ala Lys
        690                 695                 700
Gln Leu Ser Gln Ser Arg Asn Val Leu Gln Asn Gly Asp Phe Glu Ser
705                 710                 715                 720
Ala Thr Leu Gly Trp Thr Thr Ser Asp Asn Ile Thr Ile Gln Glu Asp
                725                 730                 735
Asp Pro Ile Phe Lys Gly His Tyr Leu His Met Ser Gly Ala Arg Asp
            740                 745                 750
Ile Asp Gly Thr Ile Phe Pro Thr Tyr Ile Phe Gln Lys Ile Asp Glu
        755                 760                 765
Ser Lys Leu Lys Pro Tyr Thr Arg Tyr Leu Val Arg Gly Phe Val Gly
        770                 775                 780
Ser Ser Lys Asp Val Glu Leu Val Val Ser Arg Tyr Gly Glu Glu Ile
785                 790                 795                 800
Asp Ala Ile Met Asn Val Pro Ala Asp Leu Asn Tyr Leu Tyr Pro Ser
                805                 810                 815
Thr Phe Asp Cys Glu Gly Ser Asn Arg Cys Glu Thr Ser Ala Val Pro
                820                 825                 830
```

-continued

```
Ala Asn Ile Gly Asn Thr Ser Asp Met Leu Tyr Ser Cys Gln Tyr Asp
        835                 840                 845

Thr Gly Lys Lys His Val Val Cys Gln Asp Ser His Gln Phe Ser Phe
    850                 855                 860

Thr Ile Asp Thr Gly Ala Leu Asp Thr Asn Glu Asn Ile Gly Val Trp
865                 870                 875                 880

Val Met Phe Lys Ile Ser Ser Pro Asp Gly Tyr Ala Ser Leu Asp Asn
                885                 890                 895

Leu Glu Val Ile Glu Glu Gly Pro Ile Asp Gly Ala Leu Ser Arg
            900                 905                 910

Val Lys His Met Glu Lys Lys Trp Asn Asp Gln Met Glu Ala Lys Arg
        915                 920                 925

Ser Glu Thr Gln Gln Ala Tyr Asp Val Ala Lys Gln Ala Ile Asp Ala
    930                 935                 940

Leu Phe Thr Asn Val Gln Asp Glu Ala Leu Gln Phe Asp Thr Thr Leu
945                 950                 955                 960

Ala Gln Ile Gln Tyr Ala Glu Tyr Leu Val Gln Ser Ile Pro Tyr Val
                965                 970                 975

Tyr Asn Asp Trp Leu Ser Asp Val Pro Gly Met Asn Tyr Asp Ile Tyr
            980                 985                 990

Val Glu Leu Asp Ala Arg Val Ala Gln Ala Arg Tyr Leu Tyr Asp Thr
        995                 1000                1005

Arg Asn Ile Ile Lys Asn Gly Asp Phe Thr Gln Gly Val Met Gly
    1010                1015                1020

Trp His Val Thr Gly Asn Ala Asp Val Gln Gln Ile Asp Gly Val
    1025                1030                1035

Ser Val Leu Val Leu Ser Asn Trp Ser Ala Gly Val Ser Gln Asn
    1040                1045                1050

Val His Leu Gln His Asn His Gly Tyr Val Leu Arg Val Ile Ala
    1055                1060                1065

Lys Lys Glu Gly Pro Gly Asn Gly Tyr Val Thr Leu Met Asp Cys
    1070                1075                1080

Glu Glu Asn Gln Glu Lys Leu Thr Phe Thr Ser Cys Glu Glu Gly
    1085                1090                1095

Tyr Ile Thr Lys Thr Val Asp Val Phe Pro Asp Thr Asp Arg Val
    1100                1105                1110

Arg Ile Glu Ile Gly Glu Thr Glu Gly Ser Phe Tyr Ile Glu Ser
    1115                1120                1125

Ile Glu Leu Ile Cys Met Asn Glu
    1130                1135

<210> SEQ ID NO 7
<211> LENGTH: 1932
<212> TYPE: DNA
<213> ORGANISM: Bacillus thuringiensis
<220> FEATURE:
<221> NAME/KEY: CDS
<222> LOCATION: (1)..(1932)

<400> SEQUENCE: 7 atg gaa gat agt tct tta gat act tta agt ata gtt aat gaa aca gac     48
Met Glu Asp Ser Ser Leu Asp Thr Leu Ser Ile Val Asn Glu Thr Asp
1               5                   10                  15 ttt cca tta tat aat aat tat acc gaa cct act att gcg cca gca tta     96
Phe Pro Leu Tyr Asn Asn Tyr Thr Glu Pro Thr Ile Ala Pro Ala Leu
            20                  25                  30
```

-continued

| | |
|---|---|
| ata gca gta gct ccc atc gca caa tat ctt gca aca gct ata ggg aaa<br>Ile Ala Val Ala Pro Ile Ala Gln Tyr Leu Ala Thr Ala Ile Gly Lys<br>     35                    40                   45 | 144 |
| tgg gcg gca aag gca gca ttt tca aaa gta cta tca ctt ata ttc cca<br>Trp Ala Ala Lys Ala Ala Phe Ser Lys Val Leu Ser Leu Ile Phe Pro<br>50                    55                    60 | 192 |
| ggt tct caa cct gct act atg gaa aaa gtt cgt aca gaa gtg gaa aca<br>Gly Ser Gln Pro Ala Thr Met Glu Lys Val Arg Thr Glu Val Glu Thr<br>65                    70                    75                  80 | 240 |
| ctt ata aat caa aaa tta agc caa gat cga gtc aat ata tta aac gca<br>Leu Ile Asn Gln Lys Leu Ser Gln Asp Arg Val Asn Ile Leu Asn Ala<br>                  85                    90                    95 | 288 |
| gaa tat agg ggg att att gag gtt agt gat gta ttt gat gcg tat att<br>Glu Tyr Arg Gly Ile Ile Glu Val Ser Asp Val Phe Asp Ala Tyr Ile<br>                100                 105                110 | 336 |
| aaa caa cca ggt ttt acc cct gca aca gcc aag ggt tat ttt cta aat<br>Lys Gln Pro Gly Phe Thr Pro Ala Thr Ala Lys Gly Tyr Phe Leu Asn<br>                115                 120                125 | 384 |
| cta agt ggt gct ata ata caa cga tta cct caa ttt gag gtt caa aca<br>Leu Ser Gly Ala Ile Ile Gln Arg Leu Pro Gln Phe Glu Val Gln Thr<br>         130                 135                 140 | 432 |
| tat gaa gga gta tct ata gca ctt ttt act caa atg tgt aca ctt cat<br>Tyr Glu Gly Val Ser Ile Ala Leu Phe Thr Gln Met Cys Thr Leu His<br>145                 150                 155                 160 | 480 |
| tta act tta tta aaa gac gga atc cta gca ggg agt gca tgg gga ttt<br>Leu Thr Leu Leu Lys Asp Gly Ile Leu Ala Gly Ser Ala Trp Gly Phe<br>                165                 170                175 | 528 |
| act caa gct gat gta gat tca ttt ata aaa tta ttt aat caa aaa gta<br>Thr Gln Ala Asp Val Asp Ser Phe Ile Lys Leu Phe Asn Gln Lys Val<br>         180                 185                 190 | 576 |
| tta gat tac agg acc aga tta atg aga atg tac aca gaa gag ttc gga<br>Leu Asp Tyr Arg Thr Arg Leu Met Arg Met Tyr Thr Glu Glu Phe Gly<br>                195                 200                205 | 624 |
| aga ttg tgt aaa gtc agt ctt aaa gat gga ttg acg ttc cgg aat atg<br>Arg Leu Cys Lys Val Ser Leu Lys Asp Gly Leu Thr Phe Arg Asn Met<br>210                 215                 220 | 672 |
| tgt aat tta tat gtg ttt cca ttt gct gaa gcc tgg tct tta atg aga<br>Cys Asn Leu Tyr Val Phe Pro Phe Ala Glu Ala Trp Ser Leu Met Arg<br>225                 230                 235                 240 | 720 |
| tat gaa gga tta aaa tta caa agc tct cta tca tta tgg gat tat gtt<br>Tyr Glu Gly Leu Lys Leu Gln Ser Ser Leu Ser Leu Trp Asp Tyr Val<br>                245                 250                255 | 768 |
| ggt gtc tca att cct gta aat tat aat gaa tgg gga gga cta gtt tat<br>Gly Val Ser Ile Pro Val Asn Tyr Asn Glu Trp Gly Gly Leu Val Tyr<br>         260                 265                 270 | 816 |
| aag tta tta atg ggg gaa gtt aat caa aga tta aca act gtt aaa ttt<br>Lys Leu Leu Met Gly Glu Val Asn Gln Arg Leu Thr Thr Val Lys Phe<br>                275                 280                285 | 864 |
| aat tat tct ttc act aat gaa cca gct gat ata cca gca aga gaa aat<br>Asn Tyr Ser Phe Thr Asn Glu Pro Ala Asp Ile Pro Ala Arg Glu Asn<br>         290                 295                 300 | 912 |
| att cgt ggc gtc cat cct ata tac gat cct agt tct ggg ctt aca gga<br>Ile Arg Gly Val His Pro Ile Tyr Asp Pro Ser Ser Gly Leu Thr Gly<br>305                 310                 315                 320 | 960 |
| tgg ata gga aac gga aga aca aac aat ttt aat ttt gct gat aac aat<br>Trp Ile Gly Asn Gly Arg Thr Asn Asn Phe Asn Phe Ala Asp Asn Asn<br>                325                 330                335 | 1008 |
| ggc aat gaa att atg gaa gtt aga aca caa act ttt tat caa aat cca<br>Gly Asn Glu Ile Met Glu Val Arg Thr Gln Thr Phe Tyr Gln Asn Pro | 1056 |

```
                340             345             350
aat aat gag cct ata gcg cct aga gat att ata aat caa att tta act    1104
Asn Asn Glu Pro Ile Ala Pro Arg Asp Ile Ile Asn Gln Ile Leu Thr
        355                 360                 365 gcg cca gca cca gca gac cta ttt ttt aaa aat gca gat ata aat gta    1152
Ala Pro Ala Pro Ala Asp Leu Phe Phe Lys Asn Ala Asp Ile Asn Val
370                 375                 380 aag ttc aca cag tgg ttt cag tct act cta tat ggg tgg aac att aaa    1200
Lys Phe Thr Gln Trp Phe Gln Ser Thr Leu Tyr Gly Trp Asn Ile Lys
385                 390                 395                 400 ctc ggt aca caa acg gtt tta agt agt aga acc gga aca ata cca cca    1248
Leu Gly Thr Gln Thr Val Leu Ser Ser Arg Thr Gly Thr Ile Pro Pro
            405                 410                 415 aat tat tta gca tat gat gga tat tat att cgt gct att tca gct tgc    1296
Asn Tyr Leu Ala Tyr Asp Gly Tyr Tyr Ile Arg Ala Ile Ser Ala Cys
        420                 425                 430 cca aga gga gtc tca ctt gca tat aat cac gat ctt aca aca cta aca    1344
Pro Arg Gly Val Ser Leu Ala Tyr Asn His Asp Leu Thr Thr Leu Thr
            435                 440                 445 tat aat aga ata gag tat gat tca cct act aca gaa aat att att gta    1392
Tyr Asn Arg Ile Glu Tyr Asp Ser Pro Thr Thr Glu Asn Ile Ile Val
450                 455                 460 ggg ttt gca cca gat aat act aag gac ttt tat tct aaa aaa tct cac    1440
Gly Phe Ala Pro Asp Asn Thr Lys Asp Phe Tyr Ser Lys Lys Ser His
465                 470                 475                 480 tat tta agt gaa acg aat gat agt tat gta att cct gct ctg caa ttt    1488
Tyr Leu Ser Glu Thr Asn Asp Ser Tyr Val Ile Pro Ala Leu Gln Phe
            485                 490                 495 gct gaa gtt tca gat aga tca ttt tta gaa gat acg cca gat caa gca    1536
Ala Glu Val Ser Asp Arg Ser Phe Leu Glu Asp Thr Pro Asp Gln Ala
            500                 505                 510 aca gac ggc agt att aaa ttt gca cgt act ttc att agt aat gaa gct    1584
Thr Asp Gly Ser Ile Lys Phe Ala Arg Thr Phe Ile Ser Asn Glu Ala
        515                 520                 525 aag tac tct att aga cta aac acc ggg ttt aat acg gca act aga tat    1632
Lys Tyr Ser Ile Arg Leu Asn Thr Gly Phe Asn Thr Ala Thr Arg Tyr
        530                 535                 540 aaa tta att atc agg gta aga gta cct tat cgc tta cct gct gga ata    1680
Lys Leu Ile Ile Arg Val Arg Val Pro Tyr Arg Leu Pro Ala Gly Ile
545                 550                 555                 560 cgg gta caa tct cag aat tcg gga aat aat aga atg cta ggc agt ttt    1728
Arg Val Gln Ser Gln Asn Ser Gly Asn Asn Arg Met Leu Gly Ser Phe
            565                 570                 575 act gca aat gct aat cca gaa tgg gtg gat ttt gtc aca gat gca ttt    1776
Thr Ala Asn Ala Asn Pro Glu Trp Val Asp Phe Val Thr Asp Ala Phe
            580                 585                 590 aca ttt aac gat tta ggg att aca act tca agt aca aat gct tta ttt    1824
Thr Phe Asn Asp Leu Gly Ile Thr Thr Ser Ser Thr Asn Ala Leu Phe
        595                 600                 605 agt att tct tca gat agt tta aat tct gga gaa gag tgg tat tta tcg    1872
Ser Ile Ser Ser Asp Ser Leu Asn Ser Gly Glu Glu Trp Tyr Leu Ser
        610                 615                 620 cag ttg ttt tta gta aaa gaa tcg gcc ttt acg acg caa att aat ccg    1920
Gln Leu Phe Leu Val Lys Glu Ser Ala Phe Thr Thr Gln Ile Asn Pro
625                 630                 635                 640 tta cta aag tag                                                    1932
Leu Leu Lys
```

<210> SEQ ID NO 8

-continued

```
<211> LENGTH: 643
<212> TYPE: PRT
<213> ORGANISM: Bacillus thuringiensis

<400> SEQUENCE: 8

Met Glu Asp Ser Ser Leu Asp Thr Leu Ser Ile Val Asn Glu Thr Asp
1               5                   10                  15

Phe Pro Leu Tyr Asn Asn Tyr Thr Glu Pro Thr Ile Ala Pro Ala Leu
            20                  25                  30

Ile Ala Val Ala Pro Ile Ala Gln Tyr Leu Ala Thr Ala Ile Gly Lys
        35                  40                  45

Trp Ala Lys Ala Ala Phe Ser Lys Val Leu Ser Leu Ile Phe Pro
50                  55                  60

Gly Ser Gln Pro Ala Thr Met Glu Lys Val Arg Thr Glu Val Glu Thr
65                  70                  75                  80

Leu Ile Asn Gln Lys Leu Ser Gln Asp Arg Val Asn Ile Leu Asn Ala
                85                  90                  95

Glu Tyr Arg Gly Ile Ile Glu Val Ser Asp Val Phe Asp Ala Tyr Ile
            100                 105                 110

Lys Gln Pro Gly Phe Thr Pro Ala Thr Ala Lys Gly Tyr Phe Leu Asn
        115                 120                 125

Leu Ser Gly Ala Ile Ile Gln Arg Leu Pro Gln Phe Glu Val Gln Thr
130                 135                 140

Tyr Glu Gly Val Ser Ile Ala Leu Phe Thr Gln Met Cys Thr Leu His
145                 150                 155                 160

Leu Thr Leu Leu Lys Asp Gly Ile Leu Ala Gly Ser Ala Trp Gly Phe
                165                 170                 175

Thr Gln Ala Asp Val Asp Ser Phe Ile Lys Leu Phe Asn Gln Lys Val
            180                 185                 190

Leu Asp Tyr Arg Thr Arg Leu Met Arg Met Tyr Thr Glu Glu Phe Gly
        195                 200                 205

Arg Leu Cys Lys Val Ser Leu Lys Asp Gly Leu Thr Phe Arg Asn Met
210                 215                 220

Cys Asn Leu Tyr Val Phe Pro Phe Ala Glu Ala Trp Ser Leu Met Arg
225                 230                 235                 240

Tyr Glu Gly Leu Lys Leu Gln Ser Ser Leu Ser Leu Trp Asp Tyr Val
                245                 250                 255

Gly Val Ser Ile Pro Val Asn Tyr Asn Glu Trp Gly Gly Leu Val Tyr
            260                 265                 270

Lys Leu Leu Met Gly Glu Val Asn Gln Arg Leu Thr Thr Val Lys Phe
        275                 280                 285

Asn Tyr Ser Phe Thr Asn Glu Pro Ala Asp Ile Pro Ala Arg Glu Asn
290                 295                 300

Ile Arg Gly Val His Pro Ile Tyr Asp Pro Ser Ser Gly Leu Thr Gly
305                 310                 315                 320

Trp Ile Gly Asn Gly Arg Thr Asn Asn Phe Asn Phe Ala Asp Asn Asn
                325                 330                 335

Gly Asn Glu Ile Met Glu Val Arg Thr Gln Thr Phe Tyr Gln Asn Pro
            340                 345                 350

Asn Asn Glu Pro Ile Ala Pro Arg Asp Ile Ile Asn Gln Ile Leu Thr
        355                 360                 365

Ala Pro Ala Pro Ala Asp Leu Phe Phe Lys Asn Ala Asp Ile Asn Val
370                 375                 380

Lys Phe Thr Gln Trp Phe Gln Ser Thr Leu Tyr Gly Trp Asn Ile Lys
```

-continued

```
            385                 390                 395                 400
Leu Gly Thr Gln Thr Val Leu Ser Ser Arg Thr Gly Thr Ile Pro Pro
                    405                 410                 415

Asn Tyr Leu Ala Tyr Asp Gly Tyr Tyr Ile Arg Ala Ile Ser Ala Cys
                420                 425                 430

Pro Arg Gly Val Ser Leu Ala Tyr Asn His Asp Leu Thr Thr Leu Thr
            435                 440                 445

Tyr Asn Arg Ile Glu Tyr Asp Ser Pro Thr Thr Glu Asn Ile Ile Val
        450                 455                 460

Gly Phe Ala Pro Asp Asn Thr Lys Asp Phe Tyr Ser Lys Lys Ser His
465                 470                 475                 480

Tyr Leu Ser Glu Thr Asn Asp Ser Tyr Val Ile Pro Ala Leu Gln Phe
                485                 490                 495

Ala Glu Val Ser Asp Arg Ser Phe Leu Glu Asp Thr Pro Asp Gln Ala
                500                 505                 510

Thr Asp Gly Ser Ile Lys Phe Ala Arg Thr Phe Ile Ser Asn Glu Ala
            515                 520                 525

Lys Tyr Ser Ile Arg Leu Asn Thr Gly Phe Asn Thr Ala Thr Arg Tyr
        530                 535                 540

Lys Leu Ile Ile Arg Val Arg Val Pro Tyr Arg Leu Pro Ala Gly Ile
545                 550                 555                 560

Arg Val Gln Ser Gln Asn Ser Gly Asn Asn Arg Met Leu Gly Ser Phe
                565                 570                 575

Thr Ala Asn Ala Asn Pro Glu Trp Val Asp Phe Val Thr Asp Ala Phe
                580                 585                 590

Thr Phe Asn Asp Leu Gly Ile Thr Thr Ser Thr Asn Ala Leu Phe
            595                 600                 605

Ser Ile Ser Ser Asp Ser Leu Asn Ser Gly Glu Glu Trp Tyr Leu Ser
        610                 615                 620

Gln Leu Phe Leu Val Lys Glu Ser Ala Phe Thr Thr Gln Ile Asn Pro
625                 630                 635                 640

Leu Leu Lys

<210> SEQ ID NO 9
<211> LENGTH: 334
<212> TYPE: PRT
<213> ORGANISM: Bacillus subtilis

<400> SEQUENCE: 9

Met Gly Val Ser Phe Asn Ile Met Cys Pro Asn Ser Ser Ile Tyr Ser
1               5                   10                  15

Asp Glu Lys Ser Arg Val Leu Val Asp Lys Thr Lys Ser Gly Lys Val
                20                  25                  30

Arg Pro Trp Arg Glu Lys Lys Ile Ala Asn Val Asp Tyr Phe Glu Leu
            35                  40                  45

Leu His Ile Leu Glu Phe Lys Lys Ala Glu Arg Val Lys Asp Cys Ala
        50                  55                  60

Glu Ile Leu Glu Tyr Lys Gln Asn Arg Glu Thr Gly Glu Arg Lys Leu
65                  70                  75                  80

Tyr Arg Val Trp Phe Cys Lys Ser Arg Leu Cys Pro Met Cys Asn Trp
                85                  90                  95

Arg Arg Ala Met Lys His Gly Ile Gln Ser Gln Lys Val Val Ala Glu
                100                 105                 110

Val Ile Lys Gln Lys Pro Thr Val Arg Trp Leu Phe Leu Thr Leu Thr
```

```
                115                 120                 125
Val Lys Asn Val Tyr Asp Gly Glu Glu Leu Asn Lys Ser Leu Ser Asp
            130                 135                 140

Met Ala Gln Gly Phe Arg Arg Met Met Gln Tyr Lys Lys Ile Asn Lys
145                 150                 155                 160

Asn Leu Val Gly Phe Met Arg Ala Thr Glu Val Thr Ile Asn Asn Lys
                165                 170                 175

Asp Asn Ser Tyr Asn Gln His Met His Val Leu Val Cys Val Glu Pro
            180                 185                 190

Thr Tyr Phe Lys Asn Thr Glu Asn Tyr Val Asn Gln Lys Gln Trp Ile
                195                 200                 205

Gln Phe Trp Lys Lys Ala Met Lys Leu Asp Tyr Asp Pro Asn Val Lys
210                 215                 220

Val Gln Met Ile Arg Pro Lys Asn Lys Tyr Lys Ser Asp Ile Gln Ser
225                 230                 235                 240

Ala Ile Asp Glu Thr Ala Lys Tyr Pro Val Lys Asp Thr Asp Phe Met
                245                 250                 255

Thr Asp Asp Glu Glu Lys Asn Leu Lys Arg Leu Ser Asp Leu Glu Glu
            260                 265                 270

Gly Leu His Arg Lys Arg Leu Ile Ser Tyr Gly Gly Leu Leu Lys Glu
                275                 280                 285

Ile His Lys Lys Leu Asn Leu Asp Asp Thr Glu Gly Asp Leu Ile
290                 295                 300

His Thr Asp Asp Asp Glu Lys Ala Asp Glu Asp Gly Phe Ser Ile Ile
305                 310                 315                 320

Ala Met Trp Asn Trp Glu Arg Lys Asn Tyr Phe Ile Lys Glu
                325                 330

<210> SEQ ID NO 10
<211> LENGTH: 572
<212> TYPE: DNA
<213> ORGANISM: Bacillus sp.KSM-S237

<400> SEQUENCE: 10
gatttgccga tgcaacaggc ttatatttag aggaaatttc ttttaaatt gaatacggaa      60 taaaatcagg taaacaggtc ctgattttat tttttgagt ttttagaga actgaagatt     120 gaaataaaag tagaagacaa aggacataag aaaattgcat tagttttaat tatagaaaac     180 gccttttat aattattat acctagaacg aaaatactgt ttcgaaagcg gtttactata      240
aaaccttata ttccggctct tttttaaaac aggggggtaaa aattcactct agtattctaa    300
tttcaacatg ctataataaa tttgtaagac gcaatatgca tctcttttt tacgatatat     360 gtaagcggtt aaccttgtgc tatatgccga tttaggaagg ggggtagatt gagtcaagta    420
gtaataatat agataactta aagttgttg agaagcagga gagcatctgg ttactcaca     480 agtttttta aaactttaac gaaagcactt tcggtaatgc ttatgaattt agctatttga    540
ttcaattact ttaaaaatat ttaggaggta at                                  572

<210> SEQ ID NO 11
<211> LENGTH: 545
<212> TYPE: DNA
<213> ORGANISM: Bacillus sp.KSM-S237

<400> SEQUENCE: 11
gatttgccga tgcaacaggc ttatatttag aggaaatttc ttttaaatt gaatacggaa      60
```

-continued

```
taaaatcagg taaacaggtc ctgatttat tttttttgagt ttttttagaga actgaagatt    120 gaaataaaag tagaagacaa aggacataag aaaattgcat tagttttaat tatagaaaac    180 gccttttat aattatttat acctagaacg aaaatactgt ttctataaaa ccttatattc     240
cggctctttt ttaaaacagg gggtaaaaat tcactctagt attctaattt caacatgcta    300
taataaattt gtaagacgca atatgcatct cttttttac gatatacttg tgctatatgc     360
cgatttagga aggggggtag attgagtcaa gtagtaataa tatagataac ttataagttg    420
ttgagaagca ggagagcatc tgggttactc acaagttttt ttaaaacttt aacgaaagca    480
ctttcggtaa tgcttatgaa tttagctatt tgattcaatt acttttaaaaa tatttaggag  540 gtaat                                                                545
```

<210> SEQ ID NO 12
<211> LENGTH: 193
<212> TYPE: DNA
<213> ORGANISM: Bacillus subtilis

<400> SEQUENCE: 12

```
taagaaaagt gattctggga gagccgggat cactttttta tttaccttat gcccgaaatg     60
aaagctttat gacctaattg tgtaactata tcctattttt tcaaaaaata ttttaaaaac    120
gagcaggatt tcagaaaaaa tcgtggaatt gatacactaa tgcttttata tagggaaaag   180
gtggtgaact act                                                       193
```

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
gggaattcct gttataaaaa                                                 20

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
atgatgttaa gaaagaaaac a                                               21

<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 15
ataacaggaa ttccctaaga aaagtgattc tggga                                35

<210> SEQ ID NO 16
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 16
tctttcttaa catcatagta gttcaccacc ttttcc                                   36

<210> SEQ ID NO 17
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 17
aactagttta atagattatt ggattttgg aacaaactc                                 39

<210> SEQ ID NO 18
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 18
tatttaggag gtaatatgat ggcaacaatt aatgagtt                                 38

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 19
ccggcagctc ttgcaatggc aacaattaat gagtt                                    35

<210> SEQ ID NO 20
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 20
aactagttta atagattatt gattattatt catac                                    35

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
tgcaagagct gccggaaata                                                     20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
tctattaaac tagttatagg                                                     20

<210> SEQ ID NO 23
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 23
attacctcct aaatattttt                                                   20

<210> SEQ ID NO 24
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 24
gcaacaatta atgagttgta tcc                                               23

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
cgttcaaaat catccgtaaa tg                                                22

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
aaatgcatga accacttcca c                                                 21

<210> SEQ ID NO 27
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 27
attggatttt tggaacaaac tc                                                22

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
taaaagtaga agacaaagga                                                   20

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29
cgatatatgt aagcggttaa c                                                 21
```

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
caatttaaaa tcgctaccct                                          20

<210> SEQ ID NO 31
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 31
aactcattaa ttgttgccat agtagttcac caccttttcc                    40

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tttttataac aggaattccc                                          20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ggatcaactt tgggagagag                                          20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
caagtagtaa taatatagat                                          20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
gcaacaatta atgagttgta                                          20

<210> SEQ ID NO 36
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 36
agtacaccag aaagagtaat                                                  20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
tcaaggtggt aaattagatt                                                  20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
tcacgtcctg atcaaaaaat                                                  20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
tacctgctgg aagtttctat                                                  20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
acagaggccg aaatgtagta                                                  20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
acagcatatg accaagaacg                                                  20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
gagaatatgt ggaaacacac                                                  20

```
<210> SEQ ID NO 43
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 43 catacccgtta cttgatcaaa ggttg                              25

<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 44
aacagggtta ttacaatcac agtga                               25

<210> SEQ ID NO 45
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 45
aatggtaaca atgcagttaa acttt                               25

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 46
aagcttctag agatctgcag gtcga                               25

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
attacctcct aaatattttt                                     20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
agtagttcac cacctttttcc                                    20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 49
tctattaaac tagttatagg                                               20

<210> SEQ ID NO 50
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 50
tatttaggag gtaatatgat gaatccttat caaaataa                           38

<210> SEQ ID NO 51
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 51
ggaaaaggtg gtgaactact atgaatcctt atcaaaataa                         40

<210> SEQ ID NO 52
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 52
cctataacta gtttaataga tcactcgttc atgcaaatta                         40

<210> SEQ ID NO 53
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 53
tatttaggag gtaatatgat gaattcaggc tatccgtt                           38

<210> SEQ ID NO 54
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 54
ggaaaaggtg gtgaactact atgaattcag gctatccgtt                         40

<210> SEQ ID NO 55
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 55
cctataacta gtttaataga tcactcgttc atgcaaatta                         40

<210> SEQ ID NO 56
<211> LENGTH: 38
```

```
<212> TYPE: DNA
<213> ORGANISM: Artificial Sequence
<220> FEATURE:
<223> OTHER INFORMATION: Synthetic oligonucleotide

<400> SEQUENCE: 56
tatttaggag gtaatatgat ggaagatagt tctttaga                                    38

<210> SEQ ID NO 57
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 57
ggaaaaggtg gtgaactact atggaagata gttctttaga                                  40

<210> SEQ ID NO 58
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 58
cctataacta gtttaataga ctactttagt aacggattaa                                  40
```

What is claimed is:

1. A method for producing a Cry protein or a culture product comprising the Cry protein, comprising transforming a *Bacillus* bacterium with an expression plasmid incorporating a gene encoding the Cry protein operably linked to a regulatory region comprising a σA-dependent promoter or a σH-dependent promoter, and culturing the transformed cell, wherein the expression plasmid comprises a polynucleotide encoding a replication protein consisting of the amino acid sequence set forth in SEQ ID NO: 9 or a protein having an identity of 80% or more with the amino acid sequence of the replication protein and that is involved in replication initiation,
wherein the *Bacillus* bacterium is *Bacillus subtilis*, *Bacillus megaterium* or *Bacillus brevis*, and
wherein productivity of the Cry protein is at least 1.1 g/L.

2. The method according to claim 1, wherein the regulatory region comprising the σA-dependent promoter or the σH-dependent promoter differs from the regulatory region of the gene encoding the Cry protein in the microorganism from which the gene is derived.

3. The method according to claim 1, wherein the regulatory region comprising the σA-dependent promoter is a regulatory region of a cellulase gene of *Bacillus* sp. KSM-S237 strain.

4. The method according to claim 1, wherein the regulatory region comprising the σH-dependent promoter is a regulatory region of a spoVG gene.

5. The method according to claim 1, wherein the *Bacillus* bacterium is *Bacillus subtilis*.

6. The method according to claim 5, wherein the *Bacillus subtilis* is a *Bacillus subtilis* strain having a genome in which at least one region selected from the group consisting of prophage 6 region, prophage 1 region, prophage 4 region, PBSX region, prophage 5 region, prophage 3 region, spb region, pks region, skin region, pps region, prophage 2 region, ydcL-ydeK-ydhU region, yisB-yitD region, yunA-yurT region, cgeE-ypmQ region, yeeK-yesX region, pdp-rocR region, ycxB-sipU region, SKIN-Pro7 region, sbo-ywhH region, yybP-yyaJ region, and yncM-fosB region is deleted.

7. The method according to claim 5, wherein the *Bacillus subtilis* is a *Bacillus subtilis* strain in which a gene selected from the group consisting of aprX, aprE, nprB, nprE, bpr, vpr, mpr, epr, and wprA is deleted or inactivated.

8. The method according to claim 5, wherein the *Bacillus subtilis* is a *Bacillus subtilis* strain in which a gene selected from the group consisting of sigE, sigF, and sigG is deleted or inactivated.

9. The method according to claim 5, wherein the *Bacillus subtilis* is a *Bacillus subtilis* mutant strain which is obtained by genetic modification of *Bacillus subtilis* MGB874 strain to constitutively express an abrB gene or an equivalent gene thereto and in which a kinA gene is deleted or inactivated.

10. The method according to claim 1, wherein the Cry protein is Cry5B or truncated Cry5B (Cry5Bt).

11. The method according to claim 1, wherein productivity of the Cry protein is 1.1-2.5 g/L.

12. A method for producing a Cry protein or a culture product comprising the Cry protein, comprising transforming a *Bacillus* bacterium with an expression plasmid incorporating a gene encoding the Cry protein operably linked to a regulatory region comprising a σA-dependent promoter or a σH-dependent promoter, and culturing the transformed cell, wherein the expression plasmid comprises a polynucleotide encoding a replication protein consisting of the amino acid sequence set forth in SEQ ID NO: 9 or a protein having an identity of 80% or more with the amino acid sequence of the replication protein and that is involved in replication initiation, wherein the *Bacillus* bacterium is *Bacillus subtilis*, *Bacillus megaterium* or *Bacillus brevis* and wherein the Cry protein is a mosquitocidal protein selected from the group consisting of Cry4Aa, Cry4Ba, and Cry11Aa.

* * * * *

UNITED STATES PATENT AND TRADEMARK OFFICE
CERTIFICATE OF CORRECTION

| | |
|---|---|
| PATENT NO. | : 11,661,605 B2 |
| APPLICATION NO. | : 16/961331 |
| DATED | : May 30, 2023 |
| INVENTOR(S) | : Liu et al. |

It is certified that error appears in the above-identified patent and that said Letters Patent is hereby corrected as shown below:

Delete Patent No. 11661605 in its entirety and replace with the attached Patent No. 11661605.

Signed and Sealed this
Nineteenth Day of December, 2023

Katherine Kelly Vidal
*Director of the United States Patent and Trademark Office*

CERTIFICATE OF CORRECTION (continued)

(12) United States Patent
Liu et al.

(10) Patent No.: US 11,661,605 B2
(45) Date of Patent: May 30, 2023

(54) PRODUCTION METHOD FOR PROTEIN

(71) Applicant: Kao Corporation, Tokyo (JP)

(72) Inventors: Shenghao Liu, Wakayama (JP); Yasushi Kageyama, Wakayama (JP); Mika Terai, Sakai (JP)

(73) Assignee: Kao Corporation, Tokyo (JP)

(*) Notice: Subject to any disclaimer, the term of this patent is extended or adjusted under 35 U.S.C. 154(b) by 83 days.

(21) Appl. No.: 16/961,331

(22) PCT Filed: Jan. 11, 2019

(86) PCT No.: PCT/JP2019/000618
§ 371 (c)(1),
(2) Date: Jul. 10, 2020

(87) PCT Pub. No.: WO2019/139108
PCT Pub. Date: Jul. 18, 2019

(65) Prior Publication Data
US 2020/0370059 A1    Nov. 26, 2020

(30) Foreign Application Priority Data
Jan. 12, 2018    (JP) .............................. JP2018-003491

(51) Int. Cl.
*C12N 15/75* (2006.01)
*C07K 14/32* (2006.01)

(52) U.S. Cl.
CPC .............. *C12N 15/75* (2013.01); *C07K 14/32* (2013.01)

(58) Field of Classification Search
CPC ....... C12N 15/75; C07K 14/32; C07K 14/325
See application file for complete search history.

(56) References Cited

U.S. PATENT DOCUMENTS

| | | |
|---|---|---|
| 6,270,760 B1 | 8/2001 | Adams et al. |
| 8,389,685 B2 * | 3/2013 | Takimura ............... C07K 14/32 435/243 |
| 2004/0248279 A1 | 12/2004 | Sawada et al. |
| 2005/0271642 A1 | 12/2005 | Asano et al. |
| 2009/0081726 A1 | 3/2009 | Kodama et al. |
| 2012/0183998 A1 | 7/2012 | Kawahara et al. |

FOREIGN PATENT DOCUMENTS

| | | | |
|---|---|---|---|
| JP | S62-294080 A | | 12/1987 |
| JP | S63-17687 A | | 1/1988 |
| JP | S63-133999 A | | 6/1988 |
| JP | H04278092 | * | 10/1992 |
| JP | 2007-130013 A | | 5/2007 |
| JP | 4336082 B2 | | 9/2009 |
| JP | 4485341 B2 | | 6/2010 |
| JP | 2011-160686 | * | 8/2011 |
| JP | 4955358 B2 | | 3/2012 |
| JP | 2017-79639 A | | 5/2017 |
| JP | 2018-070565 A | | 5/2018 |
| JP | 2018-177656 A | | 11/2018 |
| WO | WO 95/02695 A1 | | 1/1995 |
| WO | WO 2011/049227 A1 | | 4/2011 |
| WO | WO 2016/007355 A1 | | 1/2016 |
| WO | WO 2017/123946 A1 | | 7/2017 |
| WO | WO 2018/136459 | * | 7/2018 |

OTHER PUBLICATIONS

AddGene Plasmid: pHY300PLK Plasmid map and Description—Retrived from < https://www.addgene.org/vector-database/3107/ > on Apr. 28, 2022.*

Kodama et al., 2012. "Approaches for Improving Protein Production in Multiple Protease-Deficient Bacillus subtilis Host Strains", in Advances in Applied Biotechnology, Prof. Marian Petre (Ed.), ISBN: 978-953-307-820-5, InTech.*

NCBI B. subtilis sigA gene information. Retrieved from < www.ncbi.nlm.nih.gov/gene/937897 > Retrieved on Oct. 25, 2022.*

The extended European search report including the supplementary European search report and the European search opinion, for EP application No. 19738051.2, dated Dec. 13, 2021, from the European Patent Office, Munich, Germany.

Yoshisue H, et al., "Identification of a promoter for the crystal protein-encoding gene cryIVB from *Bacillus thuringiensis* subsp. *israelensis*," Gene. Dec. 31, 1993;137(2):247-51. doi: 10.1016/0378-1119(93)90015-u. PMID: 8299955.

Hakamada Y, et al., "Deduced amino acid sequence and possible catalytic residues of a thermostable, alkaline cellulase from an alkaliphilic *Bacillus* strain," Biosci Biotechnol Biochem. Nov. 2000;6 4(11):2281-9. doi: 10.1271/bbb.64.2281. PMID: 11193393.

Carter HL 3rd, et al., "New RNA polymerase sigma factor under *spo0* control in *Bacillus subtilis*," Proc Natl Acad Sci U S A. Dec. 1986;83(24):9438-42. doi: 10.1073/pnas.83.24.9438. PMID: 3099284; PMCID: PMC387153.

International Search Report for PCT/JP2019/000618; I.A. fd Jan. 11, 2019, dated Apr. 9, 2019, from the Japan Patent Office, Tokyo, Japan.

(Continued)

*Primary Examiner* — Suzanne M Noakes
(74) *Attorney, Agent, or Firm* — Sterne, Kessler, Goldstein & Fox P.L.L.C.

(57) ABSTRACT

Provided is a method for intracellularly producing a large amount of a Cry protein in a *Bacillus* bacterium. A method for producing a Cry protein or a culture product comprising the Cry protein, comprising transforming a *Bacillus* bacterium with an expression plasmid incorporating a gene encoding the Cry protein operably linked to a regulatory region comprising a σA-dependent promoter or a σH-dependent promoter, and culturing the transformed cell, wherein the expression plasmid comprises a polynucleotide encoding a replication protein consisting of the amino acid sequence set forth in SEQ ID NO: 9 or a protein having an identity of 80% or more or more with the amino acid sequence of the replication protein and involved in replication initiation.

12 Claims, 13 Drawing Sheets
Specification includes a Sequence Listing.

(56) References Cited

OTHER PUBLICATIONS

International Preliminary Report on Patentability (IPRP), Chapter I of the Patent Cooperation Treaty, including the Written Opinion, for PCT/JP2019/000618; I.A. fd Jan. 11, 2019, dated Jul. 14, 2020, by the International Bureau of WIPO, Geneva, Switzerland.

Singh, A. et al., "Protein recovery from inclusion bodies of *Escherichia coli* using mild solubilization process." Microb Cell Fact. 2015; 14:41. Published Mar. 25, 2015. doi:10.1186/s12934-015-0222-8.

Higashibata, H, "The elements of obtaining a high expression of heterologous protein in *E. coli*." Biotechnology, vol. 91, pp. 96-100 (2013).

Schumann, W. et al., "Production of recombinant proteins in *Escherichia coli*," Genetics and Molecular Biology (Brazil), 27, 3, 442-453 (2004).

Gomes, AR et al., "An Overview of Heterologous Expression Host Systems for the Production of Recombinant Proteins," Adv. Anim. Vet. Sci. 4(7):346-356 (2016).

Ferrer-Miralles, N. et al., "Bacterial cell factories for recombinant protein production; expanding the catalogue." Microbial Cell Factories 2013 12:113.

Agaisse, H et al., "How does *Bacillus thuringiensis* produce so much insecticidal crystal protein?" J Bacteriol. 1995;177(21):6027-6032. doi:10.1128/jb.177.21.6027-6032.1995.

Deng, C et al., "Regulation of *cry* gene expression in *Bacillus thuringiensis*." Toxins (Basel). 2014;6(7):2194-2209. Published Jul. 23, 2014. doi:10.3390/toxins6072194.

Hu, Y et al., "*Bacillus subtilis* strain engineered for treatment of soil-transmitted helminth diseases." Appl Environ Microbiol. 2013;79(18):5527-5532. doi: 10.1128/AEM.01854-13.

Durmaz, E et al., "Intracellular and Extracellular Expression of *Bacillus thuringiensis* Crystal Protein Cry5B in *Lactococcus lactis* for Use as an Anthelminthic." Appl Environ Microbiol. 2015;82(4):1286-1294. Published Dec. 18, 2015. doi:10.1128/AEM.02365-15.

Yang, CY et al., . Enterotoxigenicity and cytotoxicity of *Bacillus thuringiensis* strains and development of a process for Cry1Ac production. J Agric Food Chem. 2003;51(1):100-105. doi:10.1021/j10258631.

Shivakumar AG, et al., "Gene dosage effect on the expression of the delta-endotoxin genes of *Bacillus thuringiensis* subsp. *kurstaki* in *Bacillus subtilis* and *Bacillus megaterium*," Gene. Jun. 30, 1989; 79(1):21-31. doi: 10.1016/0378-1119(89)90089-9. PMID: 2550328.

Ochoa-Zarzosa, A. et al. Chapter 9: "Shuttle vectors of *Bacillus thuringiensis*, " in E. Sansinemea (ed.), *Bacillus thuringiensis Biotechnology*, Springer Science+Business Media B.V., 2012, pp. 175-184.

Chen, Hong, "Principles and Applications of Genetic Engineering," Beijing: China Agriculture Press, pp. 223-226, Jan. 31, 2004.

\* cited by examiner

[Figure 1-A]
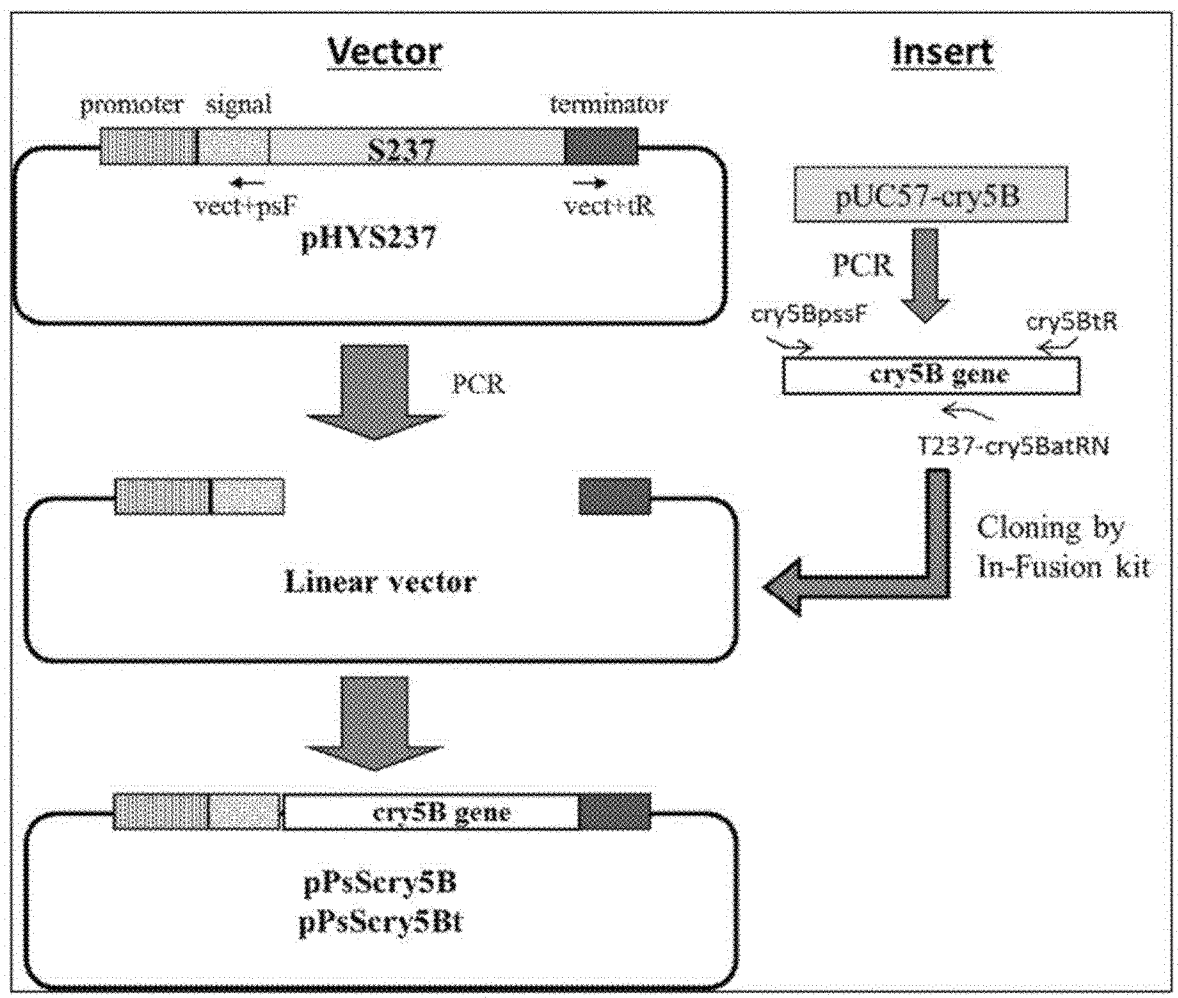

[Figure 1-B]
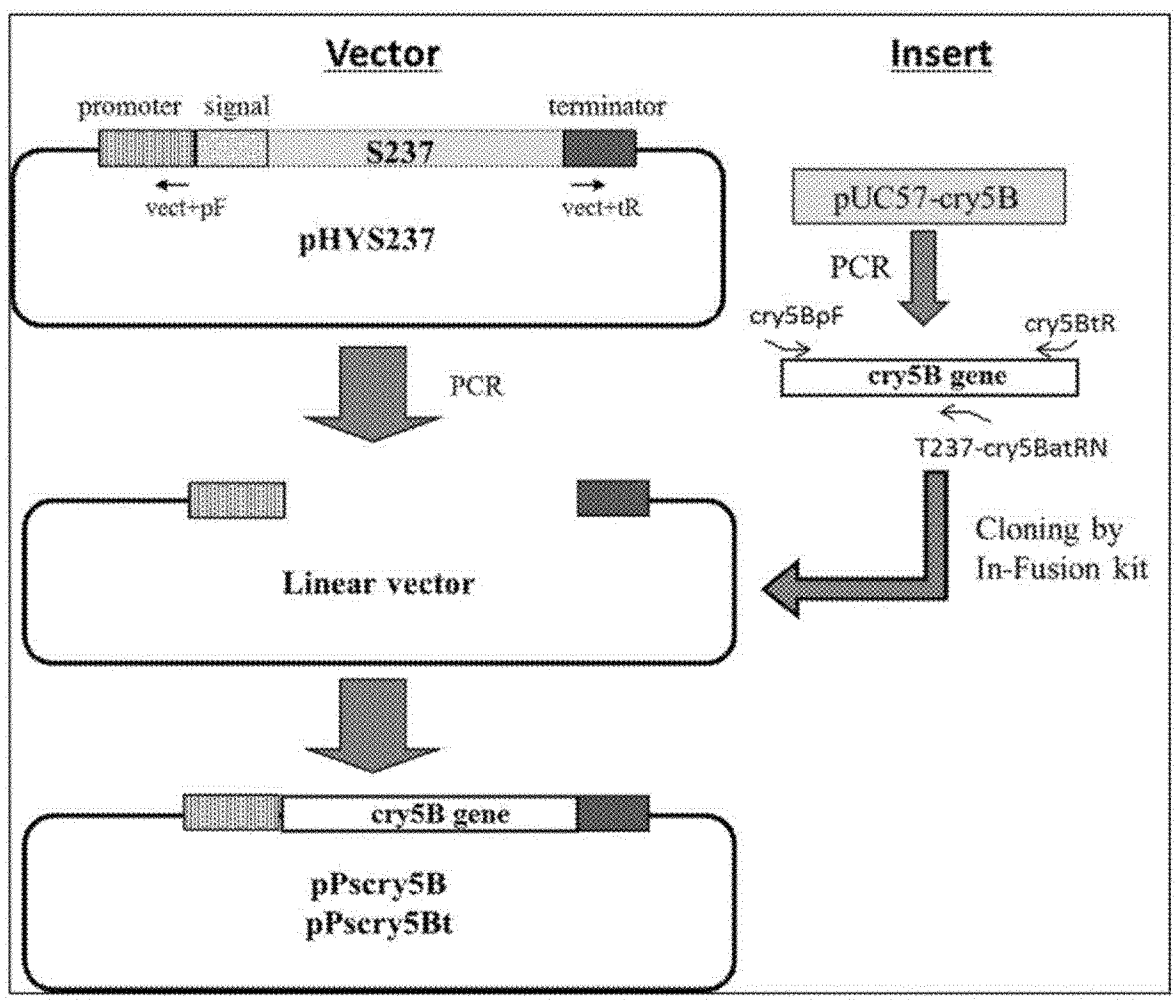

[Figure 1-C]
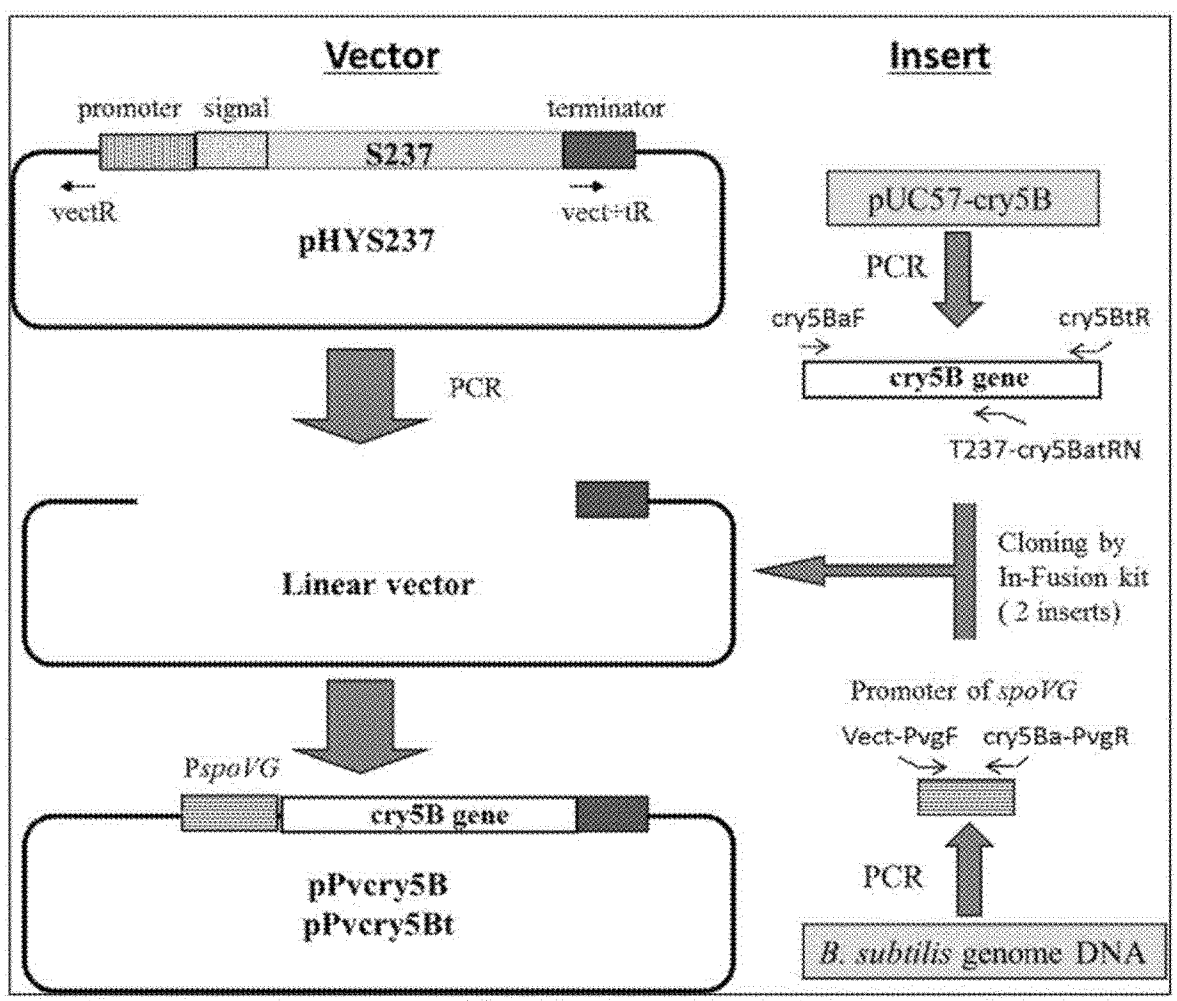

[Figure 1-D]
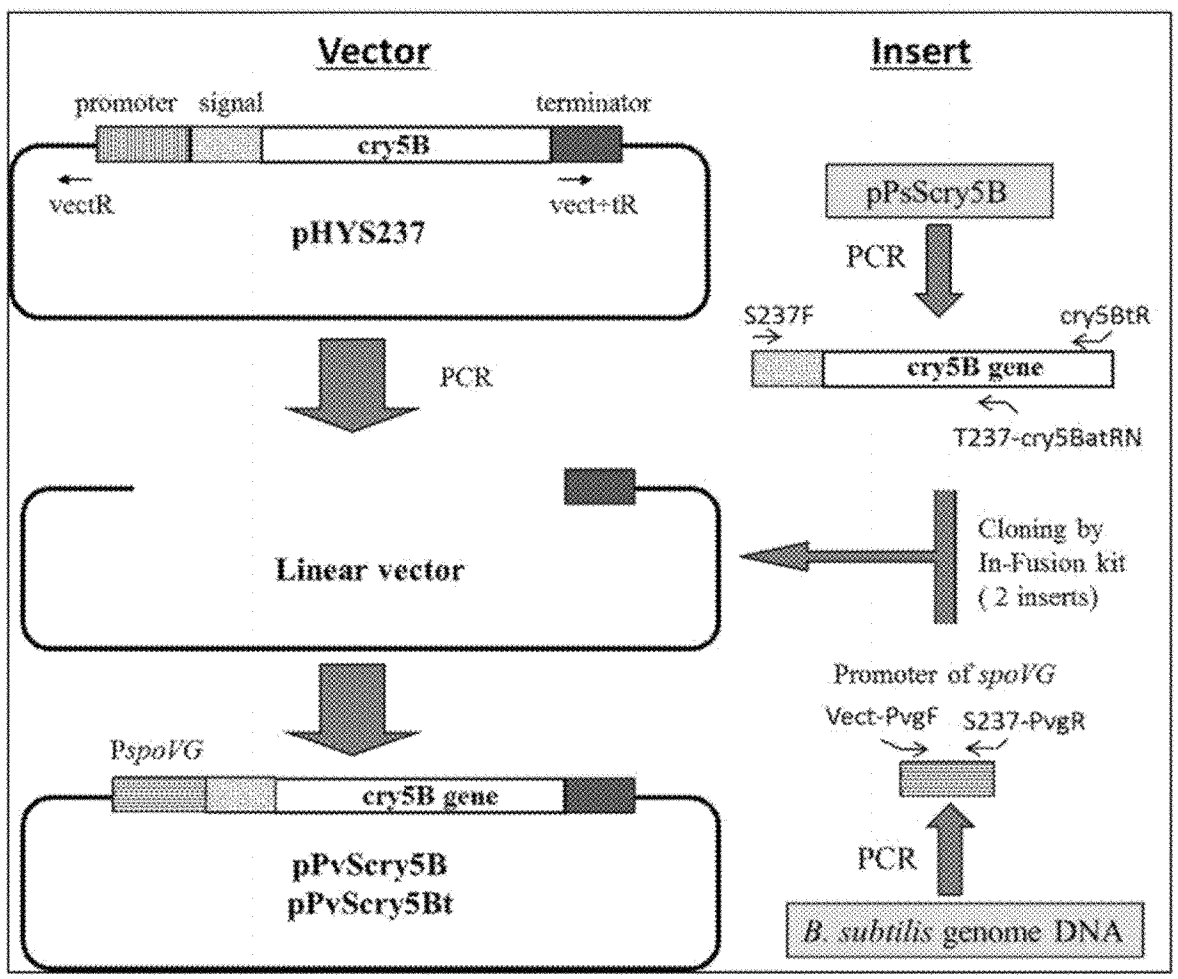

[Figure 2]
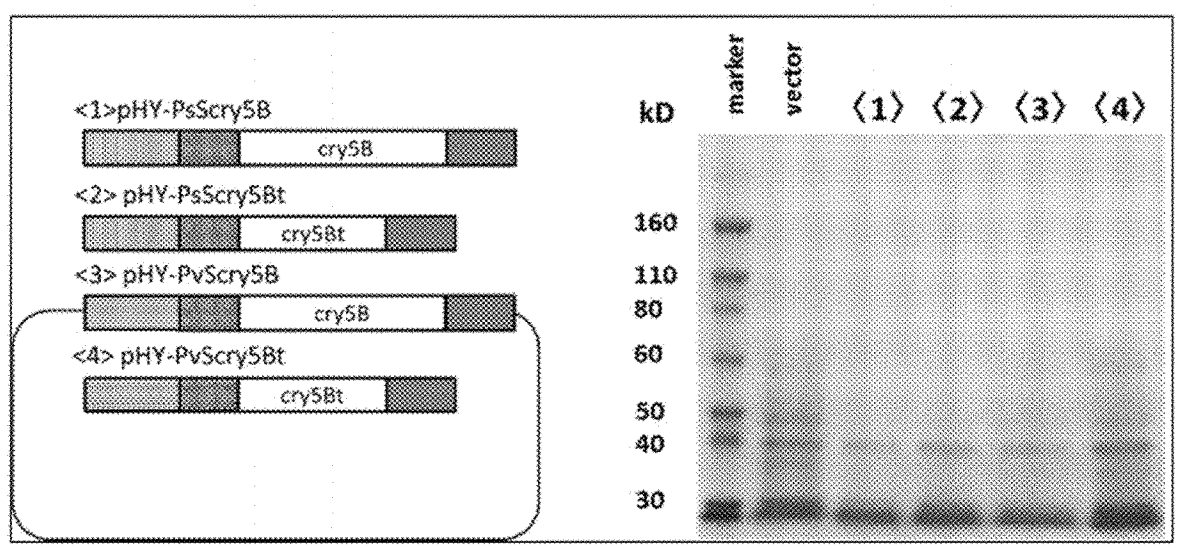

[Figure 3]
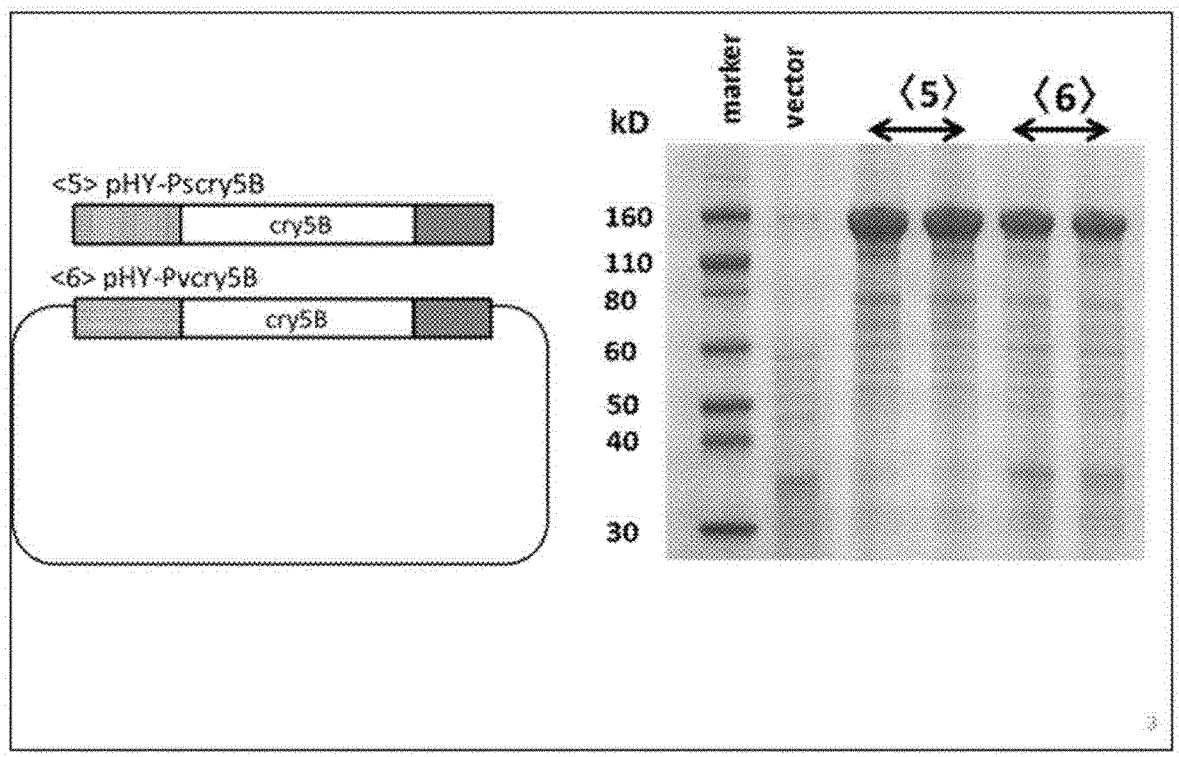

[Figure 4-A]
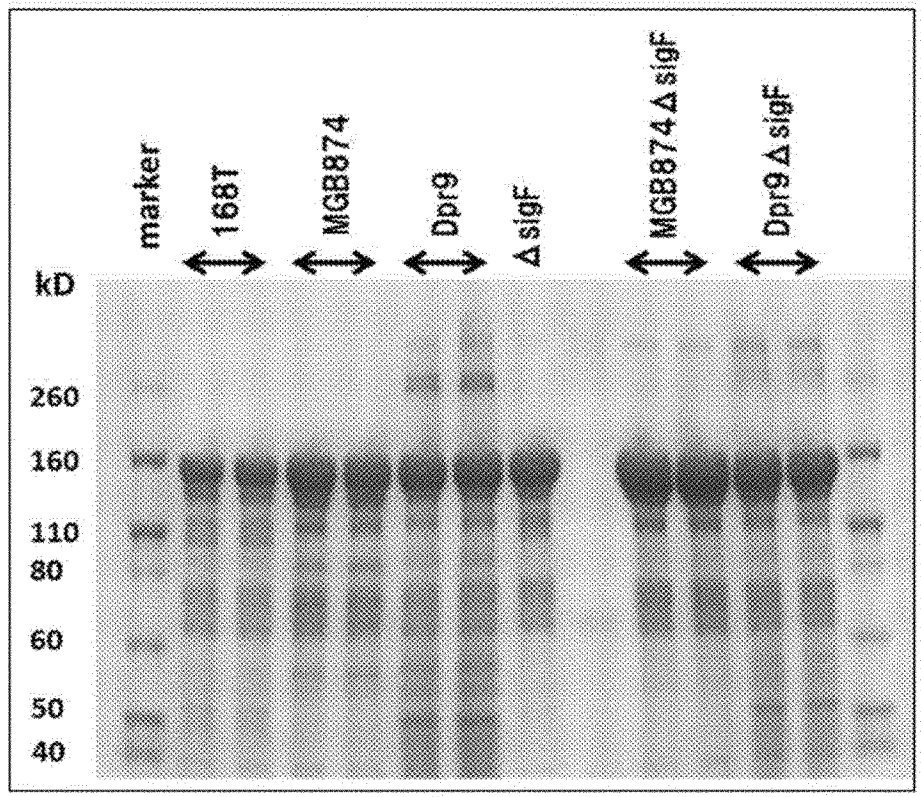

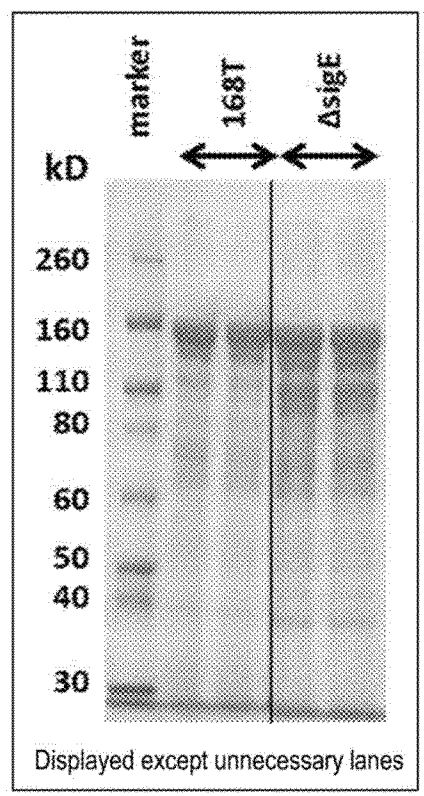
[Figure 4-B]

[Figure 5]
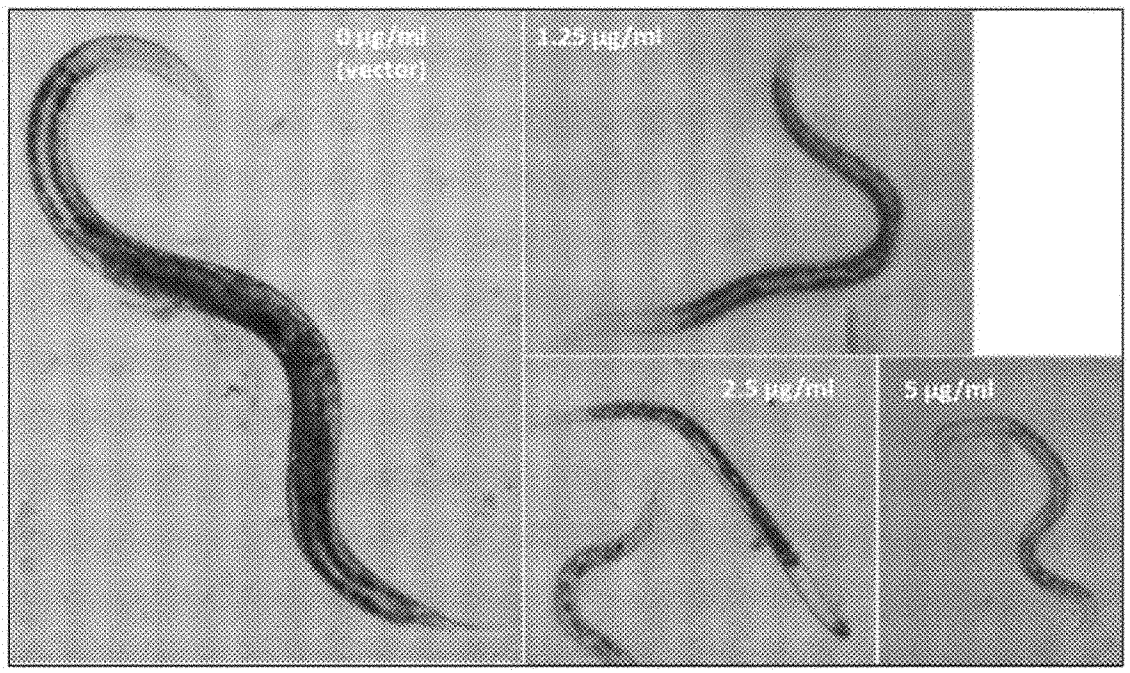

[Figure 6]
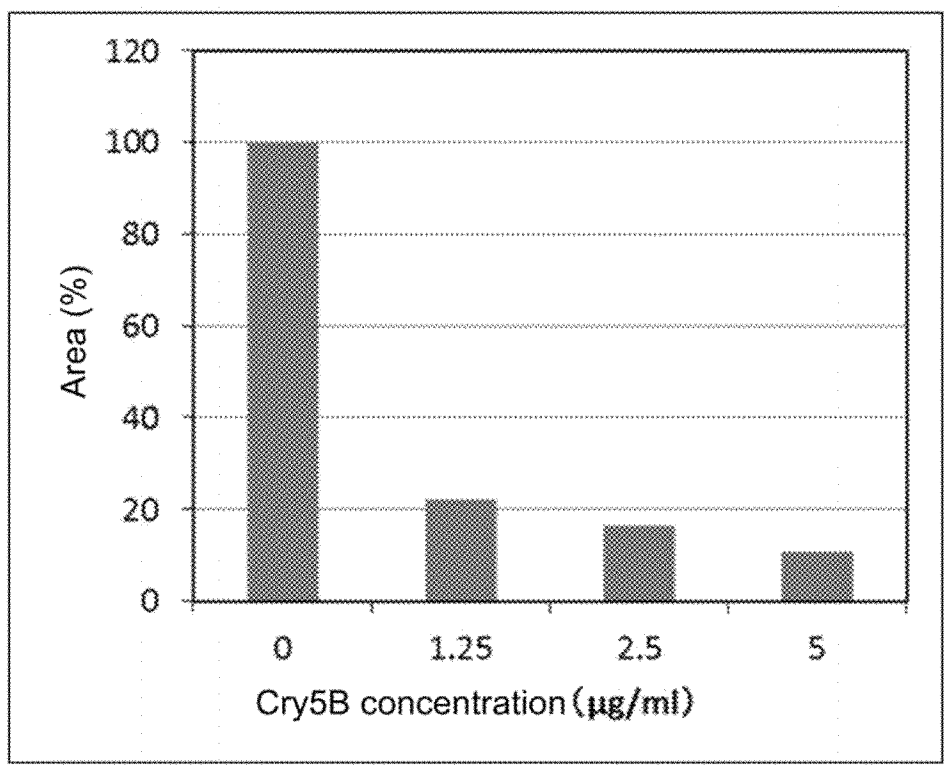

[Figure 7]
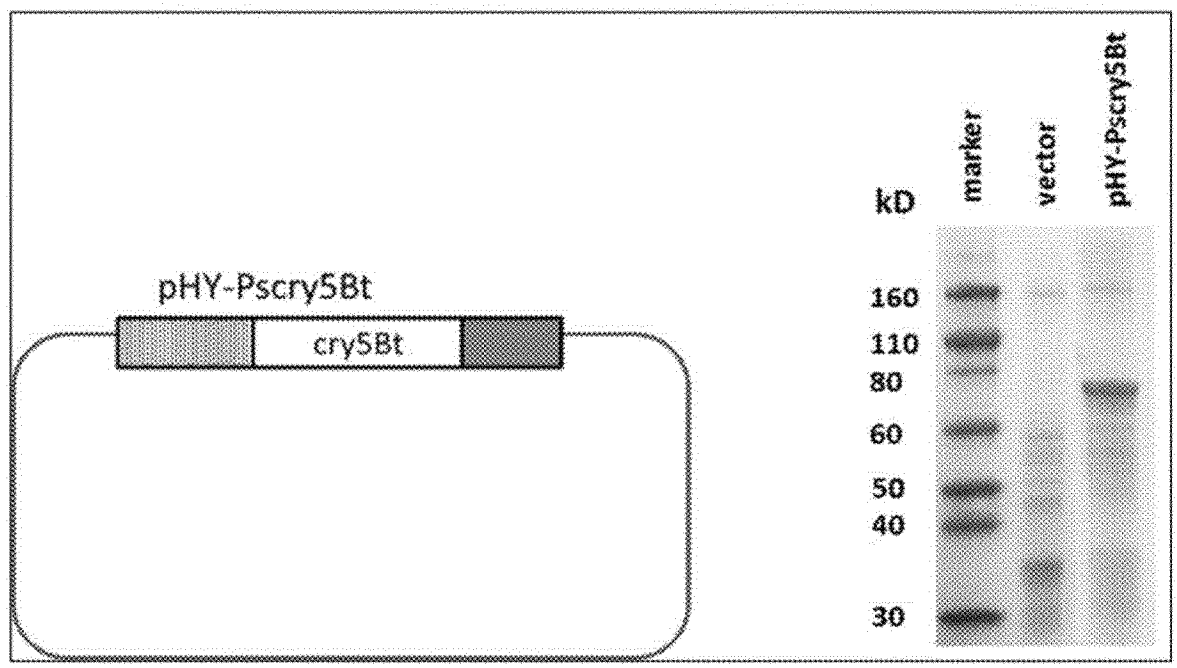

[Figure 8]
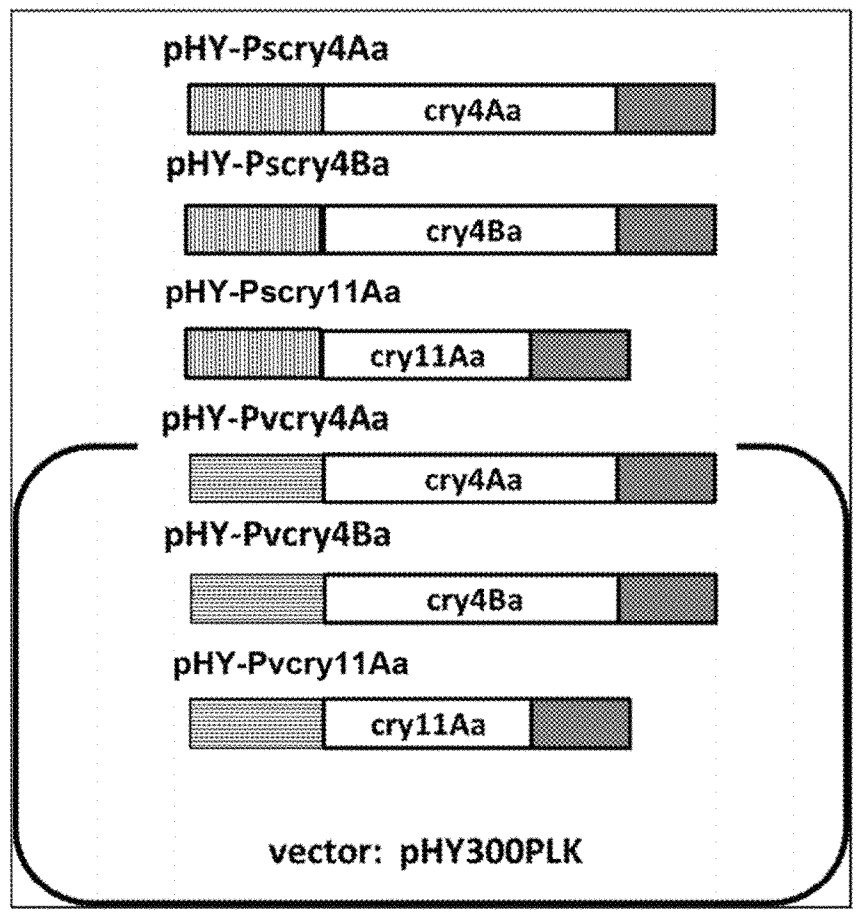

[Figure 9]
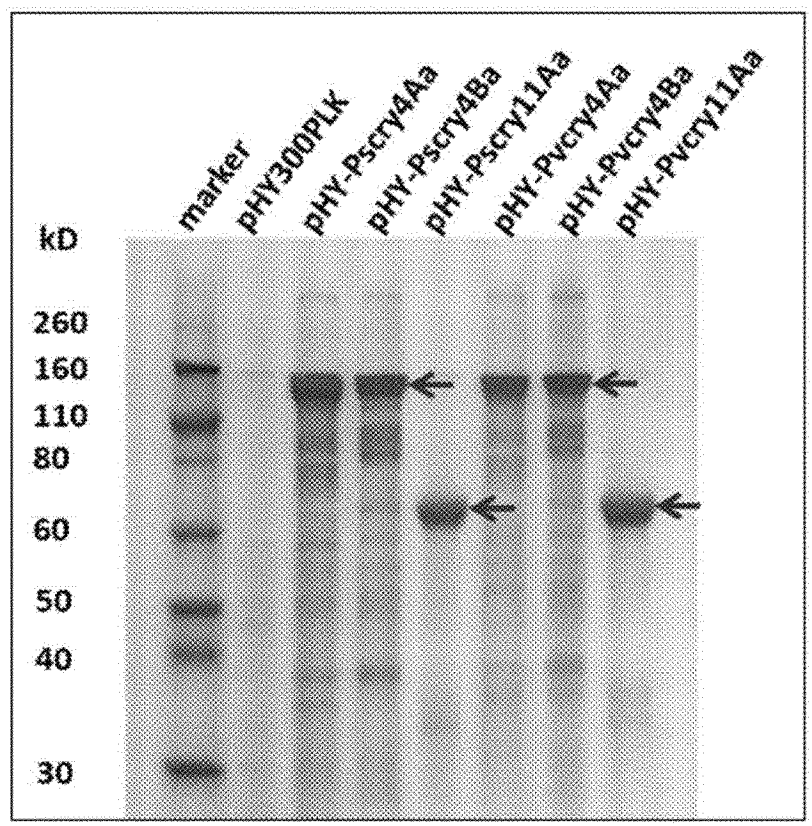

PRODUCTION METHOD FOR PROTEIN

FIELD OF THE INVENTION

The present invention relates to a method for producing a Cry protein by using a *Bacillus* bacterium.

BACKGROUND OF THE INVENTION

Generally, when a large amount of protein is intracellularly expressed by using *Escherichia coli*, the protein is often collected as an insoluble/inactive aggregate (modified protein) called an inclusion body. In this case, in order to recover a biological activity of the protein, a procedure that solubilizes the aggregate and activates (refolding) the protein is required (Non Patent Literature 1). When an active protein cannot be obtained even by the procedure, the expression level of the protein is regulated so as not to form an inclusion body (Non Patent Literatures 2, 3). In another case, when a heterologous protein is intracellularly produced, it is also necessary to adjust expression of a promoter and the copy number of plasmids, in consideration of effect of the heterologous protein on a host (Non Patent Literatures 2, 3).

In contrast, when an extracellular protein is expressed, it is not necessary to consider formation of an inclusion body and effect of concentration of the protein on a host. Up to present, studies for enhancing expression by using a high-expression promoter in combination with a high-copy-number plasmid and releasing suppression of a promoter have been conducted (Patent Literature 1). As a host suitable for extracellular production of protein, a *Bacillus* bacterium, particularly *Bacillus subtilis* has been reported (Non Patent Literatures 4, 5). In addition, *Bacillus subtilis* has been recognized particularly as a highly safe microorganism. In this respect, *Bacillus subtilis* is advantageous as a host.

*Bacillus thuringiensis* is a microorganism producing various insecticidal crystal proteins (hereinafter, referred to as "Cry proteins") and used as a biological agrochemical (Non Patent Literature 6). Generally, a plasmid encoding a Cry protein gene (cry gene) that *Bacillus thuringiensis* has is a large theta-replicating plasmid of low-copy-number. In contrast, a rolling circle replicating plasmid such as a plasmid encoding a replication protein (RepB), which is set forth in SEQ ID NO: 9 and functions to replicate *Bacillus subtilis*, is commonly known to be high copy number. In this point, the rolling circle replicating plasmid differs from the theta-replicating plasmid of low-copy-number (Non Patent Literature 7). When the Cry protein is intracellularly produced by using *Bacillus thuringiensis* from a Cry protein gene (cry gene) on its plasmid, the cry-gene copy number reaches a saturation. From this, it is suggested that the production amount is not increased by increasing the number of copies (Non Patent Literature 6). When a cry gene is cloned into a high-copy-number plasmid, physiological equilibrium changes, with the result that inhibition of sporulation is observed (Non Patent Literature 6). It is suggested that formation of a crystal structure of Cry protein and solubility thereof are influenced by various factors such as a secondary structure and additional constitution components (Non Patent Literature 6). Thus, it has been considered unlikely that a large amount of the protein can be produced simply by enhancing cry gene expression. For example, when *Bacillus thuringiensis*-derived Cry5B protein is expressed in *Bacillus subtilis* PY79, the productivity of the protein in *Bacillus subtilis* PY79 is reported to be as low as only 10 mg/L in contrast to the productivity in *Bacillus thuringiensis* is 75 mg/L (Non Patent Literature 8, Patent Literature 2). Also, it is reported that when Cry5B protein gene is expressed by using a high-copy-number plasmid under control of a high-expression promoter in *Lactococcus lactis*, the productivity of the protein in *Bacillus thuringiensis* is as low as a detection level by western blot (Non Patent Literature 9).

As described above, means that have been generally studied for improving expression of an extracellular protein are not always applicable to production of intracellular proteins, and a means for efficiently and highly expressing, in particular, Cry protein, has not yet been found.

PATENT LITERATURE

Patent Literature 1: WO2011/049227A1
Patent Literature 2: WO2016/007355A1
Patent Literature 3: WO2017/123946A1

NON PATENT LITERATURE

Non Patent Literature 1: Singh A, Upadhyay V, Upadhyay A K, Singh S M, Panda A K (2015) Protein recovery from inclusion bodies of *Escherichia coli* using mild solubilization process; Microb Cell Fact.; 25:14-41.

Non Patent Literature 2: Hiroki Higashibata (2013), ABC for highly expressing heterologous protein using *Escherichia coli* as a host; Biotechnology, 91, 96-100

Non Patent Literature 3: CHUMANN, Wolfgang and FERREIRA, Luis Carlos S. (2004) Production of recombinant proteins in *Escherichia coli*. Genet. Mol. Biol. [online]., 27 (3), 442-453.

Non Patent Literature 4: Gomes A R, Byregowda S M, Veeregowda B M, Balamurugan V (2016). An overview of heterologous expression host systems for the production of recombinant proteins; Adv. Anim. Vet. Sci. 4 (7): 346-356.

Non Patent Literature 5: Ferrer-Miralles and Villaverde (2013). Bacterial cell factories for recombinant protein production; expanding the catalogue. Microbial Cell Factories, 12: 113

Non Patent Literature 6: HERVE' A. et al. How Does *Bacillus thuringiensis* Produce SO Much Insecticidal Crystal Protein; J. of Bacteriology 1995, 177 (21), 6027-6032

Non Patent Literature 7: Deng C, Peng Q, Song F, Lereclus D (2014) Regulation of cry gene expression in *Bacillus thuringiensis*; Toxins. 6: 2194-2209

Non Patent Literature 8: Yan Hu et al. *Bacillus subtilis* Strain Engineered for Treatment of Soil-Transmitted Helminth Diseases, Applied and Environmental Microbiology 2013, 79 (18): 5527-5532

Non Patent Literature 9: Durmaz E. et al. Intracellular and Extracellular Expression of *Bacillus thuringiensis* Crystal Protein Cry5B in *Lactococcus lactis* for Use as an Anthelminthic, Applied and Environmental Microbiology 2016, 82 (4): 1286-1294

SUMMARY OF THE INVENTION

The present invention provides the following 1) and 2).

1) A method for producing a Cry protein or a culture product comprising the Cry protein, comprising transforming a *Bacillus* bacterium with an expression plasmid incorporating a gene encoding the Cry protein operably linked to a regulatory region comprising a σA-dependent promoter or a σH-dependent promoter, and culturing the transformed cell, wherein the expression plasmid comprises a polynucleotide encoding a replication protein consisting of the amino acid sequence set forth in SEQ ID NO: 9 or a protein having an identity of 80% or more with the amino acid sequence of the replication protein and involved in replication initiation.

2) An expression plasmid for expressing a Cry protein in a *Bacillus* bacterium, comprising a polynucleotide encoding a replication protein consisting of the amino acid sequence set forth in SEQ ID NO: 9 or a protein having an identity of 80% or more with the amino acid sequence of the replication protein and involved in replication initiation, wherein a gene encoding the Cry protein is operably linked to a regulatory region comprising a σA-dependent promoter or a σH-dependent promoter.

BRIEF DESCRIPTION OF DRAWINGS

FIG. 1-A shows construction of a Cry5B expression plasmid (pPsScry5B and pPsScry5Bt). The arrows represent the positions and directions of primers. The names of primers are shown above or below the arrows.

FIG. 1-B shows construction of a Cry5B expression plasmid (pPscry5B and pPscry5Bt). The arrows represent the positions and directions of primers. The names of primers are shown above and below the arrows.

FIG. 1-C shows construction of a Cry5B expression plasmid (pPvcry5B and pPvcry5Bt). The arrows represent the positions and directions of primers. The names of primers are shown above and below the arrows.

FIG. 1-D shows construction of a Cry5B expression plasmid (pPvScry5B and pPvScry5Bt). The arrows represent the positions and directions of primers. The names of primers are shown above and below the arrows.

FIG. 2 shows expression of Cry5B and Cry5Bt by a plasmid having a secretion signal.

FIG. 3 shows expression of Cry5B by a plasmid having no secretion signal.

FIG. 4-A shows expression (1) of Cry5B by using a *Bacillus subtilis* mutant strain.

FIG. 4-B shows expression (2) of Cry5B by using a *Bacillus subtilis* mutant strain.

FIG. 5 shows photographs of nematodes in L1 growth assay.

FIG. 6 shows the areas of nematodes, more specifically, values at different concentrations of Cry5B protein based on the area of a control (regarded as 100%)

FIG. 7 shows expression of Cry5Bt by a plasmid having no secretion signal.

FIG. 8 shows plasmids expressing a mosquitocidal protein (pHY-Pscry4Aa, pHY-Pscry4Ba, pHY-Pscry11Aa, pHY-Pvcry4Aa, pHY-Pvcry4Ba, pHY-Pvcry11Aa).

FIG. 9 shows expression of a mosquitocidal protein.

DETAILED DESCRIPTION OF THE INVENTION

The present invention relates to a provision of a method for intracellularly producing a large amount of a Cry protein in a *Bacillus* bacterium.

The present inventors conducted studies on intracellular production of a Cry protein by a *Bacillus* bacterium, preferably *Bacillus subtilis*. As a result, they surprisingly found that a significantly large amount of a Cry protein is intracellularly produced by using a predetermined high-expression plasmid used for extracellular production of a protein, and that the Cry protein thus produced has an activity equivalent to that of a wild-type protein.

According to the present invention, there is provided a high-expression system for a Cry protein using a *Bacillus* bacterium, preferably, *Bacillus subtilis*. Using the system, it is possible to efficiently produce a Cry protein or a culture product containing the Cry protein.

In the specification, the identities between amino acid sequences and between nucleotide sequences are calculated by the Lipman-Pearson method (Lipman, D J., Pearson. W R.: Science, 227, 1435-1441, 1985). Specifically, the identity is calculated by analysis using homology analysis (Search homology) program of genetic information processing software, Genetyx-Win (Software Development) and performed by setting the "unit size to compare (ktup)" at 2.

In the specification, the term "one or several" used in connection with deletion, substitution, addition or insertion of amino acid(s) or nucleotide(s) in an amino acid sequence or a nucleotide sequence, can be, for example, 1 to 12, preferably 1 to 8, and more preferably 1 to 4, unless otherwise specified. In the specification, "addition" of amino acid(s) or nucleotide(s) includes addition of one to several amino acids or nucleotides to one or both ends of a sequence.

In the specification, "stringent conditions" in connection with hybridization refer to conditions described in Molecular Cloning-A LABORATORY MANUAL THIRD EDITION (Joseph Sambrook, David W. Russell, Cold Spring Harbor Laboratory Press, 2001). More specifically, examples thereof include conditions where hybridization is performed by incubating a solution containing 6×SSC (1×SSC composition: 0.15 M sodium chloride, 0.015 M sodium citrate, pH 7.0), 0.5% SDS, 5×Denhardt and 100 mg/mL herring sperm DNA together with a probe at a constant temperature of 65° C. for 8 to 16 hours.

In the specification, the upstream and downstream regions of a gene refer to a region following the 5' end and 3' end of a target gene or target region, respectively. The upstream and downstream regions of a gene are not limited respectively to the upstream region and downstream region of a translation initiation site of the gene, unless otherwise specified.

In the specification, the transcription initiation regulatory region is a region containing a promoter and a transcription initiation site, and the translation initiation regulatory region is a site corresponding to the Shine-Dalgarno (SD) sequence, which forms a ribosome binding site together with an initiation codon (Shine, J., Dalgarno, L.: Proc. Natl. Acad. Sci. USA., 71, 1342-1346, 1974).

In the present invention, a Cry protein refers to a crystalline insecticidal protein produced by *Bacillus thuringiensis*. Cry proteins are classified into classes from Cry1 to Cry75 based on the primary structure of the proteins (Microbiology and Molecular Biology Reviews (1998) 62, 807-813. Revision of the Nomenclature for the *Bacillus thuringiensis* Pesticidal Crystal Proteins, www.lifesci.sussex.ac.uk/Home/Neil#Crickmore/Bt/(Dec. 7, 2017)). Each of the classes is further divided into subclasses based on the degree of sequence analogy. For example, 100 or more types of Cry proteins belong to Cry1 class. Major Cry proteins are listed in the following Tables 1-1 to 1-3. Note that, the access numbers shown in Tables are GenBank Accession Nos.

TABLE 1-1

| Cry protein | Accession No. | NCBI Protein | NCBI Nuc | Authors | Year | Strain/Other ID |
|---|---|---|---|---|---|---|
| Cry1Aa1 | AAA22353 | 142765 | 142764 | Schnepf et al | 1985 | Bt kurstaki HD1 |
| Cry1Ab1 | AAA22330 | 142720 | 142719 | Wabiko et al | 1986 | Bt berliner 1715 |
| Cry1Ba1 | CAA29898 | | | Brizzard & Whiteley | 1988 | Bt *thuringiensis* HD2 |
| Cry1Ac1 | AAA22331 | | | Adang et al | 1985 | Bt kurstaki HD73 |
| Cry2Aa1 | AAA22335 | | | Donovan et al | 1989 | Bt kurstaki |
| Cry1Fa1 | AAA22348 | | | Chambers et al | 1991 | Bt aizawai EG6346 |
| Cry2Ab1 | AAA22342 | | | Widner & Whiteley | 1989 | Bt kurstaki HD1 |
| Cry2Ba1 | KC156658 | | | Sampson et al | 2012 | ARP026 |
| Cry3Aa1 | AAA22336 | | | Herrnstadt et al | 1987 | Bt san diego |
| Cry3Ba1 | CAA34983 | | | Sick et al | 1990 | Bt tolworthi 43F |
| Cry4Aa1 | CAA68485 | | | Ward & Ellar | 1987 | Bt *israelensis* |
| Cry4Ba1 | CAA30312 | | | Chungjatpornchai et al | 1988 | Bt *israelensis* 4Q2-72 |
| Cry5Aa1 | AAA67694 | | | Narva et al | 1994 | Bt darmstadiensis PS17 |
| Cry5Ba1 | AAA68598 | | | Foncerrada & Narva | 1997 | Bt PS86Q3 |
| Cry6Aa1 | AAA22357 | | | Narva et al | 1993 | Bt PS52A1 |
| Cry6Ba1 | AAA22358 | | | Narva et al | 1991 | Bt PS69D1 |
| Cry7Aa1 | AAA22351 | | | Lambert et al | 1992 | Bt galleriae PGSI245 |
| Cry8Aa1 | AAA21117 | | | Narva & Fu | 1992 | Bt kumamotoensis |
| Cry9Aa1 | CAA41122 | | | Shevelev et al | 1991 | Bt galleriae |
| Cry10Aa1 | AAA22614 | | | Thorne et al | 1986 | Bt *israelensis* |
| Cry11Aa1 | AAA22352 | | | Donovan et al | 1988 | Bt *israelensis* |
| Cry11Ba1 | CAA60504 | | | Delecluse et al | 1995 | Bt jegathesan 367 |
| Cry12Aa1 | AAA22355 | | | Narva et al | 1991 | Bt PS33F2 |
| Cry13Aa1 | AAA22356 | | | Narva et al | 1992 | Bt PS63B |
| Cry14Aa1 | AAA21516 | | | Narva et al | 1994 | Bt sotto PS80JJ1 |
| Cry15Aa1 | AAA22333 | | | Brown & Whiteley | 1992 | Bt thompsoni |
| Cry16Aa1 | CAA63860 | | | Barloy et al | 1996 | Cb malaysia CH18 |

TABLE 1-2

| Cry protein | Accession No. | NCBI Protein | NCBI Nuc | Authors | Year | Strain/Other ID |
|---|---|---|---|---|---|---|
| Cry17Aa1 | CAA67841 | | | Barloy et al | 1998 | Cb malaysia CH18 |
| Cry18Aa1 | CAA67506 | | | Zhang et al | 1997 | *Paenibacillus popilliae* |
| Cry19Aa1 | CAA68875 | | | Rosso & Delecluse | 1996 | Bt jegathesan 367 |
| Cry20Aa1 | AAB93476 | | | Lee & Gill | 1997 | Bt fukuokaensis |
| Cry21Aa1 | I32932 | | | Payne et al | 1996 | |
| Cry21Ba1 | BAC06484 | | | Sato & Asano | 2002 | Bt roskildiensis |
| Cry22Aa1 | I34547 | | | Payne et al | 1997 | |
| Cry23Aa1 | AAF76375 | | | Donovan et al | 2000 | Bt |
| Cry24Aa1 | AAC61891 | | | Kawalek and Gill | 1998 | Bt jegathesan |
| Cry25Aa1 | AAC61892 | | | Kawalek and Gill | 1998 | Bt jegathesan |
| Cry26Aa1 | AAD25075 | | | Wojciechowska et al | 1999 | Bt finitimus B-1166 |
| Cry27Aa1 | BAA82796 | | | Saitoh | 1999 | Bt higo |
| Cry28Aa1 | AAD24189 | | | Wojciechowska et al | 1999 | Bt finitimus B-1161 |
| Cry29Aa1 | CAC80985 | | | Delecluse et al | 2000 | Bt medellin |
| Cry30Aa1 | CAC80986 | | | Delecluse et al | 2000 | Bt medellin |
| Cry31Aa1 | BAB11757 | | | Saitoh & Mizuki | 2000 | Bt 84-HS-1-11 |
| Cry32Aa1 | AAG36711 | | | Balasubramanian et al | 2001 | Bt *yunnanensis* |
| Cry33Aa1 | AAL26871 | | | Kim et al | 2001 | Bt dakota |
| Cry34Ab1 | AAG41671 | | | Moellenbeck et all | 2001 | Bt PS149B1 |
| Cry35Ab1 | AAG41672 | | | Moellenbeck et al | 2001 | Bt PS149B1 |
| Cry36Aa1 | AAK64558 | | | Rupar et al | 2001 | Bt |
| Cry39Aa1 | BAB72016 | | | Ito et al | 2001 | Bt aizawai |
| Cry40Aa1 | BAB72018 | | | Ito et al | 2001 | Bt aizawai |
| Cry41Aa1 | BAD35157 | | | Yamashita et al | 2003 | Bt A1462 |
| Cry42Aa1 | BAD35166 | | | Yamashita et al | 2003 | Bt A1462 |
| Cry43Aa1 | BAD15301 | | | Yokoyama and Tanaka | 2003 | P. *lentimorbus* semadara |
| Cry44Aa1 | BAD08532 | | | Ito et al | 2004 | Bt entomocidus INA288 |

TABLE 1-3

| Cry protein | Accession No. | NCBI Protein | NCBI Nuc | Authors | Year | Strain/Other ID |
|---|---|---|---|---|---|---|
| Cry45Aa1 | BAD22577 | | | Okumura et al | 2004 | Bt 89-T-34-22 |
| Cry46Aa1 | BAC79010 | | | Ito et al | 2004 | Bt dakota |
| Cry47Aa1 | AAY24695 | | | Kongsuwan et al | 2005 | Bt CAA890 |
| Cry48Aa1 | CAJ18351 | | | Jones and Berry | 2005 | Bs IAB59 |

TABLE 1-3-continued

| Cry protein | Accession No. | NCBI Protein | NCBI Nuc | Authors | Year | Strain/Other ID |
|---|---|---|---|---|---|---|
| Cry50Aa1 | BAE86999 | 89885725 | 89885724 | Ohgushi et al | 2006 | Bt sotto |
| Cry51Aa1 | ABI14444 | 112253719 | 112253718 | Meng et al | 2006 | Bt F14-1 |
| Cry52Aa1 | EF613489 | | | Shu et al | 2010 | Bt Y41 |
| Cry53Aa1 | EF633476 | | | Shu et al | 2010 | Bt Y41 |
| Cry54Aa1 | ACA52194 | 169261091 | 169261090 | Tan et al | 2009 | Bt MC28 |
| Cry55Aa1 | ABW88932 | | | Guo et al | 2008 | YBT 1518 |
| Cry56Aa1 | ACU57499 | 256033941 | 256033940 | Zhu et al | 2010 | Bt Ywc2-8 |
| Cry57Aa1 | ACN87261 | 225348555 | 225348554 | Noguera & Ibarra | 2009 | Bt kim |
| Cry58Aa1 | ACN87260 | 225348553 | 225348552 | Noguera & Ibarra | 2009 | Bt entomocidus |
| Cry59Aa1 | ACR43758 | 239638225 | 239638224 | Noguera & Ibarra | 2009 | Bt kim LBIT-980 |
| Cry60Aa1 | ACU24782 | 255653180 | 255653179 | Sun and Park | 2009 | Bt jegathesan |
| Cry61Aa1 | HM035087 | | 327505548 | Geng et al | 2010 | Sbt009 |
| Cry62Aa1 | HM054509 | | 302753235 | Zhu et al | 2010 | ST7 |
| Cry63Aa1 | BAI44028 | 260268375 | | Nagamatsu et al | 2010 | MO19 |
| Cry64Aa1 | BAJ05397 | 294661779 | | Ekino et al | 2010 | Bt tohokuensis |
| Cry65Aa1 | HM461868 | | 328833581 | Geng et al | 2010 | SBt 003 |
| Cry66Aa1 | AEB52311 | | 339186760 | Sun et al | 2010 | SBt 021 |
| Cry67Aa1 | HM485582 | | 339186762 | Sun et al | 2010 | SBt 009 |
| Cry68Aa1 | HQ113114 | | 327466752 | Peng Guan et al | 2012 | Bt MC28 |
| Cry69Aa1 | HQ401006 | | 332139130 | Peng Guan | 2011 | Bt MC28 |
| Cry70Aa1 | JN646781 | | | Qiao Li | 2015 | Bt hs18-1 |
| Cry71Aa1 | JX025568 | | | Qiao Li et al | 2016 | Bt Hs18-1 |
| Cry72Aa1 | JX025569 | | | Qiao Li et al | 2016 | Bt Hs18-1 |

Among the Cry proteins listed above, Cry1A protein, Cry1F protein, Cry2A protein, Cry34A protein, Cry35A protein, Cry3A protein, Cry3B protein, Cry21 protein, Cry14A protein, CryσA protein, Cry13 protein, Cry5B protein, Cry4Aa protein, Cry4Ba protein and Cry11Aa protein are more suitably produced by the method of the present invention; and Cry5B protein, Cry4Aa protein, Cry4Ba protein and Cry11Aa protein are more suitably produced.

A Cry5B protein is a nematocidal protein known to be effective to soil-transmitted helminth infections (Cappello M et al. Proc. Natl. Acad. Sci. U.S.A. 103: 15154-15159, Hu Y et al. PLoS Negl. Trop. Dis. 4: e614). For example, the amino acid sequence of Cry5B protein is set forth in SEQ ID NO: 2 in the Sequence Listing and the nucleotide sequence of a gene encoding the protein is set forth in SEQ ID NO: 1 in the Sequence Listing.

Cry4Aa protein, Cry4Ba protein and Cry11Aa protein are known as proteins having an insecticidal activity to mosquitos (FEMS Microbiol Lett 266 (2007) 163-169, Mhalakshmi A at al. Advances Microbiol. 2 (2012) 216-226).

For examples, the amino acid sequence of Cry4Aa protein is set forth in SEQ ID NO: 4 of the Sequence Listing and the nucleotide sequence of a gene encoding the protein is set forth in SEQ ID NO: 3 of the Sequence Listing.

For example, the amino acid sequence of Cry4Ba protein is set forth in SEQ ID NO: 6 of the Sequence Listing and the nucleotide sequence of a gene encoding the protein is set forth in SEQ ID NO: 5 of the Sequence Listing.

For example, the amino acid sequence of Cry11Aa protein is set forth in SEQ ID NO: 8 of the Sequence Listing and the nucleotide sequence of a gene encoding the protein is set forth in SEQ ID NO: 7 of the Sequence Listing.

Naturally occurring proteins of these are well known to have mutant proteins having one to several amino acid mutations due to gene mutations caused by difference in, e.g., ecotype, or the presence of analogous isozyme(s).

Because of this, other than the Cry proteins listed in Table 1, mutants of the Cry proteins, which have addition, substitution of one to several amino acid residues or deletion of one to several amino acid residues in the amino acid sequences consisting of the Cry proteins and have an equivalent insecticidal activity are included in the Cry protein of the present invention.

For example, in the cases of Cry5B protein, Cry4Aa protein, Cry4Ba protein and Cry11Aa protein, the following (A) to (C) are included:

(A) a protein consisting of the amino acid sequence set forth in SEQ ID NO: 2, 4, 6 or 8;

(B) a protein consisting of an amino acid having deletion, substitution, addition or insertion of one or several amino acids with respect to the amino acid sequence set forth in SEQ ID NO: 2, 4, 6 or 8 and having an insecticidal activity; and (C) A protein consisting of an amino acid sequence having an identity of 80% or more, more preferably 90% or more, more preferably 95% or more, more preferably 96% or more, more preferably 97% or more, more preferably 98% or more, and more preferably 99% or more with the amino acid sequence set forth in SEQ ID NO: 2, 4, 6 or 8 and having an insecticidal activity.

A gene encoding the Cry protein (also referred to as cry gene) of the present invention is not particularly limited in type; in other words, the gene may be any one of naturally occurring DNA, recombinant DNA and chemically synthesized DNA, and either a genomic DNA clone or a cDNA clone.

The cry gene of the present invention typically refers to any one of the cry genes listed in Table 1. Among the naturally occurring genes, a small number of mutations are present due to difference in, e.g., ecotype, or the presence of analogous isozymes, as is well known to those skilled in the art. Accordingly, examples of the cry gene of the present invention are not limited to the genes listed in Table 1 and include all genes as long as they encode the aforementioned Cry proteins.

For example, in the cases of cry5B gene, cry4Aa gene, cry4Ba gene and cry11Aa gene, the following (a) to (f) are included:

(a) a polynucleotide consisting of the nucleotide sequence set forth in SEQ ID NO: 1, 3, 5 or 7;

(b) a polynucleotide consisting of a nucleotide sequence having an identity of 80% or more, more preferably 90% or more, more preferably 95% or more, more preferably 96% or more, more preferably 97% or more, more preferably 98% or more, and more preferably 99% or more with the nucleotide sequence set forth in SEQ ID NO: 1, 3, 5 or 7 and encoding a protein having an insecticidal activity;

(c) a polynucleotide hybridizing with a complementary strand of the polynucleotide consisting of the nucleotide sequence set forth in SEQ ID NO: 1, 3, 5 or 7 under stringent conditions and encoding a protein having an insecticidal activity;

(d) a polynucleotide encoding a protein consisting of the amino acid sequence set forth in SEQ ID NO: 2, 4, 6 or 8;

(e) A polynucleotide encoding a protein consisting of an amino acid sequence having deletion, substitution, addition or insertion of one or several amino acids with respect to the amino acid set forth in SEQ ID NO: 2, 4, 6 and 8 and having an insecticidal activity; and (f) a polynucleotide encoding a protein consisting of an amino acid sequence having an identity of 80% or more, more preferably 90% or more, more preferably 95% or more, more preferably 96% or more, more preferably 97% or more, more preferably 98% or more, and more preferably 99% or more with the amino acid sequence set forth in SEQ ID NO: 2 and having an insecticidal activity.

In the present invention, a Cry protein or a culture product containing a Cry protein is produced by incorporating the cry gene mentioned above operably linked to a regulatory region containing a σA-dependent promoter or a σH-dependent promoter into an expression plasmid, transforming a *Bacillus* bacterium with the plasmid, and culturing the transformed cell. As the expression plasmid, a plasmid containing a polynucleotide encoding a replication protein consisting of the amino acid sequence set forth in SEQ ID NO: 9 or a protein having an identity of 80% or more with the amino acid sequence of the replication protein and involved in replication initiation, is used.

The replication protein (Rep) is an initiator protein functioning in replication initiation of a plasmid. The plasmid used in the present invention, contains the replication protein set forth in SEQ ID NO: 9 required for replication in *Bacillus subtilis*. For example, the replication protein set forth in SEQ ID NO: 9 is present in pAMα1. Two types of replication proteins for pAMα1 are known; however, the replication protein to be used in the present invention is a protein, which consists of the amino acid sequence set forth in SEQ ID NO: 9. Also, a protein having an identity of 80% or more, more preferably 90% or more, more preferably 95% or more, more preferably 96% or more, more preferably 97% or more, more preferably 98% or more, and more preferably 99% or more with the amino acid sequence of the replication protein and involved in replication initiation can be used similarly to the protein. As such a plasmid replication protein, for example, a protein having an amino acid having deletion, substitution or addition of one or several amino acids with respect to the amino acid sequence set forth in SEQ ID NO: 9 is included. For example, mutant proteins described in JP-B-5361484 are mentioned; more specifically, proteins, which are obtained by substituting at least one amino acid residue selected from the group consisting of amino acid residues at (a) 48-position, (b) 262-position, (c) 149-position and (d) 198-position of the amino acid sequence set forth in SEQ ID NO: 9 with a predetermined amino acid residue, are mentioned.

The above plasmid includes, other than a polynucleotide encoding a replication protein, e.g., polynucleotides encoding a protein involved in initiation replication. Other than these, the plasmid can also appropriately include e.g., a drug resistance gene and a multicloning site.

Examples of the plasmid suitably used in the present invention include pHY300PLK and the plasmids described in JP-B-5361484.

Plasmid pHY300PLK can be constructed of DNA molecules derived from *E. coli* plasmid, pACYC177, and *Streptococcus faecalis* plasmid, pAMα1, by use of a shuttle vector, which can transform DNA of both *Escherichia coli* and *Bacillus subtilis*, and RepB is contained in the replication region of pAMα1.

A gene encoding a desired Cry protein is operably linked to a regulatory region containing a σA factor-dependent promoter or a σH factor-dependent promoter in the plasmid to construct a recombinant plasmid (expression vector) which can produce a Cry protein in bacterial cells of *Bacillus subtilis*.

The "gene operably linked to a regulatory region" herein refers to a gene arranged expressibly under control of the regulatory region.

The promoter herein is present upstream of the coding region of a predetermined gene and defined as a region having a function to control transcription of the gene by interaction with RNA polymerase. More specifically, the promoter refers to a region consisting of about 200 to 600 nucleotides and present upstream of the coding region of the predetermined gene.

As the regulatory region including a promoter, a transcription initiation regulatory region and translation initiation regulatory region are mentioned. The regulatory region preferably has a function to enhance expression of a gene present downstream thereof in a host and more preferably a function to constitutively express a downstream gene or enhancing expression thereof.

The σA factor-dependent promoter and σH factor-dependent promoter are promoters working before a spore coat protein deposition period in the sporulation phase for spore-forming microorganisms.

The regulatory region containing a σA-dependent promoter or a σH-dependent promoter is preferably selected from regulatory regions different from the regulatory region of a gene encoding a Cry protein in the microorganism from which the gene is derived.

Examples of the σA factor-dependent promoter include, but are not particularly limited to, *Bacillus subtilis* phage SP01 promoter (Proc. Natl. Acd. Sci. USA. (1984) 81: 439-443.) and promoters of veg gene, amyE (amylase) gene, aprE (subtilisin) gene and S237 (S237 cellulase, JP-A-2000-210081) gene. Examples of the σH factor-dependent promoter include, but are not particularly limited to, promoters of cite gene, spoVS gene and spoVG (Proc. Natl. Acd. Sci. USA. (1986) 83: 9438-9442.) gene.

In the present invention, as the GA factor-dependent promoter, a promoter of a cellulase gene of *Bacillus* sp. KSM-S237 strain is more preferable. As the σH factor-dependent promoter, a promoter of spoVG gene (BG10112) of *Bacillus subtilis* Marburg No. 168 (*Bacillus subtilis* 168 strain) is more preferable.

As the regulatory region containing a σA factor-dependent promoter, the regulatory region of a cellulase gene of *Bacillus* sp. KSM-S237 strain is suitably mentioned. The regulatory region is more specifically a transcription initiation regulatory region and a translation initiation region (SEQ ID NO: 10) of the cellulase gene, preferably the nucleotide sequence set forth in SEQ ID NO: 10, or a nucleotide sequence having an identity of 80% or more, more preferably 90% or more, further preferably 95% or more, and still further preferably 98% or more with the nucleotide sequence set forth in SEQ ID NO: 10, or any one of the above nucleotide sequences partly having a deletion. The nucleotide sequence having an identity of 80% or more, more preferably 90% or more, further preferably 95% or more and still further preferably 98% or more with the nucleotide sequence set forth in SEQ ID NO: 10 refers to a sequence having the above identity and maintaining a function as a σA factor-dependent promoter, i.e., function involved in transcription and translation of the gene. The nucleotide sequence partly having a deletion is a sequence having a deletion but maintaining a function as a σA factor-dependent promoter, i.e., function involved in transcription and translation of the gene. Among the σA factor-dependent promoters, a more preferable σA factor-dependent promoter includes a promoter consisting of the nucleotide sequence set forth in SEQ ID NO: 11. The promoter is a promoter consisting of a sequence of the regulatory region of a cellulase gene of the *Bacillus* sp. KSM-S237 strain mentioned above, from which a Cre-like sequence has been deleted (JP-A-2011-103875), and having a sequence identity of 95% with the nucleotide sequence set forth in SEQ ID NO: 10.

Herein, the phrase "functions as a σA factor-dependent promoter" means that transcription is specifically controlled by the σA factor which is an RNA polymerase. The specificity thereof can be evaluated by ligating a reporter gene to a site downstream of the polynucleotide to be evaluated, and observing expression of the reporter gene in the presence or absence of the σA factor.

As the regulatory region containing a σH factor-dependent promoter, the regulatory region of spoVG gene of *Bacillus subtilis* Marburg No. 168 (*Bacillus subtilis* 168 strain) is preferably mentioned. The regulatory region is more specifically a transcription initiation regulatory region and a translation initiation region of the spoVG gene (BG10112) (SEQ ID NO: 12), preferably the nucleotide sequence set forth in SEQ ID NO: 12 or a nucleotide sequence having an identity of 80% or more, more preferably 90% or more, further preferably 95% or more and still further preferably 98% or more with the nucleotide sequence set forth in SEQ ID NO: 12 or any one of the above nucleotide sequences partly having a deletion. The nucleotide sequence having an identity of 80% or more, more preferably 90% or more, further preferably 95% or more and still further preferably 98% or more with the nucleotide sequence set forth in SEQ ID NO: 12 refers to a sequence having the above identity and maintaining a function as a σH factor-dependent promoter, i.e., a function involved in transcription and translation of the gene. The nucleotide sequence partly having a deletion is a sequence having a deletion but maintaining a function as a σH factor-dependent promoter, i.e., a function involved in transcription and translation of a gene. Herein, the phrase "function as a σH factor-dependent promoter" means that transcription is specifically controlled by the σH factor which is an RNA polymerase. The specificity thereof can be evaluated by ligating a reporter gene to a site downstream of the polynucleotide to be evaluated, and observing expression of the reporter gene in the presence or absence of a σH factor.

Insertion into a plasmid containing the cry gene and the regulatory region can be carried out by a method ordinarily used in the technical field. For example, fragments of the cry gene and the regulatory region may be amplified by, e.g., PCR, inserted into a plasmid by, e.g., a restriction enzyme method and linked. Alternatively, a fragment prepared by ligating the fragments of the gene and the regulatory region in advance may be inserted into a plasmid. In this case, the regulatory region fragment and the cry gene fragment are arranged on the plasmid in this order from the upstream and ligated. For convenient sake, a commercially available ligation kit (for example, manufactured by, e.g., Takara Bio Inc.) can be used.

Examples of a method for introducing a constructed plasmid into a host cell include the calcium chloride method and the calcium chloride/rubidium chloride method described in Sambrook, J. et al., Molecular Cloning, A Laboratory Manual (2nd edition), Cold Spring Harbor Laboratory, 1.74 (1989), an electroporation method, an electro-injection method, a chemical treatment method with, e.g., PEG, and a method using a gene gun.

As the host cell to which the above expression plasmid is to be introduced, a *Bacillus* bacterium, preferably *Bacillus subtilis*, *Bacillus megaterium* or *Bacillus brevis*, is used. The *Bacillus* bacterium to be used may be a wild type or a mutant type. Specific examples of the microorganism belonging to the genus *Bacillus* include *Bacillus subtilis*, *Bacillus cereus*, *Bacillus thuringiensis*, *Bacillus anthracis*, *Bacillus stearotheromophilus*, *Bacillus coagulans*, *Bacillus megaterium*, *Bacillus halodurans*, *Bacillus brevis* (*BreviBacillus brevis*), *Bacillus choshinensis* (*Brevibacillus choshinensis*), *Bacillus pumilus*, *Bacillus alcalophilus*, *Bacillus amylolyticus*, *Bacillus amyloliquefaciens*, *Bacillus liqueniformis*, *Bacillus polymyxa* (*Paenibacillus polymyxa*), *Bacillus sphaericus*, *Bacillus firmus*, *Bacillus clausii* and *Bacillus macerans*. Note that, *Bacillus brevis* is classified into the genus *Brevibacillus* and sometimes represented as, e.g., *BreviBacillus brevis* or *Brevibacillus choshinensis*, depending on the strain; *Bacillus polymyxa* is classified into the genus *Paenibacillus* and sometimes represented as *Paenibacillus polymyxa*; and *Bacillus stearotheromophilus* is classified into the genus *Geobacillus* and sometimes represented as *Geobacillus stearotheromophilus*. However, in the specification, *Bacillus brevis*, *Bacillus polymyxa*, and *Bacillus stearotheromophilus* are all defined as bacteria belonging to the genus *Bacillus*. More specifically, in the present invention, the microorganisms belonging to the genus *Bacillus* are interpreted as including microorganisms represented as *Brevibacillus brevis* and *Brevibacillus choshinensis*, a microorganism represented as *Paenibacillus polymyxa* and a microorganism represented as *Geobacillus stearotheromophilus*. Note that, microorganisms belonging to the genus *Bacillus* can be purchased from culture collections.

Examples of a wild-type *Bacillus* include *Bacillus subtilis* Marburg No. 168 (*Bacillus subtilis* 168 strain). A *Bacillus subtilis* mutant strain is not particularly limited as long as it is suitable for producing a Cry protein and, for example, a *Bacillus subtilis* strain having deletion of the regions unnecessary for survival, proliferation and protein production from the genome of the wild-type strain thereof; a *Bacillus subtilis* strain having a deletion of a predetermined protease gene; a *Bacillus subtilis* strain having a deletion of a factor gene specific to a sporulation phase, or a *Bacillus subtilis* strain having these mutations in combination, is mentioned.

A *Bacillus subtilis* mutant strain having a wide region deleted in the genome has a genome having a wide region deleted compared to the genome of a wild-type *Bacillus subtilis* strain (for example, *Bacillus subtilis* 168 strain); for example, mutant strains described in JP-B-4955358 are mentioned. Examples thereof include *Bacillus subtilis* mutant strains having a deletion of at least one region selected from the group consisting of prophage 6 (yoaV-yob0) region, prophage 1 (ybbU-ybdE) region, prophage 4 (yjcM-yjdJ) region, PBSX (ykdA-xlyA) region, prophage 5 (ynxB-dut) region, prophage 3 (ydiM-ydjC) region, spb (yodU-ypqP) region, pks (pksA-ymaC) region, skin (spoIVCB-spoIIIC) region, pps (ppsE-ppsA) region, prophage 2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, prophage 7 (yrkM-yraK, or yrkS-yraK) region, sbo-ywhH region, yybP-yyaJ region and yncM-fosB region in the genome of wild-type *Bacillus subtilis* strain; and preferably include *Bacillus subtilis* MGB874 strain having deletions of all of prophage 6 (yoaV-yob0) region, prophage 1 (ybbU-ybdE) region, prophage 4 (yjcM-yjdJ) region, PBSX (ykdA-xlyA) region, prophage 5 (ynxB-dut) region, prophage 3 (ydiM-ydjC) region, spb (yodU-ypqP) region, pks (pksA-ymaC) region, skin (spoIVCB-spoIIIC) region, pps (ppsE-ppsA) region, prophage 2 (ydcL-ydeJ) region, ydcL-ydeK-ydhU region, yisB-yitD region, yunA-yurT region, cgeE-ypmQ region, yeeK-yesX region, pdp-rocR region, ycxB-sipU region, prophage 7 (yrkS-yraK) region, sbo-ywhH region, yybP-yyaJ region and yncM-fosB region. The MGB874 strain mentioned above is available from the National Bio Resource Project (NBRP) of the National Institute of Genetics (www.shigen.nig.ac.jp/bsub/kaoListAction.do). Further, an example of an MGB874 mutant strain is a *Bacillus subtilis* mutant stain (MGB874abrB* ΔkinA) described in JP-A-2017-79639 which is obtained by genetic modification to constitutively express abrB gene or an equivalent gene thereto and in which kinA gene is deleted or inactivated.

Examples of a *Bacillus subtilis* strain having a predetermined protease gene deleted, include *Bacillus subtilis*, which is described in JP-B-4485341 and has a deletion or inactivation of aprX gene of *Bacillus subtilis* and at least one gene selected from the group consisting of aprE, nprB, nprE, bpr, vpr, mpr, epr and wprA of *Bacillus subtilis*; and preferably a *Bacillus subtilis* strain (Dpr9 strain) having nonuple deletions of aprX, aprE, nprB, nprE, bpr, vpr, mpr, epr and wprA genes.

A *Bacillus subtilis* strain having a deletion of sporulation phase-specific σ factor gene includes *Bacillus subtilis* strains, which are described in JP-B-4336082 and have a deletion or inactivation of at least one gene selected from the group consisting of sigF, sigG and sigE; preferably a sigE-deficient strain (ΔsigE strain) and a sigF-deficient strain (ΔsigF strain); and more preferably a sigF-deficient strain (ΔsigF strain).

In view of production of a Cry protein, an MGB874ΔsigF mutant strain obtained by deleting sigF from the MGB874 strain mentioned above and a Dpr9ΔsigF mutant strain obtained by deleting sigF from the Dpr9 strain mentioned above are more preferably used.

The Cry protein of the present invention can be expressed (produced) by culturing a transformed *Bacillus subtilis* containing an expression vector prepared as described above in a nutrition medium. The nutrient medium preferably contains a carbon source and an inorganic or organic nitrogen source necessary for growth of *Bacillus subtilis* (transformant). Examples of the carbon source include glucose, dextran, soluble starch, sucrose and methanol. Examples of the inorganic or organic nitrogen source include ammonium salts, nitrates, amino acids, corn steep liquor, peptone, casein, meat extract, soybean meal and potato extract. If desired, other nutrients (e.g., inorganic salts (e.g., sodium chloride, calcium chloride, sodium dihydrogen phosphate, magnesium chloride), vitamins and antibiotics (e.g., tetracycline, neomycin, kanamycin, spectinomycin, erythromycin)) may be contained. Culturing is performed by a method known in the art. Culture conditions, such as temperature, aeration/stirring conditions, medium pH and culture time, are appropriately selected so as to produce a large amount of the protein of the present invention.

A culture product containing a Cry protein of the present invention and obtained by culturing as mentioned above can be obtained by collecting host cells by a process such as centrifugation and filtration, and suspending the collected host cells in an appropriate buffer (for example, a buffer such as a Tris buffer, phosphate buffer, HEPES buffer, MES buffer having a concentration of about 10 M to 100 mM (desirably in the range of pH 5.0 to 9.0) or water. The host cells can be further crushed by appropriately using known cell disruption means such as lysozyme, freeze-thaw, sonication, French press and bead disruption in combination and subjected to centrifugation to collect the Cry protein. The above culture product can be sterilized by adding a bactericidal substance such as carvacrol followed by incubation (Patent Literature 3).

The collected Cry protein can be appropriately purified by utilizing a sucrose density gradient method, a recrystallization method, ion exchange chromatography, gel filtration, hydrophobic chromatography, isoelectric chromatography and affinity column using a polyclonal antibody against a Cry protein as a ligand.

In connection with the embodiments mentioned above, the following aspects of the present invention are further disclosed.

<1> A method for producing a Cry protein or a culture product comprising the Cry protein, comprising transforming a *Bacillus* bacterium with an expression plasmid incorporating a gene encoding the Cry protein operably linked to a regulatory region comprising a σA-dependent promoter or a σH-dependent promoter, and culturing the transformed cell, wherein the expression plasmid comprises a polynucleotide encoding a replication protein consisting of the amino acid sequence set forth in SEQ ID NO: 9 or a protein having an identity of 80% or more, more preferably 90% or more, more preferably 95% or more, more preferably 96% or more, more preferably 97% or more, more preferably 98% or more, and more preferably 99% or more with the amino acid sequence of the replication protein and involved in replication initiation.

<2> The method according to <1>, wherein the regulatory region comprising a σA-dependent promoter or a σH-dependent promoter differs from a regulatory region of a gene encoding the Cry protein in a microorganism from which the gene is derived.

<3> The method according to <1> or <2>, wherein the regulatory region comprising a σA-dependent promoter or a σH-dependent promoter is a regulatory region of spoVG gene or a regulatory region of a cellulase gene of *Bacillus* sp. KSM-S237 strain.

<4> The method according to <3>, wherein the regulatory region of a cellulase gene of *Bacillus* sp. KSM-S237 strain is a transcription initiation regulatory region and a translation initiation region of the gene.

<5> The method according to any one of <1> to <4>, wherein the *Bacillus* bacterium is *Bacillus subtilis*, *Bacillus megaterium* or *Bacillus brevis*.

<6> The method according to any one of <1> to <4>, wherein the *Bacillus* bacterium is *Bacillus subtilis*.

<7> The method according to <6>, wherein the *Bacillus subtilis* is *Bacillus subtilis* 168 strain.

<8> The method according to <6> or <7>, wherein the *Bacillus subtilis* is a *Bacillus subtilis* strain having a genome in which at least one region selected from the group consisting of prophage 6 region, prophage 1 region, prophage 4 region, PBSX region, prophage 5 region, prophage 3 region, spb region, pks region, skin region, pps region, prophage 2 region, ydcL-ydeK-ydhU region, yisB-yitD region, yunA-yurT region, cgeE-ypmQ region, yeeK-yesX region, pdp-rocR region, ycxB-sipU region, SKIN-Pro7 region, sbo-ywhH region, yybP-yyaJ region and yncM-fosB region is deleted.

<9> The method according to any one of <6> to <8>, wherein the *Bacillus subtilis* is a *Bacillus subtilis* strain in which all of aprX, aprE, nprB, nprE, bpr, vpr, mpr, epr and wprA genes are deleted or inactivated.

<10> The method according to any one of <6> to <8>, wherein the *Bacillus subtilis* is a *Bacillus subtilis* strain in which a gene selected from the group consisting of sigE, sigF and sigG is deleted.

<11> The method according to any one of <6> to <8>, wherein the *Bacillus subtilis* is a *Bacillus subtilis* strain in which a gene selected from the group consisting of sigE and sigF is deleted.

<12> The method according to any one of <6> to <8>, wherein the *Bacillus subtilis* is a *Bacillus subtilis* strain in which sigF gene is deleted.

<13> The method according to <12>, wherein the *Bacillus subtilis* is a *Bacillus subtilis* strain selected from the group consisting of *Bacillus subtilis* 168 strain, MGB874 strain and Dpr9 strain, or a *Bacillus subtilis* strain obtained by deleting sigF gene from 168 strain, MGB874 strain or Dpr9 strain.

<14> The method according to any one of <6> to <8>, wherein the *Bacillus subtilis* is a *Bacillus subtilis* mutant strain which is obtained by genetic modification of *Bacillus subtilis* MGB874 strain to constitutively express abrB gene or an equivalent gene thereto and in which kinA gene is deleted or inactivated.

<15> The method according to any one of <1> to <14>, wherein the Cry protein is Cry5B.

<16> The method according to any one of <1> to <14>, wherein the Cry protein is Cry5Bt.

<17> The method according to any one of <1> to <14>, wherein the Cry protein is a mosquitocidal protein selected from the group consisting of Cry4Aa, Cry4Ba and Cry11Aa.

<18> An expression plasmid for expressing a Cry protein in a *Bacillus* bacterium, comprising a polynucleotide encoding a replication protein consisting of the amino acid sequence set forth in SEQ ID NO: 9 or a protein having an identity of 80% or more, more preferably 90% or more, more preferably 95% or more, more preferably 96% or more, more preferably 97% or more, more preferably 98% or more, and more preferably 99% or more with the amino acid sequence of the replication protein and involved in replication initiation, wherein a gene encoding the Cry protein is operably linked to a regulatory region comprising a σA-dependent promoter or a σH-dependent promoter.

<19> The expression plasmid according to <18>, wherein the regulatory region comprising a σA-dependent promoter or a σH-dependent promoter differs from a regulatory region of a gene encoding the Cry protein in a microorganism from which the gene is derived.

<20> The expression plasmid according to <18> or <19>, wherein the regulatory region comprising a σA-dependent promoter or a σH-dependent promoter comprises a regulatory region of spoVG gene or a regulatory region of a cellulase gene of *Bacillus* sp. KSM-S237 strain.

<21> The expression plasmid according to <20>, wherein the regulatory region of a cellulase gene of *Bacillus* sp. KSM-S237 strain is a transcription initiation regulatory region and a translation initiation region of the gene.

<22> The expression plasmid according to any one of <18> to <21>, wherein the Cry protein is Cry5B.

<23> The expression plasmid according to any one of <18> to <21>, wherein the Cry protein is Cry5Bt.

<24> The expression plasmid according to any one of <18> to <21>, wherein the Cry protein is a mosquitocidal protein selected from the group consisting of Cry4Aa, Cry4Ba and Cry11Aa.

<25> A *Bacillus* bacterium comprising the expression plasmid according to any one of <18> to <24> introduced therein.

<26> The *Bacillus* bacterium according to <25>, which is *Bacillus subtilis*, *Bacillus megaterium* or *Bacillus brevis*.

<27> The *Bacillus subtilis* according to <26>, which is *Bacillus subtilis* 168 strain.

<28> The *Bacillus subtilis* according to <26> or <27>, which is a *Bacillus subtilis* strain having a genome in which at least one region selected from the group consisting of prophage 6 region, prophage 1 region, prophage 4 region, PBSX region, prophage 5 region, prophage 3 region, spb region, pks region, skin region, pps region, prophage 2 region, ydcL-ydeK-ydhU region, yisB-yitD region, yunA-yurT region, cgeE-ypmQ region, yeeK-yesX region, pdp-rocR region, ycxB-sipU region, SKIN-Pro7 region, sbo-ywhH region, yybP-yyaJ region and yncM-fosB region is deleted.

<29> The *Bacillus subtilis* according to any one of <26> to <28>, which is a *Bacillus subtilis* strain having a genome in which prophage 6 region, prophage 1 region, prophage 4 region, PBSX region, prophage 5 region, prophage 3 region, spb region, pks region, skin region, pps region, prophage 2 region, ydcL-ydeK-ydhU region, yisB-yitD region, yunA-yurT region, cgeE-ypmQ region, yeeK-yesX region, pdp-rocR region, ycxB-sipU region, SKIN-Pro7 region, sbo-ywhH region, yybP-yyaJ region and yncM-fosB region are deleted.

<30> The *Bacillus subtilis* according to any one of <26> to <29>, which is a *Bacillus subtilis* strain in which at least one gene selected from the group consisting of aprX, aprE, nprB, nprE, bpr, vpr, mpr, epr and wprA is deleted or inactivated.

<31> The *Bacillus subtilis* according to any one of <26> to <30>, which is a *Bacillus subtilis* strain in which aprX, aprE, nprB, nprE, bpr, vpr, mpr, epr and wprA genes are deleted or inactivated.

<32> The *Bacillus subtilis* according to any one of <26> to <31>, which is a *Bacillus subtilis* strain in which at least one gene selected from the group consisting of sigE, sigF and sigG is deleted or inactivated.

<33> The *Bacillus subtilis* according to any one of <26> to <32>, which is a *Bacillus subtilis* strain in which sigF gene is deleted or inactivated.

<34> The *Bacillus subtilis* according to any one of <26> to <33>, which is a *Bacillus subtilis* which is obtained by genetic modification to constitutively express abrB gene or an equivalent gene thereto and in which kinA gene is deleted or inactivated.

<35> The expression plasmid or *Bacillus subtilis* according to any one of <18> to <34>, wherein the regulatory region comprising a σA-dependent promoter is a regulatory region of a cellulase gene of *Bacillus* sp. KSM-S237 strain.

<36> The expression plasmid or *Bacillus subtilis* according to <35>, wherein the regulatory region of a cellulase gene of *Bacillus* sp. KSM-S237 strain is a sequence having an identity of 80% or more, more preferably 90% or more, further preferably 95% or more and still further preferably 98% or more with the nucleotide sequence set forth in SEQ ID NO: 10, and maintaining a function involved in transcription and a function involved in translation of the gene as a σA factor-dependent promoter.

<37> The expression plasmid or *Bacillus subtilis* according to any one of <18> to <34>, wherein the regulatory region comprising a σH-dependent promoter is a regulatory region of a spoVG gene of *Bacillus subtilis* Marburg No. 168 (*Bacillus subtilis* 168 strain).

<38> The expression plasmid or *Bacillus subtilis* according to <37>, wherein the regulatory region of spoVG gene is a sequence having a nucleotide sequence having an identity of 80% or more, more preferably 90% or more, further preferably 95% or more and still further preferably 98% or more with the nucleotide sequence set forth in SEQ ID NO: 12, and maintaining a function involved in transcription and a function involved in translation of the gene as a σH factor-dependent promoter.

EXAMPLES

Example 1

Production of Culture Product Containing Cry5B Protein

1. Synthesis of Artificial Gene

*Bacillus thuringiensis* YBT-1518-derived insecticidal protein gene cry5B (GenBank: CP005935.1, SEQ ID NO: 1) was artificially synthesized by GenScript Biotech Corporation (U.S.A.). The synthesized gene (3738 bp) was cloned into a KpnI-HindIII site of pUC57 to obtain pUC57-cry5B.

2. Construction of Expression Plasmid

In construction of all expression plasmids, pHY300PLK (Takara Bio Inc.) was used as a vector and S237 cellulase gene-derived sequence was used as a terminator. A promoter derived from S237 cellulase gene [Hakamada et al, Biosci. Biotechnol. Biochem., 64 (2000), 2281-2289] or spoVG gene of *Bacillus subtilis* 168 strain, was used. A signal sequence derived from S237 cellulase is used or not used. Full length Cry5B gene (cry5B) or truncated (cry5Bt) was used. Eight types of plasmids were prepared by using these in combination (FIGS. 1-A to D). The full length of cry5B gene (3738 bp) is set forth in SEQ ID NO: 1. The nucleotide sequence from nucleotide Nos. 2095-3738 is the region to be decomposed within the intestine of a nematode; whereas, the nucleotide sequence from nucleotide Nos. 1-2094 is a sequence encoding crystal toxin, which is activated after the decomposition [Hui et al, 2012, Biochemistry, vol 11, p 9911-21]. The full-length cry5B gene has the whole sequence of nucleotide Nos. 1-3738; whereas the truncated gene thereof has a sequence of nucleotide Nos. 1-2094.

Construction was carried out in accordance with the method instructed by the protocol of In-Fusion (R) HD EcoDry™ Cloning Kit. The processes for producing individual plasmids were shown in FIGS. 1-A to D.

2.1 Construction of pPsScry5B and pPsScry5Bt

Using a primer set of vect+psF and vect+tR, shown in Table 2 and pHYS237 DNA as a template, a vector containing the promoter, signal and terminator regions of S237 was amplified. Next, using pUC57-cry5B DNA as a template and a primer set of cry5BpssF and cry5BtR (or T237-cry5BatRN), an insert of full-length (or truncated) cry5B gene was amplified by PCR. Subsequently, using In-Fusion (R) HD EcoDry™ Cloning Kit (company: Clontech), the vector and the insert were ligated, and thereafter, *Escherichia coli* HB101 competent cells (Takara Bio Inc.) were transformed with the resultant construct. Transformants were screened based on tetracycline resistance, confirmed by colony PCR and designated as pPsScry5B (or pPsScry5Bt) (FIG. 1-A). The plasmid was extracted, further confirmed by PCR and checked for the digestion pattern of the plasmid by use of restriction enzymes EcoRI, SpeI and XbaI.

TABLE 2

| No | Name of primer | Sequence (5'-3') | SEQ ID NO: |
|---|---|---|---|
| 1 | vectR | GGGAATTCCTGTTATAAAAA | 13 |
| 2 | S237F | ATGATGTTAAGAAAGAAAACA | 14 |
| 3 | vect-PvgF | ATAACAGGAATTCCCTAAGAAAAGTGATTCTGGGA | 15 |
| 4 | S237-PvgR | TCTTTCTTAACATCATAGTAGTTCACCACCTTTTCC | 16 |
| 5 | T237-cry5BatRN | AACTAGTTTAATAGATTATTGGATTTTTGGAACAAACTC | 17 |
| 6 | cry5BpF | TATTTAGGAGGTAATATGATGGCAACAATTAATGAGTT | 18 |
| 7 | cry5BpssF | CCGGCAGCTCTTGCAATGGCAACAATTAATGAGTT | 19 |
| 8 | cry5BtR | AACTAGTTTAATAGATTATTGATTATTATTCATAC | 20 |
| 9 | vect+psF | TGCAAGAGCTGCCGGAAATA | 21 |
| 10 | vect+tR | TCTATTAAACTAGTTATAGG | 22 |
| 11 | vect+pF | ATTACCTCCTAAATATTTTT | 23 |
| 12 | cry5BaF | GCAACAATTAATGAGTTGTATCC | 24 |
| 13 | cry5BaF1 | CGTTCAAAATCATCCGTAAATG | 25 |

TABLE 2-continued

| No | Name of primer | Sequence (5'-3') | SEQ ID NO: |
|---|---|---|---|
| 14 | cry5BaR1 | AAATGCATGAACCACTTCCAC | 26 |
| 15 | cry5BatR | ATTGGATTTTTGGAACAAACTC | 27 |
| 16 | S237Pfw | TAAAAGTAGAAGACAAAGGA | 28 |
| 17 | S237fw | CGATATATGTAAGCGGTTAAC | 29 |
| 18 | S237rv | CAATTTAAAATCGCTACCCT | 30 |
| 19 | cry5Ba-PvgR | AACTCATTAATTGTTGCCATAGTAGTTCACCACCTTTTCC | 31 |
| 20 | vectR-F | TTTTTATAACAGGAATTCCC | 32 |
| 21 | SEQ-P1 | GGATCAACTTTGGGAGAGAG | 33 |
| 22 | SEQ-P2 | CAAGTAGTAATAATATAGAT | 34 |
| 23 | SEQ-P3 | GCAACAATTAATGAGTTGTA | 35 |
| 24 | SEQ-P4 | AGTACACCAGAAAGAGTAAT | 36 |
| 25 | SEQ-P5 | TCAAGGTGGTAAATTAGATT | 37 |
| 26 | SEQ-P6 | TCACGTCCTGATCAAAAAAT | 38 |
| 27 | SEQ-P7 | TACCTGCTGGAAGTTTCTAT | 39 |
| 28 | SEQ-P8 | ACAGAGGCCGAAATGTAGTA | 40 |
| 29 | SEQ-P9 | ACAGCATATGACCAAGAACG | 41 |
| 30 | SEQ-P10 | GAGAATATGTGGAAACACAC | 42 |
| 31 | frag1-F | CATACCCTTACTTGATCAAAGGTTG | 43 |
| 32 | frag1-R | AACAGGGTTATTACAATCACAGTGA | 44 |
| 33 | frag2-F | AATGGTAACAATGCAGTTAAACTTT | 45 |
| 34 | frag2-R | AAGCTTCTAGAGATCTGCAGGTCGA | 46 |

2.2 Construction of pPscry5B and pPscry5Bt

Using a primer set of vect+pF and vect+tR, shown in Table 2, and pHYS237 DNA as a template, a vector containing the promoter and terminator regions of S237 was amplified. Next, using pUC57-cry5B DNA as a template and a primer set of cry5BpF and cry5BtR (or T237-cry5BatRN), an insert of full-length (or truncated) cry5B gene was amplified by PCR. Subsequently, using In-Fusion (R) HD EcoDry™ Cloning Kit (company: Clontech), the vector and the insert were ligated and *Escherichia coli* HB101 competent cells (Takara Bio Inc.) were transformed with the resultant construct. Transformants were screened based on tetracycline resistance, confirmed by colony PCR and designated as pPscry5B (or pPscry5Bt) (FIG. 1-B). The plasmid was extracted, further confirmed by PCR and checked for the digestion pattern of the plasmid by use of restriction enzymes EcoRI, SpeI and XbaI.

2.3 Construction of pPvcry5B and pPvcry5Bt

Using a primer set of vectR and vect+tR, shown in Table 2 and pHYS237 DNA as a template, a vector containing a terminator region of S237 was amplified. Next, using pUC57-cry5B DNA as a template and a primer set of cry5BaF and cry5BtR (or T237-cry5BatRN), an insert of full-length (or truncated) cry5B gene was amplified by PCR. Also, using a primer set of Vect-PvgF and cry5Ba-PvgR, and genomic DNA of *Bacillus subtilis* 168 strain as a template, a promoter region of spoVG gene was amplified as a second insert. Subsequently, using In-Fusion (R) HD EcoDry™ Cloning Kit (company: Clontech), the vector and the second insert were ligated and *Escherichia coli* HB101 competent cells (Takara Bio Inc.) were transformed with the resultant construct. Transformants were screened based on tetracycline resistance, confirmed by colony PCR and designated as pPvcry5B (or pPvcry5Bt) (FIG. 1-C). The plasmid was extracted, further confirmed by PCR and checked for the digestion pattern of the plasmid by use of restriction enzymes EcoRI, SpeI and XbaI.

2.4 Construction of pPvScry5B and pPvScry5Bt

Using a primer set of vectR and vect+tR, shown in Table 2 and pHYS237 DNA as a template, a vector containing a terminator region of S237 was amplified. Next, using pPsScry5B DNA as a template and a primer set of S237F and cry5BtR (or T237-cry5BatRN), an insert of full-length (or truncated) cry5B gene having a signal sequence of S237 ligated thereto was amplified by PCR. Also, using a primer set of Vect-PvgF and S237-PvgR, and genomic DNA of *Bacillus subtilis* 168 strain as a template, a promoter region of spoVG gene was amplified as a second insert. Subsequently, using In-Fusion (R) HD EcoDry™ Cloning Kit (company: Clontech), the vector and the second insert were ligated, and thereafter, *Escherichia coli* HB101 competent cells (Takara Bio Inc.) were transformed with the resultant construct. Transformants were screened based on tetracycline resistance, confirmed by colony PCR and designated as pPvScry5B (or pPvScry5Bt) (FIG. 1-D). The plasmid was extracted, further confirmed by PCR and checked for the digestion pattern of the plasmid by use of restriction enzymes EcoRI, SpeI and XbaI.

3. Sequencing of Plasmid

Eight types of plasmids thus constructed were subjected to sequencing. Templates for sequencing was prepared by PCR. With respect to 4 types of full-length cry5B plasmids, 5' and 3' side fragments of each plasmid were prepared by use of primers frag1-F and frag1-R or frag2-F and frag2-R shown in Table 2. With respect to four types of truncated cry5B plasmids, fragments were prepared by use of primers frag1-F and frag2-R shown in Table 2. The PCR products of them were subjected to sequencing using 10 primers of SEQ-P1 to SEQ-P10 shown in Table 2. As a result of the analysis, no mutation was found in all plasmids. From this, it was confirmed that all plasmids were successfully constructed as designed.

4. Expression of Cry5B Protein and Truncated Cry5B (Cry5Bt) protein in Wild-Type *Bacillus Subtilis* Strain by Plasmid Having Secretion Signal Tryptophan auxotrophy-recovered *Bacillus subtilis* 168 strain (168T strain) (JP-A-2017-79640) were transformed with the four types of constructed plasmids having a secretion signal (FIGS. 1-A, D). The obtained transformants were cultured in a 2×L/mal medium containing 2% (w/v) of Bacto Tryptone, 1.0% (w/v) of yeast extract, 1.0% (w/v) of sodium chloride, 0.00075% (w/v) of manganese sulfate pentahydrate (manufactured by Wako Pure Chemical Industries, Ltd.), 7.5% (w/v) of maltose monohydrate (manufactured by Wako Pure Chemical Industries, Ltd.) and 0.0015% (w/v) of tetracycline hydrochloride for 3 days at 30° C. while shaking at 250 rpm. Each of the culture solutions (1 mL) was centrifuged at 15000 rpm and 4° C. to separate into a culture supernatant and cells. The prepared culture supernatant was checked for Cry5B expression by SDS-PAGE, and as a result, no Cry5B band was observed (FIG. 2).

5. Expression of Cry5B Protein by Plasmid Having No Secretion Signal in Wild Type *Bacillus Subtilis* Strain Among the constructed plasmids having no secretion signal (FIGS. 1-B, C), two types of plasmids <5> and <6> (FIG. 3) for expressing Cry5B protein were used herein. Tryptophan auxotrophy-recovered *Bacillus subtilis* 168 strains (168T strain) were transformed with plasmids <5> and <6>. The obtained transformants were each cultured in a 2×L/mal medium for 3 days at 30° C. while shaking at 250 rpm. Each of the culture solutions (1 mL) was centrifuged at 15000 rpm and 4° C. to separate into a culture supernatant and cells. The cell pellets were washed with 1×PBS, and then suspended in 1 mL of 1×PBS. To the suspensions, 1 mg/mL lysozyme was added and the mixtures were kept warm at 37° C. for one hour. Subsequently, the cells were crushed by sonication using BIORUPTOR (Cosmo Bio) for 30 seconds. After sonication was repeated 20 times, the crushed cells were centrifuged at 15000 rpm and 4° C. for 30 minutes. The supernatants were discarded and the precipitates were suspended in 1 mL of 1×PBS to obtain cell lysates. The prepared cell lysates were checked for Cry5B expression by SDS-PAGE, and as a result, high expression by pHY-Pscry5B (<5>) and pHY-Pvcry5B (<6>) was confirmed. Plasmids pHY-Pscry5B and pHY-Pvcry5B have a full-length of 140 kD, which matched with estimated sizes (FIG. 3).

6. Expression of Cry5B Protein in *Bacillus Subtilis* Mutant Strain (1)

A *Bacillus subtilis* mutant strain in which a large region of the genome of wild type *Bacillus subtilis* strain is deleted (MGB874 strain; JP-B-4955358), a protease deficient strain (Dpr9 strain; JP-B-4485341), sigF deficient strain (ΔsigF strain; JP-B-4336082), MGB874ΔsigF strain and Dpr9ΔsigF strain were used as hosts and each transformed with pHY-Pscry5B. MGB874ΔsigF strain and Dpr9ΔsigF strain, MGB874abrB*ΔkinA strain (JP-A-2017-79639) were prepared in the same manner as in ΔsigF strain by removing sigF from MGB874 and Dpr9 strain, respectively. Similarly to the above Section 4, culturing was carried out in a 2×L/mal medium and the prepared cell lysates were analyzed for Cry5B expression by SDS-PAGE. As a result, it was found that bands of Cry5B expressed in MGB874 strain, Dpr9 strain, sigF deficient strain, MGB874ΔsigF strain and Dpr9ΔsigF strain are clearly thick compared to that of a wild-type 168T strain (FIG. 4-A).

7. Expression of Cry5B Protein in *Bacillus Subtilis* Mutant (2)

A sigE deficient strain (ΔsigE strain; JP-B-4336082) was used as a host and transformed with pHY-Pscry5B. Similarly to the above Section 4, culturing was carried out in the 2×L/mal medium and the prepared cell lysate was analyzed for Cry5B expression by SDS-PAGE. As a result, it was found that the band of Cry5B in sigE deficient strain is apparently thick (FIG. 4-B).

8. Expression of Cry5B Protein in *Bacillus Megaterium*

Plasmid pHY-Pscry5B for expressing Cry5B protein was introduced to *Bacillus megaterium* ATCC 14581 strain (hereinafter referred to as 14581 strain) by a protoplast method. The obtained recombinant strain was cultured in the 2×L/mal medium in the same manner as in Example 1, Section 5, and the prepared cell lysate was analyzed for Cry5B expression by SDS-PAGE. As a result, in a transformant having pHY-Pscry5B introduced therein, a thick Cry5B band was observed.

9. Quantification of Cry5B Protein Expressed

Using image software, ImageJ, (rsb.info.nih.gov/ij/download.html) developed by the National Institute of Health (NIH), bands on SDS-PAGE were quantified. Bovine serum albumin (BSA) (manufactured by Wako Pure Chemical Industries, Ltd.) as a standard protein, and Cry5B expressed in pHY-Pscry5B transformant were subjected to SDS-PAGE and staining was carried out by Bio-Safe™ Coomassie (BIO-RAD) while shaking for one hour. After color was removed by ion-exchange water, the gel was photographed.

The brightness of individual bands in an image of SDS-PAGE was analyzed by ImageJ to prepare a BSA calibration curve. Based on this calibration curve, the amounts of Cry5B proteins were calculated (Table 3, Table 4, Table 5). As shown in Table 3, Cry5B productivity in wild type *Bacillus subtilis* strain was 1.1 g/L, which was found to be 15 times as high as the value (75 mg/L) produced by a recombinant and described in literatures. The productivity was further improved twice or more by using MGB874ΔsigF strain.

TABLE 3

Productivity of Cry5B protein (1)

| Host strain | Amount of Cry5B produced (g/L) |
|---|---|
| 168T | 1.1 |
| MGB874 | 1.7 |
| Dpr9 | 1.7 |
| ΔsigF | 1.8 |
| MGB874ΔsigF | 2.5 |
| Dpr9ΔsigF | 2.0 |
| MGB874abrB*ΔkinA | 1.9 |

TABLE 4

Productivity of Cry5B protein (2)

| Host strain | Amount of Cry5B produced (g/L) |
|---|---|
| 168T | 1.2 |
| ΔsigE | 1.7 |

TABLE 5

Productivity of Cry5B protein (3)

| Host strain | Amount of Cry5B produced (g/L) |
|---|---|
| 14581 strain | 1.3 |

10. Evaluation of Cry5B Activity 10.1 Preparation of Egg-Bearing Adult Insect

A solution containing 750 μL of an *Escherichia coli* (*E. coli* OP50-1) solution (1 g wet-weight/6 mL S medium), 100 μL of a streptomycin (1 mg/mL) solution and 1000 L1 larvae (*Caenorhabditis elegans*) was dropped on an NGM plate and cultured in an incubator at 20° C. for 3 to 4 days to obtain egg-bearing adult insects.

10.2 Preparation of First-Stage (L1) Larvae

The NGM plate (Table 6) on which nematodes were cultured was washed about three times with S basal buffer and all were transferred to a 15 mL centrifuge tube. The supernatant was discarded and nematodes precipitated were transferred to a 1.5 mL-Eppendorf tube. After allowed to stand still for a while, the supernatant up to 1 mL was removed. To the Eppendorf tube, 250 μL of 4M NaOH and 250 μL of a sodium hypochlorite solution (Wako) were added and slightly stirred. After allowed to stand still for 3 minutes, the tube was spun down by a bench-top mini-centrifuge for about 30 seconds. The supernatant was removed while remaining a precipitate, and S basal buffer was added up to 1.5 mL. After slightly stirred, the tube was spun down for about 30 seconds. This operation was repeated three times. The total amount of the egg precipitate thus obtained was transferred to a petri dish of 35 mm in diameter, cultured at 20° C. for about 24 hours to obtain a first-stage larvae (L1 larva) hatched.

10.3 L1 Growth Assay

In accordance with a method of Bischof et al. (Methods in Molecular Biology, vol. 331, pp 139-154, *C. elegans*: Methods and applications, Edited by: K. Strange, Humana Press), L1 growth assay was carried out. To individual wells of a 48-well flat-bottom plate, 20 μL of a 1 g/35 mL *Escherichia coli* solution, 20 μL of a 1 mg/mL streptomycin solution, 10 L1-larvae and an appropriate amount of Cry5B protein expressed in *Bacillus subtilis* were added and the total amount was adjusted with S medium (Table 7) to 200 μL. As the amount of Cry5B protein, 1.25, 2.5 and 5 μg/mL were used. As the control, *Bacillus subtilis* to which a vector (pHY300PLK) was introduced was used. After culturing was carried out at 20° C. for 3 days, the nematodes in individual wells were photographed by a camera (FIG. 5). Based on the image photographed, outlines of the nematodes were drawn by use of Image J and the area thereof was calculated. The results are shown in FIG. 6. The growth of nematode was significantly suppressed by use of Cry5B; more specifically, the growth was suppressed by about 80%, even at a concentration of 1.25 μg/mL, compared to the control. From the results, it was demonstrated that Cry5B expressed in *Bacillus subtilis* is toxic to nematodes.

Medium component (1) NGM:

TABLE 6

| <A> | |
|---|---|
| NaCl | 3.0 g |
| Agar powder | 17.0 g |
| Cholesterol (5 mL/mL in EtOH) | 1.0 mL |
| Ultrapure water | 973 mL |
| <B> | |
| 1M CaCl$_2$ | 1.0 mL |
| 1M MgSO$_4$ | 1.0 mL |
| 1M phosphate buffer solution (pH 6.0) | 25 mL |

After A and B were separately sterilized, they were mixed.

(2) S basal buffer: 0.1M NaCl, 0.05M KHPO$_4$ (pH6.0)

(3) S medium:

TABLE 7

| <A> S basal | |
|---|---|
| NaCl | 5.8 g |
| 1M phosphate buffer solution (pH 6.0) | 50 mL |
| Cholesterol (5 mg/mL in EtOH) | 1 mL |
| Ultrapure water | 923 mL |

TABLE 7-continued

<B>

| | |
|---|---|
| 1M citrate buffer solution (pH 6.0) | 10 mL |
| Aqueous trace metal solution | 10 mL |
| 1M CaCl$_2$ | 3 mL |
| 1M MgSO$_4$ | 3 mL |

*Aqueous trace metal solution:
EDTA·Na$_2$ 1.86 g
FeSO$_4$·7H$_2$O 0.69 g
MnCl$_2$·4H$_2$O 0.20 g
ZnSO$_4$·7H$_2$O 0.29 g
CuSO$_4$·5H$_2$O 0.025 g
Ultrapure water 1000 mL After A and B were separately sterilized, they were mixed.

11. Expression of Truncated Cry5B (Cry5Bt) Protein by Plasmid Having No Secretion Signal in Wild Type *Bacillus Subtilis* Strain Plasmid pHY-Pscry5Bt <7> of truncated Cry5B (Cry5Bt) having no secretion signal was used herein. A tryptophan auxotrophy-recovered *Bacillus subtilis* 168 strain (168T strain) was transformed with the plasmid, and the obtained transformant was cultured in a 2×L/mal medium for 3 days at 30° C. while shaking at 250 rpm. The culture solution (1 mL) was centrifuged at 15000 rpm and 4° C. to separate into a culture supernatant and cells. The cell pellet was washed with 1×PBS, and then suspended in 1 mL of 1×PBS. To the suspension, 1 mg/mL lysozyme was added and the mixture was kept warm at 37° C. for one hour. Subsequently, the cells were crushed by sonication using BIORUPTOR (Cosmo Bio) for 30 seconds. After sonication was repeated 20 times, the crushed cells were centrifuged at 15000 rpm and 4° C. for 30 minutes. The supernatant was discarded and the precipitate was suspended in 1 mL of 1×PBS to obtain a cell lysate. The prepared cell lysate was checked for Cry5Bt expression by SDS-PAGE (FIG. 7). As a result, it was confirmed that pHY-Pscry5Bt was highly expressed. The size of the protein band was 79 kD, which was matched with the estimated size of truncated Cry5B.

Example 2

Production of Mosquitocidal Proteins (Cry4Aa, Cry4Ba, Cry11Aa)

1. Synthesis of Artificial Gene

*Bacillus thuringiensis* serovar israelensis-derived insecticidal protein genes, cry4Aa (GenBank: YP_001573833, SEQ ID NO: 3), cry4Ba (GenBank: NC_010076, SEQ ID NO: 5) and cry11Aa (GenBank: NC_010076, SEQ ID NO: 7) were artificially synthesized by GenScript Biotech Corporation (U.S.A.). The synthesized genes were each cloned into a KpnI-HindIII site of pUC57 to obtain plasmids of pUC57-cry4Aa, pUC57-cry4Ba and pUC57-cry11Aa, respectively.

2. Construction of Expression Plasmid

In construction of all expression plasmids, pHY300PLK was used as a vector and an S237 cellulase gene-derived sequence was used as a terminator. A promoter derived from S237 cellulase gene [Hakamada et al, Biosci. Biotechnol. Biochem., 64 (2000), 2281-2289] often handled in our laboratory or derived from spoVG gene of *Bacillus subtilis* 168 strain was used. Using these in combination with the three genes: cry4Aa, cry4Ba and cry11 Aa, 6 types of plasmids shown in FIG. 8 were produced. The promoter of S237 cellulase gene was used for pHY-Pscry4Aa, pHY-Pscry4Ba and pHY-Pscry11Aa; and the promoter of the spoVG gene of *Bacillus subtilis* 168 strain was used for pHY-Pvcry4Aa, pHY-Pvcry4Ba and pHY-Pvcry11Aa. Construction was carried out in accordance with the method instructed by the protocol of In-Fusion (R) HD EcoDry™ Cloning Kit.

2.1 Construction of pHY-Pscry4Aa, pHY-Pscry4Ba and pHY-Pscry11Aa

Using a primer set of vect+pF and vect+tR shown in Table 8 and pHYS237 DNA as a template, a vector containing S237 promoter and terminator regions was amplified. Next, using pUC57-cry4Aa DNA as a template and a primer set of cry4AFPS and cry4ART, an insert of cry4Aa gene was amplified by PCR. Subsequently, using In-Fusion (R) HD EcoDry™ Cloning Kit (company: Clontech), the vector and the insert were ligated and *Escherichia coli* HB101 competent cells (Takara Bio Inc.) were transformed with the resultant construct. Transformants were screened based on tetracycline resistance, confirmed by colony PCR and designated as pHY-Pscry4Aa. The plasmid was extracted, confirmed by PCR and checked for the digestion pattern of the plasmid by use of restriction enzymes.

Similarly to the above, using pUC57-cry4Ba DNA as a template and a primer set of cry4BFPS and cry4BRT, cry4Ba gene was amplified by PCR. Further, using pUC57-cry11Aa DNA as a template and a primer set of cry11AFPS and cry11ART, an insert of cry11Aa gene was amplified by PCR. In this manner, pHY-Pscry4Ba and pHY-Pscry11Aa were constructed.

TABLE 8

| Name of primer | Sequence | SEQ ID NO: |
|---|---|---|
| vect+pF | ATTACCTCCTAAATATTTTT | 47 |
| Vect+pvgF | AGTAGTTCACCACCTTTTCC | 48 |
| vect+tR | TCTATTAAACTAGTTATAGG | 49 |
| cry4AFPS | TATTTAGGAGGTAAATATGATGAATCCT TATCAAAATAA | 50 |
| cry4AFPV | GGAAAAGGTGGTGAACTACTATGAATC CTTATCAAAATAA | 51 |
| cry4ART | CCTATAACTAGTTTAATAGATCACTCG TTCATGCAAATTA | 52 |
| cry4BFPS | TATTTAGGAGGTAAATATGAATTCA GGCTATCCGTT | 53 |
| cry4BFPV | GGAAAAGGTGGTGAACTACTATGAATT CAGGCTATCCGTT | 54 |
| cry4BRT | CCTATAACTAGTTTAATAGATCACTCG TTCATGCAAATTA | 55 |
| cry11AFPS | TATTTAGGAGGTAAATATGATGGAAGAT AGTTCTTTAGA | 56 |

TABLE 8-continued

| Name of primer | Sequence | SEQ ID NO: |
|---|---|---|
| cry11AFPV | GGAAAAGGTGGTGAACTACTATGGAAG ATAGTTCTTTAGA | 57 |
| cry11ART | CCTATAACTAGTTTAATAGACTACTTT AGTAACGGATTAA | 58 |

2.2 Construction of pHY-Pvcry4Aa, pHY-Pvcry4Ba and pHY-Pvcry11Aa

Using a primer set of vect+pvgF and vect+tR, shown in Table 8, and pHY-Pscry5B (refer to Example of Cry5B) as a template, a vector containing the promoter region of spoVG gene and the terminator region of S237 cellulase gene was amplified. Next, using pUC57-cry4Aa DNA as a template and a primer set of cry4AFPV and cry4ART, an insert of cry4Aa gene was amplified by PCR. Subsequently, using In-Fusion (R) HD EcoDry™ Cloning Kit (company: Clontech), the vector and the insert were ligated. *Escherichia coli* HB101 competent cells were transformed (Takara Bio Inc.) with the resultant construct. Transformants were screened based on tetracycline resistance, confirmed by colony PCR and designated as pHY-Pvcry4Aa. The plasmid was extracted, confirmed by PCR and check for the digestion pattern of the plasmid by use of restriction enzymes.

Similarly to the above, using pUC57-cry4Ba DNA as a template and a primer set of cry4BFPV and cry4BRT, a cry4Ba gene was amplified by PCR. Further, using pUC57-cry11Aa DNA as a template and a primer set of cry11AFPV and cry11ART, an insert of cry11Aa gene was amplified by PCR. In this manner, pHY-Pvcry4Ba and pHY-Pvcry11Aa were constructed.

3. Expression of Mosquitocidal Protein in *Bacillus Subtilis*

Six types of plasmids constructed (FIG. 8) were used herein. Tryptophan auxotrophy-recovered *Bacillus subtilis* 168 strain (168T strain) was transformed with each of the six plasmids. The obtained transformants were cultured in a 2×L/mal medium for 3 days at 30° C. while shaking at 250 rpm. The culture solution (1 mL) was centrifuged at 15000 rpm and 4° C. to separate into a culture supernatant and cells. After the cell pellets were washed with 1×PBS and suspended in 1 mL of 1×PBS. To the suspensions, 1 mg/mL lysozyme was added and the mixtures were kept warm at 37° C. for one hour. Subsequently, the cells were crushed by sonication using Biorupter (Cosmo Bio) for 30 seconds. After sonication was repeated 20 times, the crushed cells were centrifuged at 15000 rpm and 4° C. for 30 minutes. The supernatants were discarded and the precipitates were suspended in 1 mL of 1×PBS to obtain cell lysates. The prepared cell lysates were checked for protein expression by SDS-PAGE. As a result, the protein was highly expressed in all plasmids, as shown in FIG. 9.

4. Quantification of a Mosquitocidal Protein Expressed

Using image software, ImageJ, (rsb.info.nih.gov/ij/download.html) developed by the National Institute of Health (NIH), bands on SDS-PAGE were quantified. As a standard protein, bovine serum albumin (BSA) was used. The brightness of individual bands in an image of SDS-PAGE was analyzed by ImageJ to prepare a BSA calibration curve. Based on the calibration curve, the amounts of individual mosquitocidal proteins were calculated. As shown in Table 9, productivities of them were confirmed to fall within the range of 0.6 to 0.7 g/L.

TABLE 9

Productivity of Mosquitocidal protein

| Plasmid | Amount of Mosquitocidal protein produced (g/L) |
|---|---|
| pHY-Pscry4Aa | 0.70 |
| pHY-Pscry4Ba | 0.69 |
| pHY-Pscry11Aa | 0.55 |
| pHY-Pvcry4Aa | 0.58 |
| pHY-Pvcry4Ba | 0.60 |
| pHY-Pvcry11Aa | 0.59 |

5. Evaluation of Activity of Mosquitocidal Protein 5.1 Preparation of Mosquito Larva Tiger mosquito, *Aedes albopictus*, was purchased from SUMIKA TECHNOSERVICE CORPORATION, hatched and put in use. A plastic pan was filled with water up to a height of about 1 cm and a paper filter on which eggs were deposited was placed in the pan. After hatched, feed (TetraMin baby) for tropical fish was given to mosquito larvae every day. Mosquito larvae on day 5 after hatch were used for activity evaluation.

5.2 Evaluation of Mosquitocidal Activity

In accordance with the method of Leetachewa et al. (BMB reports, 47 (2014), 546-551), Cry4Aa, Cry4Ba and Cry11Aa expressed in *Bacillus subtilis* were evaluated for the mosquitocidal activity. A 24-well flat-bottom plate was used herein. To each well, 5-day-old mosquito larvae (10 larvae) were added. The concentration of a mosquitocidal protein was set at 50 µg/mL. A total amount of a sample was adjusted with water up to 1 mL. After the larvae were allowed to stand still at 25° C. for 24 hours, the number of dead mosquito larvae was counted and a mortality rate was calculated. The results are shown in Table 10. Compared to a control (a mortality rate of 0%), the mortality rates of Cry4Aa, Cry4Ba and Cry11Aa were 93.3%, 93.3% and 76.7%, respectively. From the results, it was confirmed that the mosquitocidal proteins expressed in *Bacillus subtilis* have a high mosquitocidal effect.

TABLE 10

Mosquitocidal effect of mosquitocidal protein on mosquito larvae

| Mosquitocidal protein | Mortality rate (%) |
|---|---|
| Control | 0 |
| Cry4Aa | 93.3 |
| Cry4Ba | 93.3 |
| Cry11Aa | 76.7 |

SEQUENCE LISTING

```
<160> NUMBER OF SEQ ID NOS: 58

<210> SEQ ID NO 1
<211> LENGTH: 3738
<212> TYPE: DNA
<213> ORGANISM: Bacillus thuringiensis
<220> FEATURE:
<221> NAME/KEY: CDS
<222> LOCATION: (1)..(3738)

<400> SEQUENCE: 1 atg gca aca att aat gag ttg tat cca gtt cct tat aat gtg cta gct       48
Met Ala Thr Ile Asn Glu Leu Tyr Pro Val Pro Tyr Asn Val Leu Ala
1               5                   10                  15 cat cca att aaa gaa gtc gat gat cct tat tct tgg tca aat tta tta       96
His Pro Ile Lys Glu Val Asp Asp Pro Tyr Ser Trp Ser Asn Leu Leu
            20                  25                  30 aag ggt ata caa gaa ggt tgg gaa gaa tgg gga aaa aca gga caa aaa      144
Lys Gly Ile Gln Glu Gly Trp Glu Glu Trp Gly Lys Thr Gly Gln Lys
        35                  40                  45 aaa ctt ttt gaa gac cat ctt acg att gca tgg aat ctt tat aaa aca      192
Lys Leu Phe Glu Asp His Leu Thr Ile Ala Trp Asn Leu Tyr Lys Thr
    50                  55                  60 gga aaa tta gat tat ttc gct ttg aca aaa gca tca ata tca ttg att      240
Gly Lys Leu Asp Tyr Phe Ala Leu Thr Lys Ala Ser Ile Ser Leu Ile
65                  70                  75                  80 gga ttt att cca ggg gca gaa gca gca gtt ccc ttt att aat atg ttt      288
Gly Phe Ile Pro Gly Ala Glu Ala Ala Val Pro Phe Ile Asn Met Phe
                85                  90                  95 gta gac ttt gtt tgg cct aaa tta ttt ggt gcg aat aca gaa gga aaa      336
Val Asp Phe Val Trp Pro Lys Leu Phe Gly Ala Asn Thr Glu Gly Lys
            100                 105                 110 gat caa cag ttg ttt aat gct atc atg gat gca gtt aat aaa atg gta      384
Asp Gln Gln Leu Phe Asn Ala Ile Met Asp Ala Val Asn Lys Met Val
        115                 120                 125 gat aat aag ttc tta agt tat aat ctt agt aca ctt aat aaa aca att      432
Asp Asn Lys Phe Leu Ser Tyr Asn Leu Ser Thr Leu Asn Lys Thr Ile
    130                 135                 140 gaa gga ctt caa ggt aat tta ggc cta ttt caa aat gct ata caa gta      480
Glu Gly Leu Gln Gly Asn Leu Gly Leu Phe Gln Asn Ala Ile Gln Val
145                 150                 155                 160 gcc att tgt caa ggc agt aca cca gaa aga gta att ttt gat caa aat      528
Ala Ile Cys Gln Gly Ser Thr Pro Glu Arg Val Ile Phe Asp Gln Asn
                165                 170                 175 tgt aca cca tgt aat cca aat caa cct tgt aaa gat gat ttg gat aga      576
Cys Thr Pro Cys Asn Pro Asn Gln Pro Cys Lys Asp Asp Leu Asp Arg
            180                 185                 190 gtt gct tca cgt ttt gat acg gct aat tct caa ttc aca cag cat tta      624
Val Ala Ser Arg Phe Asp Thr Ala Asn Ser Gln Phe Thr Gln His Leu
        195                 200                 205 cca gaa ttt aaa aat cct tgg tcg gat gaa aac tct act cag gaa ttt      672
Pro Glu Phe Lys Asn Pro Trp Ser Asp Glu Asn Ser Thr Gln Glu Phe
    210                 215                 220 aaa aga aca tct gtt gaa tta act tta cca atg tat aca aca gta gct      720
Lys Arg Thr Ser Val Glu Leu Thr Leu Pro Met Tyr Thr Thr Val Ala
225                 230                 235                 240 acg tta cat ctt tta tta tat aaa gga tat ata gaa ttt atg aca aaa      768
Thr Leu His Leu Leu Leu Tyr Lys Gly Tyr Ile Glu Phe Met Thr Lys
                245                 250                 255 tgg aat ttt cac aat gaa caa tat tta aat aat tta aag gta gaa tta      816
Trp Asn Phe His Asn Glu Gln Tyr Leu Asn Asn Leu Lys Val Glu Leu
```

-continued

```
                260                265                270
caa caa ttg ata cac tca tat tca gaa act gtt cgt aca agt ttc ctt      864
Gln Gln Leu Ile His Ser Tyr Ser Glu Thr Val Arg Thr Ser Phe Leu
        275                280                285 caa ttt tta cct acc ttg aat aat cgt tca aaa tca tcc gta aat gct      912
Gln Phe Leu Pro Thr Leu Asn Asn Arg Ser Lys Ser Ser Val Asn Ala
    290                295                300 tat aac cgt tat gtc cgc aat atg act gtt aac tgt tta gat att gct      960
Tyr Asn Arg Tyr Val Arg Asn Met Thr Val Asn Cys Leu Asp Ile Ala
305                310                315                320 gct aca tgg cct aca ttt gat aca cat aat tat cat caa ggt ggt aaa     1008
Ala Thr Trp Pro Thr Phe Asp Thr His Asn Tyr His Gln Gly Gly Lys
            325                330                335 tta gat tta act cgt att att ctt tca gat aca gca gga cca ata gaa     1056
Leu Asp Leu Thr Arg Ile Ile Leu Ser Asp Thr Ala Gly Pro Ile Glu
        340                345                350 gaa tat act act ggc gac aaa act tca gga cct gaa cat agt aac att     1104
Glu Tyr Thr Thr Gly Asp Lys Thr Ser Gly Pro Glu His Ser Asn Ile
    355                360                365 aca cca aat aat att cta gat aca cca tct cca aca tat cag cac tca     1152
Thr Pro Asn Asn Ile Leu Asp Thr Pro Ser Pro Thr Tyr Gln His Ser
370                375                380 ttt gta tct gtt gat tct att gta tat tct aga aaa gaa tta caa caa     1200
Phe Val Ser Val Asp Ser Ile Val Tyr Ser Arg Lys Glu Leu Gln Gln
385                390                395                400 tta gac ata gct act tat agt aca aat aat agt aat aat tgt cac cct     1248
Leu Asp Ile Ala Thr Tyr Ser Thr Asn Asn Ser Asn Asn Cys His Pro
            405                410                415 tat gga tta cga ctt tca tat aca gat gga agc aga tat gat tat gga     1296
Tyr Gly Leu Arg Leu Ser Tyr Thr Asp Gly Ser Arg Tyr Asp Tyr Gly
        420                425                430 gat aat caa cct gat ttt act act tcc aat aac aat tat tgt cat aat     1344
Asp Asn Gln Pro Asp Phe Thr Thr Ser Asn Asn Asn Tyr Cys His Asn
    435                440                445 agc tat act gcc cct att aca ctt gtg aat gca cga cat tta tat aat     1392
Ser Tyr Thr Ala Pro Ile Thr Leu Val Asn Ala Arg His Leu Tyr Asn
450                455                460 gca aaa ggc tct tta caa aat gta gaa tct tta gtg gtt agt act gta     1440
Ala Lys Gly Ser Leu Gln Asn Val Glu Ser Leu Val Val Ser Thr Val
465                470                475                480 aat ggt gga agt ggt tca tgc att tgt gat gca tgg att aat tat tta     1488
Asn Gly Gly Ser Gly Ser Cys Ile Cys Asp Ala Trp Ile Asn Tyr Leu
            485                490                495 cgt cct cct caa aca agt aaa aat gaa tca cgt cct gat caa aaa att     1536
Arg Pro Pro Gln Thr Ser Lys Asn Glu Ser Arg Pro Asp Gln Lys Ile
        500                505                510 aat gtt ttg tat cca ata aca gaa act gta aat aag ggg act gga gga     1584
Asn Val Leu Tyr Pro Ile Thr Glu Thr Val Asn Lys Gly Thr Gly Gly
    515                520                525 aat tta gga gtt att tct gcc tat gtt cca atg gaa ctt gta cca gaa     1632
Asn Leu Gly Val Ile Ser Ala Tyr Val Pro Met Glu Leu Val Pro Glu
530                535                540 aac gtt att gga gat gtt aat gct gat act aaa ttg cca ctt aca caa     1680
Asn Val Ile Gly Asp Val Asn Ala Asp Thr Lys Leu Pro Leu Thr Gln
545                550                555                560 tta aag ggc ttt cca ttt gaa aaa tat ggt tct gag tat aat aat cgg     1728
Leu Lys Gly Phe Pro Phe Glu Lys Tyr Gly Ser Glu Tyr Asn Asn Arg
            565                570                575 ggt atc tct ctt gtt cgc gaa tgg ata aat ggt aac aat gca gtt aaa     1776
```

```
                                              -continued

Gly Ile Ser Leu Val Arg Glu Trp Ile Asn Gly Asn Asn Ala Val Lys
                    580                 585                 590 ctt tct aat agt caa tct gtt ggc ata caa att acg aat caa acc aaa       1824
Leu Ser Asn Ser Gln Ser Val Gly Ile Gln Ile Thr Asn Gln Thr Lys
        595                 600                 605 caa aaa tat gaa ata cgt tgc cgt tat gcg agt aaa gga gat aat aat       1872
Gln Lys Tyr Glu Ile Arg Cys Arg Tyr Ala Ser Lys Gly Asp Asn Asn
610                 615                 620 gtt tat ttt aat gtg gat tta agt gaa aat cca ttt aga aat tcc att       1920
Val Tyr Phe Asn Val Asp Leu Ser Glu Asn Pro Phe Arg Asn Ser Ile
625                 630                 635                 640 tct ttt gga tct act gaa agt tct gtt gta gga gta caa ggt gaa aat       1968
Ser Phe Gly Ser Thr Glu Ser Ser Val Val Gly Val Gln Gly Glu Asn
        645                 650                 655 gga aag tat ata ttg aaa tca atc aca acg gta gaa ata cct gct gga       2016
Gly Lys Tyr Ile Leu Lys Ser Ile Thr Thr Val Glu Ile Pro Ala Gly
660                 665                 670 agt ttc tat gtt cat ata aca aac caa ggt tct tca gat ctc ttt tta       2064
Ser Phe Tyr Val His Ile Thr Asn Gln Gly Ser Ser Asp Leu Phe Leu
        675                 680                 685 gat cgt att gag ttt gtt cca aaa atc caa ttc caa ttc tgt gat aat       2112
Asp Arg Ile Glu Phe Val Pro Lys Ile Gln Phe Gln Phe Cys Asp Asn
        690                 695                 700 aat aat ctt cac tgt gat tgt aat aac cct gtt gac acc gat tgt aca       2160
Asn Asn Leu His Cys Asp Cys Asn Asn Pro Val Asp Thr Asp Cys Thr
705                 710                 715                 720 ttt tgt tgc gtt tgc act agt ctt act gat tgt gat tgt aat aac cct       2208
Phe Cys Cys Val Cys Thr Ser Leu Thr Asp Cys Asp Cys Asn Asn Pro
                725                 730                 735 cgt ggc cta gat tgt acg cta tgt tgt cag gta gaa aat cag cta cct       2256
Arg Gly Leu Asp Cys Thr Leu Cys Cys Gln Val Glu Asn Gln Leu Pro
        740                 745                 750 tct ttt gtg aca ctt aca gat tta caa aat att acg aca caa gta aat       2304
Ser Phe Val Thr Leu Thr Asp Leu Gln Asn Ile Thr Thr Gln Val Asn
        755                 760                 765 gca tta gtt gca tcg agc gaa cat gat aca ctt gca aca gac gtg agt       2352
Ala Leu Val Ala Ser Ser Glu His Asp Thr Leu Ala Thr Asp Val Ser
        770                 775                 780 gat tat gag att gaa gaa gtt gta ctg aaa gta gat gca tta tct ggt       2400
Asp Tyr Glu Ile Glu Glu Val Val Leu Lys Val Asp Ala Leu Ser Gly
785                 790                 795                 800 gaa gtg ttt gga aaa gag aaa aaa gca ttg cgt aaa ttg gta aat cac       2448
Glu Val Phe Gly Lys Glu Lys Lys Ala Leu Arg Lys Leu Val Asn His
                805                 810                 815 aca aaa cgt tta agc aaa gcg cgt aac ctc ttg ata gga gga aat ttt       2496
Thr Lys Arg Leu Ser Lys Ala Arg Asn Leu Leu Ile Gly Gly Asn Phe
        820                 825                 830 gat aac ttg gat gct tgg tac aga ggc cga aat gta gta aac gta tct       2544
Asp Asn Leu Asp Ala Trp Tyr Arg Gly Arg Asn Val Val Asn Val Ser
        835                 840                 845 gat cat gaa cta ttt aag agt gat cat gta tta ttg cca cca cca aca       2592
Asp His Glu Leu Phe Lys Ser Asp His Val Leu Leu Pro Pro Pro Thr
850                 855                 860 ctg tac tca tct tat atg ttc caa aaa gta gag gaa tcg aaa tta aaa       2640
Leu Tyr Ser Ser Tyr Met Phe Gln Lys Val Glu Glu Ser Lys Leu Lys
865                 870                 875                 880 gcg aat aca cgt tat act gtg tct ggt ttt att gca cat gca gaa gat       2688
Ala Asn Thr Arg Tyr Thr Val Ser Gly Phe Ile Ala His Ala Glu Asp
                885                 890                 895
```

```
tta gaa att gtt gtg tct cgt tat ggg caa gaa gtg aag aaa gtg gtt    2736
Leu Glu Ile Val Val Ser Arg Tyr Gly Gln Glu Val Lys Lys Val Val
            900                 905                 910 caa gtt cca tat gga gaa gca ttc cca ttg aca tcg agg gga gcg att    2784
Gln Val Pro Tyr Gly Glu Ala Phe Pro Leu Thr Ser Arg Gly Ala Ile
            915                 920                 925 tgt tgc cct cca cgt tct aca tgt aat gga aaa cct gct gat cca cat    2832
Cys Cys Pro Pro Arg Ser Thr Cys Asn Gly Lys Pro Ala Asp Pro His
    930                 935                 940 ttc ttt agt tac agt att gat gtg gga aca tta gat gta gaa gca aac    2880
Phe Phe Ser Tyr Ser Ile Asp Val Gly Thr Leu Asp Val Glu Ala Asn
945                 950                 955                 960 cct ggt atc gaa ttg ggt ctt cgt att gta gaa cga act gga atg gca    2928
Pro Gly Ile Glu Leu Gly Leu Arg Ile Val Glu Arg Thr Gly Met Ala
                965                 970                 975 cgt gta agt aat tta gaa att cgt gaa gat cgt cca tta aag aaa aat    2976
Arg Val Ser Asn Leu Glu Ile Arg Glu Asp Arg Pro Leu Lys Lys Asn
            980                 985                 990 gaa ctc cgc aat gta caa cgt gca  gca aga aat tgg aga  aca gca tat  3024
Glu Leu Arg Asn Val Gln Arg Ala  Ala Arg Asn Trp Arg  Thr Ala Tyr
            995                 1000                1005 gac caa gaa cgt gca gaa gta  acg gcc ttg att caa  cct gta tta      3069
Asp Gln Glu Arg Ala Glu Val  Thr Ala Leu Ile Gln  Pro Val Leu
        1010                1015                1020 aat caa atc aat gcg ttg tat  gaa aat gaa gat tgg  aat cga gca      3114
Asn Gln Ile Asn Ala Leu Tyr  Glu Asn Glu Asp Trp  Asn Arg Ala
        1025                1030                1035 att cgt tct gga gtt tct tat  cat gac tta gaa gca  att gtt tta      3159
Ile Arg Ser Gly Val Ser Tyr  His Asp Leu Glu Ala  Ile Val Leu
        1040                1045                1050 cca aca tta cca aaa tta aat  cat tgg ttt atg tct  gat atg tta      3204
Pro Thr Leu Pro Lys Leu Asn  His Trp Phe Met Ser  Asp Met Leu
        1055                1060                1065 ggg gaa caa ggt tcc att tta  gct caa ttt caa gaa  gca tta gat      3249
Gly Glu Gln Gly Ser Ile Leu  Ala Gln Phe Gln Glu  Ala Leu Asp
        1070                1075                1080 cgt gcg tat acg caa ctc gaa  gaa agt aca att ctg  cat aat ggt      3294
Arg Ala Tyr Thr Gln Leu Glu  Glu Ser Thr Ile Leu  His Asn Gly
        1085                1090                1095 cat ttc aca aca gat gca gca  aat tgg acg ata gaa  ggc gat gca      3339
His Phe Thr Thr Asp Ala Ala  Asn Trp Thr Ile Glu  Gly Asp Ala
        1100                1105                1110 cat cat gcg ata tta gaa gat  ggt aga cgc gta tta  cgt ctt cca      3384
His His Ala Ile Leu Glu Asp  Gly Arg Arg Val Leu  Arg Leu Pro
        1115                1120                1125 gat tgg tct tct agc gtt tca  caa acc att gaa ata  gaa aat ttt      3429
Asp Trp Ser Ser Ser Val Ser  Gln Thr Ile Glu Ile  Glu Asn Phe
        1130                1135                1140 gat cca gat aaa gaa tat cag  tta gtt ttc cat gca  caa gga gaa      3474
Asp Pro Asp Lys Glu Tyr Gln  Leu Val Phe His Ala  Gln Gly Glu
        1145                1150                1155 gga acg gtc tcc ctt caa cat  ggt gaa gaa gga gaa  tat gtg gaa      3519
Gly Thr Val Ser Leu Gln His  Gly Glu Glu Gly Glu  Tyr Val Glu
        1160                1165                1170 aca cac ccg cat aag tct gcg  aat ttt aca act tca  cac cgt caa      3564
Thr His Pro His Lys Ser Ala  Asn Phe Thr Thr Ser  His Arg Gln
        1175                1180                1185 gga gtc aca ttt gaa aca aat  aaa gta aca gtt gaa  att acc tca      3609
Gly Val Thr Phe Glu Thr Asn  Lys Val Thr Val Glu  Ile Thr Ser
        1190                1195                1200
```

```
gaa gat gga gaa ttc cta gtc gat cat att gcg ctt gtg gaa gct    3654
Glu Asp Gly Glu Phe Leu Val Asp His Ile Ala Leu Val Glu Ala
    1205                1210                1215 cct ctt cct aca gat gac caa agt tca gat gga aat acg act tcc    3699
Pro Leu Pro Thr Asp Asp Gln Ser Ser Asp Gly Asn Thr Thr Ser
    1220                1225                1230 aat acg aat agc aat aca agt atg aat aat aat caa taa            3738
Asn Thr Asn Ser Asn Thr Ser Met Asn Asn Asn Gln
    1235                1240                1245

<210> SEQ ID NO 2
<211> LENGTH: 1245
<212> TYPE: PRT
<213> ORGANISM: Bacillus thuringiensis

<400> SEQUENCE: 2
```

Met Ala Thr Ile Asn Gl

```
                        305                 310                 315                 320
                    Ala Thr Trp Pro Thr Phe Asp Thr His Asn Tyr His Gln Gly Gly Lys
                                    325                 330                 335

Leu Asp Leu Thr Arg Ile Ile Leu Ser Asp Thr Ala Gly Pro Ile Glu
                                    340                 345                 350

Glu Tyr Thr Thr Gly Asp Lys Thr Ser Gly Pro Glu His Ser Asn Ile
                                    355                 360                 365

Thr Pro Asn Asn Ile Leu Asp Thr Pro Ser Pro Thr Tyr Gln His Ser
                                370                 375                 380

Phe Val Ser Val Asp Ser Ile Val Tyr Ser Arg Lys Glu Leu Gln Gln
                    385                 390                 395                 400

Leu Asp Ile Ala Thr Tyr Ser Thr Asn Ser Asn Asn Cys His Pro
                                    405                 410                 415

Tyr Gly Leu Arg Leu Ser Tyr Thr Asp Gly Ser Arg Tyr Asp Tyr Gly
                                    420                 425                 430

Asp Asn Gln Pro Asp Phe Thr Thr Ser Asn Asn Tyr Cys His Asn
                                    435                 440                 445

Ser Tyr Thr Ala Pro Ile Thr Leu Val Asn Ala Arg His Leu Tyr Asn
                                450                 455                 460

Ala Lys Gly Ser Leu Gln Asn Val Glu Ser Leu Val Val Ser Thr Val
                    465                 470                 475                 480

Asn Gly Gly Ser Gly Ser Cys Ile Cys Asp Ala Trp Ile Asn Tyr Leu
                                    485                 490                 495

Arg Pro Pro Gln Thr Ser Lys Asn Glu Ser Arg Pro Asp Gln Lys Ile
                                500                 505                 510

Asn Val Leu Tyr Pro Ile Thr Glu Thr Val Asn Lys Gly Thr Gly Gly
                                    515                 520                 525

Asn Leu Gly Val Ile Ser Ala Tyr Val Pro Met Glu Leu Val Pro Glu
                                    530                 535                 540

Asn Val Ile Gly Asp Val Asn Ala Asp Thr Lys Leu Pro Leu Thr Gln
                    545                 550                 555                 560

Leu Lys Gly Phe Pro Phe Glu Lys Tyr Gly Ser Glu Tyr Asn Arg
                                    565                 570                 575

Gly Ile Ser Leu Val Arg Glu Trp Ile Asn Gly Asn Asn Ala Val Lys
                                    580                 585                 590

Leu Ser Asn Ser Gln Ser Val Gly Ile Gln Ile Thr Asn Gln Thr Lys
                                    595                 600                 605

Gln Lys Tyr Glu Ile Arg Cys Arg Tyr Ala Ser Lys Gly Asp Asn Asn
                                610                 615                 620

Val Tyr Phe Asn Val Asp Leu Ser Glu Asn Pro Phe Arg Asn Ser Ile
                    625                 630                 635                 640

Ser Phe Gly Ser Thr Glu Ser Ser Val Val Gly Val Gln Gly Glu Asn
                                    645                 650                 655

Gly Lys Tyr Ile Leu Lys Ser Ile Thr Thr Val Glu Ile Pro Ala Gly
                                    660                 665                 670

Ser Phe Tyr Val His Ile Thr Asn Gln Gly Ser Ser Asp Leu Phe Leu
                                675                 680                 685

Asp Arg Ile Glu Phe Val Pro Lys Ile Gln Phe Gln Phe Cys Asp Asn
                                    690                 695                 700

Asn Asn Leu His Cys Asp Cys Asn Asn Pro Val Asp Thr Asp Cys Thr
                    705                 710                 715                 720

Phe Cys Cys Val Cys Thr Ser Leu Thr Asp Cys Asp Cys Asn Asn Pro
                                    725                 730                 735
```

-continued

```
Arg Gly Leu Asp Cys Thr Leu Cys Cys Gln Val Glu Asn Gln Leu Pro
            740                 745                 750
Ser Phe Val Thr Leu Thr Asp Leu Gln Asn Ile Thr Thr Gln Val Asn
            755                 760                 765
Ala Leu Val Ala Ser Ser Glu His Asp Thr Leu Ala Thr Asp Val Ser
            770                 775                 780
Asp Tyr Glu Ile Glu Val Val Leu Lys Val Asp Ala Leu Ser Gly
785                 790                 795                 800
Glu Val Phe Gly Lys Glu Lys Lys Ala Leu Arg Lys Leu Val Asn His
                805                 810                 815
Thr Lys Arg Leu Ser Lys Ala Arg Asn Leu Leu Ile Gly Gly Asn Phe
            820                 825                 830
Asp Asn Leu Asp Ala Trp Tyr Arg Gly Arg Asn Val Val Asn Val Ser
            835                 840                 845
Asp His Glu Leu Phe Lys Ser Asp His Val Leu Leu Pro Pro Pro Thr
            850                 855                 860
Leu Tyr Ser Ser Tyr Met Phe Gln Lys Val Glu Glu Ser Lys Leu Lys
865                 870                 875                 880
Ala Asn Thr Arg Tyr Thr Val Ser Gly Phe Ile Ala His Ala Glu Asp
                885                 890                 895
Leu Glu Ile Val Val Ser Arg Tyr Gly Gln Glu Val Lys Lys Val Val
                900                 905                 910
Gln Val Pro Tyr Gly Glu Ala Phe Pro Leu Thr Ser Arg Gly Ala Ile
            915                 920                 925
Cys Cys Pro Pro Arg Ser Thr Cys Asn Gly Lys Pro Ala Asp Pro His
            930                 935                 940
Phe Phe Ser Tyr Ser Ile Asp Val Gly Thr Leu Asp Val Glu Ala Asn
945                 950                 955                 960
Pro Gly Ile Glu Leu Gly Leu Arg Ile Val Glu Arg Thr Gly Met Ala
                965                 970                 975
Arg Val Ser Asn Leu Glu Ile Arg Glu Asp Arg Pro Leu Lys Lys Asn
                980                 985                 990
Glu Leu Arg Asn Val Gln Arg Ala  Ala Arg Asn Trp Arg  Thr Ala Tyr
            995                 1000                1005
Asp Gln  Glu Arg Ala Glu Val  Thr Ala Leu Ile Gln  Pro Val Leu
    1010                1015                1020
Asn Gln  Ile Asn Ala Leu Tyr  Glu Asn Glu Asp Trp  Asn Arg Ala
    1025                1030                1035
Ile Arg  Ser Gly Val Ser Tyr  His Asp Leu Glu Ala  Ile Val Leu
    1040                1045                1050
Pro Thr  Leu Pro Lys Leu Asn  His Trp Phe Met Ser  Asp Met Leu
    1055                1060                1065
Gly Glu  Gln Gly Ser Ile Leu  Ala Gln Phe Gln Glu  Ala Leu Asp
    1070                1075                1080
Arg Ala  Tyr Thr Gln Leu Glu  Glu Ser Thr Ile Leu  His Asn Gly
    1085                1090                1095
His Phe  Thr Thr Asp Ala Ala  Asn Trp Thr Ile Glu  Gly Asp Ala
    1100                1105                1110
His His  Ala Ile Leu Glu Asp  Gly Arg Arg Val Leu  Arg Leu Pro
    1115                1120                1125
Asp Trp  Ser Ser Ser Val Ser  Gln Thr Ile Glu Ile  Glu Asn Phe
    1130                1135                1140
```

```
Asp Pro Asp Lys Glu Tyr Gln Leu Val Phe His Ala Gln Gly Glu
    1145                1150                1155

Gly Thr Val Ser Leu Gln His Gly Glu Gly Glu Tyr Val Glu
    1160                1165                1170

Thr His Pro His Lys Ser Ala Asn Phe Thr Thr Ser His Arg Gln
    1175                1180                1185

Gly Val Thr Phe Glu Thr Asn Lys Val Thr Val Glu Ile Thr Ser
    1190                1195                1200

Glu Asp Gly Glu Phe Leu Val Asp His Ile Ala Leu Val Glu Ala
    1205                1210                1215

Pro Leu Pro Thr Asp Asp Gln Ser Ser Asp Gly Asn Thr Thr Ser
    1220                1225                1230

Asn Thr Asn Ser Asn Thr Ser Met Asn Asn Asn Gln
    1235                1240                1245

<210> SEQ ID NO 3
<211> LENGTH: 3543
<212> TYPE: DNA
<213> ORGANISM: Bacillus thuringiensis
<220> FEATURE:
<221> NAME/KEY: CDS
<222> LOCATION: (1)..(3543)

<400> SEQUENCE: 3 atg aat cct tat caa aat aa

```
cct cct aat cct agt gat tgc gat tac tat aac ata cta gta tta tct    624
Pro Pro Asn Pro Ser Asp Cys Asp Tyr Tyr Asn Ile Leu Val Leu Ser
        195                 200                 205 agt tat gca caa gca gca aac tta cat ctg act gta tta aat caa gcc    672
Ser Tyr Ala Gln Ala Ala Asn Leu His Leu Thr Val Leu Asn Gln Ala
    210                 215                 220 gtc aaa ttt gaa gcg tat tta aaa aac aat cga caa ttc gat tat tta    720
Val Lys Phe Glu Ala Tyr Leu Lys Asn Asn Arg Gln Phe Asp Tyr Leu
225                 230                 235                 240 gag cct ttg cca aca gca att gat tat tat cca gta ttg act aaa gct    768
Glu Pro Leu Pro Thr Ala Ile Asp Tyr Tyr Pro Val Leu Thr Lys Ala
                245                 250                 255 ata gaa gat tac act aat tat tgt gta aca act tat aaa aaa gga tta    816
Ile Glu Asp Tyr Thr Asn Tyr Cys Val Thr Thr Tyr Lys Lys Gly Leu
            260                 265                 270 aat tta att aaa acg acg cct gat agt aat ctt gat gga aat ata aac    864
Asn Leu Ile Lys Thr Thr Pro Asp Ser Asn Leu Asp Gly Asn Ile Asn
        275                 280                 285 tgg aac aca tac aat acg tat cga aca aaa atg act act gct gta tta    912
Trp Asn Thr Tyr Asn Thr Tyr Arg Thr Lys Met Thr Thr Ala Val Leu
    290                 295                 300 gat ctt gtt gca ctc ttt cct aat tat gat gta ggt aaa tat cca ata    960
Asp Leu Val Ala Leu Phe Pro Asn Tyr Asp Val Gly Lys Tyr Pro Ile
305                 310                 315                 320 ggt gtc caa tct gaa ctt act cga gaa att tat cag gta ctt aac ttc    1008
Gly Val Gln Ser Glu Leu Thr Arg Glu Ile Tyr Gln Val Leu Asn Phe
                325                 330                 335 gaa gaa agc ccc tat aaa tat tat gac ttt caa tat caa gag gat tca    1056
Glu Glu Ser Pro Tyr Lys Tyr Tyr Asp Phe Gln Tyr Gln Glu Asp Ser
            340                 345                 350 ctt aca cgt aga ccg cat tta ttt act tgg ctt gat tct ttg aat ttt    1104
Leu Thr Arg Arg Pro His Leu Phe Thr Trp Leu Asp Ser Leu Asn Phe
        355                 360                 365 tat gaa aaa gcg caa act act cct aat aat ttt ttc acc agc cat tat    1152
Tyr Glu Lys Ala Gln Thr Thr Pro Asn Asn Phe Phe Thr Ser His Tyr
    370                 375                 380 aat atg ttt cat tac aca ctt gat aat ata tcc caa aaa tct agt gtt    1200
Asn Met Phe His Tyr Thr Leu Asp Asn Ile Ser Gln Lys Ser Ser Val
385                 390                 395                 400 ttt gga aat cac aat gta act gat aaa tta aaa tct ctt ggt ttg gca    1248
Phe Gly Asn His Asn Val Thr Asp Lys Leu Lys Ser Leu Gly Leu Ala
                405                 410                 415 aca aat att tat att ttt tta tta aat gtc ata agc tta gat aat aaa    1296
Thr Asn Ile Tyr Ile Phe Leu Leu Asn Val Ile Ser Leu Asp Asn Lys
            420                 425                 430 tat cta aat gat tat aat aat att agt aaa atg gat ttt ttt ata act    1344
Tyr Leu Asn Asp Tyr Asn Asn Ile Ser Lys Met Asp Phe Phe Ile Thr
        435                 440                 445 aat ggt act aga ctt ttg gag aaa gaa ctt aca gca gga tct ggg caa    1392
Asn Gly Thr Arg Leu Leu Glu Lys Glu Leu Thr Ala Gly Ser Gly Gln
    450                 455                 460 ata act tat gat gta aat aaa aat att ttc ggg tta cca att ctt aaa    1440
Ile Thr Tyr Asp Val Asn Lys Asn Ile Phe Gly Leu Pro Ile Leu Lys
465                 470                 475                 480 cga aga gag aat caa gga aac cct acc ctt ttt cca aca tat gat aac    1488
Arg Arg Glu Asn Gln Gly Asn Pro Thr Leu Phe Pro Thr Tyr Asp Asn
                485                 490                 495 tat agt cat att tta tca ttt att aaa agt ctt agt atc cct gca aca    1536
Tyr Ser His Ile Leu Ser Phe Ile Lys Ser Leu Ser Ile Pro Ala Thr
```

-continued

```
              500                 505                 510
tat aaa act caa gtg tat acg ttt gct tgg aca cac tct agt gtt gat    1584
Tyr Lys Thr Gln Val Tyr Thr Phe Ala Trp Thr His Ser Ser Val Asp
        515                 520                 525 cct aaa aat aca att tat aca cat tta act acc caa att cca gct gta    1632
Pro Lys Asn Thr Ile Tyr Thr His Leu Thr Thr Gln Ile Pro Ala Val
530                 535                 540 aaa gcg aat tca ctt ggg act gct tct aag gtt gtt caa gga cct ggt    1680
Lys Ala Asn Ser Leu Gly Thr Ala Ser Lys Val Val Gln Gly Pro Gly
545                 550                 555                 560 cat aca gga ggg gat tta att gat ttc aaa gat cat ttc aaa att aca    1728
His Thr Gly Gly Asp Leu Ile Asp Phe Lys Asp His Phe Lys Ile Thr
                565                 570                 575 tgt caa cac tca aat ttt caa caa tcg tat ttt ata aga att cgt tat    1776
Cys Gln His Ser Asn Phe Gln Gln Ser Tyr Phe Ile Arg Ile Arg Tyr
                580                 585                 590 gct tca aat gga agc gca aat act cga gct gtt ata aat ctt agt atc    1824
Ala Ser Asn Gly Ser Ala Asn Thr Arg Ala Val Ile Asn Leu Ser Ile
            595                 600                 605 cca ggg gta gca gaa ctg ggt atg gca ctc aac ccc act ttt tct ggt    1872
Pro Gly Val Ala Glu Leu Gly Met Ala Leu Asn Pro Thr Phe Ser Gly
    610                 615                 620 aca gat tat acg aat tta aaa tat aaa gat ttt cag tac tta gaa ttt    1920
Thr Asp Tyr Thr Asn Leu Lys Tyr Lys Asp Phe Gln Tyr Leu Glu Phe
625                 630                 635                 640 tct aac gag gtg aaa ttt gct cca aat caa aac ata tct ctt gtg ttt    1968
Ser Asn Glu Val Lys Phe Ala Pro Asn Gln Asn Ile Ser Leu Val Phe
                645                 650                 655 aat cgt tcg gat gta tat aca aac aca aca gta ctt att gat aaa att    2016
Asn Arg Ser Asp Val Tyr Thr Asn Thr Thr Val Leu Ile Asp Lys Ile
                660                 665                 670 gaa ttt ctg cca att act cgt tct ata aga gag gat aga gag aaa caa    2064
Glu Phe Leu Pro Ile Thr Arg Ser Ile Arg Glu Asp Arg Glu Lys Gln
            675                 680                 685 aaa tta gaa aca gta caa caa ata att aat aca ttt tat gca aat cct    2112
Lys Leu Glu Thr Val Gln Gln Ile Ile Asn Thr Phe Tyr Ala Asn Pro
    690                 695                 700 ata aaa aac act tta caa tca gaa ctt aca gat tat gac ata gat caa    2160
Ile Lys Asn Thr Leu Gln Ser Glu Leu Thr Asp Tyr Asp Ile Asp Gln
705                 710                 715                 720 gcc gca aat ctt gtg gaa tgt att tct gaa gaa tta tat cca aaa gaa    2208
Ala Ala Asn Leu Val Glu Cys Ile Ser Glu Glu Leu Tyr Pro Lys Glu
                725                 730                 735 aaa atg ctg tta tta gat gaa gtt aaa aat gcg aaa caa ctt agt caa    2256
Lys Met Leu Leu Leu Asp Glu Val Lys Asn Ala Lys Gln Leu Ser Gln
                740                 745                 750 tct cga aat gta ctt caa aac ggg gat ttt gaa tcg gct acg ctt ggt    2304
Ser Arg Asn Val Leu Gln Asn Gly Asp Phe Glu Ser Ala Thr Leu Gly
            755                 760                 765 tgg aca aca agt gat aat atc aca att caa gaa gat gat cct att ttt    2352
Trp Thr Thr Ser Asp Asn Ile Thr Ile Gln Glu Asp Asp Pro Ile Phe
    770                 775                 780 aaa ggg cat tac ctt cat atg tct ggg gcg aga gac att gat ggt acg    2400
Lys Gly His Tyr Leu His Met Ser Gly Ala Arg Asp Ile Asp Gly Thr
785                 790                 795                 800 ata ttt ccg acc tat ata ttc caa aaa att gat gaa tca aaa tta aaa    2448
Ile Phe Pro Thr Tyr Ile Phe Gln Lys Ile Asp Glu Ser Lys Leu Lys
                805                 810                 815 ccg tat aca cgt tac cta gta agg gga ttt gta gga agt agt aaa gat    2496
```

```
                                                                -continued

Pro Tyr Thr Arg Tyr Leu Val Arg Gly Phe Val Gly Ser Ser Lys Asp
            820                 825                 830 gta gaa cta gtg gtt tca cgc tat ggg gaa gaa att gat gcc atc atg    2544
Val Glu Leu Val Val Ser Arg Tyr Gly Glu Glu Ile Asp Ala Ile Met
            835                 840                 845 aat gtt cca gct gat tta aac tat ctg tat cct tct acc ttt gat tgt    2592
Asn Val Pro Ala Asp Leu Asn Tyr Leu Tyr Pro Ser Thr Phe Asp Cys
        850                 855                 860 gaa ggg tct aat cgt tgt gag acg tcc gct gtg ccg gct aac att ggg    2640
Glu Gly Ser Asn Arg Cys Glu Thr Ser Ala Val Pro Ala Asn Ile Gly
865                 870                 875                 880 aac act tct gat atg ttg tat tca tgc caa tat gat aca ggg aaa aag    2688
Asn Thr Ser Asp Met Leu Tyr Ser Cys Gln Tyr Asp Thr Gly Lys Lys
                885                 890                 895 cat gtc gta tgt cag gat tcc cat caa ttt agt ttc act att gat aca    2736
His Val Val Cys Gln Asp Ser His Gln Phe Ser Phe Thr Ile Asp Thr
            900                 905                 910 ggg gca tta gat aca aat gaa aat ata ggg gtt tgg gtc atg ttt aaa    2784
Gly Ala Leu Asp Thr Asn Glu Asn Ile Gly Val Trp Val Met Phe Lys
            915                 920                 925 ata tct tct cca gat gga tac gca tca tta gat aat tta gaa gta att    2832
Ile Ser Ser Pro Asp Gly Tyr Ala Ser Leu Asp Asn Leu Glu Val Ile
    930                 935                 940 gaa gaa ggg cca ata gat ggg gaa gca ctg tca cgc gtg aaa cac atg    2880
Glu Glu Gly Pro Ile Asp Gly Glu Ala Leu Ser Arg Val Lys His Met
945                 950                 955                 960 gag aag aaa tgg aac gat caa atg gaa gca aaa cgt tcg gaa aca caa    2928
Glu Lys Lys Trp Asn Asp Gln Met Glu Ala Lys Arg Ser Glu Thr Gln
                965                 970                 975 caa gca tat gat gta gcg aaa caa gcc att gat gct tta ttc aca aat    2976
Gln Ala Tyr Asp Val Ala Lys Gln Ala Ile Asp Ala Leu Phe Thr Asn
            980                 985                 990 gta caa gat gag gct tta cag ttt gat acg aca ctc gct caa att cag    3024
Val Gln Asp Glu Ala Leu Gln Phe Asp Thr Thr Leu Ala Gln Ile Gln
            995                 1000                1005 tac gct gag tat ttg gta caa tcg att cca tat gtg tac aat gat        3069
Tyr Ala Glu Tyr Leu Val Gln Ser Ile Pro Tyr Val Tyr Asn Asp
    1010                1015                1020 tgg ttg tca gat gtt cca ggt atg aat tat gat atc tat gta gag        3114
Trp Leu Ser Asp Val Pro Gly Met Asn Tyr Asp Ile Tyr Val Glu
    1025                1030                1035 ttg gat gca cga gtg gca caa gcg cgt tat ttg tat gat aca aga        3159
Leu Asp Ala Arg Val Ala Gln Ala Arg Tyr Leu Tyr Asp Thr Arg
    1040                1045                1050 aat att att aaa aat ggt gat ttt aca caa ggg gta atg ggg tgg        3204
Asn Ile Ile Lys Asn Gly Asp Phe Thr Gln Gly Val Met Gly Trp
    1055                1060                1065 cat gta act gga aat gca gac gta caa caa ata gat ggt gtt tct        3249
His Val Thr Gly Asn Ala Asp Val Gln Gln Ile Asp Gly Val Ser
    1070                1075                1080 gta ttg gtt cta tct aat tgg agt gct ggc gta tct caa aat gtc        3294
Val Leu Val Leu Ser Asn Trp Ser Ala Gly Val Ser Gln Asn Val
    1085                1090                1095 cat ctc caa cat aat cat ggg tat gtc tta cgt gtt att gcc aaa        3339
His Leu Gln His Asn His Gly Tyr Val Leu Arg Val Ile Ala Lys
    1100                1105                1110 aaa gaa gga cct gga aat ggg tat gtc acg ctt atg gat tgt gag        3384
Lys Glu Gly Pro Gly Asn Gly Tyr Val Thr Leu Met Asp Cys Glu
    1115                1120                1125
```

-continued

```
gag aat caa gaa aaa ttg acg ttt acg tct tgt gaa gaa gga tat      3429
Glu Asn Gln Glu Lys Leu Thr Phe Thr Ser Cys Glu Glu Gly Tyr
    1130                1135                1140 att acg aag aca gta gat gta ttc cca gat aca gat cgt gta cga      3474
Ile Thr Lys Thr Val Asp Val Phe Pro Asp Thr Asp Arg Val Arg
    1145                1150                1155 att gag ata ggc gaa acc gaa ggt tcg ttt tat atc gaa agc att      3519
Ile Glu Ile Gly Glu Thr Glu Gly Ser Phe Tyr Ile Glu Ser Ile
    1160                1165                1170 gaa tta att tgc atg aac gag tga                                  3543
Glu Leu Ile Cys Met Asn Glu
    1175                1180

<210> SEQ ID NO 4
<211> LENGTH: 1180
<212> TYPE: PRT
<213> ORGANISM: Bacillus thuringiensis

<400> SEQUENCE: 4

Met Asn Pro Tyr Gln Asn Lys Asn Glu Tyr Glu Thr Leu Asn Ala Ser
1               5                   10                  15

Gln Lys Lys Leu Asn Ile Ser Asn Asn Tyr Thr Arg Tyr Pro Ile Glu
            20                  25                  30

Asn Ser Pro Lys Gln Leu Leu Gln Ser Thr Asn Tyr Lys Asp Trp Leu
        35                  40                  45

Asn Met Cys Gln Gln Asn Gln Gln Tyr Gly Gly Asp Phe Glu Thr Phe
    50                  55                  60

Ile Asp Ser Gly Glu Leu Ser Ala Tyr Thr Ile Val Val Gly Thr Val
65                  70                  75                  80

Leu Thr Gly Phe Gly Phe Thr Thr Pro Leu Gly Leu Ala Leu Ile Gly
                85                  90                  95

Phe Gly Thr Leu Ile Pro Val Leu Phe Pro Ala Gln Asp Gln Ser Asn
            100                 105                 110

Thr Trp Ser Asp Phe Ile Thr Gln Thr Lys Asn Ile Ile Lys Lys Glu
        115                 120                 125

Ile Ala Ser Thr Tyr Ile Ser Asn Ala Asn Lys Ile Leu Asn Arg Ser
    130                 135                 140

Phe Asn Val Ile Ser Thr Tyr His Asn His Leu Lys Thr Trp Glu Asn
145                 150                 155                 160

Asn Pro Asn Pro Gln Asn Thr Gln Asp Val Arg Thr Gln Ile Gln Leu
                165                 170                 175

Val His Tyr His Phe Gln Asn Val Ile Pro Glu Leu Val Asn Ser Cys
            180                 185                 190

Pro Pro Asn Pro Ser Asp Cys Asp Tyr Tyr Asn Ile Leu Val Leu Ser
        195                 200                 205

Ser Tyr Ala Gln Ala Ala Asn Leu His Leu Thr Val Leu Asn Gln Ala
    210                 215                 220

Val Lys Phe Glu Ala Tyr Leu Lys Asn Asn Arg Gln Phe Asp Tyr Leu
225                 230                 235                 240

Glu Pro Leu Pro Thr Ala Ile Asp Tyr Tyr Pro Val Leu Thr Lys Ala
                245                 250                 255

Ile Glu Asp Tyr Thr Asn Tyr Cys Val Thr Thr Tyr Lys Lys Gly Leu
            260                 265                 270

Asn Leu Ile Lys Thr Thr Pro Asp Ser Asn Leu Asp Gly Asn Ile Asn
        275                 280                 285

Trp Asn Thr Tyr Asn Thr Tyr Arg Thr Lys Met Thr Thr Ala Val Leu
```

-continued

```
                290                 295                 300
Asp Leu Val Ala Leu Phe Pro Asn Tyr Asp Val Gly Lys Tyr Pro Ile
305                 310                 315                 320
Gly Val Gln Ser Glu Leu Thr Arg Glu Ile Tyr Gln Val Leu Asn Phe
                325                 330                 335
Glu Glu Ser Pro Tyr Lys Tyr Tyr Asp Phe Gln Tyr Gln Glu Asp Ser
                340                 345                 350
Leu Thr Arg Arg Pro His Leu Phe Thr Trp Leu Asp Ser Leu Asn Phe
                355                 360                 365
Tyr Glu Lys Ala Gln Thr Thr Pro Asn Asn Phe Phe Thr Ser His Tyr
                370                 375                 380
Asn Met Phe His Tyr Thr Leu Asp Asn Ile Ser Gln Lys Ser Ser Val
385                 390                 395                 400
Phe Gly Asn His Asn Val Thr Asp Lys Leu Lys Ser Leu Gly Leu Ala
                405                 410                 415
Thr Asn Ile Tyr Ile Phe Leu Leu Asn Val Ile Ser Leu Asp Asn Lys
                420                 425                 430
Tyr Leu Asn Asp Tyr Asn Asn Ile Ser Lys Met Asp Phe Phe Ile Thr
                435                 440                 445
Asn Gly Thr Arg Leu Leu Glu Lys Glu Leu Thr Ala Gly Ser Gly Gln
450                 455                 460
Ile Thr Tyr Asp Val Asn Lys Asn Ile Phe Gly Leu Pro Ile Leu Lys
465                 470                 475                 480
Arg Arg Glu Asn Gln Gly Asn Pro Thr Leu Phe Pro Thr Tyr Asp Asn
                485                 490                 495
Tyr Ser His Ile Leu Ser Phe Ile Lys Ser Leu Ser Ile Pro Ala Thr
                500                 505                 510
Tyr Lys Thr Gln Val Tyr Thr Phe Ala Trp Thr His Ser Ser Val Asp
                515                 520                 525
Pro Lys Asn Thr Ile Tyr Thr His Leu Thr Thr Gln Ile Pro Ala Val
                530                 535                 540
Lys Ala Asn Ser Leu Gly Thr Ala Ser Lys Val Val Gln Gly Pro Gly
545                 550                 555                 560
His Thr Gly Gly Asp Leu Ile Asp Phe Lys Asp His Phe Lys Ile Thr
                565                 570                 575
Cys Gln His Ser Asn Phe Gln Gln Ser Tyr Phe Ile Arg Ile Arg Tyr
                580                 585                 590
Ala Ser Asn Gly Ser Ala Asn Thr Arg Ala Val Ile Asn Leu Ser Ile
                595                 600                 605
Pro Gly Val Ala Glu Leu Gly Met Ala Leu Asn Pro Thr Phe Ser Gly
                610                 615                 620
Thr Asp Tyr Thr Asn Leu Lys Tyr Lys Asp Phe Gln Tyr Leu Glu Phe
625                 630                 635                 640
Ser Asn Glu Val Lys Phe Ala Pro Asn Gln Asn Ile Ser Leu Val Phe
                645                 650                 655
Asn Arg Ser Asp Val Tyr Thr Asn Thr Thr Val Leu Ile Asp Lys Ile
                660                 665                 670
Glu Phe Leu Pro Ile Thr Arg Ser Ile Arg Glu Asp Arg Glu Lys Gln
                675                 680                 685
Lys Leu Glu Thr Val Gln Gln Ile Ile Asn Thr Phe Tyr Ala Asn Pro
                690                 695                 700
Ile Lys Asn Thr Leu Gln Ser Glu Leu Thr Asp Tyr Asp Ile Asp Gln
705                 710                 715                 720
```

-continued

```
Ala Ala Asn Leu Val Glu Cys Ile Ser Glu Glu Leu Tyr Pro Lys Glu
            725                 730                 735
Lys Met Leu Leu Leu Asp Glu Val Lys Asn Ala Lys Gln Leu Ser Gln
            740                 745                 750
Ser Arg Asn Val Leu Gln Asn Gly Asp Phe Glu Ser Ala Thr Leu Gly
            755                 760                 765
Trp Thr Thr Ser Asp Asn Ile Thr Ile Gln Glu Asp Asp Pro Ile Phe
            770                 775                 780
Lys Gly His Tyr Leu His Met Ser Gly Ala Arg Asp Ile Asp Gly Thr
785                 790                 795                 800
Ile Phe Pro Thr Tyr Ile Phe Gln Lys Ile Asp Glu Ser Lys Leu Lys
                    805                 810                 815
Pro Tyr Thr Arg Tyr Leu Val Arg Gly Phe Val Gly Ser Lys Asp
                    820                 825                 830
Val Glu Leu Val Val Ser Arg Tyr Gly Glu Glu Ile Asp Ala Ile Met
                    835                 840                 845
Asn Val Pro Ala Asp Leu Asn Tyr Leu Tyr Pro Ser Thr Phe Asp Cys
850                 855                 860
Glu Gly Ser Asn Arg Cys Glu Thr Ser Ala Val Pro Ala Asn Ile Gly
865                 870                 875                 880
Asn Thr Ser Asp Met Leu Tyr Ser Cys Gln Tyr Asp Thr Gly Lys Lys
                    885                 890                 895
His Val Val Cys Gln Asp Ser His Gln Phe Ser Phe Thr Ile Asp Thr
                    900                 905                 910
Gly Ala Leu Asp Thr Asn Glu Asn Ile Gly Val Trp Val Met Phe Lys
            915                 920                 925
Ile Ser Ser Pro Asp Gly Tyr Ala Ser Leu Asp Asn Leu Glu Val Ile
            930                 935                 940
Glu Glu Gly Pro Ile Asp Gly Glu Ala Leu Ser Arg Val Lys His Met
945                 950                 955                 960
Glu Lys Lys Trp Asn Asp Gln Met Glu Ala Lys Arg Ser Glu Thr Gln
                    965                 970                 975
Gln Ala Tyr Asp Val Ala Lys Gln Ala Ile Asp Ala Leu Phe Thr Asn
            980                 985                 990
Val Gln Asp Glu Ala Leu Gln Phe Asp Thr Thr Leu Ala Gln Ile Gln
            995                 1000                1005
Tyr Ala Glu Tyr Leu Val Gln Ser Ile Pro Tyr Val Tyr Asn Asp
    1010                1015                1020
Trp Leu Ser Asp Val Pro Gly Met Asn Tyr Asp Ile Tyr Val Glu
    1025                1030                1035
Leu Asp Ala Arg Val Ala Gln Ala Arg Tyr Leu Tyr Asp Thr Arg
    1040                1045                1050
Asn Ile Ile Lys Asn Gly Asp Phe Thr Gln Gly Val Met Gly Trp
    1055                1060                1065
His Val Thr Gly Asn Ala Asp Val Gln Gln Ile Asp Gly Val Ser
    1070                1075                1080
Val Leu Val Leu Ser Asn Trp Ser Ala Gly Val Ser Gln Asn Val
    1085                1090                1095
His Leu Gln His Asn His Gly Tyr Val Leu Arg Val Ile Ala Lys
    1100                1105                1110
Lys Glu Gly Pro Gly Asn Gly Tyr Val Thr Leu Met Asp Cys Glu
    1115                1120                1125
```

```
Glu Asn Gln Glu Lys Leu Thr  Phe Thr Ser Cys Glu  Glu Gly Tyr
    1130             1135                1140

Ile Thr  Lys Thr Val Asp Val  Phe Pro Asp Thr Asp  Arg Val Arg
    1145             1150                1155

Ile Glu  Ile Gly Glu Thr Glu  Gly Ser Phe Tyr Ile  Glu Ser Ile
    1160             1165                1170

Glu Leu  Ile Cys Met Asn Glu
    1175             1180

<210> SEQ ID NO 5
<211> LENGTH: 3411
<212> TYPE: DNA
<213> ORGANISM: Bacillus thuringiensis
<220> FEATURE:
<221> NAME/KEY: CDS
<222> LOCATION: (1)..(3411)

<400> SEQUENCE: 5 atg aat tca ggc tat ccg tta gcg aat gac tta caa ggg tca atg aaa     48
Met Asn Ser Gly Tyr Pro Leu Ala Asn Asp Leu Gln Gly Ser Met Lys
1               5                   10                  15 aac acg aac tat aaa gat tgg cta gcc atg tgt gaa aat aac caa cag     96
Asn Thr Asn Tyr Lys Asp Trp Leu Ala Met Cys Glu Asn Asn Gln Gln
            20                  25                  30 tat ggc gtt aat cca gct gcg att aat tct tct tca gtt agt acc gct    144
Tyr Gly Val Asn Pro Ala Ala Ile Asn Ser Ser Ser Val Ser Thr Ala
        35                  40                  45 tta aaa gta gct gga gct atc ctt aaa ttt gta aac cca cct gca ggt    192
Leu Lys Val Ala Gly Ala Ile Leu Lys Phe Val Asn Pro Pro Ala Gly
    50                  55                  60 act gtc tta acc gta ctt agc gcg gtg ctt cct att ctt tgg ccg act    240
Thr Val Leu Thr Val Leu Ser Ala Val Leu Pro Ile Leu Trp Pro Thr
65                  70                  75                  80 aat act cca acg cct gaa aga gtt tgg aat gat ttc atg acc aat aca    288
Asn Thr Pro Thr Pro Glu Arg Val Trp Asn Asp Phe Met Thr Asn Thr
                85                  90                  95 ggg aat ctt att gat caa act gta aca gct tat gta cga aca gat gca    336
Gly Asn Leu Ile Asp Gln Thr Val Thr Ala Tyr Val Arg Thr Asp Ala
            100                 105                 110 aat gca aaa atg acg gtt gtg aaa gat tat tta gat caa tat aca act    384
Asn Ala Lys Met Thr Val Val Lys Asp Tyr Leu Asp Gln Tyr Thr Thr
        115                 120                 125 aaa ttt aac act tgg aaa aga gag cct aat aac cag tcc tat aga aca    432
Lys Phe Asn Thr Trp Lys Arg Glu Pro Asn Asn Gln Ser Tyr Arg Thr
    130                 135                 140 gca gta ata act caa ttt aac tta acc agt gcc aaa ctt cga gag acc    480
Ala Val Ile Thr Gln Phe Asn Leu Thr Ser Ala Lys Leu Arg Glu Thr
145                 150                 155                 160 gca gtt tat ttt agc aac tta gta ggt tat gaa tta ttg tta tta cca    528
Ala Val Tyr Phe Ser Asn Leu Val Gly Tyr Glu Leu Leu Leu Leu Pro
                165                 170                 175 ata tac gca caa gta gca aat ttc aat tta ctt tta ata aga gat ggc    576
Ile Tyr Ala Gln Val Ala Asn Phe Asn Leu Leu Leu Ile Arg Asp Gly
            180                 185                 190 ctc ata aat gca caa gaa tgg tct tta gca cgt agt gct ggt gac caa    624
Leu Ile Asn Ala Gln Glu Trp Ser Leu Ala Arg Ser Ala Gly Asp Gln
        195                 200                 205 cta tat aac act atg gtg cag tac act aaa gaa tat att gca cat agc    672
Leu Tyr Asn Thr Met Val Gln Tyr Thr Lys Glu Tyr Ile Ala His Ser
    210                 215                 220
```

```
att aca tgg tat aat aaa ggt tta gat gta ctt aga aat aaa tct aat    720
Ile Thr Trp Tyr Asn Lys Gly Leu Asp Val Leu Arg Asn Lys Ser Asn
225                 230                 235                 240 gga caa tgg att acg ttt aat gat tat aaa aga gag atg act att caa    768
Gly Gln Trp Ile Thr Phe Asn Asp Tyr Lys Arg Glu Met Thr Ile Gln
            245                 250                 255 gta tta gat ata ctc gct ctt ttt gcc agt tat gat cca cgt cga tac    816
Val Leu Asp Ile Leu Ala Leu Phe Ala Ser Tyr Asp Pro Arg Arg Tyr
        260                 265                 270 cct gcg gac aaa ata gat aat acg aaa cta tca aaa aca gaa ttt aca    864
Pro Ala Asp Lys Ile Asp Asn Thr Lys Leu Ser Lys Thr Glu Phe Thr
    275                 280                 285 aga gag att tat aca gct tta gta gaa tct cct tct agt aaa tct ata    912
Arg Glu Ile Tyr Thr Ala Leu Val Glu Ser Pro Ser Ser Lys Ser Ile
290                 295                 300 gca gca ctg gag gca gca ctt aca cga gat gtt cat tta ttc act tgg    960
Ala Ala Leu Glu Ala Ala Leu Thr Arg Asp Val His Leu Phe Thr Trp
305                 310                 315                 320 cta aag aga gta gat ttc tgg acc aat act ata tat caa gat tta aga    1008
Leu Lys Arg Val Asp Phe Trp Thr Asn Thr Ile Tyr Gln Asp Leu Arg
            325                 330                 335 ttt tta tct gcc aat aaa att ggg ttt tca tat aca aat tct tct gca    1056
Phe Leu Ser Ala Asn Lys Ile Gly Phe Ser Tyr Thr Asn Ser Ser Ala
        340                 345                 350 atg caa gaa agt gga att tat gga agt tct ggt ttt ggt tca aat ctt    1104
Met Gln Glu Ser Gly Ile Tyr Gly Ser Ser Gly Phe Gly Ser Asn Leu
    355                 360                 365 act cat caa att caa ctt aat tct aat gtt tat aaa act tct atc aca    1152
Thr His Gln Ile Gln Leu Asn Ser Asn Val Tyr Lys Thr Ser Ile Thr
370                 375                 380 gat act agc tcc ccc tct aat cga gtt aca aaa atg gat ttc tac aaa    1200
Asp Thr Ser Ser Pro Ser Asn Arg Val Thr Lys Met Asp Phe Tyr Lys
385                 390                 395                 400 att gat ggt act ctt gcc tct tat aat tca aat ata aca cca act cct    1248
Ile Asp Gly Thr Leu Ala Ser Tyr Asn Ser Asn Ile Thr Pro Thr Pro
            405                 410                 415 gaa ggt tta agg acc aca ttt ttt gga ttt tca aca aat gag aac aca    1296
Glu Gly Leu Arg Thr Thr Phe Phe Gly Phe Ser Thr Asn Glu Asn Thr
        420                 425                 430 cct aat caa cca act gta aat gat tat acg cat att tta agc tat ata    1344
Pro Asn Gln Pro Thr Val Asn Asp Tyr Thr His Ile Leu Ser Tyr Ile
    435                 440                 445 aaa act gat gtt ata gat tat aac agt aac agg gtt tca ttt gct tgg    1392
Lys Thr Asp Val Ile Asp Tyr Asn Ser Asn Arg Val Ser Phe Ala Trp
450                 455                 460 aca cat aag att gtt gac cct aat aat caa ata tac aca gat gct atc    1440
Thr His Lys Ile Val Asp Pro Asn Asn Gln Ile Tyr Thr Asp Ala Ile
465                 470                 475                 480 aca caa gtt ccg gcc gta aaa tct aac ttc ttg aat gca aca gct aaa    1488
Thr Gln Val Pro Ala Val Lys Ser Asn Phe Leu Asn Ala Thr Ala Lys
            485                 490                 495 gta atc aag gga cct ggt cat aca ggg ggg gat cta gtt gct ctt aca    1536
Val Ile Lys Gly Pro Gly His Thr Gly Gly Asp Leu Val Ala Leu Thr
        500                 505                 510 agc aat ggt act cta tca ggc aga atg gag att caa tgt aaa aca agt    1584
Ser Asn Gly Thr Leu Ser Gly Arg Met Glu Ile Gln Cys Lys Thr Ser
    515                 520                 525 att ttt aat gat cct aca aga agt tac gga tta cgc ata cgt tat gct    1632
Ile Phe Asn Asp Pro Thr Arg Ser Tyr Gly Leu Arg Ile Arg Tyr Ala
530                 535                 540
```

-continued

```
gca aat agt cca att gta ttg aat gta tca tat gta tta caa gga gtt    1680
Ala Asn Ser Pro Ile Val Leu Asn Val Ser Tyr Val Leu Gln Gly Val
545                 550                 555                 560 tct aga gga aca acg att agt aca gaa tct acg ttt tca aga cct aat    1728
Ser Arg Gly Thr Thr Ile Ser Thr Glu Ser Thr Phe Ser Arg Pro Asn
            565                 570                 575 aat ata ata cct aca gat tta aaa tat gaa gag ttt aga tac aaa gat    1776
Asn Ile Ile Pro Thr Asp Leu Lys Tyr Glu Glu Phe Arg Tyr Lys Asp
        580                 585                 590 cct ttt gat gca att gta ccg atg aga tta tct tct aat caa ctg ata    1824
Pro Phe Asp Ala Ile Val Pro Met Arg Leu Ser Ser Asn Gln Leu Ile
    595                 600                 605 act ata gct att caa cca tta aac atg act tca aat aat caa gtg att    1872
Thr Ile Ala Ile Gln Pro Leu Asn Met Thr Ser Asn Asn Gln Val Ile
610                 615                 620 att gac aga atc gaa att att cca atc act caa tct gta tta gat gag    1920
Ile Asp Arg Ile Glu Ile Ile Pro Ile Thr Gln Ser Val Leu Asp Glu
625                 630                 635                 640 aca gag aac caa aat tta gaa tca gaa cga gaa gtt gtg aat gca ctg    1968
Thr Glu Asn Gln Asn Leu Glu Ser Glu Arg Glu Val Val Asn Ala Leu
            645                 650                 655 ttt aca aat gac gcg aaa gat gca tta aac att gga acg aca gat tat    2016
Phe Thr Asn Asp Ala Lys Asp Ala Leu Asn Ile Gly Thr Thr Asp Tyr
        660                 665                 670 gac ata gat caa gcc gca aat ctt gtg gaa tgt att tct gaa gaa tta    2064
Asp Ile Asp Gln Ala Ala Asn Leu Val Glu Cys Ile Ser Glu Glu Leu
    675                 680                 685 tat cca aaa gaa aaa atg ctg tta tta gat gaa gtt aaa aat gcg aaa    2112
Tyr Pro Lys Glu Lys Met Leu Leu Leu Asp Glu Val Lys Asn Ala Lys
690                 695                 700 caa ctt agt caa tct cga aat gta ctt caa aac ggg gat ttt gaa tcg    2160
Gln Leu Ser Gln Ser Arg Asn Val Leu Gln Asn Gly Asp Phe Glu Ser
705                 710                 715                 720 gct acg ctt ggt tgg aca aca agt gat aat atc aca att caa gaa gat    2208
Ala Thr Leu Gly Trp Thr Thr Ser Asp Asn Ile Thr Ile Gln Glu Asp
            725                 730                 735 gat cct att ttt aaa ggg cat tac ctt cat atg tct ggg gcg aga gac    2256
Asp Pro Ile Phe Lys Gly His Tyr Leu His Met Ser Gly Ala Arg Asp
        740                 745                 750 att gat ggt acg ata ttt ccg acc tat ata ttc caa aaa att gat gaa    2304
Ile Asp Gly Thr Ile Phe Pro Thr Tyr Ile Phe Gln Lys Ile Asp Glu
    755                 760                 765 tca aaa tta aaa ccg tat aca cgt tac cta gta agg gga ttt gta gga    2352
Ser Lys Leu Lys Pro Tyr Thr Arg Tyr Leu Val Arg Gly Phe Val Gly
770                 775                 780 agt agt aaa gat gta gaa cta gtg gtt tca cgc tat ggg gaa gaa att    2400
Ser Ser Lys Asp Val Glu Leu Val Val Ser Arg Tyr Gly Glu Glu Ile
785                 790                 795                 800 gat gcc atc atg aat gtt cca gct gat tta aac tat ctg tat cct tct    2448
Asp Ala Ile Met Asn Val Pro Ala Asp Leu Asn Tyr Leu Tyr Pro Ser
            805                 810                 815 acc ttt gat tgt gaa ggg tct aat cgt tgt gag acg tcc gct gtg ccg    2496
Thr Phe Asp Cys Glu Gly Ser Asn Arg Cys Glu Thr Ser Ala Val Pro
        820                 825                 830 gct aac att ggg aac act tct gat atg ttg tat tca tgc caa tat gat    2544
Ala Asn Ile Gly Asn Thr Ser Asp Met Leu Tyr Ser Cys Gln Tyr Asp
    835                 840                 845 aca ggg aaa aag cat gtc gta tgt cag gat tcc cat caa ttt agt ttc    2592
Thr Gly Lys Lys His Val Val Cys Gln Asp Ser His Gln Phe Ser Phe
```

```
                850                855                860
act att gat aca ggg gca tta gat aca aat gaa aat ata ggg gtt tgg     2640
Thr Ile Asp Thr Gly Ala Leu Asp Thr Asn Glu Asn Ile Gly Val Trp
865                870                875                880 gtc atg ttt aaa ata tct tct cca gat gga tac gca tca tta gat aat     2688
Val Met Phe Lys Ile Ser Ser Pro Asp Gly Tyr Ala Ser Leu Asp Asn
            885                890                895 tta gaa gta att gaa gaa ggg cca ata gat ggg gaa gca ctg tca cgc     2736
Leu Glu Val Ile Glu Glu Gly Pro Ile Asp Gly Glu Ala Leu Ser Arg
        900                905                910 gtg aaa cac atg gag aag aaa tgg aac gat caa atg gaa gca aaa cgt     2784
Val Lys His Met Glu Lys Lys Trp Asn Asp Gln Met Glu Ala Lys Arg
    915                920                925 tcg gaa aca caa caa gca tat gat gta gcg aaa caa gcc att gat gct     2832
Ser Glu Thr Gln Gln Ala Tyr Asp Val Ala Lys Gln Ala Ile Asp Ala
930                935                940 tta ttc aca aat gta caa gat gag gct tta cag ttt gat acg aca ctc     2880
Leu Phe Thr Asn Val Gln Asp Glu Ala Leu Gln Phe Asp Thr Thr Leu
945                950                955                960 gct caa att cag tac gct gag tat ttg gta caa tcg att cca tat gtg     2928
Ala Gln Ile Gln Tyr Ala Glu Tyr Leu Val Gln Ser Ile Pro Tyr Val
            965                970                975 tac aat gat tgg ttg tca gat gtt cca ggt atg aat tat gat atc tat     2976
Tyr Asn Asp Trp Leu Ser Asp Val Pro Gly Met Asn Tyr Asp Ile Tyr
        980                985                990 gta gag ttg gat gca cga gtg gca  caa gcg cgt tat ttg  tat gat aca   3024
Val Glu Leu Asp Ala Arg Val Ala  Gln Ala Arg Tyr Leu  Tyr Asp Thr
    995                1000                1005 aga aat  att att aaa aat ggt  gat ttt aca caa ggg  gta atg ggg      3069
Arg Asn  Ile Ile Lys Asn Gly  Asp Phe Thr Gln Gly  Val Met Gly
    1010                1015                1020 tgg cat  gta act gga aat gca  gac gta caa caa ata  gat ggt gtt      3114
Trp His  Val Thr Gly Asn Ala  Asp Val Gln Gln Ile  Asp Gly Val
    1025                1030                1035 tct gta  ttg gtt cta tct aat  tgg agt gct ggc gta  tct caa aat      3159
Ser Val  Leu Val Leu Ser Asn  Trp Ser Ala Gly Val  Ser Gln Asn
    1040                1045                1050 gtc cat  ctc caa cat aat cat  ggg tat gtc tta cgt  gtt att gcc      3204
Val His  Leu Gln His Asn His  Gly Tyr Val Leu Arg  Val Ile Ala
    1055                1060                1065 aaa aaa  gaa gga cct gga aat  ggg tat gtc acg ctt  atg gat tgt      3249
Lys Lys  Glu Gly Pro Gly Asn  Gly Tyr Val Thr Leu  Met Asp Cys
    1070                1075                1080 gag gag  aat caa gaa aaa ttg  acg ttt acg tct tgt  gaa gaa gga      3294
Glu Glu  Asn Gln Glu Lys Leu  Thr Phe Thr Ser Cys  Glu Glu Gly
    1085                1090                1095 tat att  acg aag aca gta gat  gta ttc cca gat aca  gat cgt gta      3339
Tyr Ile  Thr Lys Thr Val Asp  Val Phe Pro Asp Thr  Asp Arg Val
    1100                1105                1110 cga att  gag ata ggc gaa acc  gaa ggt tcg ttt tat  atc gaa agc      3384
Arg Ile  Glu Ile Gly Glu Thr  Glu Gly Ser Phe Tyr  Ile Glu Ser
    1115                1120                1125 att gaa  tta att tgc atg aac  gag tga                               3411
Ile Glu  Leu Ile Cys Met Asn  Glu
    1130                1135

<210> SEQ ID NO 6
<211> LENGTH: 1136
<212> TYPE: PRT
<213> ORGANISM: Bacillus thuringiensis
```

<400> SEQUENCE: 6

```
Met Asn Ser Gly Tyr Pro Leu Ala Asn Asp Leu Gln Gly Ser Met Lys
1               5                   10                  15

Asn Thr Asn Tyr Lys Asp Trp Leu Ala Met Cys Glu Asn Asn Gln Gln
            20                  25                  30

Tyr Gly Val Asn Pro Ala Ala Ile Asn Ser Ser Ser Val Ser Thr Ala
        35                  40                  45

Leu Lys Val Ala Gly Ala Ile Leu Lys Phe Val Asn Pro Pro Ala Gly
    50                  55                  60

Thr Val Leu Thr Val Leu Ser Ala Val Leu Pro Ile Leu Trp Pro Thr
65                  70                  75                  80

Asn Thr Pro Thr Pro Glu Arg Val Trp Asn Asp Phe Met Thr Asn Thr
                85                  90                  95

Gly Asn Leu Ile Asp Gln Thr Val Thr Ala Tyr Val Arg Thr Asp Ala
            100                 105                 110

Asn Ala Lys Met Thr Val Val Lys Asp Tyr Leu Asp Gln Tyr Thr Thr
        115                 120                 125

Lys Phe Asn Thr Trp Lys Arg Glu Pro Asn Asn Gln Ser Tyr Arg Thr
    130                 135                 140

Ala Val Ile Thr Gln Phe Asn Leu Thr Ser Ala Lys Leu Arg Glu Thr
145                 150                 155                 160

Ala Val Tyr Phe Ser Asn Leu Val Gly Tyr Glu Leu Leu Leu Leu Pro
                165                 170                 175

Ile Tyr Ala Gln Val Ala Asn Phe Asn Leu Leu Leu Ile Arg Asp Gly
            180                 185                 190

Leu Ile Asn Ala Gln Glu Trp Ser Leu Ala Arg Ser Ala Gly Asp Gln
        195                 200                 205

Leu Tyr Asn Thr Met Val Gln Tyr Thr Lys Glu Tyr Ile Ala His Ser
    210                 215                 220

Ile Thr Trp Tyr Asn Lys Gly Leu Asp Val Leu Arg Asn Lys Ser Asn
225                 230                 235                 240

Gly Gln Trp Ile Thr Phe Asn Asp Tyr Lys Arg Glu Met Thr Ile Gln
                245                 250                 255

Val Leu Asp Ile Leu Ala Leu Phe Ala Ser Tyr Asp Pro Arg Arg Tyr
            260                 265                 270

Pro Ala Asp Lys Ile Asp Asn Thr Lys Leu Ser Lys Thr Glu Phe Thr
        275                 280                 285

Arg Glu Ile Tyr Thr Ala Leu Val Glu Ser Pro Ser Ser Lys Ser Ile
    290                 295                 300

Ala Ala Leu Glu Ala Ala Leu Thr Arg Asp Val His Leu Phe Thr Trp
305                 310                 315                 320

Leu Lys Arg Val Asp Phe Trp Thr Asn Thr Ile Tyr Gln Asp Leu Arg
                325                 330                 335

Phe Leu Ser Ala Asn Lys Ile Gly Phe Ser Tyr Thr Asn Ser Ser Ala
            340                 345                 350

Met Gln Glu Ser Gly Ile Tyr Gly Ser Ser Gly Phe Gly Ser Asn Leu
        355                 360                 365

Thr His Gln Ile Gln Leu Asn Ser Asn Val Tyr Lys Thr Ser Ile Thr
    370                 375                 380

Asp Thr Ser Ser Pro Ser Asn Arg Val Thr Lys Met Asp Phe Tyr Lys
385                 390                 395                 400

Ile Asp Gly Thr Leu Ala Ser Tyr Asn Ser Asn Ile Thr Pro Thr Pro
```

```
                        405                 410                 415
Glu Gly Leu Arg Thr Thr Phe Phe Gly Phe Ser Thr Asn Glu Asn Thr
                420                 425                 430
Pro Asn Gln Pro Thr Val Asn Asp Tyr Thr His Ile Leu Ser Tyr Ile
            435                 440                 445
Lys Thr Asp Val Ile Asp Tyr Asn Ser Asn Arg Val Ser Phe Ala Trp
        450                 455                 460
Thr His Lys Ile Val Asp Pro Asn Asn Gln Ile Tyr Thr Asp Ala Ile
465                 470                 475                 480
Thr Gln Val Pro Ala Val Lys Ser Asn Phe Leu Asn Ala Thr Ala Lys
                485                 490                 495
Val Ile Lys Gly Pro Gly His Thr Gly Gly Asp Leu Val Ala Leu Thr
            500                 505                 510
Ser Asn Gly Thr Leu Ser Gly Arg Met Glu Ile Gln Cys Lys Thr Ser
        515                 520                 525
Ile Phe Asn Asp Pro Thr Arg Ser Tyr Gly Leu Arg Ile Arg Tyr Ala
        530                 535                 540
Ala Asn Ser Pro Ile Val Leu Asn Val Ser Tyr Val Leu Gln Gly Val
545                 550                 555                 560
Ser Arg Gly Thr Thr Ile Ser Thr Glu Ser Thr Phe Ser Arg Pro Asn
                565                 570                 575
Asn Ile Ile Pro Thr Asp Leu Lys Tyr Glu Glu Phe Arg Tyr Lys Asp
            580                 585                 590
Pro Phe Asp Ala Ile Val Pro Met Arg Leu Ser Ser Asn Gln Leu Ile
        595                 600                 605
Thr Ile Ala Ile Gln Pro Leu Asn Met Thr Ser Asn Asn Gln Val Ile
    610                 615                 620
Ile Asp Arg Ile Glu Ile Ile Pro Ile Thr Gln Ser Val Leu Asp Glu
625                 630                 635                 640
Thr Glu Asn Gln Asn Leu Glu Ser Glu Arg Glu Val Val Asn Ala Leu
                645                 650                 655
Phe Thr Asn Asp Ala Lys Asp Ala Leu Asn Ile Gly Thr Thr Asp Tyr
            660                 665                 670
Asp Ile Asp Gln Ala Ala Asn Leu Val Glu Cys Ile Ser Glu Glu Leu
        675                 680                 685
Tyr Pro Lys Glu Lys Met Leu Leu Leu Asp Glu Val Lys Asn Ala Lys
    690                 695                 700
Gln Leu Ser Gln Ser Arg Asn Val Leu Gln Asn Gly Asp Phe Glu Ser
705                 710                 715                 720
Ala Thr Leu Gly Trp Thr Thr Ser Asp Asn Ile Thr Ile Gln Glu Asp
                725                 730                 735
Asp Pro Ile Phe Lys Gly His Tyr Leu His Met Ser Gly Ala Arg Asp
            740                 745                 750
Ile Asp Gly Thr Ile Phe Pro Thr Tyr Ile Phe Gln Lys Ile Asp Glu
        755                 760                 765
Ser Lys Leu Lys Pro Tyr Thr Arg Tyr Leu Val Arg Gly Phe Val Gly
    770                 775                 780
Ser Ser Lys Asp Val Glu Leu Val Val Ser Arg Tyr Gly Glu Glu Ile
785                 790                 795                 800
Asp Ala Ile Met Asn Val Pro Ala Asp Leu Asn Tyr Leu Tyr Pro Ser
                805                 810                 815
Thr Phe Asp Cys Glu Gly Ser Asn Arg Cys Glu Thr Ser Ala Val Pro
            820                 825                 830
```

```
Ala Asn Ile Gly Asn Thr Ser Asp Met Leu Tyr Ser Cys Gln Tyr Asp
            835                 840                 845

Thr Gly Lys Lys His Val Val Cys Gln Asp Ser His Gln Phe Ser Phe
    850                 855                 860

Thr Ile Asp Thr Gly Ala Leu Asp Thr Asn Glu Asn Ile Gly Val Trp
865                 870                 875                 880

Val Met Phe Lys Ile Ser Ser Pro Asp Gly Tyr Ala Ser Leu Asp Asn
                885                 890                 895

Leu Glu Val Ile Glu Gly Pro Ile Asp Gly Glu Ala Leu Ser Arg
            900                 905                 910

Val Lys His Met Glu Lys Lys Trp Asn Asp Gln Met Glu Ala Lys Arg
            915                 920                 925

Ser Glu Thr Gln Gln Ala Tyr Asp Val Ala Lys Gln Ala Ile Asp Ala
    930                 935                 940

Leu Phe Thr Asn Val Gln Asp Glu Ala Leu Gln Phe Asp Thr Thr Leu
945                 950                 955                 960

Ala Gln Ile Gln Tyr Ala Glu Tyr Leu Val Gln Ser Ile Pro Tyr Val
                965                 970                 975

Tyr Asn Asp Trp Leu Ser Asp Val Pro Gly Met Asn Tyr Asp Ile Tyr
            980                 985                 990

Val Glu Leu Asp Ala Arg Val Ala  Gln Ala Arg Tyr Leu Tyr Asp Thr
            995                 1000                 1005

Arg Asn Ile Ile Lys Asn Gly  Asp Phe Thr Gln Gly  Val Met Gly
        1010                 1015                 1020

Trp His Val Thr Gly Asn Ala  Asp Val Gln Gln Ile  Asp Gly Val
        1025                 1030                 1035

Ser Val Leu Val Leu Ser Asn  Trp Ser Ala Gly Val  Ser Gln Asn
        1040                 1045                 1050

Val His Leu Gln His Asn His  Gly Tyr Val Leu Arg  Val Ile Ala
        1055                 1060                 1065

Lys Lys Glu Gly Pro Gly Asn  Gly Tyr Val Thr Leu  Met Asp Cys
        1070                 1075                 1080

Glu Glu Asn Gln Glu Lys Leu  Thr Phe Thr Ser Cys  Glu Glu Gly
        1085                 1090                 1095

Tyr Ile Thr Lys Thr Val Asp  Val Phe Pro Asp Thr  Asp Arg Val
        1100                 1105                 1110

Arg Ile Glu Ile Gly Glu Thr  Glu Gly Ser Phe Tyr  Ile Glu Ser
        1115                 1120                 1125

Ile Glu Leu Ile Cys Met Asn  Glu
        1130                 1135

<210> SEQ ID NO 7
<211> LENGTH: 1932
<212> TYPE: DNA
<213> ORGANISM: Bacillus thuringiensis
<220> FEATURE:
<221> NAME/KEY: CDS
<222> LOCATION: (1)..(1932)

<400> SEQUENCE: 7 atg gaa gat agt tct tta

```
ata gca gta gct ccc atc gca caa tat ctt gca aca gct ata ggg aaa    144
Ile Ala Val Ala Pro Ile Ala Gln Tyr Leu Ala Thr Ala Ile Gly Lys
         35                  40                  45 tgg gcg gca aag gca gca ttt tca aaa gta cta tca ctt ata ttc cca    192
Trp Ala Ala Lys Ala Ala Phe Ser Lys Val Leu Ser Leu Ile Phe Pro
 50                  55                  60 ggt tct caa cct gct act atg gaa aaa gtt cgt aca gaa gtg gaa aca    240
Gly Ser Gln Pro Ala Thr Met Glu Lys Val Arg Thr Glu Val Glu Thr
 65                  70                  75                  80 ctt ata aat caa aaa tta agc caa gat cga gtc aat ata tta aac gca    288
Leu Ile Asn Gln Lys Leu Ser Gln Asp Arg Val Asn Ile Leu Asn Ala
                 85                  90                  95 gaa tat agg ggg att att gag gtt agt gat gta ttt gat gcg tat att    336
Glu Tyr Arg Gly Ile Ile Glu Val Ser Asp Val Phe Asp Ala Tyr Ile
                100                 105                 110 aaa caa cca ggt ttt acc cct gca aca gcc aag ggt tat ttt cta aat    384
Lys Gln Pro Gly Phe Thr Pro Ala Thr Ala Lys Gly Tyr Phe Leu Asn
            115                 120                 125 cta agt ggt gct ata ata caa cga tta cct caa ttt gag gtt caa aca    432
Leu Ser Gly Ala Ile Ile Gln Arg Leu Pro Gln Phe Glu Val Gln Thr
    130                 135                 140 tat gaa gga gta tct ata gca ctt ttt act caa atg tgt aca ctt cat    480
Tyr Glu Gly Val Ser Ile Ala Leu Phe Thr Gln Met Cys Thr Leu His
145                 150                 155                 160 tta act tta tta aaa gac gga atc cta gca ggg agt gca tgg gga ttt    528
Leu Thr Leu Leu Lys Asp Gly Ile Leu Ala Gly Ser Ala Trp Gly Phe
                165                 170                 175 act caa gct gat gta gat tca ttt ata aaa tta ttt aat caa aaa gta    576
Thr Gln Ala Asp Val Asp Ser Phe Ile Lys Leu Phe Asn Gln Lys Val
                180                 185                 190 tta gat tac agg acc aga tta atg aga atg tac aca gaa gag ttc gga    624
Leu Asp Tyr Arg Thr Arg Leu Met Arg Met Tyr Thr Glu Glu Phe Gly
            195                 200                 205 aga ttg tgt aaa gtc agt ctt aaa gat gga ttg acg ttc cgg aat atg    672
Arg Leu Cys Lys Val Ser Leu Lys Asp Gly Leu Thr Phe Arg Asn Met
    210                 215                 220 tgt aat tta tat gtg ttt cca ttt gct gaa gcc tgg tct tta atg aga    720
Cys Asn Leu Tyr Val Phe Pro Phe Ala Glu Ala Trp Ser Leu Met Arg
225                 230                 235                 240 tat gaa gga tta aaa tta caa agc tct cta tca tta tgg gat tat gtt    768
Tyr Glu Gly Leu Lys Leu Gln Ser Ser Leu Ser Leu Trp Asp Tyr Val
                245                 250                 255 ggt gtc tca att cct gta aat tat aat gaa tgg gga gga cta gtt tat    816
Gly Val Ser Ile Pro Val Asn Tyr Asn Glu Trp Gly Gly Leu Val Tyr
                260                 265                 270 aag tta tta atg ggg gaa gtt aat caa aga tta aca act gtt aaa ttt    864
Lys Leu Leu Met Gly Glu Val Asn Gln Arg Leu Thr Thr Val Lys Phe
            275                 280                 285 aat tat tct ttc act aat gaa cca gct gat ata cca gca aga gaa aat    912
Asn Tyr Ser Phe Thr Asn Glu Pro Ala Asp Ile Pro Ala Arg Glu Asn
    290                 295                 300 att cgt ggc gtc cat cct ata tac gat cct agt tct ggg ctt aca gga    960
Ile Arg Gly Val His Pro Ile Tyr Asp Pro Ser Ser Gly Leu Thr Gly
305                 310                 315                 320 tgg ata gga aac gga aga aca aac aat ttt aat ttt gct gat aac aat   1008
Trp Ile Gly Asn Gly Arg Thr Asn Asn Phe Asn Phe Ala Asp Asn Asn
                325                 330                 335 ggc aat gaa att atg gaa gtt aga aca caa act ttt tat caa aat cca   1056
Gly Asn Glu Ile Met Glu Val Arg Thr Gln Thr Phe Tyr Gln Asn Pro
```

```
                340                 345                 350
aat aat gag cct ata gcg cct aga gat att ata aat caa att tta act    1104
Asn Asn Glu Pro Ile Ala Pro Arg Asp Ile Ile Asn Gln Ile Leu Thr
        355                 360                 365 gcg cca gca cca gca gac cta ttt ttt aaa aat gca gat ata aat gta    1152
Ala Pro Ala Pro Ala Asp Leu Phe Phe Lys Asn Ala Asp Ile Asn Val
370                 375                 380 aag ttc aca cag tgg ttt cag tct act cta tat ggg tgg aac att aaa    1200
Lys Phe Thr Gln Trp Phe Gln Ser Thr Leu Tyr Gly Trp Asn Ile Lys
385                 390                 395                 400 ctc ggt aca caa acg gtt tta agt agt aga acc gga aca ata cca cca    1248
Leu Gly Thr Gln Thr Val Leu Ser Ser Arg Thr Gly Thr Ile Pro Pro
            405                 410                 415 aat tat tta gca tat gat gga tat tat att cgt gct att tca gct tgc    1296
Asn Tyr Leu Ala Tyr Asp Gly Tyr Tyr Ile Arg Ala Ile Ser Ala Cys
        420                 425                 430 cca aga gga gtc tca ctt gca tat aat cac gat ctt aca aca cta aca    1344
Pro Arg Gly Val Ser Leu Ala Tyr Asn His Asp Leu Thr Thr Leu Thr
    435                 440                 445 tat aat aga ata gag tat gat tca cct act aca gaa aat att att gta    1392
Tyr Asn Arg Ile Glu Tyr Asp Ser Pro Thr Thr Glu Asn Ile Ile Val
450                 455                 460 ggg ttt gca cca gat aat act aag gac ttt tat tct aaa aaa tct cac    1440
Gly Phe Ala Pro Asp Asn Thr Lys Asp Phe Tyr Ser Lys Lys Ser His
465                 470                 475                 480 tat tta agt gaa acg aat gat agt tat gta att cct gct ctg caa ttt    1488
Tyr Leu Ser Glu Thr Asn Asp Ser Tyr Val Ile Pro Ala Leu Gln Phe
            485                 490                 495 gct gaa gtt tca gat aga tca ttt tta gaa gat acg cca gat caa gca    1536
Ala Glu Val Ser Asp Arg Ser Phe Leu Glu Asp Thr Pro Asp Gln Ala
        500                 505                 510 aca gac ggc agt att aaa ttt gca cgt act ttc att agt aat gaa gct    1584
Thr Asp Gly Ser Ile Lys Phe Ala Arg Thr Phe Ile Ser Asn Glu Ala
    515                 520                 525 aag tac tct att aga cta aac acc ggg ttt aat acg gca act aga tat    1632
Lys Tyr Ser Ile Arg Leu Asn Thr Gly Phe Asn Thr Ala Thr Arg Tyr
530                 535                 540 aaa tta att atc agg gta aga gta cct tat cgc tta cct gct gga ata    1680
Lys Leu Ile Ile Arg Val Arg Val Pro Tyr Arg Leu Pro Ala Gly Ile
545                 550                 555                 560 cgg gta caa tct cag aat tcg gga aat aat aga atg cta ggc agt ttt    1728
Arg Val Gln Ser Gln Asn Ser Gly Asn Asn Arg Met Leu Gly Ser Phe
            565                 570                 575 act gca aat gct aat cca gaa tgg gtg gat ttt gtc aca gat gca ttt    1776
Thr Ala Asn Ala Asn Pro Glu Trp Val Asp Phe Val Thr Asp Ala Phe
        580                 585                 590 aca ttt aac gat tta ggg att aca act tca agt aca aat gct tta ttt    1824
Thr Phe Asn Asp Leu Gly Ile Thr Thr Ser Ser Thr Asn Ala Leu Phe
    595                 600                 605 agt att tct tca gat agt tta aat tct gga gaa gag tgg tat tta tcg    1872
Ser Ile Ser Ser Asp Ser Leu Asn Ser Gly Glu Glu Trp Tyr Leu Ser
610                 615                 620 cag ttg ttt tta gta aaa gaa tcg gcc ttt acg acg caa att aat ccg    1920
Gln Leu Phe Leu Val Lys Glu Ser Ala Phe Thr Thr Gln Ile Asn Pro
625                 630                 635                 640 tta cta aag tag                                                    1932
Leu Leu Lys

<210> SEQ ID NO 8
```

<211> LENGTH: 643
<212> TYPE: PRT
<213> ORGANISM: Bacillus thuringiensis

<400> SEQUENCE: 8

```
Met Glu Asp Ser Ser Leu Asp Thr Leu Ser Ile Val Asn Glu Thr Asp
1               5                   10                  15

Phe Pro Leu Tyr Asn Asn Tyr Thr Glu Pro Thr Ile Ala Pro Ala Leu
            20                  25                  30

Ile Ala Val Ala Pro Ile Ala Gln Tyr Leu Ala Thr Ala Ile Gly Lys
        35                  40                  45

Trp Ala Ala Lys Ala Ala Phe Ser Lys Val Leu Ser Leu Ile Phe Pro
50                  55                  60

Gly Ser Gln Pro Ala Thr Met Glu Lys Val Arg Thr Glu Val Glu Thr
65                  70                  75                  80

Leu Ile Asn Gln Lys Leu Ser Gln Asp Arg Val Asn Ile Leu Asn Ala
                85                  90                  95

Glu Tyr Arg Gly Ile Ile Glu Val Ser Asp Val Phe Asp Ala Tyr Ile
            100                 105                 110

Lys Gln Pro Gly Phe Thr Pro Ala Thr Ala Lys Gly Tyr Phe Leu Asn
        115                 120                 125

Leu Ser Gly Ala Ile Ile Gln Arg Leu Pro Gln Phe Glu Val Gln Thr
130                 135                 140

Tyr Glu Gly Val Ser Ile Ala Leu Phe Thr Gln Met Cys Thr Leu His
145                 150                 155                 160

Leu Thr Leu Leu Lys Asp Gly Ile Leu Ala Gly Ser Ala Trp Gly Phe
                165                 170                 175

Thr Gln Ala Asp Val Asp Ser Phe Ile Lys Leu Phe Asn Gln Lys Val
            180                 185                 190

Leu Asp Tyr Arg Thr Arg Leu Met Arg Met Tyr Thr Glu Glu Phe Gly
        195                 200                 205

Arg Leu Cys Lys Val Ser Leu Lys Asp Gly Leu Thr Phe Arg Asn Met
210                 215                 220

Cys Asn Leu Tyr Val Phe Pro Phe Ala Glu Ala Trp Ser Leu Met Arg
225                 230                 235                 240

Tyr Glu Gly Leu Lys Leu Gln Ser Ser Leu Ser Leu Trp Asp Tyr Val
                245                 250                 255

Gly Val Ser Ile Pro Val Asn Tyr Asn Glu Trp Gly Gly Leu Val Tyr
            260                 265                 270

Lys Leu Leu Met Gly Glu Val Asn Gln Arg Leu Thr Thr Val Lys Phe
        275                 280                 285

Asn Tyr Ser Phe Thr Asn Glu Pro Ala Asp Ile Pro Ala Arg Glu Asn
290                 295                 300

Ile Arg Gly Val His Pro Ile Tyr Asp Pro Ser Ser Gly Leu Thr Gly
305                 310                 315                 320

Trp Ile Gly Asn Gly Arg Thr Asn Asn Phe Asn Phe Ala Asp Asn Asn
                325                 330                 335

Gly Asn Glu Ile Met Glu Val Arg Thr Gln Thr Phe Tyr Gln Asn Pro
            340                 345                 350

Asn Asn Glu Pro Ile Ala Pro Arg Asp Ile Ile Asn Gln Ile Leu Thr
        355                 360                 365

Ala Pro Ala Pro Ala Asp Leu Phe Phe Lys Asn Ala Asp Ile Asn Val
370                 375                 380

Lys Phe Thr Gln Trp Phe Gln Ser Thr Leu Tyr Gly Trp Asn Ile Lys
```

```
385                 390                 395                 400

Leu Gly Thr Gln Thr Val Leu Ser Ser Arg Thr Gly Thr Ile Pro Pro
                405                 410                 415

Asn Tyr Leu Ala Tyr Asp Gly Tyr Tyr Ile Arg Ala Ile Ser Ala Cys
            420                 425                 430

Pro Arg Gly Val Ser Leu Ala Tyr Asn His Asp Leu Thr Thr Leu Thr
        435                 440                 445

Tyr Asn Arg Ile Glu Tyr Asp Ser Pro Thr Thr Glu Asn Ile Ile Val
    450                 455                 460

Gly Phe Ala Pro Asp Asn Thr Lys Asp Phe Tyr Ser Lys Lys Ser His
465                 470                 475                 480

Tyr Leu Ser Glu Thr Asn Asp Ser Tyr Val Ile Pro Ala Leu Gln Phe
                485                 490                 495

Ala Glu Val Ser Asp Arg Ser Phe Leu Glu Asp Thr Pro Asp Gln Ala
            500                 505                 510

Thr Asp Gly Ser Ile Lys Phe Ala Arg Thr Phe Ile Ser Asn Glu Ala
        515                 520                 525

Lys Tyr Ser Ile Arg Leu Asn Thr Gly Phe Asn Thr Ala Thr Arg Tyr
    530                 535                 540

Lys Leu Ile Ile Arg Val Arg Val Pro Tyr Arg Leu Pro Ala Gly Ile
545                 550                 555                 560

Arg Val Gln Ser Gln Asn Ser Gly Asn Asn Arg Met Leu Gly Ser Phe
                565                 570                 575

Thr Ala Asn Ala Asn Pro Glu Trp Val Asp Phe Val Thr Asp Ala Phe
            580                 585                 590

Thr Phe Asn Asp Leu Gly Ile Thr Thr Ser Ser Thr Asn Ala Leu Phe
        595                 600                 605

Ser Ile Ser Ser Asp Ser Leu Asn Ser Gly Glu Glu Trp Tyr Leu Ser
    610                 615                 620

Gln Leu Phe Leu Val Lys Glu Ser Ala Phe Thr Thr Gln Ile Asn Pro
625                 630                 635                 640

Leu Leu Lys

<210> SEQ ID NO 9
<211> LENGTH: 334
<212> TYPE: PRT
<213> ORGANISM: Bacillus subtilis

<400> SEQUENCE: 9

Met Gly Val Ser Phe Asn Ile Met Cys Pro Asn Ser Ser Ile Tyr Ser
1               5                   10                  15

Asp Glu Lys Ser Arg Val Leu Val Asp Lys Thr Lys Ser Gly Lys Val
            20                  25                  30

Arg Pro Trp Arg Glu Lys Lys Ile Ala Asn Val Asp Tyr Phe Glu Leu
        35                  40                  45

Leu His Ile Leu Glu Phe Lys Lys Ala Glu Arg Val Lys Asp Cys Ala
    50                  55                  60

Glu Ile Leu Glu Tyr Lys Gln Asn Arg Glu Thr Gly Glu Arg Lys Leu
65                  70                  75                  80

Tyr Arg Val Trp Phe Cys Lys Ser Arg Leu Cys Pro Met Cys Asn Trp
                85                  90                  95

Arg Arg Ala Met Lys His Gly Ile Gln Ser Gln Lys Val Val Ala Glu
            100                 105                 110

Val Ile Lys Gln Lys Pro Thr Val Arg Trp Leu Phe Leu Thr Leu Thr
```

```
            115                 120                 125
Val Lys Asn Val Tyr Asp Gly Glu Glu Leu Asn Lys Ser Leu Ser Asp
    130                 135                 140

Met Ala Gln Gly Phe Arg Arg Met Met Gln Tyr Lys Lys Ile Asn Lys
145                 150                 155                 160

Asn Leu Val Gly Phe Met Arg Ala Thr Glu Val Thr Ile Asn Asn Lys
                165                 170                 175

Asp Asn Ser Tyr Asn Gln His Met His Val Leu Val Cys Val Glu Pro
            180                 185                 190

Thr Tyr Phe Lys Asn Thr Glu Asn Tyr Val Asn Gln Lys Gln Trp Ile
        195                 200                 205

Gln Phe Trp Lys Lys Ala Met Lys Leu Asp Tyr Asp Pro Asn Val Lys
    210                 215                 220

Val Gln Met Ile Arg Pro Lys Asn Lys Tyr Lys Ser Asp Ile Gln Ser
225                 230                 235                 240

Ala Ile Asp Glu Thr Ala Lys Tyr Pro Val Lys Asp Thr Asp Phe Met
                245                 250                 255

Thr Asp Asp Glu Glu Lys Asn Leu Lys Arg Leu Ser Asp Leu Glu Glu
            260                 265                 270

Gly Leu His Arg Lys Arg Leu Ile Ser Tyr Gly Gly Leu Leu Lys Glu
        275                 280                 285

Ile His Lys Lys Leu Asn Leu Asp Asp Thr Glu Gly Asp Leu Ile
    290                 295                 300

His Thr Asp Asp Asp Glu Lys Ala Asp Glu Asp Gly Phe Ser Ile Ile
305                 310                 315                 320

Ala Met Trp Asn Trp Glu Arg Lys Asn Tyr Phe Ile Lys Glu
                325                 330

<210> SEQ ID NO 10
<211> LENGTH: 572
<212> TYPE: DNA
<213> ORGANISM: Bacillus sp.KSM-S237

<400> SEQUENCE: 10
gatttgccga tgcaacaggc ttatatttag aggaaatttc tttttaaatt gaatacggaa    60
taaaatcagg taaacaggtc ctgatttat tttttgagt ttttagaga actgaagatt       120 gaaataaaag tagaagacaa aggacataag aaaattgcat tagtttaat tatagaaaac    180 gcctttttat aattatttat acctagaacg aaaatactgt ttcgaaagcg gtttactata    240
aaaccttata ttccggctct tttttaaaac aggggggtaaa aattcactct agtattctaa   300
tttcaacatg ctataataaa tttgtaagac gcaatatgca tctcttttttt tacgatatat   360 gtaagcggtt aaccttgtgc tatatgccga tttaggaagg ggggtagatt gagtcaagta    420
gtaataatat agataactta taagttgttg agaagcagga gagcatctgg gttactcaca    480
agttttttta aaactttaac gaaagcactt tcggtaatgc ttatgaattt agctatttga    540
ttcaattact ttaaaaatat ttaggaggta at                                   572

<210> SEQ ID NO 11
<211> LENGTH: 545
<212> TYPE: DNA
<213> ORGANISM: Bacillus sp.KSM-S237

<400> SEQUENCE: 11
gatttgccga tgcaacaggc ttatatttag aggaaatttc tttttaaatt gaatacggaa    60
```

```
taaaatcagg taaacaggtc ctgattttat ttttttgagt tttttagaga actgaagatt    120
gaaataaaag tagaagacaa aggacataag aaaattgcat tagttttaat tatagaaaac    180 gccttttat aattatttat acctagaacg aaaatactgt ttctataaaa ccttatattc     240
cggctctttt ttaaaacagg gggtaaaaat tcactctagt attctaattt caacatgcta    300
taataaattt gtaagacgca atatgcatct ctttttttac gatatacttg tgctatatgc    360
cgatttagga aggggggtag attgagtcaa gtagtaataa tatagataac ttataagttg    420
ttgagaagca ggagagcatc tgggttactc acaagttttt ttaaaacttt aacgaaagca    480
ctttcggtaa tgcttatgaa tttagctatt tgattcaatt actttaaaaa tatttaggag    540
gtaat                                                                545

<210> SEQ ID NO 12
<211> LENGTH: 193
<212> TYPE: DNA
<213> ORGANISM: Bacillus subtilis

<400> SEQUENCE: 12
taagaaaagt gattctggga gagccgggat cacttttta tttaccttat gcccgaaatg     60
aaagctttat gacctaattg tgtaactata tcctatttt tcaaaaaata ttttaaaaac    120
gagcaggatt tcagaaaaaa tcgtggaatt gatacactaa tgcttttata tagggaaaag   180
gtggtgaact act                                                      193

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
gggaattcct gttataaaaa                                                20

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
atgatgttaa gaaagaaaac a                                              21

<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 15
ataacaggaa ttccctaaga aaagtgattc tggga                               35

<210> SEQ ID NO 16
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 16
```

```
tctttcttaa catcatagta gttcaccacc ttttcc                         36

<210> SEQ ID NO 17
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 17
aactagttta atagattatt ggattttggg aacaaactc                      39

<210> SEQ ID NO 18
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 18
tatttaggag gtaatatgat ggcaacaatt aatgagtt                       38

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 19
ccggcagctc ttgcaatggc aacaattaat gagtt                          35

<210> SEQ ID NO 20
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 20
aactagttta atagattatt gattattatt catac                          35

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
tgcaagagct gccggaaata                                           20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
tctattaaac tagttatagg                                           20

<210> SEQ ID NO 23
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 23
attacctcct aaatattttt                                              20

<210> SEQ ID NO 24
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 24
gcaacaatta atgagttgta tcc                                          23

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
cgttcaaaat catccgtaaa tg                                           22

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
aaatgcatga accacttcca c                                            21

<210> SEQ ID NO 27
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 27
attggatttt tggaacaaac tc                                           22

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
taaaagtaga agacaaagga                                              20

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29
cgatatatgt aagcggttaa c                                            21
```

```
<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
caatttaaaa tcgctaccct                                                   20

<210> SEQ ID NO 31
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 31
aactcattaa ttgttgccat agtagttcac cacctttcc                              40

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
tttttataac aggaattccc                                                   20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ggatcaactt tgggagagag                                                   20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
caagtagtaa taatatagat                                                   20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
gcaacaatta atgagttgta                                                   20

<210> SEQ ID NO 36
<211> LENGTH: 20
<212> TYPE: DNA
<213> ORGANISM: Artificial Sequence
<220> FEATURE:
```

-continued

```
<223> OTHER INFORMATION: Synthetic oligonucleotide

<400> SEQUENCE: 36
agtacaccag aaagagtaat                                        20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
tcaaggtggt aaattagatt                                        20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
tcacgtcctg atcaaaaaat                                        20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
tacctgctgg aagtttctat                                        20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
acagaggccg aaatgtagta                                        20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
acagcatatg accaagaacg                                        20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
gagaatatgt ggaaacacac                                        20
```

```
<210> SEQ ID NO 43
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 43
cataccctta cttgatcaaa ggttg                                25

<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 44
aacagggtta ttacaatcac agtga                                25

<210> SEQ ID NO 45
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 45
aatggtaaca atgcagttaa acttt                                25

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 46
aagcttctag agatctgcag gtcga                                25

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
attacctcct aaatatttt                                       20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
agtagttcac cacctttcc                                       20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 49
tctattaaac tagttatagg                                          20

<210> SEQ ID NO 50
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 50
tatttaggag gtaatatgat gaatccttat caaaataa                      38

<210> SEQ ID NO 51
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 51
ggaaaaggtg gtgaactact atgaatcctt atcaaaataa                    40

<210> SEQ ID NO 52
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 52
cctataacta gtttaataga tcactcgttc atgcaaatta                    40

<210> SEQ ID NO 53
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 53
tatttaggag gtaatatgat gaattcaggc tatccgtt                      38

<210> SEQ ID NO 54
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 54
ggaaaaggtg gtgaactact atgaattcag gctatccgtt                    40

<210> SEQ ID NO 55
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 55
cctataacta gtttaataga tcactcgttc atgcaaatta                    40

<210> SEQ ID NO 56
<211> LENGTH: 38
```

```
<212> TYPE: DNA
<213> ORGANISM: Artificial Sequence
<220> FEATURE:
<223> OTHER INFORMATION: Synthetic oligonucleotide

<400> SEQUENCE: 56
tatttaggag gtaatatgat ggaagatagt tctttaga                              38

<210> SEQ ID NO 57
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 57
ggaaaaggtg gtgaactact atggaagata gttctttaga                           40

<210> SEQ ID NO 58
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 58
cctataacta gtttaataga ctactttagt aacggattaa                           40
```

What is claimed is:

1. A method for producing a Cry protein or a culture product comprising the Cry protein, comprising transforming a *Bacillus* bacterium with an expression plasmid incorporating a gene encoding the Cry protein operably